US011576986B2

(12) United States Patent
Salter et al.

(10) Patent No.: US 11,576,986 B2
(45) Date of Patent: Feb. 14, 2023

(54) MACROCYCLIC CHELATORS AND METHODS OF USE THEREOF

(71) Applicant: Janssen Biotech, Inc., Horsham, PA (US)

(72) Inventors: Rhys Salter, Doylestown, PA (US); Vadim Dudkin, Chalfont, PA (US); Fengbin Song, Doylestown, PA (US); Wei Zhang, Malvern, PA (US); Shalom Goldberg, Merion Station, PA (US); John Keith, San Diego, CA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 16/869,771

(22) Filed: May 8, 2020

(65) Prior Publication Data

US 2020/0353105 A1    Nov. 12, 2020

Related U.S. Application Data

(60) Provisional application No. 62/846,044, filed on May 10, 2019.

(51) Int. Cl.
*A61K 51/02* (2006.01)
*A61K 51/04* (2006.01)
*A61K 51/10* (2006.01)

(52) U.S. Cl.
CPC ........ *A61K 51/025* (2013.01); *A61K 51/0482* (2013.01); *A61K 51/1027* (2013.01); *A61K 51/1093* (2013.01)

(58) Field of Classification Search
CPC ....... A61K 51/02; A61K 51/04; A61K 51/511
See application file for complete search history.

(56) References Cited

U.S. PATENT DOCUMENTS

| | | | |
|---|---|---|---|
| 10,100,125 | B2 | 10/2018 | Timmermand et al. |
| 2013/0266512 | A1 | 10/2013 | Fox et al. |
| 2016/0287734 | A1 | 10/2016 | Rashidian et al. |
| 2020/0024360 | A1 | 1/2020 | Anderson et al. |
| 2020/0157087 | A1 | 5/2020 | Babich et al. |

FOREIGN PATENT DOCUMENTS

| | | | | |
|---|---|---|---|---|
| WO | WO 2015/073746 | A2 | 5/2015 | |
| WO | WO 2018/183906 | A | 10/2018 | |
| WO | WO 2018/187631 | A1 | 10/2018 | |
| WO | WO 2018183906 | * | 10/2018 | |
| WO | WO-2019090242 | A1 * | 5/2019 | ........... A61K 31/215 |
| WO | WO 2019/125982 | A1 | 6/2019 | |
| WO | WO 2020/106886 | A1 | 5/2020 | |

OTHER PUBLICATIONS

International Search Report relating to corresponding PCT Patent Application No. PCT/IB2020/054381, filed May 8, 2020, dated Jul. 2, 2020.

Written Opinion relating to corresponding PCT Patent Application No. PCT/IB2020/054381, filed May 8, 2020, dated Jul. 2, 2020.
Maguire et al., "Efficient 1-Step 1,2,4-28 Radiolabeling of Monoclonal Antibodies to High Specific Activity with $^{225}$Ac for α-Particle Radioimmunotherapy of Cancer", The Journal of Nuclear Medicine, Jun. 30, 2014,pp. 1491-1498, vol. 55(9), XP055568060.
Agarwal, P. and Bertozzi, C.R., "Site-specific antibody-drug conjugates: the nexus of bioorthogonal chemistry, protein engineering, and drug development.", Bioconjug Chem, 2015, pp. 176-192, vol. 26(2).
Babb et al., "Synthesis of Hydroxymethyl-Functionalized Diazacrowns and Cryptands.", Journal of Heterocyclic Chemistry, 1986, pp. 609-613, vol. 23(2).
Ban et al., "Facile and Stabile Linkages through Tyrosine: Bioconjugation Strategies with the Tyrosine-Click Reaction.", Bioconjugate Chemistry, 2013, pp. 520-532, vol. 24.
Bradshaw et al., "Synthesis of (AUyloxy)methyl-Substituted Diaza-18-crown-6 Compounds for Attachment to Silica Gel.", Journal of Organic Chemistry, 1988, pp. 3190-3195, vol. 53(14).
Bronson et al., "Efficient Immobilization of a Cadmium Chemosensor in a Thin Film: Generation of a Cadmium Sensor Prototype.", Org. Lett. 2005, pp. 1105-1108, vol. 7(6).
Debets et al., "Bioconjugation with strained alkenes and alkynes.", Acc Chem Res, 2011, pp. 805-815, vol. 44(9).
Hu et al.,"Towards the next generation of biomedicines by site-selective conjugation.", Chem Soc Rev 2016, pp. 1691-1719, vol. 45(6).
Kolb et al., "Click Chemistry: Diverse Chemical Function from a Few Good Reactions.", Angewandte Chemie International Edition, 2001, pp. 2004-2021, vol. 40.
Kwekkeboom et al., "[$^{177}$Lu-DOTA$^0$,Tyr$^3$]octreotate: comparison with [$^{111}$In-DTPA$^0$]octreotide in patients.", Eur J Nucl Med., Sep. 2001, pp. 1319-1325, vol. 28(9).
Li et al., "Preparation of well-defined antibody-drug conjugates through glycan remodeling and strain-promoted azide-alkyne cycloadditions.", Angew Chem Int Ed Engl, 2014, pp. 7179-7182, vol. 53.
Lin et al., "Redox-Based reagents for chemoselective methionine bioconjugation.", Science, 2017, pp. 597-602, vol. 355.
Miederer et al., "Realizing the potential of the Actinium-225 radionuclide generator in targeted alpha particle therapy applications.", Adv Drug Deliv Rev, 2008, pp. 71-82, vol. 60.

(Continued)

*Primary Examiner* — Michael G. Hartley
*Assistant Examiner* — Jagadishwar R Samala
(74) *Attorney, Agent, or Firm* — Brian C. Trinque; Lathrop GPM LLP

(57) ABSTRACT

Macrocyclic chelators for chelation of alpha-emitting radiometal ions, such as actinium-225 are provided. Also provided are radiometal complexes containing an alpha-emitting radiometal ion bound to the macrocyclic chelator via coordinate bonding, and radioimmunoconjugates containing the radiometal complexes covalently linked to a targeting ligand, such as an antibody or antigen binding fragment thereof. The radioimmunoconjugates can be produced by click chemistry reactions. Methods of using the radiocomplexes and radioimmunoconjugates for selectively targeting neoplastic cells for radiotherapy and for treating neoplastic diseases and disorders are also described.

22 Claims, 3 Drawing Sheets

Figure 1B:
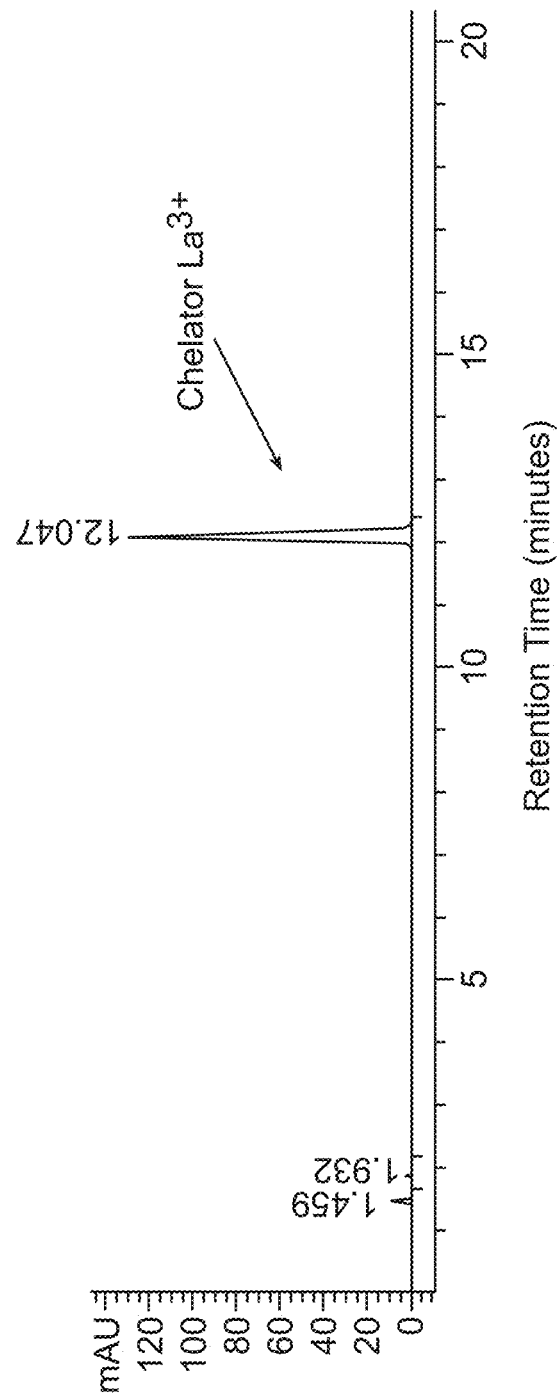

Specification includes a Sequence Listing.

(56) References Cited

OTHER PUBLICATIONS

Park et al., "Peptide-directed photocrosslinking for site-specific conjugation of IgG.", Bioconjugate Chem, 2018, pp. 1-14, 3240.
Pham et al., "Tuning a Protein-Labeling Reaction to Achieve Highly SiteSelective Lysine Conjugation.", Chembiochem, 2018, pp. 799-804, vol. 19.
Rabuka, D., "Chemoenzymatic methods for site-specific protein modification.", Curr Opin Chem Biol, 2010, pp. 790-796, vol. 14.
Roca-Sabio et al., "Macrocyclic Receptor Exhibiting Unprecedented Selectivity for Light Lanthanides.", J. Am. Chem. Soc., 2009, pp. 3331-3341, vol. 131.
Spicer et al., "Selective chemical protein modification.", Nature Communications, 2014, pp. 1-14, vol. 5.
Thiele et al., "An Eighteen-Membered Macrocyclic Ligand for Actinium-225 Targeted Alpha Therapy.", Angew. Chem. Int. Ed., 2017, pp. 14712-14717, vol. 56.
Toda et al., "Rapid, Stable, Chemoselective Labeling of Thiols with Julia-Kocienski-like Reagents: A Serum-Stable Alternative to Maleimide-Based Protein Conjugation**.", Angew Chemie, 2013, pp. 12592-12596, vol. 52.
Xiao et al., Genetic incorporation of multiple unnatural amino acids into proteins in mammalian cells., Angew Chem Int Ed Engl, 2013, pp. 14080-14083, vol. 52.
Deal et al., "Improved in vivo stability of actinium-225 macrocyclic complexes.", J Med Chem, 1999, pp. 2988-2892, vol. 42(15).
Thiele et al., "Implementing f-Block Metal Ions in Medicine: Tuning the Size Selectivity of Expanded Macrocycles.", Inorganic Chemistry, Aug. 19, 2019, pp. 10483-10500, vol. 58(16).
Brinkley, M., "A Brief Survey of Methods for Preparing Protein Conjugates with Dyes, Haptens, and Cross-Linking Reagents", *Bioconjugate Chem.*, 3:2-13, 1992.
Kim et al., "An overview of targeted alpha therapy", *Tumor Biol.*, 33:573-590, 2012.

* cited by examiner

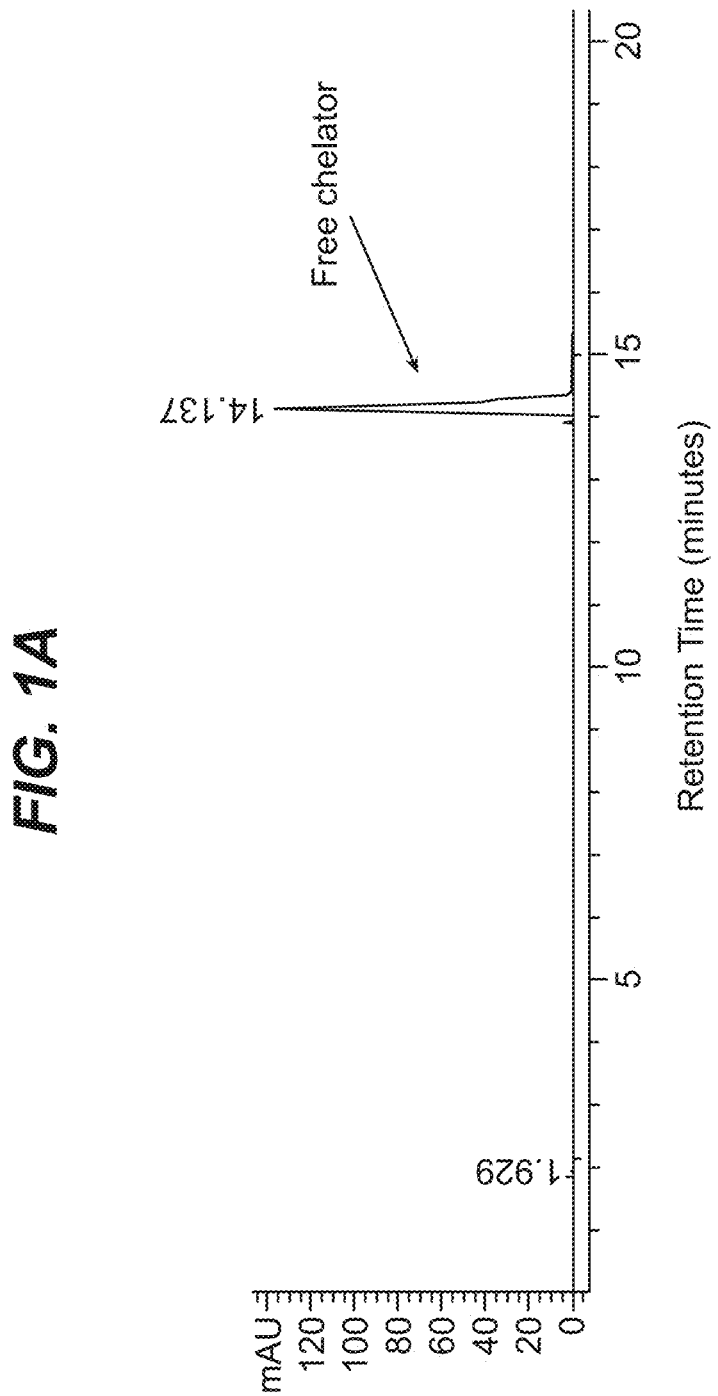

```
                            SEQUENCE LISTING

<160> NUMBER OF SEQ ID NOS: 22

<210> SEQ ID NO 1
<211> LENGTH: 447
<212> TYPE: PRT
<213> ORGANISM: Artificial Sequence
<220> FEATURE:
<223> OTHER INFORMATION: Control mAb HC

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 2
<211> LENGTH: 219
<212> TYPE: PRT
<213> ORGANISM: Artificial Sequence
<220> FEATURE:
<223> OTHER INFORMATION: Control mAb LC

<400> SEQUENCE: 2

Asp Ile Val Met Thr Gln Ser Pro Asp Ser Leu Ala Val Ser Leu Gly
1               5                   10                  15

Glu Arg Asn Ala Thr Ile Asn Cys Arg Ala Ser Gln Ser Val Asp Tyr
                20                  25                  30

Asn Gly Ile Ser Tyr Met His Trp Tyr Gln Gln Lys Pro Gly Gln Pro
            35                  40                  45

Pro Lys Leu Leu Ile Tyr Ala Ala Ser Asn Pro Glu Ser Gly Val Pro
        50                  55                  60

Asp Arg Phe Ser Gly Ser Gly Ser Gly Thr Asp Phe Thr Leu Thr Ile
```

```
                65                  70                  75                  80
Ser Ser Leu Gln Ala Glu Asp Val Ala Val Tyr Tyr Cys Gln Gln Ile
                    85                  90                  95

Ile Glu Asp Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 3
<211> LENGTH: 5
<212> TYPE: PRT
<213> ORGANISM: Artificial Sequence
<220> FEATURE:
<223> OTHER INFORMATION: Anti-PSMA mAb (PSMB127) HC CDR1

<400> SEQUENCE: 3

Ser Asp Ala Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Anti-PSMA mAb (PSMB127) HC CDR2

<400> SEQUENCE: 4

Glu Ile Ser Gly Ser Gly Gly Tyr Thr Asn Tyr Ala Asp Ser Val Lys
1               5                   10                  15

Gly

<210> SEQ ID NO 5
<211> LENGTH: 15
<212> TYPE: PRT
<213> ORGANISM: Artificial Sequence
<220> FEATURE:
<223> OTHER INFORMATION: Anti-PSMA mAb (PSMB127) HC CDR3

<400> SEQUENCE: 5

Asp Ser Tyr Asp Ser Ser Leu Tyr Val Gly Asp Tyr Phe Asp Tyr
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Anti-PSMA mAb (PSMB127) LC CDR1

<400> SEQUENCE: 6
```

```
Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Anti-PSMA mAb (PSMB127) LC CDR2

<400> SEQUENCE: 7

Asp Ala Ser Asn Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Anti-PSMA mAb (PSMB127) LC CDR3

<400> SEQUENCE: 8

Gln Gln Arg Ser Asn Trp Pro Leu Thr
1               5

<210> SEQ ID NO 9
<211> LENGTH: 451
<212> TYPE: PRT
<213> ORGANISM: Artificial Sequence
<220> FEATURE:
<223> OTHER INFORMATION: Anti-PSMA mAb (PSMB127) HC

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
                20                  25                  30

Ala Met His Trp Val Arg Gln Ala Pro Gly Lys Gly Leu Glu Trp Val
            35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205
```

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Anti-PSMA mAb (PSMB127) LC

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 6
<212> TYPE: PRT
<213> ORGANISM: Artificial Sequence
<220> FEATURE:
<223> OTHER INFORMATION: H11B6 CDR sequence

<400> SEQUENCE: 11

Ser Asp Tyr Ala Trp Asn
1               5

<210> SEQ ID NO 12
<211> LENGTH: 16
<212> TYPE: PRT
<213> ORGANISM: Artificial Sequence
<220> FEATURE:
<223> OTHER INFORMATION: H11B6 CDR sequence

<400> SEQUENCE: 12

Tyr Ile Ser Tyr Ser Gly Ser Thr Thr Tyr Asn Pro Ser Leu Lys Ser
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: H11B6 CDR sequence

<400> SEQUENCE: 13

Gly Tyr Tyr Tyr Gly Ser Gly Phe
1               5

<210> SEQ ID NO 14
<211> LENGTH: 15
<212> TYPE: PRT
<213> ORGANISM: Artificial Sequence
<220> FEATURE:
<223> OTHER INFORMATION: H11B6 CDR sequence

<400> SEQUENCE: 14

Lys Ala Ser Glu Ser Val Glu Tyr Phe Gly Thr Ser Leu Met His
1               5                   10                  15

<210> SEQ ID NO 15
<211> LENGTH: 7
<212> TYPE: PRT
<213> ORGANISM: Artificial Sequence
<220> FEATURE:
```

<223> OTHER INFORMATION: H11B6 CDR sequence

<400> SEQUENCE: 15

Ala Ala Ser Asn Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: H11B6 CDR sequence

<400> SEQUENCE: 16

Gln Gln Thr Arg Lys Val Pro Tyr Thr
1               5

<210> SEQ ID NO 17
<211> LENGTH: 117
<212> TYPE: PRT
<213> ORGANISM: Artificial Sequence
<220> FEATURE:
<223> OTHER INFORMATION: H11B6 HC variable region sequence

<400> SEQUENCE: 17

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115

<210> SEQ ID NO 18
<211> LENGTH: 111
<212> TYPE: PRT
<213> ORGANISM: Artificial Sequence
<220> FEATURE:
<223> OTHER INFORMATION: H11B6 LC variable region sequence

<400> SEQUENCE: 18

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
            85                  90                  95

Lys Val Pro Tyr Thr Phe Gly Gln Gly Thr Lys Leu Glu Ile Lys
            100                 105                 110

<210> SEQ ID NO 19
<211> LENGTH: 330
<212> TYPE: PRT
<213> ORGANISM: Artificial Sequence
<220> FEATURE:
<223> OTHER INFORMATION: H11B6 HC constant region sequence

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 107
<212> TYPE: PRT
<213> ORGANISM: Artificial Sequence
<220> FEATURE:
<223> OTHER INFORMATION: H11B6 LC constant region sequence

<400> SEQUENCE: 20

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 21
<211> LENGTH: 447
<212> TYPE: PRT
<213> ORGANISM: Artificial Sequence
<220> FEATURE:
<223> OTHER INFORMATION: H11B6 HC sequence

<400> SEQUENCE: 21

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 22
<211> LENGTH: 218
<212> TYPE: PRT
<213> ORGANISM: Artificial Sequence
<220> FEATURE:
<223> OTHER INFORMATION: H11B6 LC sequence

<400> SEQUENCE: 22

Asp Ile Val Leu Thr Gln Ser Pro Asp Ser Leu Ala Val Ser Leu Gly
1               5                   10                  15
Glu Arg Ala Thr Ile Asn Cys Lys Ala Ser Glu Ser Val Glu Tyr Phe
            20                  25                  30
Gly Thr Ser Leu Met His Trp Tyr Gln Gln Lys Pro Gly Gln Pro Pro
        35                  40                  45
Lys Leu Leu Ile Tyr Ala Ala Ser Asn Arg Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Thr Arg
                85                  90                  95
Lys Val Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130             135                 140

Pro Arg Glu Ala Lys Val Gln Trp Lys Val Asp Asn Ala Leu Gln Ser
145             150                 155                 160

Gly Asn Ser Gln Glu Ser Val Thr Glu Gln Asp Ser Lys Asp Ser Thr
            165                 170             175

Tyr Ser Leu Ser Ser Thr Leu Thr Leu Ser Lys Ala Asp Tyr Glu Lys
            180                 185             190

His Lys Val Tyr Ala Cys Glu Val Thr His Gln Gly Leu Ser Ser Pro
        195             200                 205

Val Thr Lys Ser Phe Asn Arg Gly Glu Cys
    210                 215
```

MACROCYCLIC CHELATORS AND METHODS OF USE THEREOF

CROSS-REFERENCE TO RELATED APPLICATIONS

This application claims the benefit of priority of U.S. Provisional Patent Application No. 62/846,044, filed on May 10, 2019, which is incorporated by reference herein, in its entirety and for all purposes.

REFERENCE TO SEQUENCE LISTING SUBMITTED ELECTRONICALLY

This application contains a sequence listing, which is submitted electronically via EFS-Web as an ASCII formatted sequence listing with a file name "JBI6072USNP1_SeqListing.txt" and a creation date of May 1, 2020 and having a size of 26 kb. The sequence listing submitted via EFS-Web is part of the specification and is herein incorporated by reference in its entirety.

BACKGROUND OF THE INVENTION

Alpha particle-emitting radionuclides have great promise for cancer therapy due to their combination of high energy with short-range action, providing the possibility of potent killing that is mostly localized to tumor cells (Kim, Y. S. and M. W. Brechbiel, An overview of targeted alpha therapy. *Tumour Biol*, 2012. 33(3): p. 573-90). Targeted delivery of alpha-emitters, using an antibody, scaffold protein, small molecule ligand, aptamer, or other binding moiety that is specific for a cancer antigen, provides a method of selective delivery of the radionuclide to tumors to enhance their potency and mitigate off-target effects. In common practice, the binding moiety is attached to a chelator which binds to the alpha-emitting radiometal to produce a radiocomplex. Many such examples use a monoclonal antibody (mAb) as the targeting ligand, to produce what is known as a radioimmunoconjugate.

Actinium-225 ($^{225}$Ac) is an alpha-emitting radioisotope that is of particular interest for medical applications (Miederer et al., Realizing the potential of the Actinium-225 radionuclide generator in targeted alpha particle therapy applications. *Adv Drug Deliv Rev*, 2008. 60(12):71-82). The 10-day half-life of $^{225}$Ac is long enough to facilitate radioconjugate production, but short enough to match the circulation pharmacokinetics of delivery vehicles such as antibodies. As such, $^{225}$Ac radioimmunoconjugates are of particular interest. Additionally, $^{225}$Ac decays in a series of steps that ultimately emits 4 alpha particles before reaching a stable isotope, $^{209}$Bi, thereby increasing the potency. Another radioisotope of interest for medical applications is Lutetium-177 ($^{177}$Lu), which emits both gamma-irradiation suitable for imaging and medium-energy beta-irradiation suitable for radiotherapy. It has been shown that $^{177}$Lu-labeled peptides demonstrate reduced normal tissue damage, and that $^{177}$Lu-labeling makes it possible to use a single radiolabeled agent for both therapy and imaging (Kwekkeboom D J, et al. [$^{177}$Lu-DOTA$^0$,Tyr$^3$]octreotide: comparison with [$^{111}$In-DTPA]octreotide in patients. *Eur J Nucl Med*. 2001; 28: p. 1319-1325). Other radioisotopes that are used for therapeutic applications include, e.g., beta or alpha emitters, such as, e.g., $^{32}$P, $^{47}$Sc, $^{67}$Cu, $^{77}$As, $^{89}$Sr, $^{90}$Y, $^{99}$Tc, $^{105}$Rh, $^{109}$Pd, $^{111}$Ag, $^{131}$I, $^{149}$Tb, $^{152}$Tb, $^{155}$Tb, $^{153}$Sm, $^{159}$Gd, $^{165}$Dy, $^{166}$Ho, $^{169}$Er, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{255}$Fm and $^{227}$Th. Other radioisotopes that are used for imaging applications include gamma-emitting radioisotopes, such as, e.g., $^{62}$Cu, $^{64}$Cu, $^{67}$Ga, $^{68}$Ga, $^{86}$Y, $^{89}$Zr, and $^{111}$In.

Currently, the most widely used chelator for Actinium-225 and lanthanides is DOTA (1,4,7,10-Tetraazacyclododecane-1,4,7,10-tetraacetic acid; tetraxaten), and previous clinical and pre-clinical programs have largely used 1,4,7,10-tetraazacyclododecane-1,4,7,10-tetraacetic acid (DOTA) for actinium chelation. However, it is known that DOTA chelation of actinium can be challenging (Deal, K. A., et al., Improved in vivo stability of actinium-225 macrocyclic complexes. *J Med Chem*, 1999. 42(15): p. 2988-92). For example, DOTA allows for a chelation ratio of at best >500:1 DOTA:Actinium-225 when attached to targeting ligands, such as proteins or antibodies, and often requires either harsh conditions or high levels of DOTA per antibody. Other macrocyclic chelators for lanthanides and actinium-225 have been described in, for example, International Patent Application Publication WO 2018/183906; Thiele et al. "An Eighteen-Membered Macrocyclic Ligand for Actinium-225 Targeted Alpha Therapy" *Angew. Chem. Int. Ed*. (2017) 56, 14712-14717; Roca-Sabio et al. "Macrocyclic Receptor Exhibiting Unprecedented Selectivity for Light Lanthanides" *J. Am. Chem. Soc*. (2009) 131, 3331-3341.

Site-specificity has become a key area of focus in the antibody-drug conjugate (ADC) field (Agarwal, P. and C. R. Bertozzi, Site-specific antibody-drug conjugates: the nexus of bioorthogonal chemistry, protein engineering, and drug development, *Bioconjug Chem*, 2015. 26(2): p. 176-92), as it has been demonstrated that both efficacy and safety of ADCs can be increased with site-specific methods as compared to random conjugation. It is thought that similar safety and efficacy benefits could be achieved for radioimmunoconjugates.

BRIEF SUMMARY OF THE INVENTION

Accordingly, there is a need in the art for novel chelators that bind radiometals, preferably alpha-emitting radiometals, such as actinium-225 ($^{225}$Ac), and can be used to produce stable radioimmunoconjugates with high specific activity and high yield. The invention satisfies this need by providing a macrocyclic chelator capable of binding radiometals, such as alpha-emitting radiometals, particularly $^{225}$Ac, irrespective of the specific activity or most common metal impurities. Chelators of the invention can be used to produce radioimmunoconjugates having high stability in vitro and in vivo by conjugation to a targeting ligand, such as an antibody, protein, aptamer, small molecule, etc., preferably in a site-specific manner using "click chemistry." Radioimmunoconjugates produced by conjugation of the chelator of the invention to a targeting ligand can be used for targeted radiotherapy, such as for targeted radiotherapy of a neoplastic cell and/or targeted treatment of a neoplastic disease or disorder, including cancer.

In one general aspect, the invention relates to a chelator of formula (I):

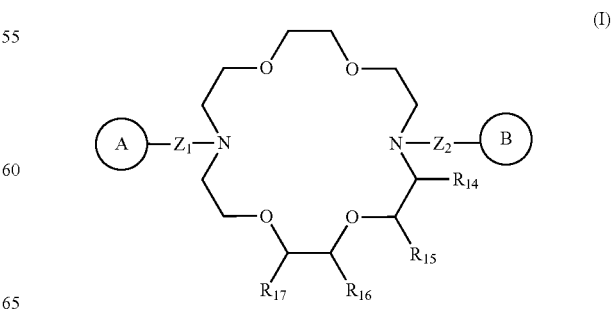

(I)

wherein:
each of ring A and ring B is independently a 6-10 membered aryl or a 5-10 membered heteroaryl, wherein each of ring A and ring B is optionally substituted with one or more substituents independently selected from the group consisting of halo, alkyl, alkenyl, cycloalkyl, cycloalkenyl, aryl, heterocyclyl, heteroaryl, —$OR_{13}$, —$SR_{13}$, —$(CH_2)_pCOOR_{13}$, —$OC(O)R_{13}$, —$N(R_{13})_2$, —$CON(R_{13})_2$, —$NO_2$, —CN, —$OC(O)N(R_{13})_2$, and X;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X,
or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
provided that the chelator comprises at least one X, and when X is present on ring A or ring B, $L_1$ is a linker or at least one of $R_{12}$ and $R_{14}$-$R_{17}$ is not hydrogen.

In alternative embodiments, it is contemplated that each of ring A and ring B is an optionally substituted heterocyclyl ring, such as oxazoline.

In one embodiment, a chelator of the invention is a chelator of formula (II):

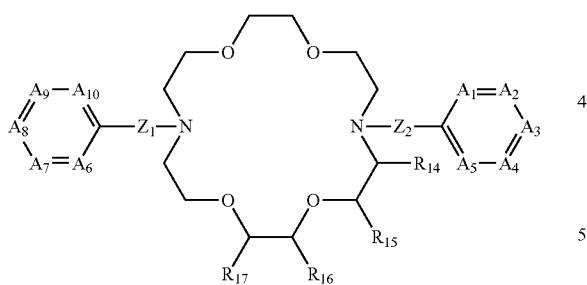

(II)

wherein:
$A_1$ is N or $CR_1$ or is absent;
$A_2$ is N or $CR_2$;
$A_3$ is N or $CR_3$;
$A_4$ is N or $CR_4$;
$A_5$ is N or $CR_5$;
$A_6$ is N or $CR_6$ or is absent;
$A_7$ is N or $CR_7$;
$A_8$ is N or $CR_8$;
$A_9$ is N or $CR_9$;
$A_{10}$ is N or $CR_{10}$;
provided that no more than three of $A_1$, $A_2$, $A_3$, $A_4$, and $A_5$ are N, and no more than three of $A_6$, $A_7$, $A_8$, $A_9$, and $A_{10}$ are N;

each of $R_1$, $R_2$, $R_3$, $R_4$, $R_5$, $R_6$, $R_7$, $R_8$, $R_9$, and $R_{10}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_pCOOR_{13}$, —$OC(O)R_{13}$, —$N(R_{13})_2$, —$CON(R_{13})_2$, —$NO_2$, —CN, —$OC(O)N(R_{13})_2$, and —X,
or, alternatively, any two directly adjacent $R_1$, $R_2$, $R_3$, $R_4$, $R_5$, $R_6$, $R_7$, $R_8$, $R_9$, and $R_{10}$ are taken together with the atoms to which they are attached to form a five or six-membered substituted or unsubstituted carbocyclic or nitrogen-containing ring;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X,
or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
provided that the chelator comprises at least one X, and when any one of $R_1$, $R_2$, $R_3$, $R_4$, $R_5$, $R_6$, $R_7$, $R_8$, $R_9$, and $R_{10}$ is X, then $L_1$ is a linker.

In one embodiment, a chelator of the invention is a chelator of formula (III):

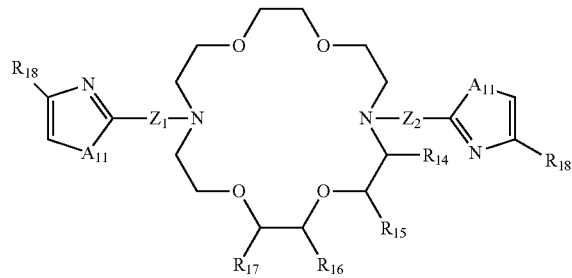

(III)

wherein:
each $A_{11}$ is independently O, S, NMe, or NH;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X, or alternatively R$_{14}$ and R$_{15}$ and/or R$_{16}$ and R$_{17}$ are taken together with the carbon atoms to which they are attached to form a 5- or 6-membered cycloalkyl ring optionally substituted with X;

each R$_{18}$ is independently selected from the group consisting of hydrogen, halo, alkyl, alkenyl, cycloalkyl, cycloalkenyl, aryl, heterocyclyl, heteroaryl, —OR$_{13}$, —SR$_{13}$, —(CH$_2$)$_p$COOR$_{13}$, —OC(O)R$_{13}$, —N(R$_{13}$)$_2$, —CON(R$_{13}$)$_2$, —NO$_2$, —CN, —OC(O)N(R$_{13}$)$_2$, and —X, provided that the chelator comprises at least one X, and when R$_{18}$ is X, then L$_1$ is a linker or at least one of R$_{12}$ and R$_{14}$-R$_{17}$ is not hydrogen.

In particular embodiments, a chelator is:

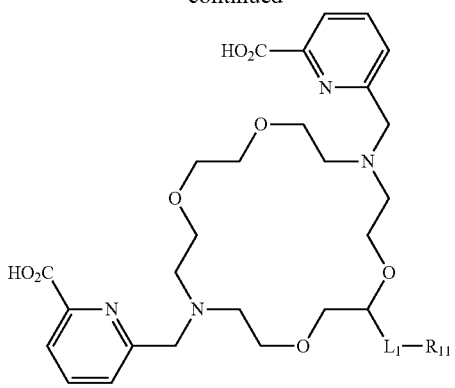

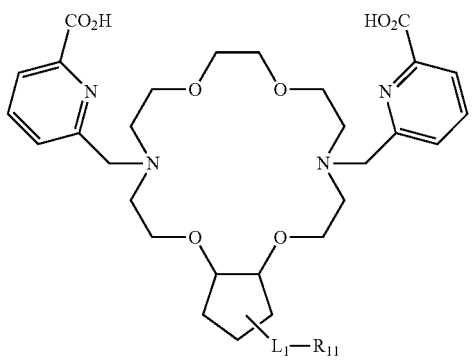

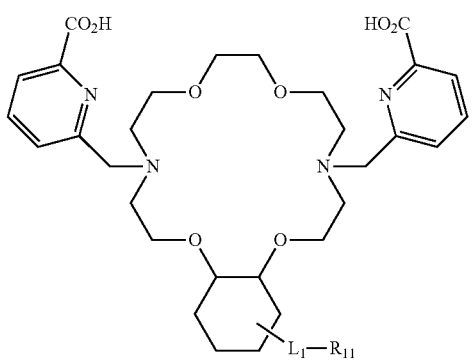

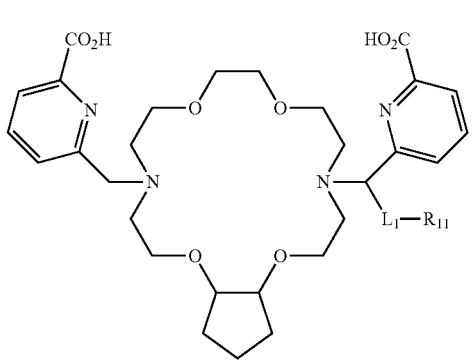

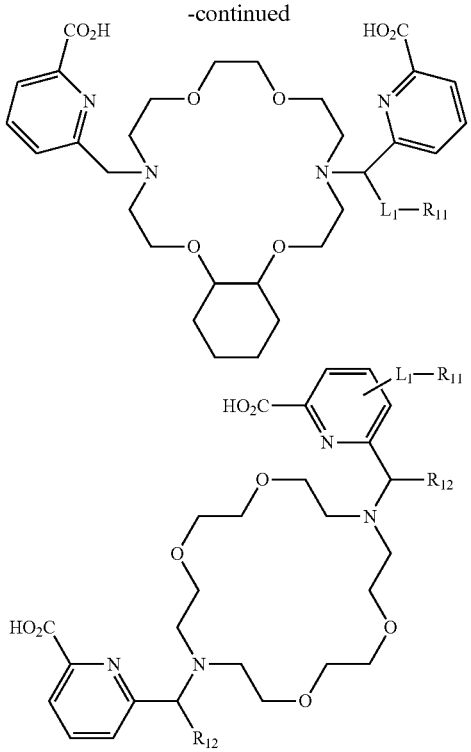

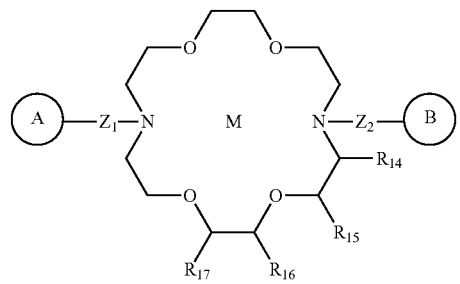

wherein:
L₁ is absent or a linker;
R₁₁ is a nucleophilic moiety or an electrophilic moiety, or R₁₁ comprises a targeting ligand; and
each R₁₂ is independently hydrogen, —CH₃ or —CH₂CH₃, provided that at least one R₁₂ is —CH₃ or CH₂CH₃.

In some embodiments, R₁₁ is —NH₂, —NCS, —NCO, —N₃, alkynyl, cycloalkynyl, —C(O)R₁₃, —COOR₁₃, —CON(R₁₃)₂, maleimido, acyl halide, tetrazine, or trans-cyclooctene.

In certain embodiments, R₁₁ is cyclooctynyl or a cyclooctynyl derivative selected from the group consisting of bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

In particular embodiments, R₁₁ is DBCO or BCN.

In some embodiments, R₁₁ comprises a targeting ligand, wherein the targeting ligand comprises an antibody or antigen binding fragment thereof, scaffold protein, small molecule, or aptamer.

In particular embodiments, a targeting ligand is an antibody or antigen binding fragment thereof.

In another aspect, the invention relates to a radiometal complex comprising a chelator of the invention comprising a radiometal ion bound to the chelator via coordinate bonding.

In one embodiment, a radiometal complex of the invention has the structure of formula (I-m):

wherein:
M is a radiometal ion, preferably an alpha-emitting radiometal ion;
each of ring A and ring B is independently a 6-10 membered aryl or a 5-10 membered heteroaryl, wherein each of ring A and ring B is optionally substituted with one or more substituents independently selected from the group consisting of halo, alkyl, alkenyl, cycloalkyl, cycloalkenyl, aryl, heterocyclyl, heteroaryl, —OR₁₃, —SR₁₃, —(CH₂)$_p$COOR₁₃, —OC(O)R₁₃, —N(R₁₃)₂, —CON(R₁₃)₂, —NO₂, —CN —OC(O)N(R₁₃)₂, and X;
each of Z₁ and Z₂ is independently —(C(R₁₂)₂)$_m$— or —(CH₂)$_n$—C(R₁₂)(X)—(CH₂)$_n$—;
each X is independently -L₁-R₁₁;
each n is independently 0, 1, 2, 3, 4, or 5;
each m is independently 1, 2, 3, 4, or 5;
each p is independently 0 or 1;
L₁ is absent or a linker;
R₁₁ is a nucleophilic moiety or an electrophilic moiety, or R₁₁ comprises a targeting ligand;
each R₁₂ is independently hydrogen, alkyl, cycloalkyl, aryl, heterocyclyl, or heteroaryl;
each R₁₃ is independently hydrogen or alkyl;
each of R₁₄, R₁₅, R₁₆, and R₁₇ is independently hydrogen, alkyl, or X,
or alternatively R₁₄ and R₁₅ and/or R₁₆ and R₁₇ are taken together with the carbon atoms to which they are attached to form a 5- or 6-membered cycloalkyl ring optionally substituted with X;
provided that the radiometal complex comprises at least one X, and when X is present on ring A or ring B, L₁ is a linker or at least one of R₁₂ and R₁₄-R₁₇ is not hydrogen.

In alternative embodiments, it is contemplated that each of ring A and ring B is an optionally substituted heterocyclyl ring, such as oxazoline.

In one embodiment, a radiometal complex of the invention is a radiometal complex of formula (II-m):

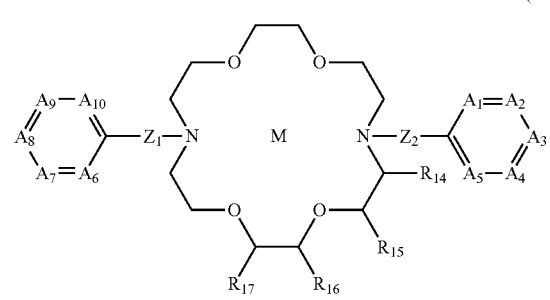

wherein:
M is a radiometal ion, preferably an alpha-emitting radiometal ion;
$A_1$ is N or $CR_1$ or is absent;
$A_2$ is N or $CR_2$;
$A_3$ is N or $CR_3$;
$A_4$ is N or $CR_4$;
$A_5$ is N or $CR_5$;
$A_6$ is N or $CR_6$ or is absent;
$A_7$ is N or $CR_7$;
$A_8$ is N or $CR_8$;
$A_9$ is N or $CR_9$;
$A_{10}$ is N or $CR_{10}$;
provided that no more than three of $A_1$, $A_2$, $A_3$, $A_4$, and $A_5$ are N, and no more than three of $A_6$, $A_7$, $A_8$, $A_9$, and $A_{10}$ are N;
each of $R_1$, $R_2$, $R_3$, $R_4$, $R_5$, $R_6$, $R_7$, $R_8$, $R_9$, and $R_{10}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_pCOOR_{13}$, —$OC(O)R_{13}$, —$N(R_{13})_2$, —$CON(R_{13})_2$, —$NO_2$, —CN —$OC(O)N(R_{13})_2$, and —X,
or, alternatively, any two directly adjacent $R_1$, $R_2$, $R_3$, $R_4$, $R_5$, $R_6$, $R_7$, $R_8$, $R_9$, and $R_{10}$ are taken together with the atoms to which they are attached to form a five or six-membered substituted or unsubstituted carbocyclic or nitrogen-containing ring;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X,
or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
provided that the radiometal complex comprises at least one X, and when any one of $R_1$, $R_2$, $R_3$, $R_4$, $R_5$, $R_6$, $R_7$, $R_8$, $R_9$, and $R_{10}$ is X, then $L_1$ is a linker or at least one or $R_{12}$ and $R_{14}$-$R_{17}$ is not hydrogen.

In one embodiment, a radiometal complex of the invention is a radiometal complex of formula (III-m):

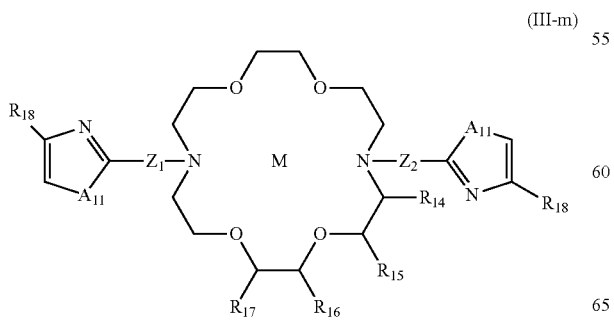

(III-m)

wherein:
M is a radiometal ion, preferably an alpha-emitting radiometal ion;
each $A_{11}$ is independently O, S, NMe, or NH;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X,
or alternatively $R_{14}$ and $R_{15}$ and/or $R_{16}$ and $R_{17}$ are taken together with the carbon atoms to which they are attached to form a 5- or 6-membered cycloalkyl ring optionally substituted with X; and
each $R_{18}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_pCOOR_{13}$, —$OC(O)R_{13}$, —$N(R_{13})_2$, —$CON(R_{13})_2$, —$NO_2$, —CN —$OC(O)N(R_{13})_2$, and —X,
provided that the radiometal complex comprises at least one X, and when $R_{18}$ is X, then $L_1$ is a linker or at least one of $R_{12}$ and $R_{14}$-$R_{17}$ is not hydrogen.

In certain embodiments, the alpha-emitting radiometal ion is actinium-225 ($^{225}$Ac).

In particular embodiments, a radiometal complex of the invention is selected from the group consisting of:

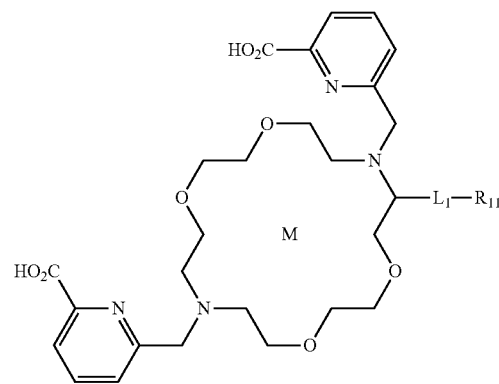

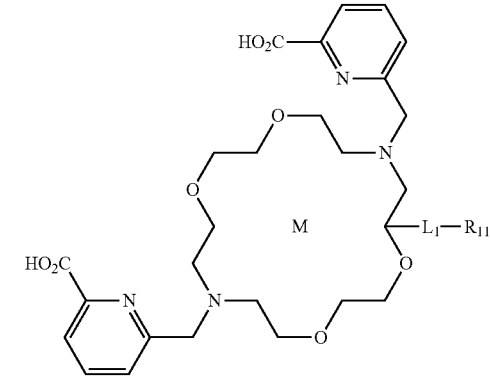

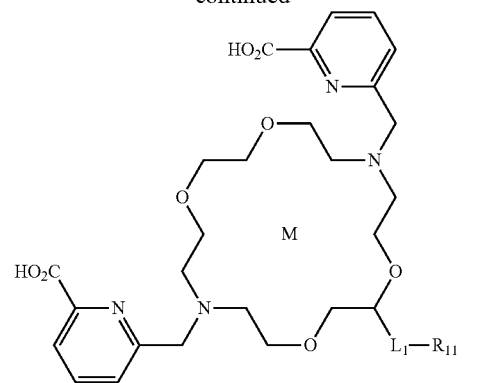

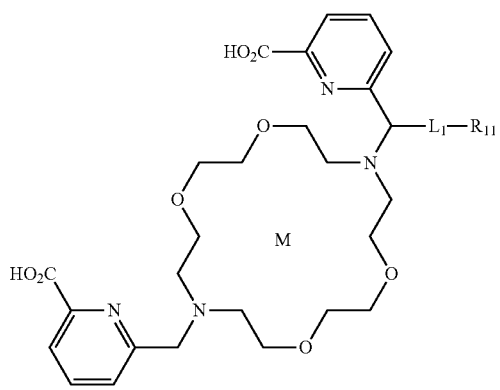

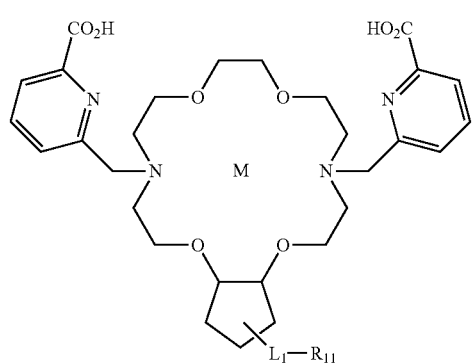

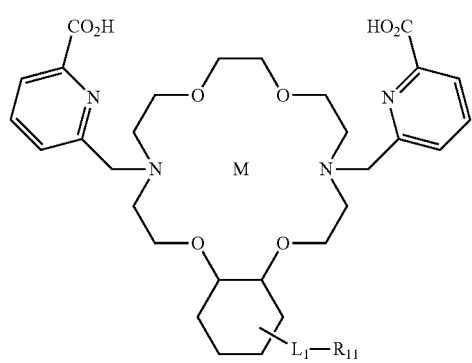

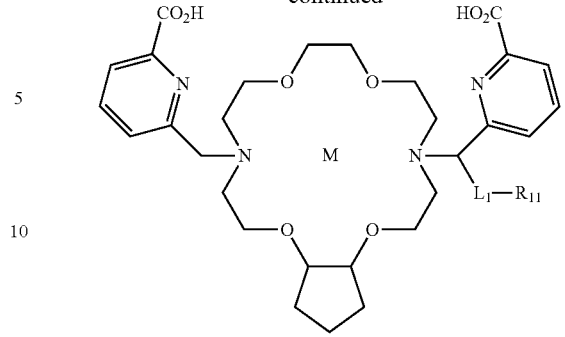

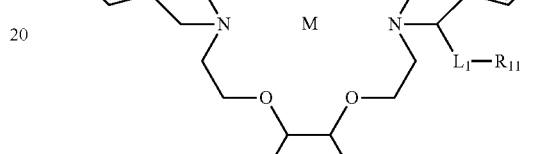

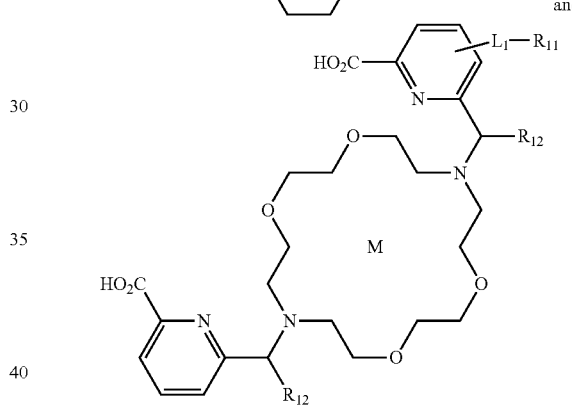

and

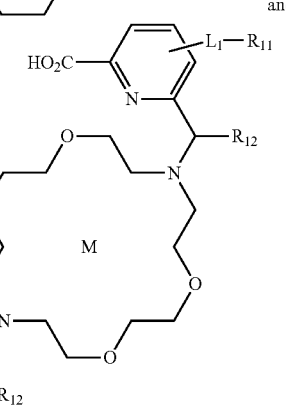

wherein:

M is a radiometal ion, preferably an alpha-emitting radiometal ion, more preferably actinium-225 ($^{225}$Ac), $L_1$ is absent or a linker;

$R_{11}$ is a nucleophilic moiety or an electrophilic moiety, or $R_{11}$ comprises a targeting ligand; and each $R_{12}$ is independently hydrogen, —$CH_3$ or —$CH_2CH_3$, provided that at least one $R_{12}$ is —$CH_3$ or $CH_2CH_3$.

In another general aspect, the invention relates to an immunoconjugate comprising a chelator of the invention covalently linked via $R_{11}$ to a targeting ligand, preferably an antibody or antigen binding fragment thereof.

In yet another general aspect, the invention relates to a radioimmunoconjugate comprising a radiometal complex of the invention covalently linked via $R_{11}$ to a targeting ligand, preferably an antibody or antigen binding fragment thereof.

In one embodiment, a radioimmunoconjugate comprises a radiometal complex of the invention covalently linked to a targeting ligand, particularly an antibody or antigen binding fragment thereof, via a triazole moiety.

In particular embodiments, a radioimmunoconjugate of the invention is selected from the group consisting of:

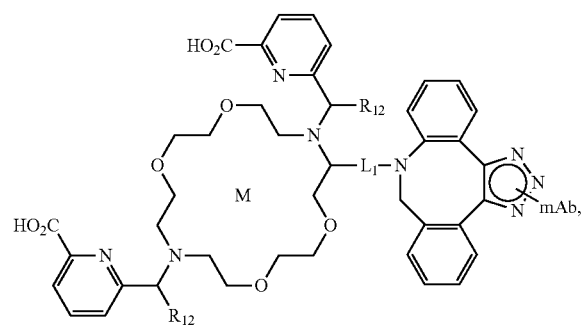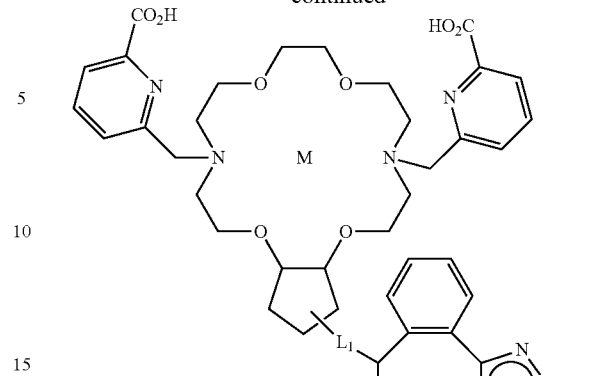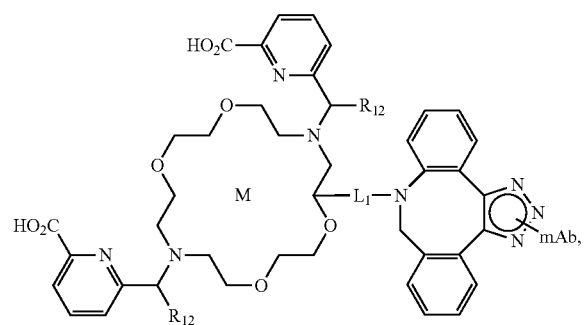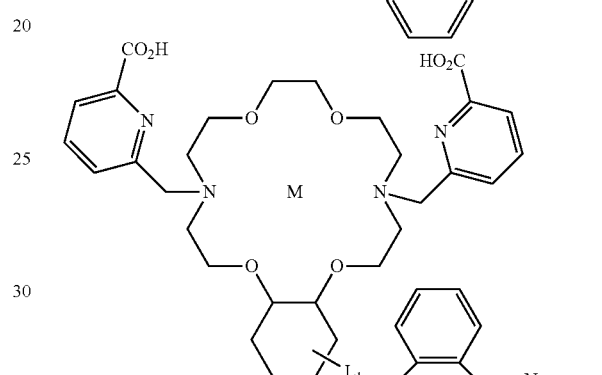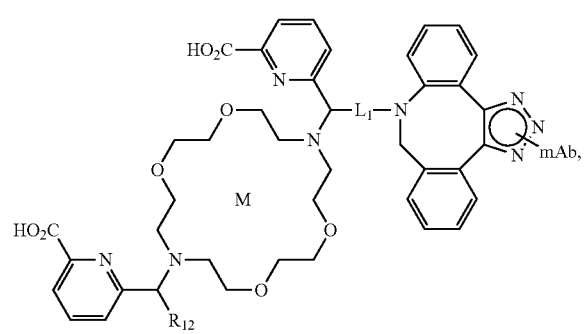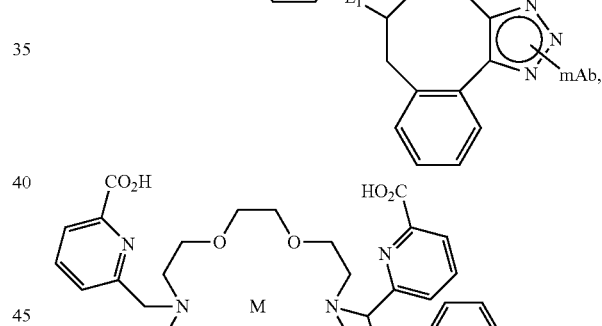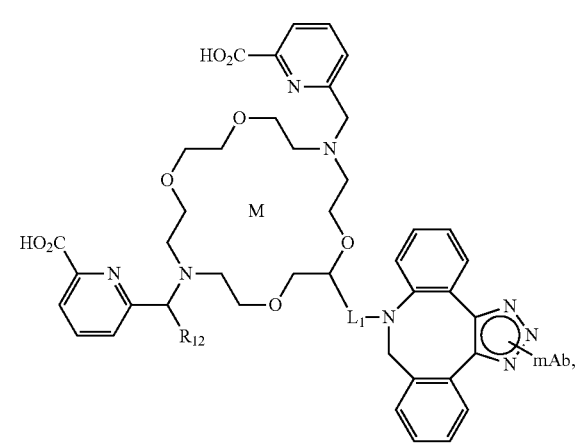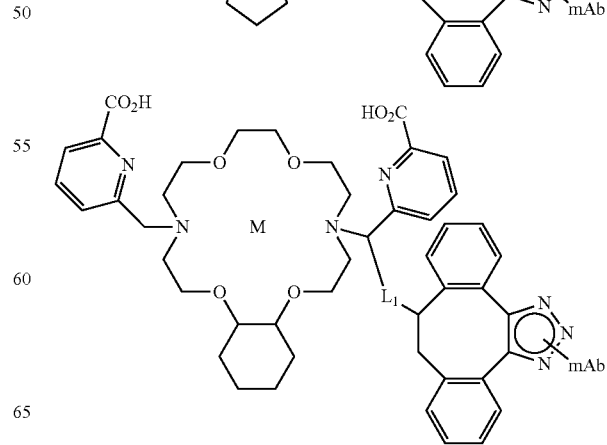

-continued

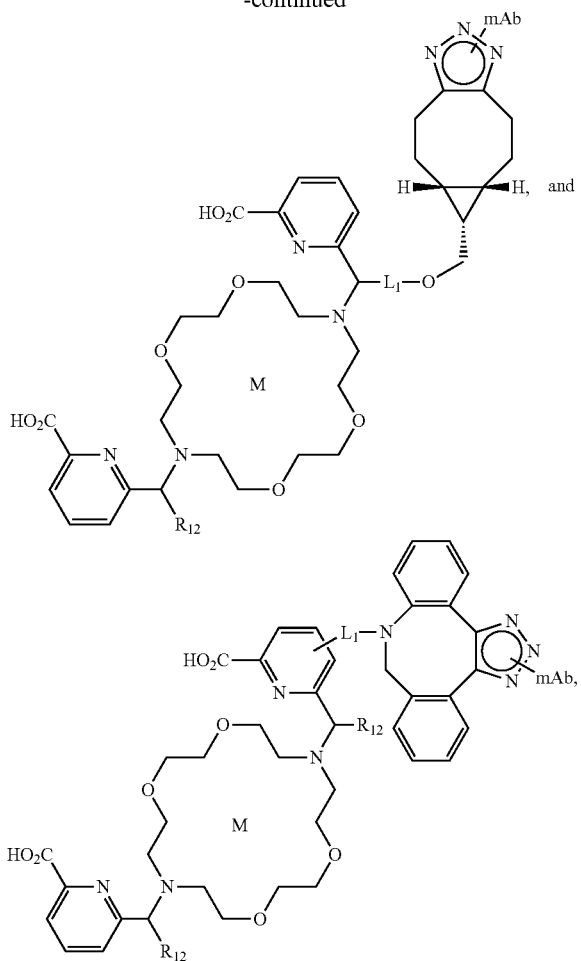

wherein $L_1$ is a linker; mAb is an antibody or antigen binding fragment thereof, preferably the mAb is an antibody or antigen binding fragment that binds specifically to a tumor cell, more preferably to a tumor antigen selected from the group consisting of prostate-specific membrane antigen (PSMA), BCMA, Her2, EGFR, KLK2, CD19, CD22, CD30, CD33, CD79b, and Nectin-4; and each $R_{12}$ is independently hydrogen, —$CH_3$, or —$CH_2CH_3$, provided at least one $R_{12}$ is —$CH_3$ or —$CH_2CH_3$.

In another general aspect, the invention relates to methods of preparing an immunoconjugate or a radioimmunoconjugate of the invention, comprising covalently linking a chelator or a radiometal complex of the invention with a targeting ligand, preferably via $R_{11}$ of the chelator or radiometal complex to an antibody or antigen binding fragment thereof.

In a particular embodiment, a method of preparing a radioimmunoconjugate of the invention comprises a "one-step direct radiolabeling" method (e.g., as illustrated in FIG. 2C) comprising:
(i) providing a modified polypeptide comprising the polypeptide (e.g., antibody or antigen binding fragment thereof) covalently linked to a first click reaction partner (e.g., an azido group);
(ii) providing a chelator complex comprising a chelator of the present invention covalently linked to a second click reaction partner (e.g., an alkynyl group or cycloalkynyl group);
(iii) contacting the modified polypeptide with the chelator complex under a condition to allow the first click reaction partner (e.g., azido group) to react with the second click reaction partner (e.g., alkynyl group or cycloalkynyl group) to thereby form a polypeptide-chelator complex (i.e., immunoconjugate); and
(iv) contacting the polypeptide-chelator complex with a radiometal ion to thereby prepare the radioimmunoconjugate (wherein the radioimmunoconjugate comprises the polypeptide labeled with the radiometal ion, e.g., a modified antibody or antigen binding fragment thereof labeled with an alpha-emitting radiometal ion bound to the chelator via coordinate bonding).

According to particular embodiments, step (iv) is performed without metal-free conditions. Preferably, the method is carried out in a site-specific manner as described herein.

In an alternative embodiment, a method of preparing a radioimmunoconjugate of the invention comprises a "click radiolabeling" method (e.g., as illustrated in FIG. 2D):
(i) providing a modified antibody or antigen binding fragment thereof comprising the antibody or antigen binding fragment thereof covalently linked to an azido group;
(ii) providing a radiocomplex of the invention comprising an alpha-emitting radiometal ion bound to a chelator via coordinate bonding, wherein the chelator is covalently linked to an alkynyl group or cycloalkynyl group; and
(iii) contacting the modified antibody or antigen binding fragment thereof with the radiocomplex under a condition to allow the azido group to react with the alkynyl group or cycloalkynyl group to thereby prepare the radioimmunoconjugate.

In some embodiments, the cycloalkynyl group is cyclooctynyl or a cyclooctynyl derivative selected from the group consisting of bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

In yet another general aspect, the invention relates to a pharmaceutical composition comprising a radioimmunoconjugate of the invention, and a pharmaceutically acceptable carrier. The pharmaceutical composition may comprise one or more pharmaceutically acceptable excipients.

In yet another general aspect, the invention relates to methods of using the radioimmunoconjugates and pharmaceutical compositions of the invention for targeted radiotherapy.

In one embodiment, provided is a method of selectively targeting neoplastic cells for radiotherapy in a subject in need thereof, the method comprising administering to the subject a pharmaceutical composition of the invention.

In one embodiment, provided is a method of treating a neoplastic disease or disorder in a subject in need thereof, the method comprising administering to the subject a pharmaceutical composition of the invention.

DETAILED DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

Figure 2:
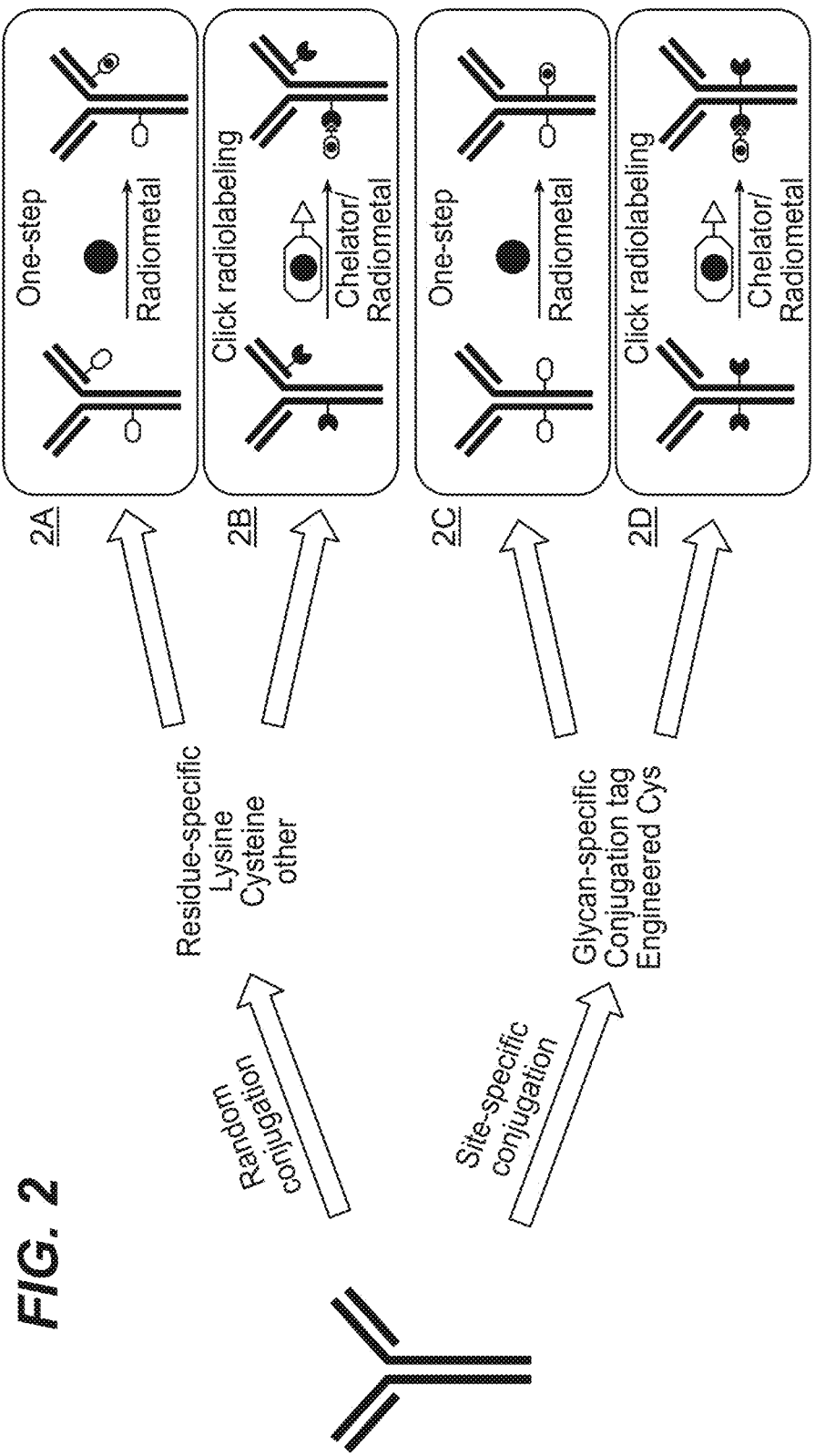

In the drawings:

FIGS. 1A-1B shows HPLC chromatograms from the chelation test with $La^{3+}$ described in Example 1; FIG. 1A shows HPLC chromatograms of H2bp18c6-benzyl-phenyl prior to mixing (top) and subsequent to mixing with $La^{3+}$; the shift in retention time from 14.137 minutes to 12.047 minutes subsequent to mixing with $La^{3+}$ indicates rapid chelation of $La^{3+}$ by H2bp18c6-benzyl-phenyl; FIG. 1B shows HPLC chromatograms of H2bp18c6-benzyl-isopentyl prior to mixing (top) and subsequent to mixing with $La^{3+}$; the shift in retention time from 17.181 minutes to 15.751 minutes subsequent to mixing with $La^{3+}$ indicates rapid chelation of $La^{3+}$ by H2bp18c6-benzyl-isopentyl; and FIG. 2 shows a schematic representation of radiolabeling an antibody to produce a radioimmunoconjugate according to embodiments of the invention by random conjugation methods (e.g., methods for labeling of lysine residues, cysteine residues, etc.) or site-specific conjugation methods (e.g., glycan-specific methods, conjugation tag methods, or engineered cysteine methods); FIG. 2A schematically illustrates random conjugation via one-step direct radiolabeling; FIG. 2B schematically illustrates random conjugation via click radiolabeling; FIG. 2C schematically illustrates site-specific conjugation via one-step direct radiolabeling; and FIG. 2D schematically illustrates site-specific conjugation via click radiolabeling.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

In an attempt to help the reader of the application, the description has been separated into various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

Unless otherwise stated, any numerical value, such as a concentration or a concentration range described herein, are to be understood as being modified in all instances by the term "about." Thus, a numerical value typically includes 10% of the recited value. For example, the recitation of "10-fold" includes 9-fold and 11-fold. As used herein, the use of a numerical range expressly includes all possible subranges, all individual numerical values within that range, including integers within such ranges and fractions of the values unless the context clearly indicates otherwise.

As used herein, "subject" means any animal, preferably a mammal, most preferably a human, to whom will be or has been administered a radioimmunoconjugate of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

As used herein, the term "alkyl" means a saturated, monovalent, unbranched or branched hydrocarbon chain. Examples of alkyl groups include, but are not limited to, methyl (Me), ethyl (Et), propyl (e.g., n-propyl, isopropyl), butyl (e.g., n-butyl, isobutyl, tert-butyl), and pentyl (e.g., n-pentyl, isopentyl, neopentyl), etc.

The term "cycloalkyl" refers to a mono- or polycyclic alkyl group having from 3 to 12, more preferably from 3 to 8 carbon atoms in the ring(s). Examples of monocyclic cycloalkyl rings include, but are not limited to, cyclopropyl, cyclobutyl, cyclopentyl, cyclohexyl, cyclohexyl, cycloheptyl, cyclooctyl, etc.

The term "alkoxy" as used herein refers to an —O-alkyl group or —OR group in which is R alkyl, wherein alkyl is as defined above. An alkoxy group is attached to the parent molecule through an oxygen atom. Examples of alkoxy include, but are not limited to, methoxy, ethoxy, propoxy (e.g., n-propoxy, isopropoxy), butoxy (e.g., n-butoxy, isobutoxy, tert-butoxy), pentyloxy (e.g., n-pentyloxy, isopentyloxy, neopentyloxy), etc. An alkoxy group can be unsubstituted or substituted with one or more suitable substituents. Similarly, "alkylthio" or "thioalkoxy" refers to an —SR group in which R is an alkyl attached to the parent molecule through a sulfur bridge, for example, —S-methyl, —S-ethyl, etc. Representative examples of alkylthio include, but are not limited to, —SCH$_3$, —SCH$_2$CH$_3$, etc.

As used herein, the term "halogen" means fluorine, chlorine, bromine, or iodine. Correspondingly, the term "halo" means fluoro, chloro, bromo, or iodo.

The terms "hydroxy" and "hydroxyl" can be used interchangeably and refer to —OH.

The term "carboxy" refers to —COOH.
The term "cyano" refers to —CN.
The term "nitro" refers to —NO$_2$.
The term "isothiocyanate" refers to —N=C=S.
The term "isocyanate" refers to —N=C=O.
The term "azido" refers to —N$_3$.

The term "alkenyl" refers to straight or branched hydrocarbon chain having at least two carbon atoms, such as 2 to 10 carbon atoms, and comprising at least one double bond between two carbon atoms. An alkenyl can have one carbon-carbon double bond, or multiple carbon-carbon double bonds, such as 2, 3, 4 or more carbon-carbon double bonds. Examples of alkenyl groups include, but are not limited to methenyl, ethenyl, propenyl, butenyl, etc.

The term "cycloalkenyl" refers to a mono- or polycyclic alkyl group having from 3 to 12, more preferably from 3 to 8 carbon atoms in the ring(s) and comprising at least one double bond between two carbon atoms. A cycloalkenyl can have one carbon-carbon double bond, or multiple carbon-carbon double bonds, such as 2, 3, 4, or more carbon-carbon double bonds. Examples of cycloalkenyl groups include, but are not limited to cyclopropenyl, cyclobutenyl, cycloheptenyl, cyclohexenyl, etc.

As used herein, the term "alkynyl," "alkyne group" or "alkyne moiety" refers to a straight or branched hydrocarbon chain having at least two carbon atoms, such as 2 to 10 carbon atoms, and comprising at least one triple bond between two carbon atoms. An alkynyl group can be a terminal alkynyl group, or a cyclic alkynyl group. A terminal alkyne has at least one hydrogen atom bonded to a triply bonded carbon atom. A "cyclic alkyne" or "cycloalkynyl" is a cycloalkyl ring comprising at least one triple bond between two carbon atoms. Examples of cyclic alkynes or cycloalkynyl groups include, but are not limited to, cyclooctyne and cyclooctyne derivatives, such as bicyclononyne (BCN), difluorinated cyclooctyne (DIFO), dibenzocyclooctyne (DIBO), keto-DIBO, biarylazacyclooctynone (BARAC), dibenzoazacyclooctyne (DIBAC), dimethoxyazacyclooctyne (DIMAC), difluorobenzocyclooctyne (DIFBO), monobenzocyclooctyne (MOBO), and tetramethoxy DIBO (TMDIBO).

The term "amino" refers to —NH$_2$. The term "alkylamino" refers to an amino group in which one or both of the hydrogen atoms attached to nitrogen is substituted with an alkyl group. An alkylamine group can be represented as —NR$_2$ in which each R is independently a hydrogen or alkyl group. For example, alkylamine includes methylamine (—NHCH$_3$), dimethylamine (—N(CH$_3$)$_2$), —NHCH$_2$CH$_3$, etc. The term "aminoalkyl" as used herein is intended to include both branched and straight-chain saturated aliphatic hydrocarbon groups substituted with one or more amino groups. Representative examples of aminoalkyl groups include, but are not limited to, —CH$_2$NH$_2$, —CH$_2$CH$_2$NH$_2$, and —CH$_2$CH(NH$_2$)CH$_3$.

As used herein, "amide" refers to —C(O)N(R)$_2$, wherein each R is independently an alkyl group or a hydrogen. Examples of amides include, but are not limited to, —C(O)NH$_2$, —C(O)NHCH$_3$, and —C(O)N(CH$_3$)$_2$.

The terms "hydroxylalkyl" and "hydroxyalkyl" are used interchangeably, and refer to an alkyl group substituted with one or more hydroxyl groups. The alkyl can be a branched or straight-chain aliphatic hydrocarbon. Examples of hydroxylalkyl include, but are not limited to, hydroxylmethyl (—CH$_2$OH), hydroxylethyl (—CH$_2$CH$_2$OH), etc.

The term "aryl" as used herein is a group that contains any carbon-based aromatic group including, but not limited to, phenyl, naphthyl, anthracenyl, phenanthranyl, and the like. Aryl moieties are well known and described, for example, in Lewis, R. J., ed., *Hawley's Condensed Chemical Dictionary*, 13$^{th}$ Edition, John Wiley & Sons, Inc., New York (1997). An aryl group can be a single ring structure (i.e., monocyclic) or comprise multiple ring structures (i.e., polycyclic) that are fused ring structures. Preferably, an aryl group is a monocyclic aryl group.

As used herein, the term "heterocyclyl" includes stable monocyclic and polycyclic hydrocarbons that contain at least one heteroatom ring member, such as sulfur, oxygen, or nitrogen. As used herein, the term "heteroaryl" includes stable monocyclic and polycyclic aromatic hydrocarbons that contain at least one heteroatom ring member such as sulfur, oxygen, or nitrogen. Heteroaryl can be monocyclic or polycyclic, e.g., bicyclic or tricyclic. Each ring of a heterocyclyl or heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups which are polycyclic, e.g., bicyclic or tricyclic must include at least one fully aromatic ring but the other fused ring or rings can be aromatic or non-aromatic. The heterocyclyl or heteroaryl group can be attached at any available nitrogen or carbon atom of any ring of the heterocyclyl or heteroaryl group. Preferably, the term "heteroaryl" refers to 5- or 6-membered monocyclic groups and 9- or 10-membered bicyclic groups which have at least one heteroatom (O, S, or N) in at least one of the rings, wherein the heteroatom-containing ring preferably has 1, 2, or 3 heteroatoms, more preferably 1 or 2 heteroatoms, selected from O, S, and/or N. The nitrogen heteroatom(s) of a heteroaryl can be substituted or unsubstituted. Additionally, the nitrogen and sulfur heteroatom(s) of a heteroaryl can optionally be oxidized (i.e., N→O and S(O)$_r$, wherein r is 0, 1 or 2).

The term "ester" refers to —C(O)$_2$R, wherein R is alkyl.
The term "carbamate" refers to —OC(O)NR$_2$, wherein each R is independently alkyl or hydrogen.
The term "aldehyde" refers to —C(O)H.
The term "carbonate" refers to —OC(O)OR, wherein R is alkyl.

The term "maleimide" refers to a group with the chemical formula H$_2$C$_2$(CO)$_2$NH. The term "maleimido" refers to a maleimide group covalently linked to another group or molecule. Preferably, a maleimido group is N-linked, for example:

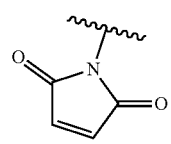 [SMILES: *N1C(=O)C=CC1=O]

The term "acyl halide" refers to —C(O)X, wherein X is halo (e.g., Br, Cl). Exemplary acyl halides include acyl chloride (—C(O)Cl) and acyl bromide (—C(O)Br).

As referred to herein, the term "substituted" means that at least one hydrogen atom is replaced with a non-hydrogen group, provided that all normal valencies are maintained and that the substitution results in a stable compound. When a particular group is "substituted," that group can have one or more substituents, preferably from one to five substituents, more preferably from one to three substituents, most preferably from one to two substituents, independently selected from the list of substituents. The term "independently" when used in reference to substituents, means that when more than one of such substituents is possible, such substituents can be the same or different from each other. Any of the substituent groups described herein (e.g., alkyl, cycloalkyl, alkoxy, alkenyl, cycloalkenyl, alkynyl, cycloalkynyl, aryl, heterocyclyl, heteroaryl, etc.) can be unsubstituted or substituted with one or more suitable substituents. Examples of suitable substituents include, but are not limited to, alkyl, halogen, hydroxy, alkoxy, amide, alkylthio, amino, alkylamino, aminoalkyl, hydroxyalkyl, hydroxyl, carboxyl, etc.

In accordance with convention used in the art:

is used in structural formulas herein to depict the bond that is the point of attachment of the moiety, functional group, or substituent to the core, parent, or backbone structure, such as a chelator or targeting ligand.

When any variable occurs more than one time in any constituent or formula for a compound, its definition at each occurrence is independent of its definition at every other occurrence. Thus, for example, if a group is shown to be substituted with 0-3 R groups, then said group can be optionally substituted with up to three R groups, and at each occurrence, R is selected independently from the definition of R.

When a bond to a substituent is shown to cross a bond connecting two atoms in a ring, then such substituent can be bonded to any atom on the ring.

As used herein, the term "radiometal ion" or "radioactive metal ion" refers to one or more isotopes of the elements that emit particles and/or photons. Any radiometal ion known to those skilled in the art in view of the present disclosure can be used in the invention. Examples of radiometal ions suitable for use in the invention include, but are not limited to, $^{32}P$, $^{47}Sc$, $^{62}Cu$, $^{64}Cu$, $^{67}Cu$, $^{67}Ga$, $^{68}Ga$, $^{77}As$, $^{86}Y$, $^{89}Zr$, $^{89}Sr$, $^{90}Y$, $^{99}Tc$, $^{105}Rh$, $^{109}Pd$, $^{111}Ag$, $^{111}In$, $^{117}Sn$, $^{131}I$, $^{149}Tb$, $^{152}Tb$, $^{155}Tb$, $^{153}Sm$, $^{159}Gd$, $^{165}Dy$, $^{166}Ho$, $^{169}Er$, $^{177}Lu$, $^{186}Re$, $^{188}Re$, $^{194}Ir$, $^{198}Au$, $^{199}Au$, $^{211}At$, $^{212}Pb$, $^{212}Bi$, $^{213}Bi$, $^{223}Ra$, $^{225}Ac$, $^{227}Th$, and $^{255}Fm$. Preferably, the radiometal ion is a "therapeutic emitter," meaning a radiometal ion that is useful in therapeutic applications. Examples of therapeutic emitters include, but are not limited to, beta or alpha emitters, such as $^{32}P$, $^{47}Sc$, $^{67}Cu$, $^{77}As$, $^{89}Sr$, $^{90}Y$, $^{99}Tc$, $^{15}Rh$, $^{109}Pd$, $^{111}Ag$, $^{131}I$, $^{149}Tb$, $^{152}Tb$, $^{155}Tb$, $^{153}Sm$, $^{159}Gd$, $^{165}Dy$, $^{166}Ho$, $^{169}Er$, $^{177}Lu$, $^{186}Re$, $^{188}Re$, $^{194}Ir$, $^{198}Au$, $^{199}Au$, $^{211}At$, $^{212}Pb$, $^{212}Bi$, $^{213}Bi$, $^{223}Ra$, $^{225}Ac$, $^{255}Fm$ and $^{227}Th$. Preferably, a radiometal ion used in the invention is an alpha-emitting radiometal ion, such as actinium-225 ($^{225}Ac$).

As used herein, the term "chelator" or "chelant" refers to a chemical compound to which a metal, preferably a radiometal, can be chelated via coordinate bonding. In a typical embodiment, a chelator is a macrocyclic ring containing one or more heteroatoms, e.g., oxygen and/or nitrogen as ring atoms. Preferably, a chelator is a derivative of 4,13-diaza-18-crown-6.

A "radiometal complex" as used herein refers to a complex comprising a radiometal ion associated with a chelator. Typically, a radiometal ion is bound to or coordinated to a chelator via coordinate bonding. Heteroatoms of the macrocyclic ring can participate in coordinate bonding of a radiometal ion to a chelator. A chelator can be substituted with one or more substituent groups, and the one or more substituent groups can also participate in coordinate bonding of a radiometal ion to a chelator in addition to, or alternatively to the heteroatoms of the macrocyclic ring.

As used herein, the term "click chemistry" refers to a chemical philosophy introduced by Sharpless, describing chemistry tailored to generate covalent bonds quickly and reliably by joining small units comprising reactive groups together (see Kolb, et al., *Angewandte Chemie International Edition* (2001) 40: 2004-2021). Click chemistry does not refer to a specific reaction, but to a concept including, but not limited to, reactions that mimic reactions found in nature. In some embodiments, click chemistry reactions are modular, wide in scope, give high chemical yields, generate inert byproducts, are stereospecific, exhibit a large thermodynamic driving force to favor a reaction with a single reaction product, and/or can be carried out under physiological conditions. In some embodiments, a click chemistry reaction can be carried out under simple reaction conditions, uses readily available starting materials and reagents, uses non-toxic solvents or uses a solvent that is benign or easily removed, such as water, and/or provides simple product isolation by non-chromatographic methods, such as crystallization or distillation.

Click chemistry reactions utilize reactive groups that are rarely found in naturally-occurring biomolecules and are chemically inert towards biomolecules, but when the click chemistry partners are reacted together, the reaction can take place efficiently under biologically relevant conditions, for example in cell culture conditions, such as in the absence of excess heat and/or harsh reagents. In general, click chemistry reactions require at least two molecules comprising click reaction partners that can react with each other. Such click reaction partners that are reactive with each other are sometimes referred to herein as click chemistry handle pairs, or click chemistry pairs. In some embodiments, the click reaction partners are an azide and a strained alkyne, e.g. cycloalkyne such as a cyclooctyne or cyclooctyne derivative, or any other alkyne. In other embodiments, the click reaction partners are reactive dienes and suitable tetrazine dienophiles. For example, trans-cyclooctene, norbornene, or biscyclononene can be paired with a suitable tetrazine dienophile as a click reaction pair. In yet other embodiments, tetrazoles can act as latent sources of nitrile imines, which can pair with unactivated alkenes in the presence of ultraviolet light to create a click reaction pair, termed a "photo-click" reaction pair. In other embodiments, the click reaction partners are a cysteine and a maleimide. For example the cysteine from a peptide (e.g., GGGC) can be reacted with a maleimide that is associated with a chelating agent (e.g., NOTA). Other suitable click chemistry handles are known to those of skill in the art (see, e.g., Spicer et al., Selective chemical protein modification. *Nature Communications*. 2014; 5: p. 4740). In other embodiments, the click reaction partners are Staudinger ligation components, such as phosphine and azide. In other embodiments, the click reaction partners are Diels-Alder reaction components, such as dienes (e.g., tetrazine) and alkenes (e.g., trans-cyclooctene (TCO) or norbornene). Exemplary click reaction partners are described in US20130266512 and in WO2015073746, the relevant description on click reaction partners in both of which are incorporated by reference herein.

According to preferred embodiments, a click chemistry reaction utilizes an azide group and an alkyne group, more preferably a strained alkyne group, e.g., cycloalkyne such as a cyclooctyne or cyclooctyne derivative, as the click chemistry pair or reaction partners. In such embodiments, the click chemistry reaction is a Huisgen cycloaddition or 1,3-dipolar cycloaddition between the azide ($-N_3$) and alkyne moiety to form a 1,2,3-triazole linker. Click chemistry reactions between alkynes and azides typically require the addition of a copper catalyst to promote the 1,3-cycloaddition reaction, and are known as copper-catalyzed azide-alkyne cycloaddition (CuAAC) reactions. However, click chemistry reactions between cyclooctyne or cyclooctyne derivatives and azides typically do not require the addition of a copper catalyst, and instead proceed via strain-promoted azide-alkyne cycloaddition (SPAAC) (Debets, M. F., et al., Bioconjugation with strained alkenes and alkynes. *Acc Chem Res,* 2011. 44(9): p. 805-15).

As used herein the term "targeting ligand" refers to any molecule that provides an enhanced affinity for a selected target, e.g., an antigen, a cell, cell type, tissue, organ, region of the body, or a compartment (e.g., a cellular, tissue or organ compartment). Targeting ligands include, but are not limited to, antibodies or antigen binding fragments thereof, small molecules, aptamers, polypeptides, and scaffold proteins. Preferably, a targeting ligand is a polypeptide, more preferably an antibody or antigen binding fragment thereof, engineered domain, or scaffold protein.

As used herein, the term "polypeptide" refers to a polymer composed of amino acid residues, related naturally occurring structural variants, and synthetic non-naturally occurring analogs thereof linked via peptide bonds. The term refers to a polypeptide of any size, structure, or function. Typically, a polypeptide is at least three amino acids long. A polypeptide can be naturally occurring, recombinant, or synthetic, or any combination thereof. Synthetic polypeptides can be synthesized, for example, using an automated polypeptide synthesizer. According to preferred embodiments, the polypeptide is an antibody, preferably a monoclonal antibody, or a fragment thereof, such as an antigen-binding fragment thereof. According to preferred embodiments, the antibody or fragment thereof is specific for a cancer antigen. According to other embodiments, the polypeptide is an engineered domain or a scaffold protein.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies, and antigen-binding fragments thereof.

In general, antibodies are proteins or peptide chains that exhibit binding specificity to a specific antigen, referred to herein as a "target." Antibody structures are well known. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibodies used in the invention can be of any of the five major classes or corresponding sub-classes. Antibody light chains of any vertebrate species can be assigned to one of two clearly distinct types, namely kappa and lambda, based on the amino acid sequences of their constant domains. According to particular embodiments, antibodies used in the invention include heavy and/or light chain constant regions from mouse antibodies or human antibodies. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody useful for the invention can have no or minimal effector function, but retain its ability to bind FcRn.

As used herein, the term "antigen-binding fragment" refers to an antibody fragment such as, for example, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "scaffold" or "scaffold protein" refers to any protein that has a target binding domain and that can bind to a target. A scaffold contains a "framework", which is largely structural, and a "binding domain" which makes contact with the target and provides for specific binding. The binding domain of a scaffold need not be defined by one contiguous sequence of the scaffold. In certain cases, a scaffold may be part of larger binding protein, which, itself, may be part of a multimeric binding protein that contains multiple scaffolds. Certain binding proteins can be bi- or multi-specific in that they can bind to two or more different epitopes. A scaffold can be derived from a single chain antibody, or a scaffold may be not antibody-derived.

As used herein, the term "aptamer" refers to a single-stranded oligonucleotide (single-stranded DNA or RNA molecule) that can bind specifically to its target with high affinity. The aptamer can be used as a molecule targeting various organic and inorganic materials.

As used herein, the term "small molecule ligand" refers to a low molecular weight organic compound. Small molecule ligands, as used herein, can refer to compounds that have a size of less than about 1000 daltons, and can be synthesized in the laboratory or found in nature.

Chelators

In one general aspect, the invention relates to a chelator, preferably a chelator to which radiometals can be chelated via coordinate bonding. According to embodiments of the invention, a chelator has the structure of formula (I):

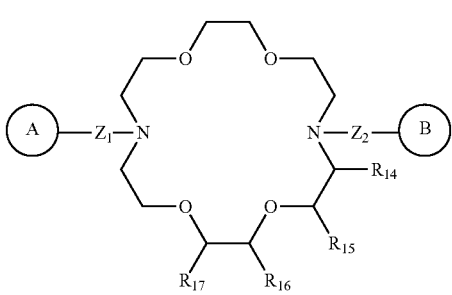

wherein:
- each of ring A and ring B is independently a 6-10 membered aryl or a 5-10 membered heteroaryl, wherein each of ring A and ring B is optionally substituted with one or more substituents independently selected from the group consisting of halo, alkyl, alkenyl, cycloalkyl, cycloalkenyl, aryl, heterocyclyl, heteroaryl, $-OR_{13}$, $-SR_{13}$, $-(CH_2)_pCOOR_{13}$, $-OC(O)R_{13}$, $-N(R_{13})_2$, $-CON(R_{13})_2$, $-NO_2$, $-CN$ $-OC(O)N(R_{13})_2$, and X;
- each of $Z_1$ and $Z_2$ is independently $-(C(R_{12})_2)_m-$ or $-(CH_2)_n-C(R_{12})(X)-(CH_2)_n-$;
- each X is independently $-L_1-R_{11}$;
- each n is independently 0, 1, 2, 3, 4, or 5;
- each m is independently 1, 2, 3, 4, or 5;
- each p is independently 0 or 1;
- $L_1$ is absent or a linker;
- $R_{11}$ is a nucleophilic moiety or an electrophilic moiety, or $R_{11}$ comprises a targeting ligand;
- each $R_{12}$ is independently hydrogen, alkyl, cycloalkyl, aryl, heterocyclyl, or heteroaryl;
- each $R_{13}$ is independently hydrogen or alkyl;
- each of $R_{14}$, $R_{15}$, $R_{16}$, and $R_{17}$ is independently hydrogen, alkyl, or X,
- or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
- provided that the chelator comprises at least one X, and when X is present on ring A or ring B, $L_1$ is a linker or at least one of $R_{12}$ and $R_{14}$-$R_{17}$ is not hydrogen.

According to embodiments of the invention, a chelator comprises at least one X group, wherein X is $-L_1-R_{11}$, wherein $L_1$ is absent or a linker, and $R_{11}$ is an electrophilic moiety or a nucleophilic moiety, or $R_{11}$ comprises a targeting ligand. When $R_{11}$ is a nucleophilic or electrophilic moiety, such moiety can be used for attachment of the chelator to a targeting ligand, directly or indirectly via a linker.

In certain embodiments, a chelator comprises a single X group, and preferably $L_1$ of the X group is a linker.

A chelator of the invention can be substituted with X at any one of the carbon atoms of the macrocyclic ring, the $Z_1$ or $Z_2$ position, or on ring A or ring B, provided that when ring or ring B comprises an X group, $L_1$ is a linker or at least one of $R_{12}$ and $R_{14}$-$R_{17}$ is not hydrogen (i.e., at least one of the carbon atoms of $Z_1$, $Z_2$, and/or the carbons of the macrocyclic ring is substituted for instance with an alkyl group, such as methyl or ethyl). Preferably, substitution at such positions does not affect the chelation efficiency of the chelator for radiometal ions, particularly [225]Ac, and in some embodiments, the substitutions can enhance chelation efficiency.

In some embodiments, $L_1$ is absent. When $L_1$ is absent, $R_{11}$ is directly bound (e.g., via covalent linkage) to the chelator.

In some embodiments, $L_1$ is a linker. As used herein, the term "linker" refers to a chemical moiety that joins a chelator to a nucleophilic moiety, electrophilic moiety, or targeting ligand. Any suitable linker known to those skilled in the art in view of the present disclosure can be used in the invention. The linkers can contain, for example, a substituted or unsubstituted alkyl, a substituted or unsubstituted heteroalkyl moiety, a substituted or unsubstituted aryl or heteroaryl, a polyethylene glycol (PEG) linker, a peptide linker, a sugar-based linker, or a cleavable linker, such as a disulfide linkage or a protease cleavage site such as valine-citrulline-p-aminobenzyl (PAB). Exemplary linker structures suitable for use in the invention include, but are not limited to:

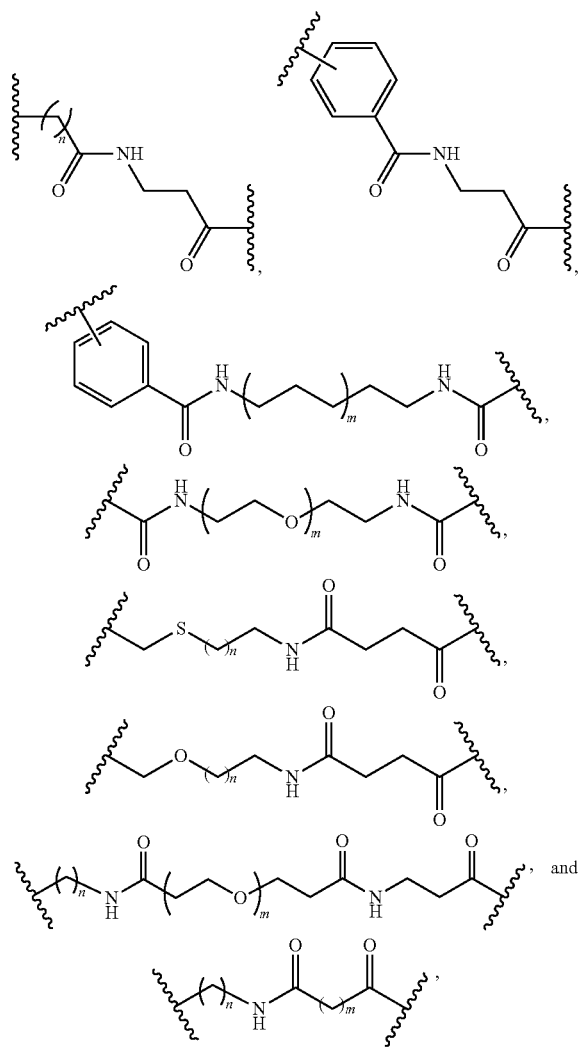

wherein n is an integer of 0 to 10, preferably an integer of 1 to 4; and m is an integer of 0 to 12, preferably an integer of 0 to 6.

In some embodiments, $R_{11}$ is a nucleophilic moiety or an electrophilic moiety. A "nucleophilic moiety" or "nucleophilic group" refers to a functional group that donates an electron pair to form a covalent bond in a chemical reaction.

An "electrophilic moiety" or "electrophilic group" refers to a functional group that accepts an electron pair to form a covalent bond in a chemical reaction. Nucleophilic groups react with electrophilic groups, and vice versa, in chemical reactions to form new covalent bonds. Reaction of the nucleophilic group or electrophilic group of a chelator of the invention with a targeting ligand or other chemical moiety (e.g., linker) comprising the corresponding reaction partner allows for covalent linkage of the targeting ligand or chemical moiety to the chelator of the invention.

Exemplary examples of nucleophilic groups include, but are not limited to, azides, amines, and thiols. Exemplary examples of electrophilic groups include, but are not limited to amine-reactive groups, thiol-reactive groups, alkynyls and cycloalkynyls. An amine-reactive group preferably reacts with primary amines, including primary amines that exist at the N-terminus of each polypeptide chain and in the side-chain of lysine residues. Examples of amine-reactive groups suitable for use in the invention include, but are not limited to, N-hydroxy succinimide (NHS), substituted NHS (such as sulfo-NHS), isothiocyanate (—NCS), isocyanate (—NCO), esters, carboxylic acid, acyl halides, amides, alkylamides, and tetra- and per-fluoro phenyl ester. A thiol-reactive group reacts with thiols, or sulfhydryls, preferably thiols present in the side-chain of cysteine residues of polypeptides. Examples of thiol-reactive groups suitable for use in the invention include, but are not limited to, Michael acceptors (e.g., maleimide), haloacetyl, acyl halides, activated disulfides, and phenyloxadiazole sulfone.

In particular embodiments, $R_{11}$ is —$NH_2$, —NCS (isothiocyanate), —NCO (isocyanate), —$N_3$ (azido), alkynyl, cycloalkynyl, carboxylic acid, ester, amido, alkylamide, maleimido, acyl halide, tetrazine, or trans-cyclooctene, more particularly —NCS, —NCO, —$N_3$, alkynyl, cycloalkynyl, —C(O)$R_{13}$, —COO$R_{13}$, —CON($R_{13}$)$_2$, maleimido, acyl halide (e.g., —C(O)Cl, —C(O)Br), tetrazine, or trans-cyclooctene wherein each $R_{13}$ is independently hydrogen or alkyl.

In some embodiments, $R_{11}$ is an alkynyl, cycloalkynyl, or azido group thus allowing for attachment of the chelator to a targeting ligand or other chemical moiety (e.g., linker) using a click chemistry reaction. In such embodiments, the click chemistry reaction that can be performed is a Huisgen cycloaddition or 1,3-dipolar cycloaddition between an azido (—$N_3$) and an alkynyl or cycloalkynyl group to form a 1,2,4-triazole linker or moiety. In one embodiment, the chelator comprises an alkynyl or cycloalkynyl group and the targeting ligand or other chemical moiety comprises an azido group. In another embodiment, the chelator comprises an azido group and the targeting ligand or other chemical moiety comprises an alkynyl or cycloalkynyl group.

In certain embodiments, $R_{11}$ is an alkynyl group, more preferably a terminal alkynyl group or cycloalkynyl group that is reactive with an azide group, particularly via strain-promoted azide-alkyne cycloaddition (SPAAC). Examples of cycloalkynyl groups that can react with azide groups via SPAAC include, but are not limited to cyclooctynyl or a bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

In a particular embodiment, $R_{11}$ is dibenzoazacyclooctynyl (DIBAC, DBCO, ADIBO), which has the following structure:

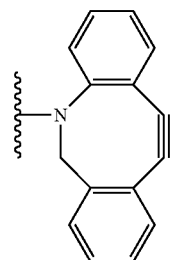

In such embodiments in which $R_{11}$ is DBCO, the DBCO can be covalently linked to a chelator directly or indirectly via a linker, and is preferably attached to the chelator indirectly via a linker.

In some embodiments, $R_{11}$ comprises a targeting ligand. The targeting ligand can be linked to the chelator directly via a covalent linkage, or indirectly via a linker. The targeting ligand can be a polypeptide, e.g., antibody or antigen binding fragment thereof, small molecule, aptamer, or scaffold protein, etc. In preferred embodiments, the targeting ligand is an antibody or antigen binding fragment thereof, such as antibody or antigen binding fragment thereof, e.g., monoclonal antibody (mAb) or antigen binding fragment thereof, which specifically binds an antigen associated with a neoplastic disease or disorder, such as a cancer antigen, which can be prostate-specific membrane antigen (PSMA), BCMA, Her2, EGFR, KLK2, CD19, CD22, CD30, CD33, CD79b, or Nectin-4.

According to embodiments of the invention, each of ring A and ring B is independently a 6-10 membered aryl or a 5-10 membered heteroaryl. In alternative embodiments, it is contemplated that each of ring A and ring B is an optionally substituted heterocyclyl ring, such as oxazoline. Each of ring A and ring B can be optionally and independently substituted with one or more substituent groups independently selected from the group consisting of halo, alkyl, alkenyl, cycloalkyl, cycloalkenyl, aryl, heterocyclyl, heteroaryl, —O$R_{13}$, —S$R_{13}$, —(CH$_2$)$_p$COO$R_{13}$, —OC(O)$R_{13}$, —N($R_{13}$)$_2$, —CON($R_{13}$)$_2$, —NO$_2$, —CN —OC(O)N($R_{13}$)$_2$, and X. Examples of 6-10 membered aryl groups suitable for this purpose include, but are not limited to, phenyl and naphthyl. Examples of 5 to 10 membered heteroaryl groups suitable for this purpose include, but are not limited to pyridinyl, thiazolyl, isothiazolyl, oxazolyl, isoxazolyl, and imidazolyl. Examples of suitable substituents of the 5 to 10 membered heteroaryl and 6 to 10 membered aryl groups include, but are not limited to —COOH, tetrazolyl, and —CH$_2$COOH. In preferred embodiments, a substituent group is —COOH or tetrazolyl, which is an isostere of —COOH.

In certain embodiments, each of ring A and ring B are independently and optionally substituted with one or more carboxyl groups, including but not limited to, —COOH and —CH$_2$COOH.

In certain embodiments, each of ring A and ring B are independently and optionally substituted with tetrazolyl.

In one embodiment, ring A and ring B are the same, e.g., both ring A and ring B are pyridinyl. In another embodiment, ring A and ring B are different, e.g., one of ring A and ring is pyridinyl and the other is phenyl.

In a particular embodiment, both ring A and ring B are pyridinyl substituted with —COOH.

In a particular embodiment, both ring A and ring B are pyridinyl substituted with tetrazolyl.

In another particular embodiment, both ring A and ring B are picolinic acid groups having the following structure:

[Structure of picolinic acid group with HOOC attached to pyridine ring]

According to embodiments of the invention, each of $Z_1$ and $Z_2$ is independently —(C(R$_{12}$)$_2$)$_m$— or —(CH$_2$)$_n$—C(R$_{12}$)(X)—(CH$_2$)$_n$—; each X is independently -L$_1$-R$_{11}$; each R$_{12}$ is independently hydrogen, alkyl, cycloalkyl, aryl, heterocyclyl, or heteroaryl; each n is independently 0, 1, 2, 3, 4, or 5; and each m is independently 1, 2, 3, 4, or 5.

In some embodiments, each $R_{12}$ is independently hydrogen or alkyl, more preferably hydrogen, —CH$_3$, or —CH$_2$CH$_3$.

In some embodiments, each $R_{12}$ is hydrogen.

In some embodiments, both $Z_1$ and $Z_2$ are —(CH$_2$)$_m$—, wherein each m is preferably 1. In such embodiments, a carbon atom of the macrocyclic ring, ring A, or ring B is substituted with an X group.

In some embodiments, one of $Z_1$ and $Z_2$ is —(CH$_2$)$_n$—C(R$_{12}$)(X)—(CH$_2$)$_n$— and the other is —(CH$_2$)$_m$—.

In some embodiments, one of $Z_1$ and $Z_2$ —(CH$_2$)$_n$—C(R$_{12}$)(X)—(CH$_2$)$_n$— and the other is —(CH$_2$)$_m$—; each n is 0; m is 1; X is -L$_1$-R$_{11}$; and L$_1$ is a linker.

In some embodiments, both $Z_1$ and $Z_2$ are —(CH$_2$)$_m$—; each m is independently 0, 1, 2, 3, 4, or 5, preferably each m is 1; and one of $R_{14}$, $R_{15}$, $R_{16}$, and $R_{17}$ is X, and the rest of $R_{14}$, $R_{15}$, $R_{16}$, and $R_{17}$ are each hydrogen.

In some embodiments, $R_{14}$ and $R_{15}$ are taken together with the carbon atoms to which they are attached to form a 5- or 6-membered cycloalkyl ring (i.e., cyclopentyl or cyclohexyl). Such 5- or 6-membered cycloalkyl ring can be substituted with an X group.

In some embodiments $R_{16}$ and $R_{17}$ are taken together with the carbon atoms to which they are attached to form a 5- or 6-membered cycloalkyl ring (i.e., cyclopentyl or cyclohexyl). Such 5- or 6-membered cycloalkyl ring can be substituted with an X group.

In certain embodiments, a chelator has the structure of formula (II):

[Structure of formula (II) showing macrocyclic chelator with A$_1$-A$_{10}$, Z$_1$, Z$_2$, N atoms, O atoms, and R$_{14}$-R$_{17}$ substituents]

(II)

wherein:
$A_1$ is N or CR$_1$ or is absent;
$A_2$ is N or CR$_2$;
$A_3$ is N or CR$_3$;
$A_4$ is N or CR$_4$;
$A_5$ is N or CR$_5$;
$A_6$ is N or CR$_6$ or is absent;
$A_7$ is N or CR$_7$;
$A_8$ is N or CR$_8$;
$A_9$ is N or CR$_9$;
$A_{10}$ is N or CR$_{10}$;
provided that no more than three of $A_1$, $A_2$, $A_3$, $A_4$, and $A_5$ are N, and no more than three of $A_6$, $A_7$, $A_8$, $A_9$, and $A_{10}$ are N;
each of $R_1$, $R_2$, $R_3$, $R_4$, $R_5$, $R_6$, $R_7$, $R_8$, $R_9$, and $R_{10}$ is independently selected from the group consisting of hydrogen, halo, alkyl, alkenyl, cycloalkyl, cycloalkenyl, aryl, heterocyclyl, heteroaryl, —OR$_{13}$, —SR$_{13}$, —(CH$_2$)$_p$COOR$_{13}$, —OC(O)R$_{13}$, —N(R$_{13}$)$_2$, —CON(R$_{13}$)$_2$, —NO$_2$, —CN, —OC(O)N(R$_{13}$)$_2$, and —X,
or, alternatively, any two directly adjacent $R_1$, $R_2$, $R_3$, $R_4$, $R_5$, $R_6$, $R_7$, $R_8$, $R_9$, and $R_{10}$ are taken together with the atoms to which they are attached to form a five or six-membered substituted or unsubstituted carbocyclic or nitrogen-containing ring;
and $Z_1$, $Z_2$, X, n, m, p, L$_1$, and R$_{11}$-R$_{17}$ are as described above for formula (I),
provided that the chelator comprises at least one X, and when any one of $R_1$, $R_2$, $R_3$, $R_4$, $R_5$, $R_6$, $R_7$, $R_8$, $R_9$, and $R_{10}$ is X, then L$_1$ is a linker or at least one of $R_{12}$ and $R_{14}$-$R_{17}$ is not hydrogen.

In some embodiments, any two directly adjacent $R_1$, $R_2$, $R_3$, $R_4$, $R_5$, $R_6$, $R_7$, $R_8$, $R_9$, and $R_{10}$ are taken together with the atoms to which they are attached to form a five or six-membered substituted or unsubstituted carbocyclic or nitrogen-containing ring. Examples of such carbocyclic rings that can be formed include, but are not limited to, naphthyl. Examples of such nitrogen-containing rings that can be formed include, but are not limited to, quinolinyl. The carbocyclic or nitrogen-containing rings can be unsubstituted or substituted with one or more suitable substituents, e.g., —COOH, —CH$_2$COOH, tetrazolyl etc.

In some embodiments, L$_1$ is absent. When L$_1$ is absent, R$_{11}$ is directly bound (e.g., via covalent linkage) to the chelator.

In some embodiments, L$_1$ is a linker. Any suitable linker known to those skilled in the art in view of the present disclosure can be used in the invention, such as those described above.

In some embodiments, one of $A_1$, $A_2$, $A_3$, $A_4$, and $A_5$ is nitrogen, one of $A_1$, $A_2$, $A_3$, $A_4$, and $A_5$ is carbon substituted with —COOH and the rest are CH, i.e., forming a pyridinyl ring substituted with carboxylic acid.

In some embodiments, one of $A_6$, $A_7$, $A_8$, $A_9$, and $A_{10}$ is nitrogen, one of $A_6$, $A_7$, $A_8$, $A_9$, and $A_{10}$ is carbon substituted with —COOH, and the rest are CH, i.e., forming a pyridinyl ring substituted with carboxylic acid.

In one embodiment, at least one of $R_1$, $R_2$, $R_3$, $R_4$ and $R_5$ is —COOH. In one embodiment, at least one of $R_6$, $R_7$, $R_8$, $R_9$, and $R_{10}$ is —COOH. In another embodiment, at least one of $R_1$, $R_2$, $R_3$, $R_4$ and $R_5$ is —COOH; and at least one of $R_6$, $R_7$, $R_8$, $R_9$, and $R_{10}$ is —COOH. In some embodiments, each of $A_1$ and $A_{10}$ is nitrogen; $A_2$ is CR$_2$ and R$_2$ is —COOH; $A_9$ is CR$_9$ and R$_9$ is —COOH; each of $A_3$-$A_8$ is CR$_2$, CR$_3$, CR$_4$, CR$_5$, CR$_6$, CR$_7$, and CR$_8$, respectively; and each of $R_3$ to $R_8$ is hydrogen.

In some embodiments, one of $A_1$, $A_2$, $A_3$, $A_4$, and $A_5$ is nitrogen, one of $A_1$, $A_2$, $A_3$, $A_4$, and $A_5$ is carbon substituted with tetrazolyl and the rest are CH.

In some embodiments, one of $A_6$, $A_7$, $A_8$, $A_9$, and $A_{10}$ is nitrogen, one of $A_6$, $A_7$, $A_8$, $A_9$, and $A_{10}$ is carbon substituted with tetrazolyl, and the rest are CH.

In one embodiment, at least one of $R_1$, $R_2$, $R_3$, $R_4$ and $R_5$ is tetrazolyl. In one embodiment, at least one of $R_6$, $R_7$, $R_8$, $R_9$, and $R_{10}$ is tetrazolyl. In another embodiment, at least one of $R_1$, $R_2$, $R_3$, $R_4$ and $R_5$ is tetrazolyl; and at least one of $R_6$, $R_7$, $R_8$, $R_9$, and $R_{10}$ is tetrazolyl.

In some embodiments, each $R_{12}$ is hydrogen.

In some embodiments, $R_{11}$ is an alkynyl group or cycloalkynyl group, preferably cyclooctynyl or a cyclooctynyl derivative, e.g., DBCO.

In particular embodiments of a chelator of formula (II):
each of $A_1$ and $A_{10}$ is nitrogen;
$A_2$ is $CR_2$ and $R_2$ is —COOH;
$A_9$ is $CR_9$ and $R_9$ is —COOH;
each of $A_3$-$A_8$ is $CR_2$, $CR_3$, $CR_4$, $CR_5$, $CR_6$, $CR_7$, and $CR_8$, respectively;
each of $R_3$ to $R_8$ is hydrogen;
one of $Z_1$ and $Z_2$ is —$(CH_2)_m$— and the other of $Z_1$ and $Z_2$ is —$(CH_2)_n$—$C(R_2)(X)$—$(CH_2)_n$—;
$R_{12}$ is hydrogen;
m is 1;
each n is 0;
X is -$L_1$-$R_1$, wherein $L_1$ is a linker and —$R_{11}$ is an electrophilic group, e.g., cyclooctynyl or cyclooctynyl derivative such as DBCO; and
each of $R_{14}$-$R_{17}$ is hydrogen, or alternatively $R_{16}$ and $R_{17}$ are taken together with the carbon atoms to which they are attached to form a 5- or 6-membered cycloalkyl ring.

In certain embodiments, a chelator has the structure of formula (III):

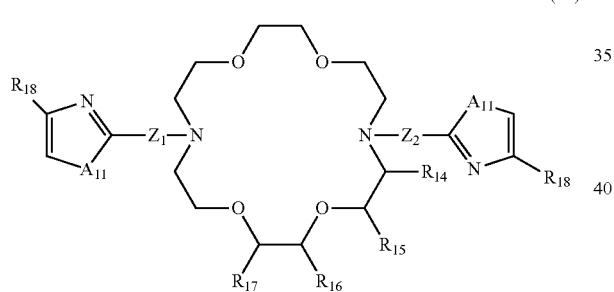

(III)

wherein:
each $A_{11}$ is independently O, S, NMe, or NH;
each $R_{18}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$COOR_{13}$, —$OC(O)R_{13}$, —$N(R_{13})_2$, —$CON(R_{13})_2$, —$NO_2$, —$CN$ —$OC(O)N(R_{13})_2$, and —X,
and $Z_1$, $Z_2$, X, n, m, $L_1$, $R_{11}$-$R_{17}$ are as described above for formula (I),
provided that the chelator comprises at least one X, and when $R_{18}$ is X, then $L_1$ is a linker or at least one of $R_{12}$ and $R_{14}$-$R_{17}$ is not hydrogen.

In some embodiments, each $A_{11}$ is the same, and each $A_{11}$ is O, S, NMe, or NH. For example, each Au can be S. In other embodiments, each $A_{11}$ is different and each is independently selected from O, S, NMe, and NH.

In some embodiments, each $R_{18}$ is independently —$(CH_2)_p$—$COOR_{13}$ or tetrazolyl, wherein $R_{13}$ is hydrogen and each p is independently 0 or 1.

In some embodiments, each $R_{18}$ is —COOH.
In some embodiments, each $R_{18}$ is —$CH_2COOH$.
In some embodiments, each $R_{18}$ is tetrazolyl.

In particular embodiments of a chelator of formula (III):
each $R_{18}$ is COOH;
one of $Z_1$ and $Z_2$ is —$(CH_2)_m$— and the other of $Z_1$ and $Z_2$ is —$(CH_2)_n$—$C(R_2)(X)$—$(CH_2)_n$—;
$R_{12}$ is hydrogen;
m is 1; each n is 0;
X is -$L_1$-$R_1$, wherein $L_1$ is a linker and —$R_{11}$ is an electrophilic group, e.g., cyclooctynyl or cyclooctynyl derivative such as DBCO, or BCN; and
each of $R_{14}$-$R_{17}$ is hydrogen, or alternatively $R_{16}$ and $R_{17}$ are taken together with the carbon atoms to which they are attached to form a 5- or 6-membered cycloalkyl ring.

In particular embodiments of the invention, a chelator is selected from the group consisting of:

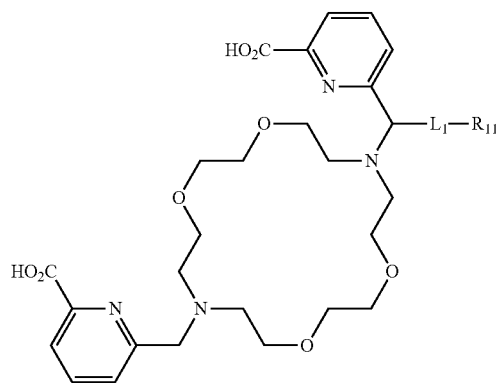

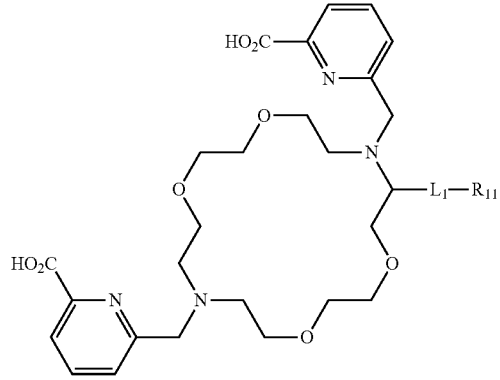

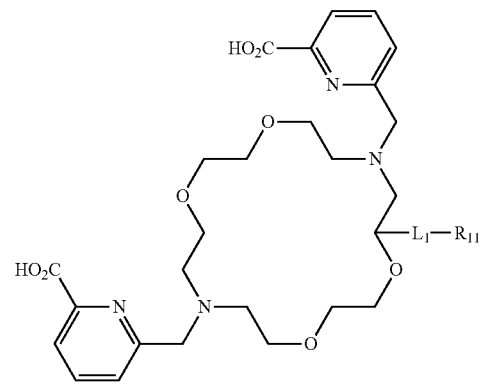

-continued

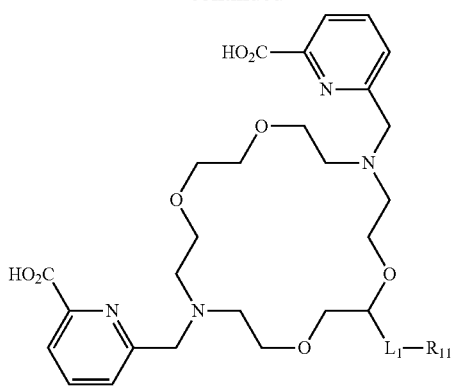

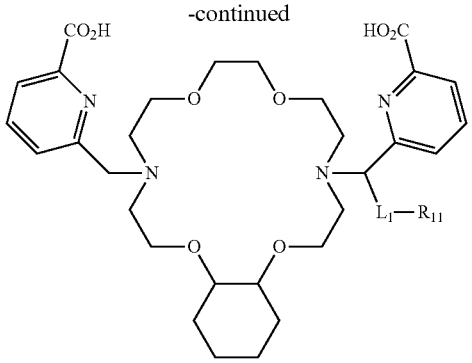

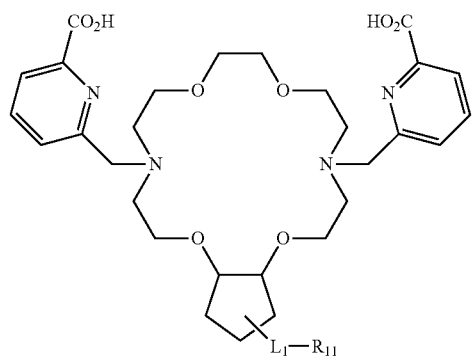

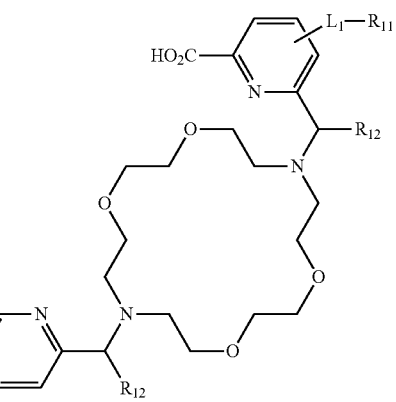

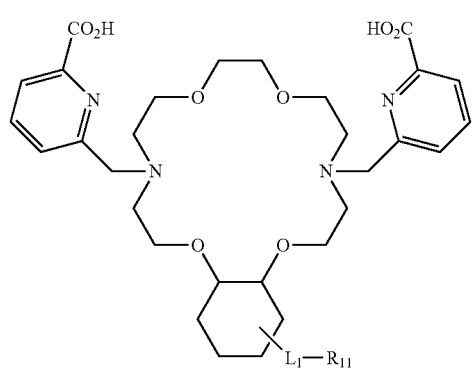

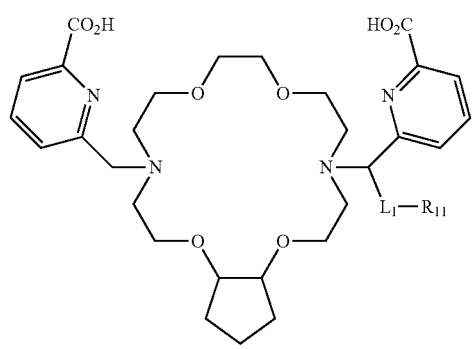

wherein:

$L_1$ is absent or a linker;

$R_{11}$ is a nucleophilic moiety or an electrophilic moiety, or $R_{11}$ comprises a targeting ligand; and each $R_{12}$ is independently hydrogen, —CH$_3$, or —CH$_2$CH$_3$, provided at least one $R_{12}$ is —CH$_3$ or —CH$_2$CH$_3$.

In some embodiments, $R_{11}$ is —NH$_2$, —NCS, —NCO, —N$_3$, alkynyl, cycloalkynyl, —C(O)R$_3$, —COOR$_{13}$, —CON(R$_{13}$)$_2$, maleimido, acyl halide, tetrazine, or trans-cyclooctene.

In certain embodiments, $R_{11}$ is cyclooctynyl or a cyclooctynyl derivative selected from the group consisting of bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

Preferably, $R_{11}$ is an alkynyl group or cycloalkynyl group, more preferably a cycloalkynyl group, e.g., DBCO or BCN.

Exemplary chelators of the invention include, but are not limited to:

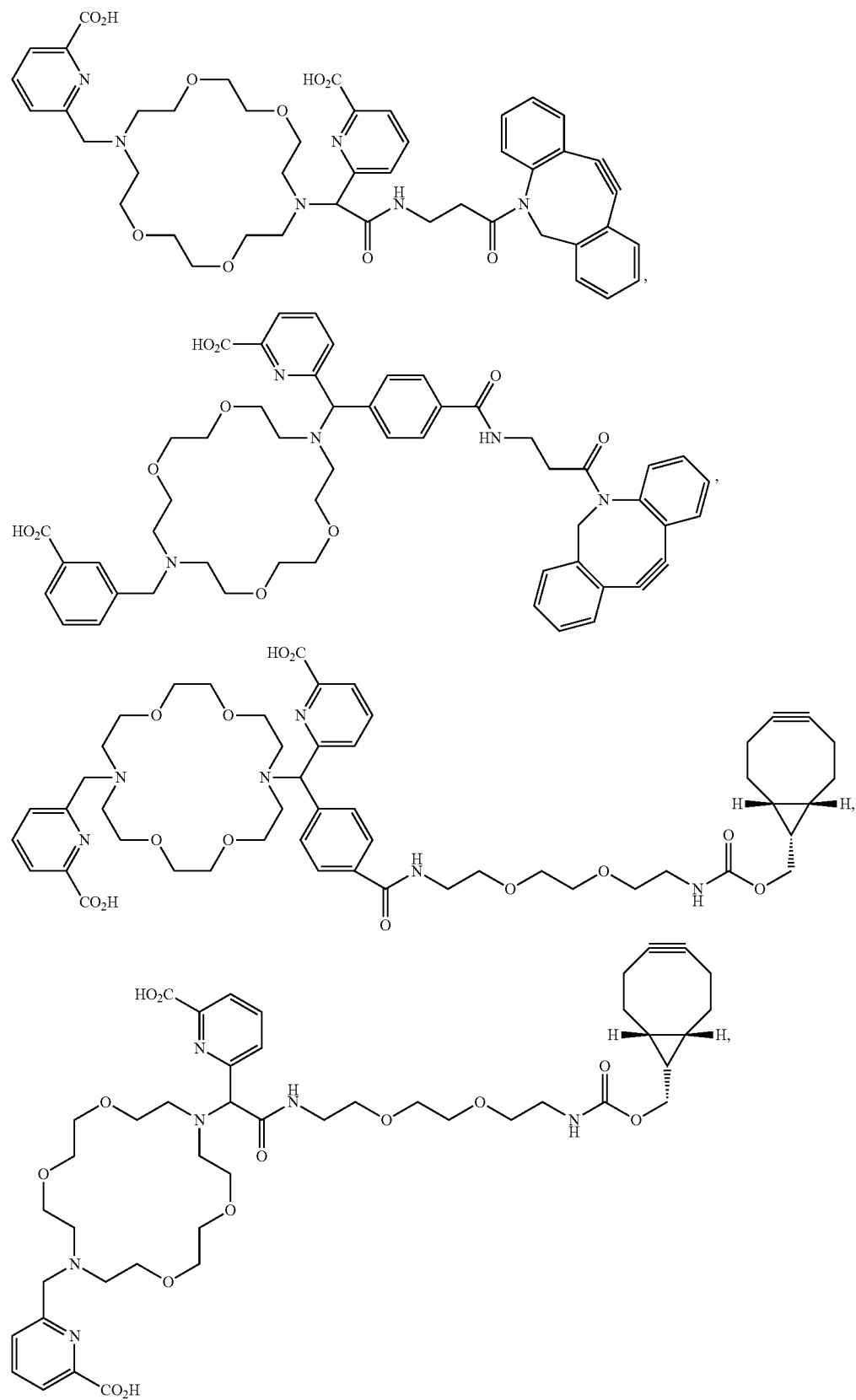

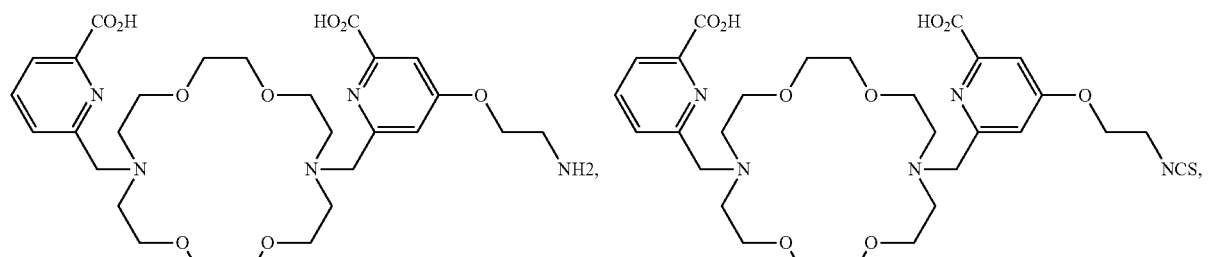
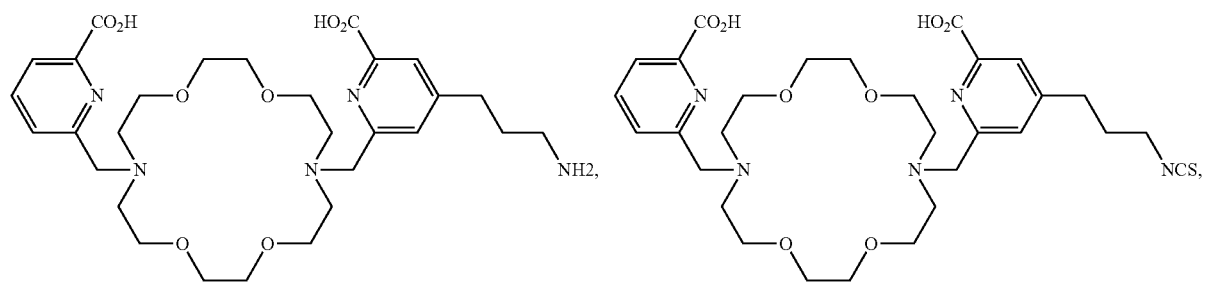
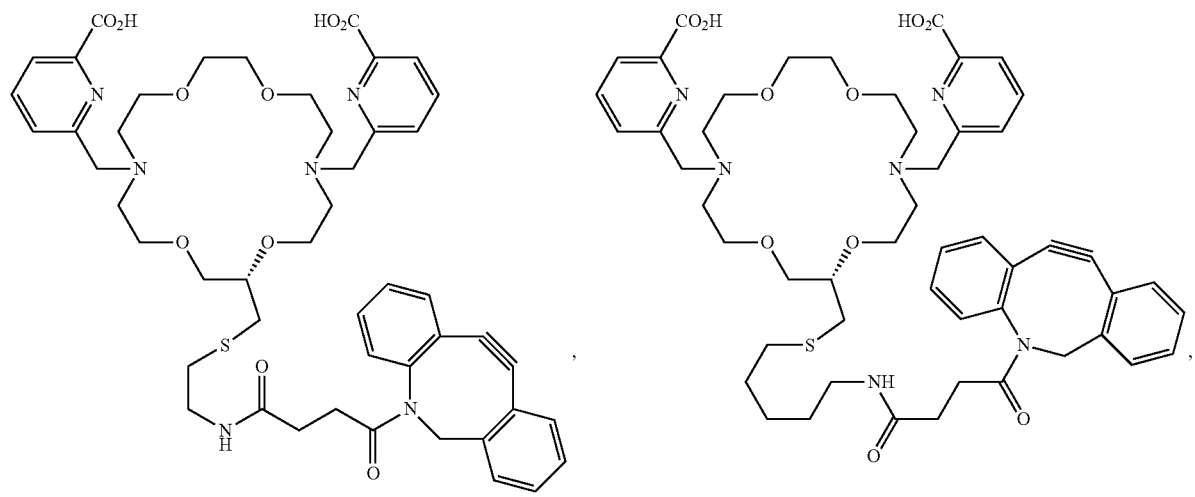
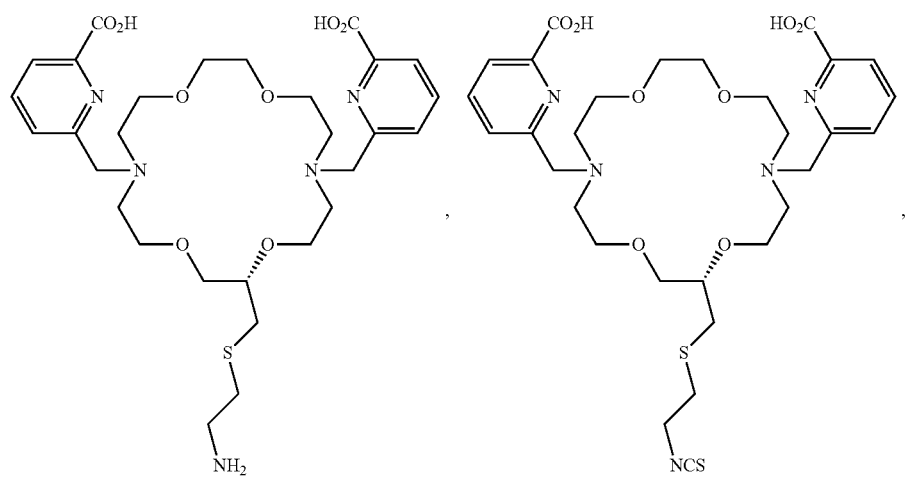

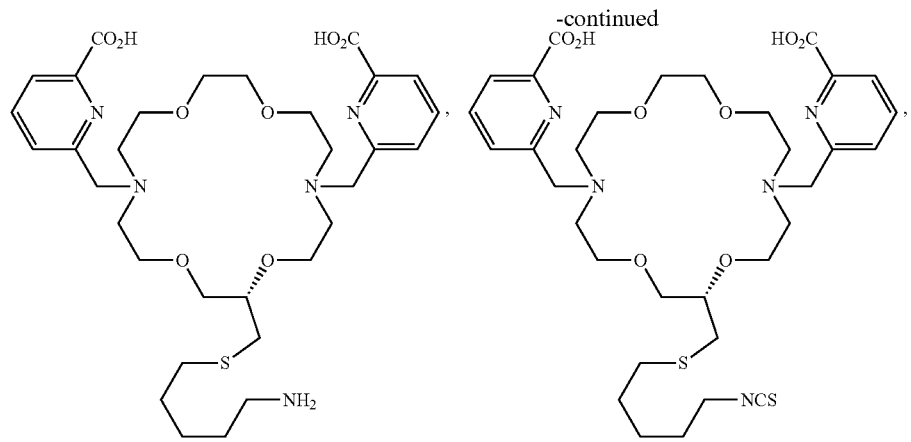

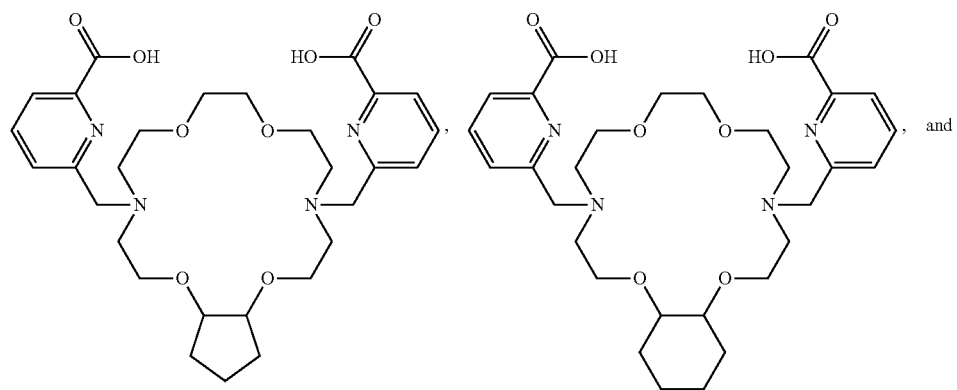

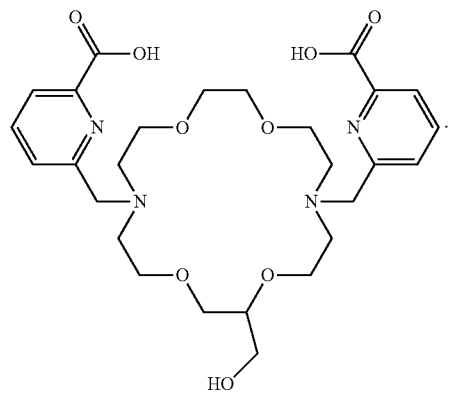

Such chelators can be covalently attached to a targeting ligand (e.g., an antibody or antigen binding fragment thereof) to form immunoconjugates or radioimmunoconjugates by reacting the chelator with an azide-labeled targeting ligand to form a 1,2,3-triazole linker via a click chemistry reaction as described in more detail below.

Chelators of the invention can be produced by any method known in the art in view of the present disclosure. For example, the pendant aromatic/heteroaromatic groups can be attached to the macrocyclic ring portion by methods known in the art, such as those exemplified and described below.

Radiometal Complexes

In another general aspect, the invention relates to a radiometal complex comprising a radiometal ion coordinated to a chelator of the invention via coordinate bonding. Any of the chelators of the invention described herein can comprise a radiometal ion. Preferably, the radiometal ion is an alpha-emitting radiometal ion, more preferably $^{225}$Ac. Chelators of the invention can robustly chelate radiometal ions, particularly $^{225}$Ac at any specific activity irrespective of metal impurities, thus forming a radiometal complex having high chelation stability in vivo and in vitro and which is stable to challenge agents, e.g., diethylene triamine pentaacetic acid (DTPA).

According to embodiments of the invention, a radiometal complex has the structure of formula (I-m):

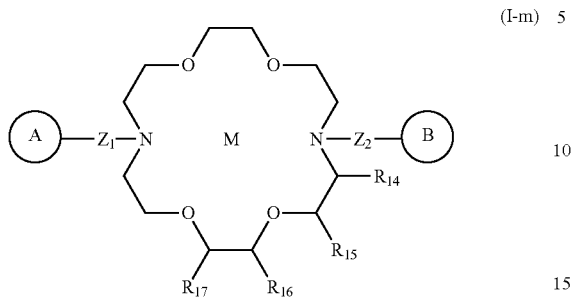

(I-m)

wherein the variable groups are as defined above in the chelators of the invention, e.g., the chelator of formula (I); and M is a radiometal ion. The radiometal ion M is bound to the chelator via coordinate bonding to form the radiometal complex. Heteroatoms of the macrocyclic ring of the chelator as well as any functional groups of the pendant arms (i.e., —$Z_1$-ring A and/or —$Z_2$-ring B) can participate in coordinate bonding of the radiometal ion.

Any of the chelators of formula (I) described above can be used to form radiometal complexes of formula (I-m).

In certain embodiments, the radiometal ion M is an alpha-emitting radiometal ion Preferably, the alpha-emitting radiometal ion is $^{225}$Ac.

According to embodiments of the invention, a radiometal complex comprises at least one X group, wherein X is -$L_1$-$R_1$, wherein $L_1$ is absent or a linker, and $R_{11}$ is an electrophilic moiety or a nucleophilic moiety, or $R_{11}$ comprises a targeting ligand. When $R_{11}$ is a nucleophilic or electrophilic moiety, such moiety can be used for attachment of the radiometal complex to a targeting ligand, directly or indirectly via a linker.

In certain embodiments, a radiometal comprises a single X group, and preferably $L_1$ of the X group is a linker.

In particular embodiments, $R_{11}$ is —$NH_2$, —NCS (isothiocyanate), —NCO (isocyanate), —$N_3$ (azido), alkynyl, cycloalkynyl, carboxylic acid, ester, amido, alkylamide, maleimido, acyl halide, tetrazine, or trans-cyclooctene, more particularly —NCS, —NCO, —$N_3$, alkynyl, cycloalkynyl, —C(O)$R_{13}$, —COO$R_{13}$, —CON($R_{13}$)$_2$, maleimido, or acyl halide (e.g., —C(O)Cl or —C(O)Br), wherein each $R_{13}$ is independently hydrogen or alkyl.

In some embodiments, $R_{11}$ is an alkynyl, cycloalkynyl, or azido group thus allowing for attachment of the chelator to a targeting ligand or other chemical moiety (e.g., linker) using a click chemistry reaction.

In certain embodiments, $R_{11}$ is an alkynyl group, more preferably a terminal alkynyl group or cycloalkynyl group that is reactive with an azido group, particularly via strain-promoted azide-alkyne cycloaddition (SPAAC). Examples of cycloalkynyl groups that can react with azide groups via SPAAC include, but are not limited to cyclooctynyl or a cyclooctynyl derivative, such as bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

In a particular embodiment, $R_{11}$ is dibenzoazacyclooctynyl (DIBAC, DBCO, ADIBO), which has the following structure:

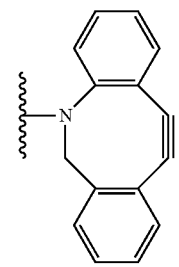 [SMILES: *N1Cc2ccccc2C#Cc2ccccc21]

In such embodiments in which $R_{11}$ is DBCO, the DBCO can be covalently linked to a radiometal complex directly or indirectly via a linker, and is preferably attached to the radiometal complex indirectly via a linker.

In another particular embodiment, $R_{11}$ is bicyclononynyl (BCN).

According to embodiments of the invention, each of ring A and ring B is independently a 6-10 membered aryl or a 5-10 membered heteroaryl. In alternative embodiments, it is contemplated that each of ring A and ring B is an optionally substituted heterocyclyl ring, such as oxazoline. Each of ring A and ring B can be optionally and independently substituted with one or more substituent groups independently selected from the group consisting of halo, alkyl, alkenyl, cycloalkyl, cycloalkenyl, aryl, heterocyclyl, heteroaryl, —O$R_{13}$, —S$R_{13}$, —(CH$_2$)$_p$COO$R_{13}$, —OC(O)$R_{13}$, —N($R_{13}$)$_2$, —CON($R_{13}$)$_2$, —NO$_2$, —CN —OC(O)N($R_{13}$)$_2$, and X. Examples of 6-10 membered aryl groups suitable for this purpose include, but are not limited to, phenyl and naphthyl. Examples of 5 to 10 membered heteroaryl groups suitable for this purpose include, but are not limited to pyridinyl, isothiazolyl, isoxazolyl, and imidazolyl. Examples of suitable substituents of the 5 to 10 membered heteroaryl and 6 to 10 membered aryl groups include, but are not limited to —COOH, tetrazolyl, and —CH$_2$COOH.

In certain embodiments, each of ring A and ring B are independently and optionally substituted with one or more carboxyl groups, including but not limited to, —COOH and —CH$_2$COOH.

In one embodiment, ring A and ring B are the same, e.g., both ring A and ring B are pyridinyl. In another embodiment, ring A and ring B are different, e.g., one of ring A and ring is pyridinyl and the other is phenyl.

In a particular embodiment, both ring A and ring B are pyridinyl substituted with —COOH.

In a particular embodiment, both ring A and ring B are pyridinyl substituted with tetrazolyl.

In another particular embodiment, both ring A and ring B are picolinic acid groups having the following structure:

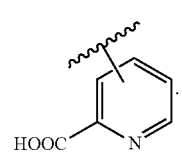

According to embodiments of the invention, each of $Z_1$ and $Z_2$ is independently —(C($R_{12}$)$_2$)$_m$— or —(CH$_2$)$_n$—C($R_2$)(X)—(CH$_2$)$_n$—; each X is independently -$L_1$-$R_{11}$; each n is independently 0, 1, 2, 3, 4, or 5; and each m is independently 1, 2, 3, 4, or 5.

In some embodiments, both $Z_1$ and $Z_2$ are —(CH$_2$)$_m$—, wherein each m is preferably 1. In such embodiments, a carbon atom of the macrocyclic ring, ring A, or ring B is substituted with an X group.

In some embodiments, one of $Z_1$ and $Z_2$ is —(CH$_2$)$_n$—C(R$_{12}$)(X)—(CH$_2$)$_n$— and the other is —(CH$_2$)$_m$—.

In some embodiments, one of $Z_1$ and $Z_2$—(CH$_2$)$_n$—C(R$_{12}$)(X)—(CH$_2$)$_n$— and the other is —(CH$_2$)$_m$—; each n is 0; m is 1; X is -L$_1$-R$_{11}$; and L$_1$ is a linker.

In some embodiments, both $Z_1$ and $Z_2$ are —(CH$_2$)$_m$—; each m is independently 0, 1, 2, 3, 4, or 5, preferably each m is 1; and one of R$_{14}$, R$_{15}$, R$_{16}$, and R$_{17}$ is X, and the rest of R$_{14}$, R$_{15}$, R$_{16}$, and R$_{17}$ are each hydrogen.

In some embodiments, R$_{14}$ and R$_{15}$ are taken together with the carbon atoms to which they are attached to form a 5- or 6-membered cycloalkyl ring (e.g., cyclopentyl or cyclohexyl). Such 5- or 6-membered cycloalkyl ring can be substituted with an X group.

In some embodiments R$_{16}$ and R$_{17}$ are taken together with the carbon atoms to which they are attached to form a 5- or 6-membered cycloalkyl ring (e.g., cyclopentyl or cyclohexyl). Such 5- or 6-membered cycloalkyl ring can be substituted with an X group.

In certain embodiments a radiometal complex has the structure of formula (II-m):

(II-m)

wherein the variable groups are as defined above in the chelators of the invention, e.g., the chelator of formula (II); and M is a radiometal ion, preferably an alpha-emitting radiometal ion, more preferably $^{225}$Ac.

Any of the chelators of formula (II) described above can be used to form radiometal complexes of formula (II-m).

In some embodiments, one of A$_1$, A$_2$, A$_3$, A$_4$, and A$_5$ is nitrogen, one of A$_1$, A$_2$, A$_3$, A$_4$, and A$_5$ is carbon substituted with —COOH and the rest are CH, i.e., forming a pyridinyl ring substituted with carboxylic acid.

In some embodiments, one of A$_6$, A$_7$, A$_8$, A$_9$, and A$_{10}$ is nitrogen, one of A$_6$, A$_7$, A$_8$, A$_9$, and A$_{10}$ is carbon substituted with —COOH, and the rest are CH, i.e., forming a pyridinyl ring substituted with carboxylic acid.

In one embodiment, at least one of R$_1$, R$_2$, R$_3$, R$_4$ and R$_5$ is —COOH. In one embodiment, at least one of R$_6$, R$_7$, R$_8$, R$_9$, and R$_{10}$ is —COOH. In another embodiment, at least one of R$_1$, R$_2$, R$_3$, R$_4$ and R$_5$ is —COOH; and at least one of R$_6$, R$_7$, R$_8$, R$_9$, and R$_{10}$ is —COOH.

In some embodiments, each of A$_1$ and A$_{10}$ is nitrogen; A$_2$ is CR$_2$ and R$_2$ is —COOH; A$_9$ is CR$_9$ and R$_9$ is —COOH; each of A$_3$-A$_8$ is CR$_2$, CR$_3$, CR$_4$, CR$_5$, CR$_6$, CR$_7$, and CR$_8$, respectively; and each of R$_3$ to R$_8$ is hydrogen.

In one embodiment, at least one of R$_1$, R$_2$, R$_3$, R$_4$ and R$_5$ is tetrazolyl. In one embodiment, at least one of R$_6$, R$_7$, R$_8$, R$_9$, and R$_{10}$ is tetrazolyl. In another embodiment, at least one of R$_1$, R$_2$, R$_3$, R$_4$ and R$_5$ is tetrazolyl; and at least one of R$_6$, R$_7$, R$_8$, R$_9$, and R$_{10}$ is tetrazolyl.

In some embodiments, each R$_{12}$ is hydrogen.

In some embodiments, R$_{11}$ is an alkynyl group or cycloalkynyl group, preferably cyclooctynyl or a cyclooctynyl derivative, e.g., DBCO.

In particular embodiments of a radiometal complex of formula (II-m):
  M is $^{225}$Ac;
  each of A$_1$ and A$_{10}$ is nitrogen;
  A$_2$ is CR$_2$ and R$_2$ is —COOH;
  A$_9$ is CR$_9$ and R$_9$ is —COOH;
  each of A$_3$-A$_8$ is CR$_2$, CR$_3$, CR$_4$, CR$_5$, CR$_6$, CR$_7$, and CR$_8$, respectively;
  each of R$_3$ to R$_8$ is hydrogen;
  one of $Z_1$ and $Z_2$ is —(CH$_2$)$_m$— and the other of $Z_1$ and $Z_2$ is —(CH$_2$)$_n$—C(R$_2$)(X)—(CH$_2$)$_n$—;
  R$_{12}$ is hydrogen;
  m is 1;
  each n is 0;
  X is -L$_1$-R$_{11}$, wherein L$_1$ is a linker and —R$_{11}$ is an electrophilic group, e.g., cyclooctynyl or cyclooctynyl derivative such as DBCO; and
  each of R$_{14}$-R$_{17}$ is hydrogen, or alternatively R$_{16}$ and R$_{17}$ are taken together with the carbon atoms to which they are attached to form a 5- or 6-membered cycloalkyl ring.

In certain embodiments, a radiometal complex has the structure of formula (III-m):

(III-m)

wherein the variable groups are as defined above in the chelators of the invention, e.g., the chelator of formula (III); and M is a radiometal ion, preferably an alpha-emitting radiometal ion, more preferably $^{225}$Ac.

Any of the chelators of formula (III) described above can be used to form radiometal complexes of formula (III-m).

In some embodiments, each A$_{11}$ is the same, and each A$_{11}$ is O, S, NMe, or NH. For example, each Au can be S. In other embodiments, each A$_{11}$ is different and each is independently selected from O, S, NMe, and NH.

In some embodiments, each R$_{18}$ is independently —(CH$_2$)$_p$—COOR$_{13}$, wherein R$_{13}$ is hydrogen and each p is independently 0 or 1.

In some embodiments, each R$_{18}$ is —COOH.

In some embodiments, each R$_{18}$ is —CH$_2$COOH.

In some embodiments, each R$_{18}$ is tetrazolyl.

In particular embodiments of a radiometal complex of formula (III-m):
  each R$_{18}$ is COOH;
  one of $Z_1$ and $Z_2$ is —(CH$_2$)$_m$— and the other of $Z_1$ and $Z_2$ is —(CH$_2$)$_n$—C(R$_{12}$)(X)—(CH$_2$)$_n$—;

$R_{12}$ is hydrogen;

m is 1; each n is 0;

X is -$L_1$-$R_1$, wherein $L_1$ is a linker and —$R_{11}$ is an electrophilic group, e.g., cyclooctynyl or cyclooctynyl derivative such as DBCO; and each of $R_{14}$-$R_{17}$ is hydrogen, or alternatively $R_{16}$ and $R_{17}$ are taken together with the carbon atoms to which they are attached to form a 5- or 6-membered cycloalkyl ring.

In particular embodiments of the invention, a radiometal complex has one of the following structures:

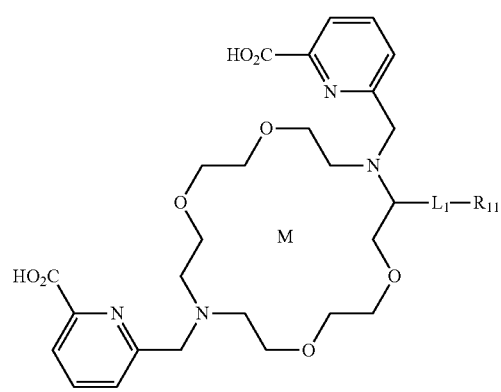

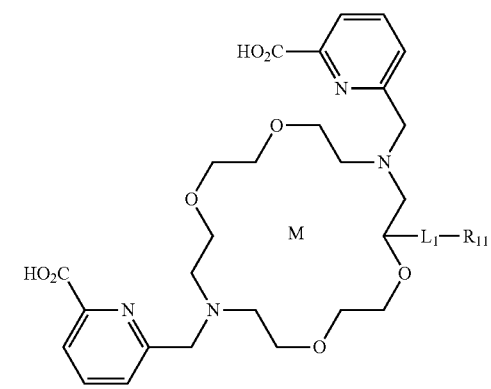

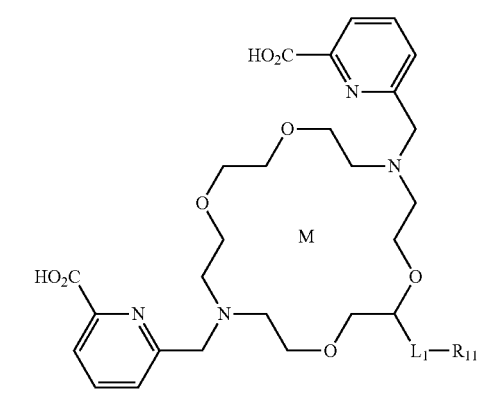

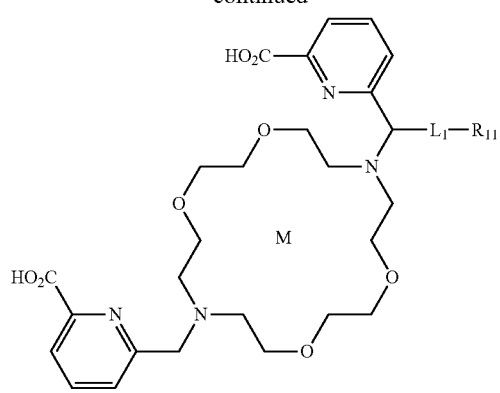

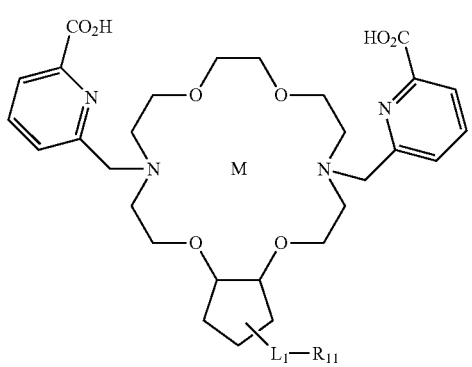

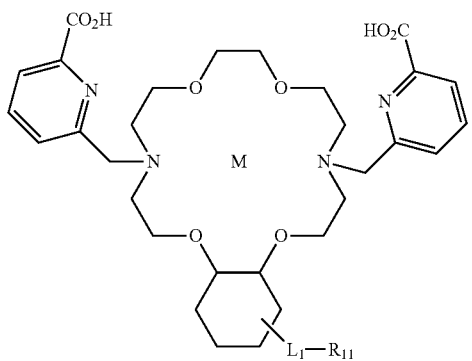

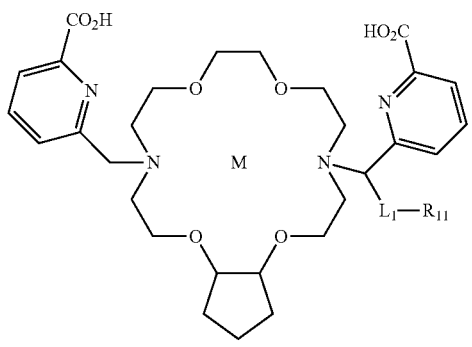

-continued

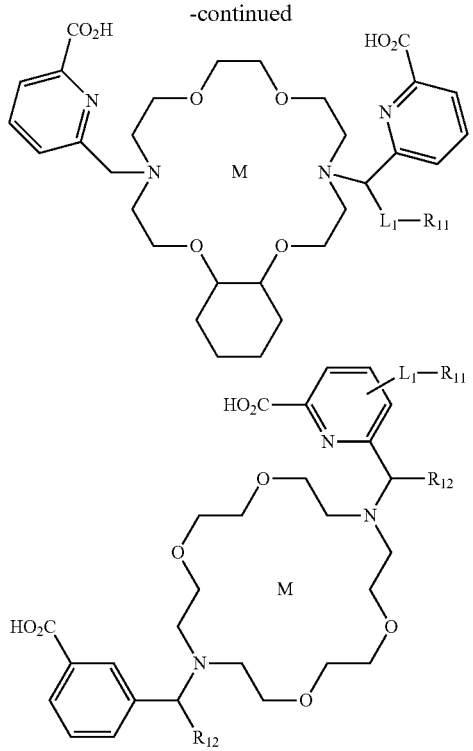

wherein:

M is actinium-225 ($^{225}$Ac), $L_1$ is absent or a linker;
$R_{11}$ is a nucleophilic moiety or an electrophilic moiety, or $R_{11}$ comprises a targeting ligand; and
each $R_{12}$ is independently hydrogen, —$CH_3$, or —$CH_2CH_3$, provided at least one $R_{12}$ is —$CH_3$ or —$CH_2CH_3$.

Radiometal complexes can be produced by any method known in the art in view of the present disclosure. For example, a chelator of the invention can be mixed with a radiometal ion and the mixture incubated to allow for formation of the radiometal complex. In an exemplary embodiment, a chelator is mixed with a solution of $^{225}$Ac $(NO_3)_3$ to form a radiocomplex comprising $^{225}$Ac bound to the chelator via coordinate bonding. As described above, chelators of in the invention efficiently chelate radiometals, particularly $^{225}$Ac. Thus, in particular embodiments, a chelator of the invention is mixed with a solution of $^{225}$Ac ion at a ratio by concentration of chelator to $^{225}$Ac ion of 1:1000, 1:500, 1:400, 1:300, 1:200, 1:100, 1:50, 1:10, or 1:5, preferably 1:5 to 1:200, more preferably 1:5 to 1:100. Thus, in some embodiments, the ratio of a chelator of the invention to $^{225}$Ac which can be used to form a radiometal complex is much lower than that which can be achieved with other known $^{225}$Ac chelators, e.g., DOTA. The radiocomplex can be characterized by instant thin layer chromatography (e.g., iTLC-SG), HPLC, LC-MS, etc. Exemplary methods are described herein, e.g., in the Examples below.

Immunoconjugates and Radioimmunoconjugates

In another general aspect, the invention relates to immunoconjugates and radioimmunoconjugates. Chelators and radiometal complexes of the invention can be conjugated to (i.e., covalently linked to) targeting ligands, such as an immune substance to produce immunoconjugates and/or radioimmunoconjugates that are suitable, for example, for medicinal applications in subjects, e.g., humans, such as targeted radiotherapy. Using the chelators and radiometal complexes of the invention, targeting ligands, particularly antibodies or antigen binding fragments thereof that can bind specifically to targets of interest (such as cancer cells), can be site-specifically labeled with radiometal ions to produce radioimmunoconjugates. In particular, using the chelators and/or radiometal complexes of the invention, radioimmunoconjugates having high yield chelation of radiometal ions, particularly $^{225}$Ac, and desired chelator-antibody ratio (CAR) can be produced. According to particular embodiments, methods of the present invention provide an average CAR of less than 10, less than 8, less than 6, or less than 4; or a CAR of between about 2 to about 8, or about 2 to about 6, or about 2 to about 4, or about 2 to about 3; or a CAR of about 2, or about 3, or about 4, or about 5, or about 6, or about 7, or about 8.

As used herein, an "immunoconjugate" is an antibody or antigen binding fragment thereof conjugated to (e.g., bound via a covalent bond) to a second molecule, such as a toxin, drug, radiometal ion, chelator, radiometal complex, etc. A "radioimmunoconjugate" in particular is an immunoconjugate in which an antibody or antigen binding fragment thereof is labeled with a radiometal or conjugated to a radiometal complex.

According to embodiments of the invention, an immunoconjugate comprises a chelator of the invention, e.g., a chelator of formula (I), formula (II), or formula (III) as described herein, covalently linked to an antibody or antigen binding fragment thereof, preferably via a linker. Numerous modes of attachment with different linkages between the chelator and antibody or antigen binding fragment thereof are possible depending on the reactive functional groups (i.e., nucleophiles and electrophiles) on the chelator and antibody or antigen binding fragment thereof.

According to embodiments of the invention, a radioimmunoconjugate comprises a radiometal complex of the invention, e.g., a radiometal complex of formula (I-m), formula (II-m), or formula (III-m) as described herein, covalently linked to an antibody or antigen binding fragment thereof, preferably via a linker.

Any of the chelators or radiometal complexes of the invention, such as those described herein, can be used to produce immunoconjugates or radioimmunoconjugates of the invention.

In some embodiments, a radiometal complex of a radioimmunoconjugate of the invention comprises an alpha-emitting radiometal ion coordinated to the chelator moiety of the radiocomplex. Preferably, the alpha-emitting radiometal ion is $^{225}$Ac.

In particular embodiments, an antibody or antigen binding fragment thereof is linked to a radiocomplex via a triazole moiety to form a radioimmunoconjugate of the invention.

In particular embodiments, the antibody or antigen binding fragment in an immunoconjugate or radioimmunoconjugate of the application can bind specifically to a tumor antigen. Preferably, the antibody or antigen binding fragment binds specifically to a cancer antigen. Examples of cancer antigens include, but are not limited to, prostate-specific membrane antigen (PSMA), BCMA, Her2, EGFR, KLK2, CD19, CD22, CD30, CD33, CD79b, and Nectin-4.

In one embodiment, the antibody binds specifically to PSMA. Preferably, the antibody is PSMB127. A human IgG4 antibody that binds to human prostate-specific membrane antigen (PSMA), referred to herein as "anti-PSMA mAb" with designation "PSMB127", has a heavy chain (HC) CDR1 sequence of SEQ ID NO: 3, a HC CDR2 sequence of SEQ ID NO: 4, a HC CDR3 sequence of SEQ ID NO: 5, a light chain (LC) CDR1 sequence of SEQ ID NO: 6, a LC CDR2 sequence of SEQ ID NO: 7, and a LC CDR3 sequence of SEQ ID NO: 8, and has a HC sequence of SEQ ID NO: 9 and a LC sequence of SEQ ID NO: 10. Anti-PSMA mAb was expressed and purified using standard chromatography methods. The antibody PSMB127, its biologic activities, uses or other related information thereof are described, for example, in U.S. Patent Application Publication No. US 20200024360A1, the contents of which are hereby incorporated by reference in their entireties.

In another embodiment, the antibody binds specifically to human kallikrein-2 (KLK2). Preferably, the antibody is H11B6. The H11B6 antibody, biologic activities, uses or other related information thereof are described in U.S. Pat. No. 10,100,125, the contents of which are hereby incorporated by reference in their entireties. As described therein, the H11B6 antibody polypeptide comprises a heavy chain (HC) variable region comprising the amino acid sequences of SEQ ID NO: 11 and SEQ ID NO: 12 and SEQ ID NO: 13 and a light chain (LC) variable region comprising the amino acid sequences of SEQ ID NO: 14 and SEQ ID NO: 15 and SEQ ID NO: 16. The H11B6 antibody can further have a heavy chain variable region which comprises the amino acid sequence of SEQ ID NO: 17 and a light chain variable region which comprises the amino acid sequence of SEQ ID NO: 18, or have a heavy chain constant region which comprises the amino acid sequence of SEQ ID NO: 19 and a light chain constant region which comprises the amino acid sequence of SEQ ID NO: 20, or have a heavy chain comprising the amino acid sequence of SEQ ID NO:21 and a light chain comprising the amino acid sequence of SEQ ID NO:22.

The commercial antibodies trastuzumab (Herceptin), cetuximab (Erbitux), pertuzumab (Perjeta), and panitumumab (Vectibix) were purchased from Roche, Lilly, Roche, and Amgen, respectively. Trastuzumab and pertuzumab bind to human Her2. Cetuximab and panitumumab bind to human EGFR.

Immunoconjugates and radioimmunoconjugates of the invention can be prepared by any method known in the art in view of the present disclosure for conjugating ligands, e.g., antibodies, to chelators, including chemical and/or enzymatic methods. For example, immunoconjugates and radioimmunoconjugates can be prepared by a coupling reaction, including by not limited to, formation of esters, thioesters, or amides from activated acids or acyl halides; nucleophilic displacement reactions (e.g., such as nucleophilic displacement of a halide ring or ring opening of a strained ring system); azide-alkyne Huisgen cycloaddition (e.g., 1,3-dipolar cycloaddition between an azide and alkyne to form a 1,2,3-triazole linker); thiolyne addition; imine formation; Diels-Alder reactions between tetrazines and trans-cycloctene (TCO); and Michael additions (e.g., maleimide addition). Numerous other modes of attachment, with different linkages, are possible depending on the reactive functional group used. The attachment of a ligand can be performed on a chelator that is coordinated to a radiometal ion, or on a chelator which is not coordinated to a radiometal ion.

According to an embodiment, a radioimmunoconjugate can be produced by covalently linking a radiometal complex of the invention to an antibody or antigen binding fragment thereof by, for example, a click chemistry reaction (see, e.g., FIGS. 2B and 2D, referred to as "click radiolabeling"). Alternatively, a radioimmunoconjugate can be produced by first preparing an immunoconjugate of the invention by covalently linking a chelator of the invention to an antibody or antigen-binding fragment thereof by, for example, a click chemistry reaction; the immunoconjugate can subsequently be labeled with a radiometal ion to produce a radioimmunoconjugate (see, e.g., FIGS. 2A and 2C, referred to as "one-step direct radiolabeling"). Both residue-specific (e.g., FIGS. 2A and 2B) and site-specific methods (e.g., FIGS. 2C and 2D) of conjugation can be used to produce immunoconjugate and radioimmunoconjugates of the invention.

Residue-specific methods for conjugation to proteins are well established and most commonly involve either lysine side chains, using an activated ester or isothiocyanate, or cysteine side chains with a maleimide, haloacetyl derivative or activated disulfide (Brinkley Bioconjugate Chem 1992:2). Since most proteins have multiple lysine and cysteine residues, heterogeneous mixtures of product with different numbers of conjugated molecules at a variety of amino acid positions are typically obtained using such methods. Additional methods have been established including tyrosine-specific conjugation (Ban et al. *Bioconjugate Chemistry* 2013:520), methionine-specific methods (Lin et al. *Science* 2017 (355) 597), additional cysteine-focused approaches (Toda et al. *Angew Chemie* 2013:12592), and others.

More recently, site-selective and site-specific conjugation methods have been established for monoclonal antibodies and other proteins (Agarwal, P. and C. R. Bertozzi, *Bioconjug Chem,* 2015. 26(2): p. 176-92; Rabuka et al. *Curr Opin Chem Biol* 2010:790). These include incorporation of unnatural amino acids; fusion of the protein of interest to a 'self-labeling tag' such as SNAP or DHFR or a tag that is recognized and modified specifically by another enzyme such as sortase A, lipoic acid ligase and formylglycine-generating enzyme; enzymatic modification of the glycan to allow conjugation of payloads of interest (Hu et al. *Chem Soc Rev* 2016:1691); use of microbial transglutaminase to selectively recognize defined positions on the antibody; and additional methods using molecular recognition and/or chemical approaches to affect selective conjugation (Yamada et al. 2019:5592; Park et al. *Bioconjugate Chem* 2018:3240; Pham et al. *Chembiochem* 2018:799).

In some embodiments, an immunoconjugate or radioimmunoconjugate of the invention is produced using residue specific methods for conjugation of a chelator of the invention to an antibody or antigen binding fragment thereof. Such residue specific methods typically result in an immunoconjugate or radioimmunoconjugate covalently linked to a chelator or radiometal complex at a variety of positions of the antibody. Any residue specific method for forming protein or antibody conjugates known to those skilled in the art in view of the present disclosure can be used. Examples of residue specific methods for conjugation that can be used include, but are not limited to, conjugation of a chelator or radiometal complex to lysine residues of the antibody using a chelator or radiometal complex comprising, e.g., an activated ester or isothiocyanate group; conjugation to cysteine residues of the antibody using a chelator or radiometal complex comprising, e.g., a maleimide, haloacetyl derivative, acyl halide, activated disulfide group, or methylsulfonyl phenyloxadiazole group; conjugation to tyrosine resides of the antibody using a chelator or radiometal complex comprising, e.g., 4-phenyl-3H-1,2,4-triazoline-3,5(4H)-diones (PTADs); and conjugation to methionine residues of the antibody using a chelator or radiometal complex comprising, e.g., an oxaziridine derivative. It is also possible to label the antibody at a particular residue with a biorthogonal reactive functional group using one or more of the above described methods prior to conjugating to a chelator or radiometal complex of the invention. For example, tyrosine residues can be site-specifically labeled with a biorthogonal reactive functional group using an oxaziridine derivative linked to the biorthogonal reactive functional group, e.g., azido, alkynyl, or cycloalkynyl, and then the antibody containing the labeled tyrosine residues can be conjugated to a chelator or radiometal complex of the invention using a chelator or radiometal complex bearing a compatible reactive functional group.

In some embodiments, an immunoconjugate or radioimmunoconjugate of the invention is produced using site-specific or site-selective methods for conjugation of a chelator of the invention to an antibody or antigen binding fragment thereof. In contrast to residue specific methods, "site-specific" or "site-selective" methods typically result in an immunoconjugate or radioimmunoconjugate covalently linked to a chelator or radiometal complex at a specified position of the antibody. Any site-specific method for forming protein or antibody conjugates known to those skilled in the art in view of the present disclosure can be used. For example, an unnatural amino acid (e.g., azido- or alkynyl-amino acid) can be site-specifically incorporated into an antibody using a mutant aminoacyl t-RNA synthetase that can selectively aminoacylate its tRNA with an unnatural amino acid of interest. The mutant acylated tRNA together with an amber suppressor tRNA can then be used to site-specifically incorporate the unnatural amino acid into a protein in response to an amber nonsense codon. An antibody that is site-specifically labeled by one or more of the above described methods can subsequently be conjugated to a chelator or radiometal complex of the invention bearing a compatible reactive functional group.

According to embodiments of the invention, a method of producing a radioimmunoconjugate comprises reacting a chelator or radiocomplex of the invention, wherein $R_{11}$ is a nucleophilic or electrophilic moiety, with an antibody or antigen binding fragment thereof, or a modified antibody or antigen binding fragment thereof comprising a nucleophilic or electrophilic moiety.

In one embodiment, a method comprises reacting a chelator of the invention with an antibody or antigen binding fragment thereof, or a modified antibody or antigen binding fragment thereof comprising a nucleophilic or electrophilic functional group, to form an immunoconjugate having a covalent linkage between the chelator and antibody or antigen binding fragment thereof, or modified antibody or antigen binding fragment thereof, and reacting the immunoconjugate with a radiometal ion such that the radiometal ion binds the chelator of the immunoconjugate via coordinate binding, thereby forming the radioimmunoconjugate. This embodiment may be referred to as a "one-step direct radiolabeling" method (e.g., as schematically illustrated in FIG. 2C) because there is only one chemical reaction step involving the radiometal.

In another embodiment, a method comprises reacting a radiocomplex of the invention with an antibody or antigen binding fragment thereof, or a modified antibody or antigen binding fragment thereof comprising a nucleophilic or electrophilic functional group, thereby forming the radioimmunoconjugate. This embodiment may be referred to as a "click radiolabeling" method (e.g., as schematically illustrated in FIG. 2D). A modified antibody or antigen binding fragment thereof can be produced by any method known in the art in view of the present disclosure, e.g., by labeling an antibody at a particular residue with a biorthogonal reactive functional group using one or more of the above described methods, or by site-specifically incorporating an unnatural amino acid (e.g., azido- or alkynyl-amino acid) into an antibody using one or more of the above described methods.

The degree of labeling (DOL), sometimes called degree of substitution (DOS), is a particularly useful parameter for characterizing and optimizing bioconjugates, such as antibody modified by unnatural amino acid. It is expressed as an average number of the unnatural amino acid coupled to a protein molecule (e.g. an antibody), or as a molar ratio in the form of label/protein. The DOL can be determined from the absorption spectrum of the labeled antibody by any known method in the filed.

In certain embodiments, as described herein, immunoconjugates and radioimmunoconjugates of the invention are prepared using a click chemistry reaction. For example, radioimmunoconjugates of the invention can be prepared using a click chemistry reaction referred to as "click radiolabeling" (see, e.g., FIGS. 2B and 2D). Click radiolabeling uses click chemistry reaction partners, preferably an azide and alkyne (e.g., cyclooctyne or cyclooctyne derivative) to form a covalent triazole linkage between the radiocomplex (radiometal ion bound to the chelator) and antibody or antigen binding fragment thereof. Click radiolabeling methods of antibodies are described in, e.g., International Patent Application No. PCT/US18/65913, entitled "Radiolabeling of Polypeptides" of which the relevant description is incorporated herein by reference. In other embodiments referred to as "one-step direct radiolabeling," an immunoconjugate is prepared using a click chemistry reaction between an antibody or antigen binding fragment thereof and a chelator; the immunoconjugate is then contacted with a radiometal ion to form the radioimmunoconjugate (see, e.g., FIGS. 2A and 2C).

According to an embodiment, a method of preparing a radioimmunoconjugate comprises binding a radiometal ion to a chelator of the invention (e.g., via coordinate bonding).

An embodiment of the "one-step direct radiolabeling" method may be described as a method of preparing a radioimmunoconjugate comprising: contacting an immunoconjugate (i.e., polypeptide-chelator complex) with a radiometal ion to thereby form the radioimmunoconjugate, wherein the immunoconjugate comprises a chelator of the present invention. According to particular embodiments, the immunoconjugate has been formed via a click chemistry reaction between the chelator of the present invention and the polypeptide. According to particular embodiments, the radioimmunoconjugate has been formed without metal-free conditions (e.g., without any step(s) of removing or actively excluding common metal impurities from the reaction mixture). This is contrary to certain conventional methods in which it is necessary to radiolabel an antibody under strict metal-free conditions to avoid competitive (non-productive) chelation of common metals such as iron, zinc and copper, which introduce significant challenges into the production process.

In a particular embodiment, a method of preparing a radioimmunoconjugate of the invention comprises a "one-step direct radiolabeling" method comprising:
(i) providing a modified polypeptide comprising the polypeptide (e.g., antibody or antigen binding fragment thereof) covalently linked to a first click reaction partner (e.g., an azido group);
(ii) providing a chelator complex comprising a chelator of the present invention covalently linked to a second click reaction partner (e.g., an alkynyl group or cycloalkynyl group);
(iii) contacting the modified polypeptide with the chelator complex under a condition to allow the first click reaction partner (e.g., azido group) to react with the second click reaction partner (e.g., alkynyl group or cycloalkynyl group) to thereby form a polypeptide-chelator complex (i.e., immunoconjugate); and (iv) contacting the polypeptide-chelator complex with a radiometal ion to thereby prepare the radioimmunoconjugate (wherein the radioimmunoconjugate comprises the polypeptide labeled with the radiometal ion, e.g., a modified antibody or antigen binding fragment thereof labeled with an alpha-emitting radiometal ion bound to the chelator via coordinate bonding).

According to particular embodiments, step (iv) is performed without metal-free conditions.

In an alternative embodiment, a method of preparing a radioimmunoconjugate comprises a "click radiolabeling" method (e.g., as illustrated in FIG. 2D) comprising:

(i) providing a modified antibody or antigen binding fragment thereof comprising the antibody or antigen binding fragment thereof covalently linked to an azido group;

(ii) providing a radiocomplex comprising an alpha-emitting radiometal ion bound to a chelator via coordinate bonding, wherein the chelator is covalently linked to an alkynyl group or cycloalkynyl group; and (iii) contacting the modified antibody or antigen binding fragment thereof with the radiocomplex under a condition to allow the azido group to react with the alkynyl group or cycloalkynyl group to thereby prepare the radioimmunoconjugate.

Conditions for carrying out click chemistry reactions are known in the art, and any conditions for carrying out click chemistry reactions known to those skilled in the art in view of the present disclosure can be used in the invention. Examples of conditions include, but are not limited to, incubating the modified polypeptide and the radiocomplex at a ratio of 1:1 to 1000:1 at a pH of 4 to 10 and a temperature of 20° C. to 70° C.

The click radiolabeling methods described above allow for chelation of the radiometal ion under low or high pH and/or high temperature conditions to maximize efficiency, which can be accomplished without the risk of inactivating the alkyne reaction partner. The efficient chelation and efficient SPAAC reaction between an azide-labeled antibody or antigen binding fragment thereof and the radiocomplex allows radioimmunoconjugates to be produced with high radiochemical yield even with low azide: antibody ratios. The only step in which trace metals must be excluded is the radiometal ion chelation to the chelating moiety; the antibody production, purification, and conjugation steps do not need to be conducted under metal free conditions.

Chelators and radiometal complexes of the invention can also be used in the production of site-specific radiolabeled polypeptides, e.g., antibodies. The click radiolabeling methods described herein facilitate site-specific production of radioimmunoconjugates by taking advantage of established methods to install azide groups site-specifically on antibodies (Li, X., et al. Preparation of well-defined antibody-drug conjugates through glycan remodeling and strain-promoted azide-alkyne cycloadditions. *Angew Chem Int Ed Engl*, 2014. 53(28): p. 7179-82; Xiao, H., et al., Genetic incorporation of multiple unnatural amino acids into proteins in mammalian cells. *Angew Chem Int Ed Engl*, 2013. 52(52): p. 14080-3). Methods of attaching molecules to proteins or antibodies in a site-specific manner are known in the art, and any method of site-specifically labeling an antibody known to those skilled in the art can be used in the invention in view of the present disclosure. Examples of methods to site-specifically modify antibodies suitable for use in the invention include, but are not limited to, incorporation of engineered cysteine residues (e.g., THIOMAB™), use of non-natural amino acids or glycans (e.g., seleno cysteine, p-AcPhe, formylglycine generating enzyme (FGE, SMARTag™), etc.), and enzymatic methods (e.g., use of glycotransferase, endoglycosidase, microbial or bacterial transglutaminase (MTG or BTG), sortase A, etc.).

In some embodiments, a modified antibody or antigen binding fragment thereof for use in producing an immunoconjugate or radioimmunoconjugate of the invention is obtained by trimming the antibody or antigen binding fragment thereof with a bacterial endoglycosidase specific for the β-1,4 linkage between a core GlcNac residue in an Fc-glycosylation site of the antibody, such as GlycINATOR (Genovis), which leaves the inner most GlcNAc intact on the Fc, allowing for the site-specific incorporation of azido sugars at that site. The trimmed antibody or antigen binding fragment thereof can then be reacted with an azide-labeled sugar, such as UDP-N-azidoacetylgalactosamine (UDP-GalNAz) or UDP-6-azido 6-deoxy GalNAc, in the presence of a sugar transferase, such as GalT galactosyltransferase or GaNAc transferase, to thereby obtain the modified antibody or antigen binding fragment thereof.

In other embodiments, a modified antibody or antigen binding fragment thereof for use in producing an immunoconjugate or radioimmunoconjugate of the invention is obtained by deglycosylating the antibody or antigen binding fragment thereof with an amidase. The resulting deglycosylated antibody or antigen binding fragment thereof can then be reacted with an azido amine, preferably 3-azido propylamine, 6-azido hexylamine, or any azido-linker-amine or any azido-alkyl/heteroalkyl-amine, such as an azido-polyethylene glycol (PEG)-amine, for example, O-(2-aminoethyl)-O'-(2-azidoethyl)tetraethylene glycol, O-(2-aminoethyl)-O'-(2-azidoethyl)pentaethylene glycol, O-(2-aminoethyl)-O'-(2-azidoethyl)triethylene glycol, etc., or in the presence of a microbial transglutaminase to thereby obtain the modified antibody or antigen binding fragment thereof.

Any radiometal complex described herein can be used to produce a radioimmunoconjugate of the invention. In particular embodiments, the radiometal complex has the structure of formula (I-m), formula (II-m), or formula (III-m). In preferred embodiments, the radiometal complex has a structure selected from the group consisting of:

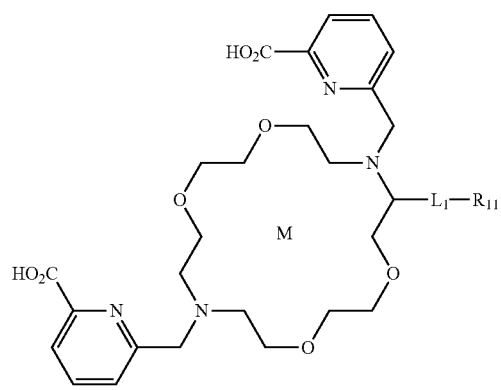

-continued

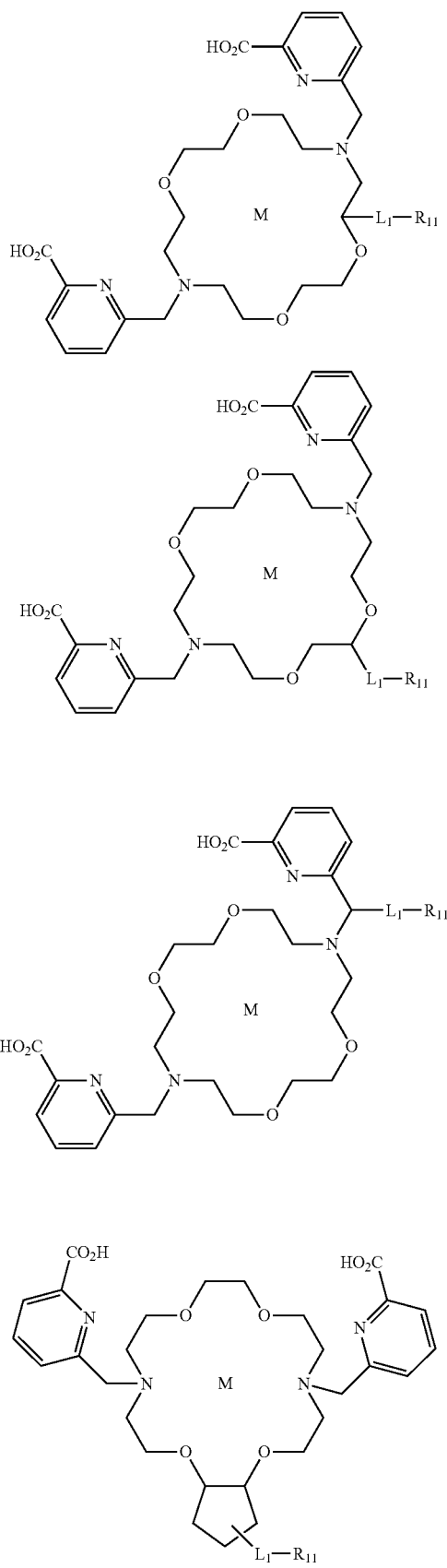

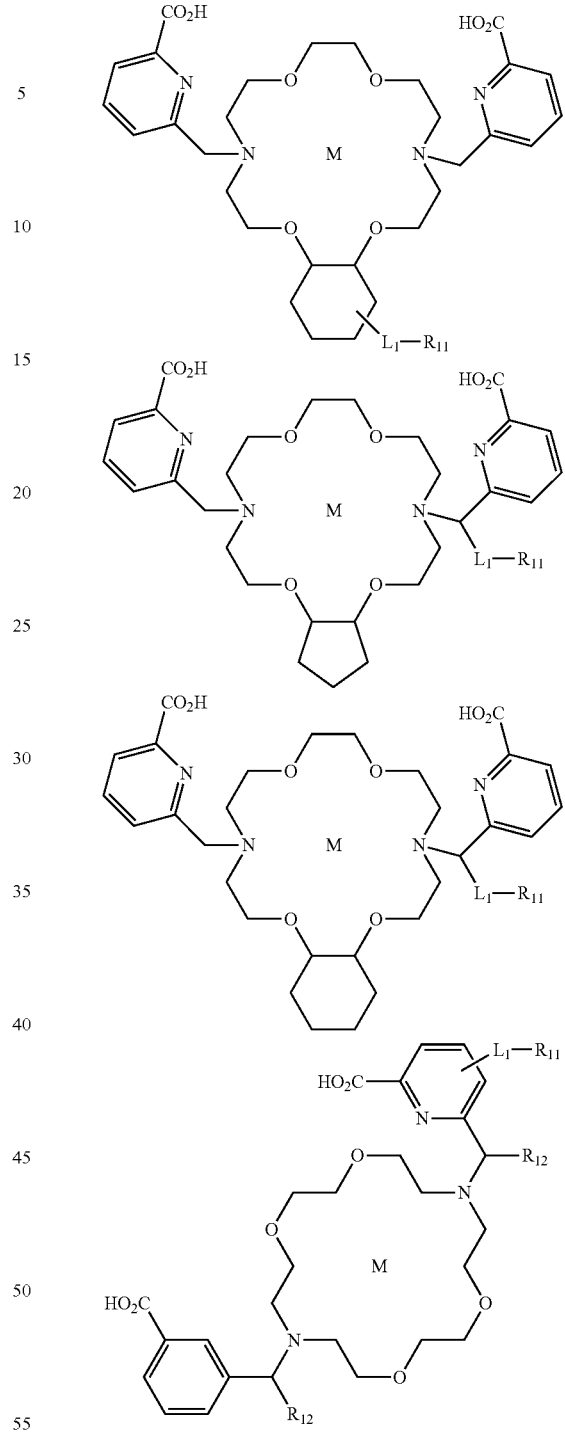

wherein M is a radiometal ion, preferably an alpha-emitting radiometal ion, more preferably actinium-225 ($^{225}$Ac), R is cyclooctynyl or a cyclooctynyl derivative, such as bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

In some embodiments, an antibody or antigen binding fragment thereof is covalently linked to an azido group using any method for chemical or enzymatic modification of antibodies and polypeptides known to those skilled in the art in view of the present disclosure. The azido-labeled antibody or antigen binding fragment thereof is reacted with a chelator or radiometal complex of the invention comprising an alkynyl or cycloalkynyl group, preferably a cyclooctynyl group and more preferably DBCO under conditions sufficient for the azido and alkynyl or cycloalkynyl group to undergo a click chemistry reaction to form a 1,2,3-triazole moiety.

In particular embodiments, the radioimmunoconjugates of the application include, but are not limited to:

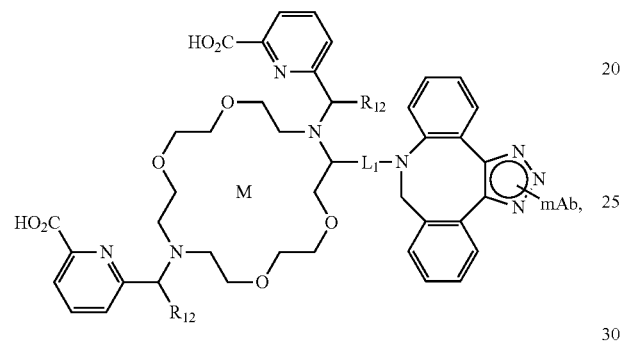

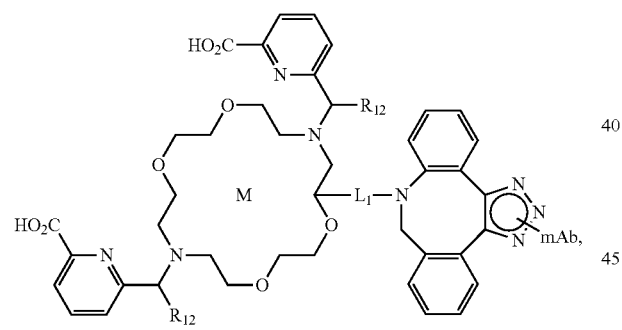

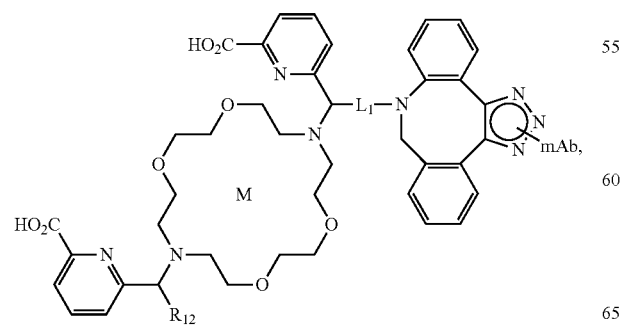

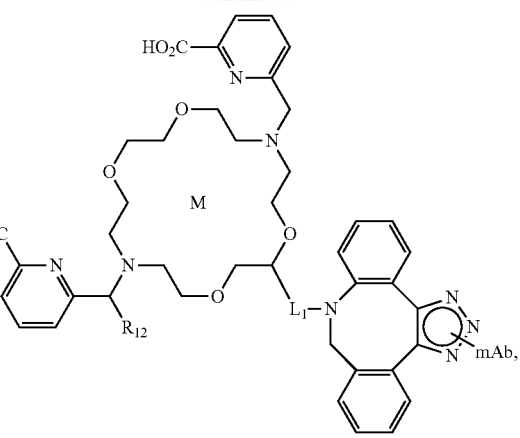

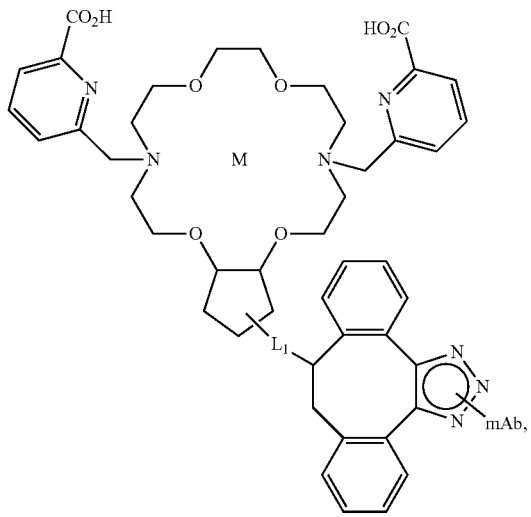

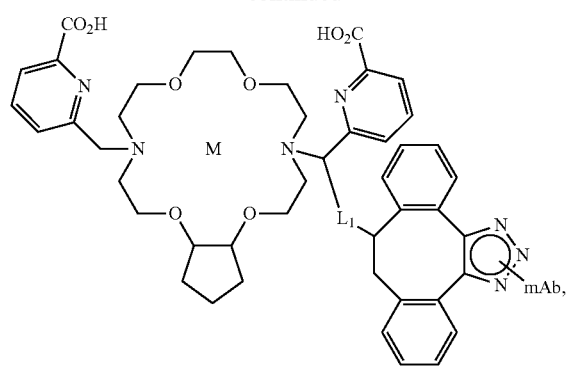
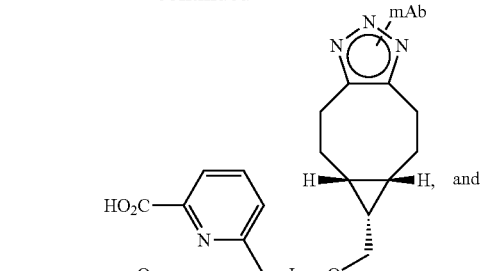
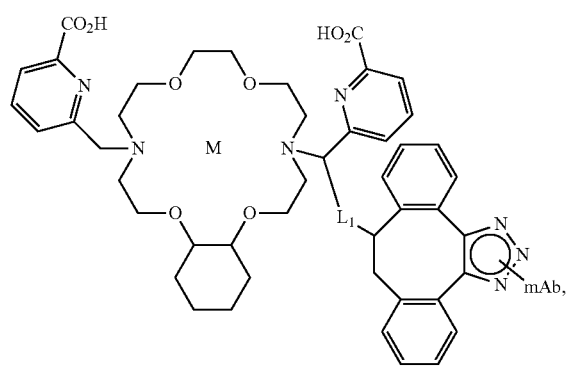
wherein mAb is an antibody or antigen binding fragment thereof; $L_1$ is absent or a linker, preferably a linker; each $R_{12}$ is independently hydrogen, $CH_3$ or $CH_2CH_3$, provided at least one $R_{12}$ is $-CH_3$ or $-CH_2CH_3$; and M is an alpha-emitting radionuclide, preferably $^{225}Ac$.
Examples of radioimmunoconjugates of the application include, but are not limited to:
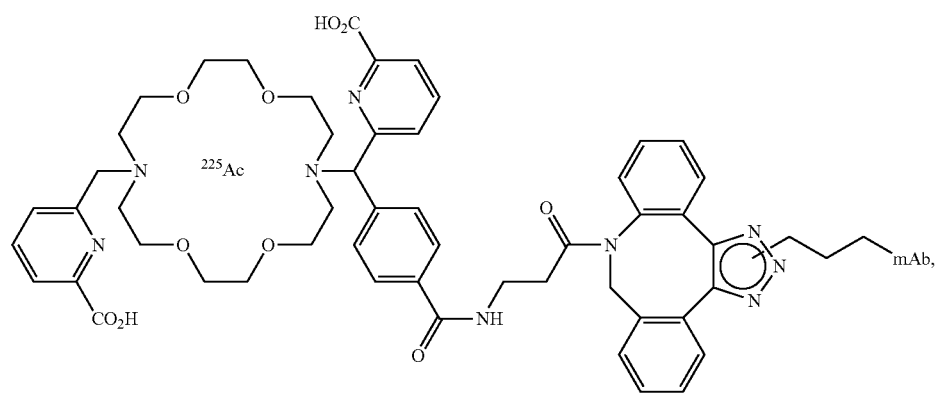

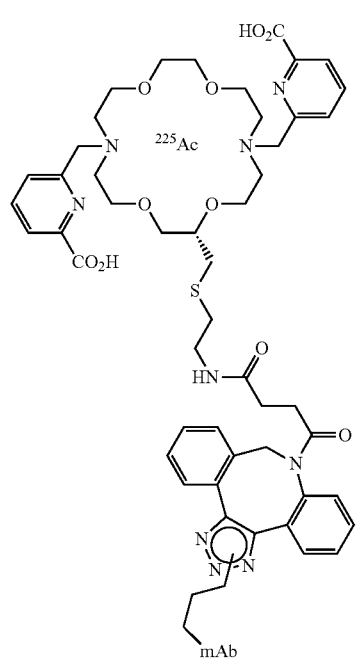
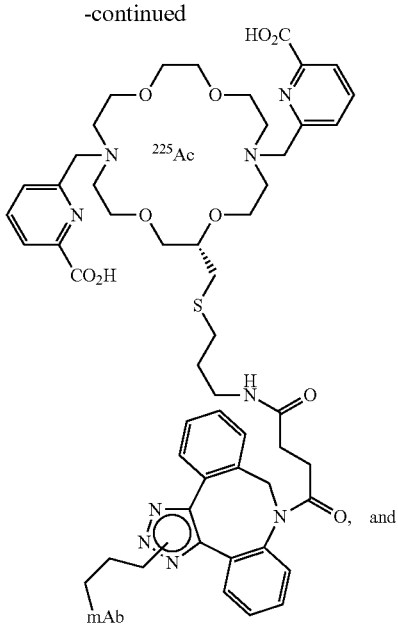
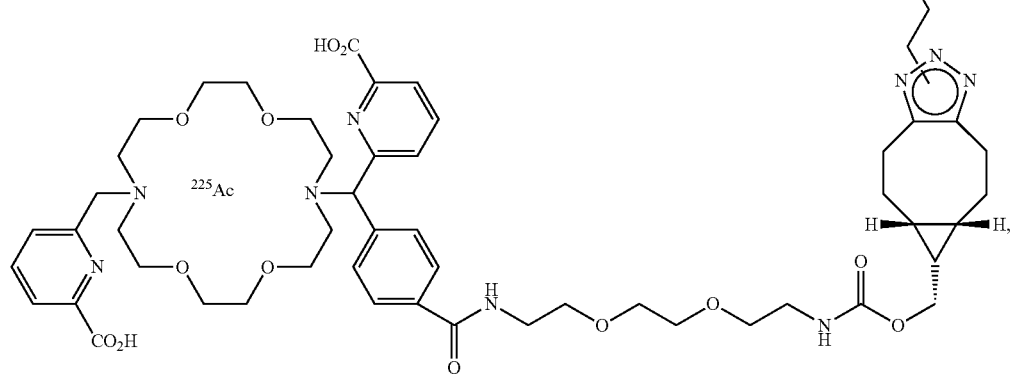

preferably the mAb is selected from PSMB127, Pertuzumab, Cetuximab, Panitumumab, Herceptin, or H11B6.

Radioimmunoconjugates produced by the methods described herein can be analyzed using methods known to those skilled in the art in view of the present disclosure. For example, LC/MS analysis can be used to determine the ratio of the chelator to the labeled polypeptide, e.g., antibody or antigen binding fragment thereof, analytical size-exclusion chromatography can be used to determine the oligomeric state of the polypeptides and polypeptide conjugates, e.g., antibody and antibody conjugates; radiochemical yield can be determined by instant thin layer chromatography (e.g., iTLC-SG), and radiochemical purity can be determined by size-exclusion HPLC. Exemplary methods are described herein, e.g., in the Examples below.

Pharmaceutical Compositions and Methods of Use

In another general aspect, the invention relates to a pharmaceutical composition comprising a chelator, radiometal complex, an immunoconjugate, or radioimmunoconjugate of the invention, and a pharmaceutically acceptable carrier. The pharmaceutical composition may comprise one or more pharmaceutically acceptable excipients.

In one embodiment, a pharmaceutical composition comprises a radiometal complex of the invention, and a pharmaceutically acceptable carrier.

In another embodiment, a pharmaceutical composition comprises a radioimmunoconjugate of the invention, and a pharmaceutically acceptable carrier.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody-based, or a radiocomplex-based pharmaceutical composition can be used in the invention.

According to particular embodiments, the compositions described herein are formulated to be suitable for the intended route of administration to a subject. For example, the compositions described herein can be formulated to be suitable for parenteral administration, e.g., intravenous, subcutaneous, intramuscular or intratumoral administration.

In other general aspects, the invention relates to methods of selectively targeting neoplastic cells for radiotherapy and treating neoplastic diseases or disorders. Any of the radiocomplexes or radioimmunoconjugates, and pharmaceutical compositions thereof described herein can be used in the methods of the invention.

A "neoplasm" is an abnormal mass of tissue that results when cells divide more than they should or do not die when they should. Neoplasms can be benign (not cancer) or malignant (cancer). A neoplasm is also referred to as a tumor. A neoplastic disease or disorder is a disease or disorder associated with a neoplasm, such as cancer. Examples of neoplastic disease or disorders include, but are not limited to, disseminated cancers and solid tumor cancers.

According to an embodiment, a method of treating prostate cancer (e.g., metastatic prostate cancer, or metastatic castration-resistant prostate cancer) in a subject in need thereof comprises administering to the subject a therapeutically effective amount of a radioimmunoconjugate as described herein, wherein the radioimmunoconjugate comprises a radiometal complex as described herein conjugated to H11B6.

Other examples of diseases to be treated or targeted for radiotherapy by the methods described herein include, but are not limited to, hypertrophy, a coronary disease, or a vascular occlusive disease, a disease or disorder associated with an infected cell, a microbe or a virus, or a disease or disorder associated with an inflammatory cell, such as rheumatoid arthritis (RA).

In an embodiment of the invention, a method of selectively targeting neoplastic cells for radiotherapy comprises administering to a subject in need thereof a radioimmunoconjugate or pharmaceutical composition of the invention to the subject.

In an embodiment of the invention, a method of treating a neoplastic disease or disorder comprises administering to a subject in need thereof a radioimmunoconjugate or pharmaceutical composition of the invention to the subject.

In an embodiment of the invention, a method of treating cancer in a subject in need thereof comprises administering to the subject in need thereof a radioimmunoconjugate or pharmaceutical composition of the invention to the subject.

Radioimmunoconjugates carry radiation directly to, for example, cells, etc., targeted by the targeting ligand. Preferably, the radioimmunoconjugates carry alpha-emitting radiometal ions, such as $^{225}$Ac. Upon targeting, alpha particles from the alpha-emitting radiometal ions, e.g., $^{225}$Ac and daughters thereof, are delivered to the targeted cells and cause a cytotoxic effect thereto, thereby selectively targeting neoplastic cells for radiotherapy and/or treating the neoplastic disease or disorder.

Pre-targeting approaches for selectively targeting neoplastic cells for radiotherapy and for treating a neoplastic disease or disorder are also contemplated by the invention. According to a pre-targeting approach, an azide-labeled antibody or antigen binding fragment thereof is dosed, binds to cells bearing the target antigen of the antibody, and is allowed to clear from circulation over time or removed with a clearing agent. Subsequently, a radiocomplex of the invention, preferably a radiocomplex comprising a cyclooctyne or cyclooctyne derivative, e.g., DBCO, is administered and undergoes a SPAAC reaction with azide-labeled antibody bound at the target site, while the remaining unbound radiocomplex clears rapidly from circulation. The pre-targeting technique provides a method of enhancing radiometal ion localization at a target site in a subject.

In other embodiments, a modified polypeptide, e.g., azide-labeled antibody or antigen binding fragment thereof, and a radiocomplex of the invention are administered to a subject in need of targeted radiotherapy or treatment of a neoplastic disease or disorder in the same composition, or in different compositions.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the terms "treat," "treating," and "treatment" are all intended to refer to an amelioration or reversal of at least one measurable physical parameter related to a disease, disorder, or condition in which administration of a radiometal ion would be beneficial, such as a neoplastic disease or disorder, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition in which administration of a radiometal ion would be beneficial, such as a neoplastic disease or disorder. In a particular embodiment, "treat," "treating," and "treatment" refer to prevention of the recurrence of a neoplastic disease, disorder, or condition. In a particular embodiment, "treat," "treating," and "treatment" refer to an increase in the survival of a subject having a neoplastic disease, disorder, or condition. In a particular embodiment, "treat," "treating," and "treatment" refer to elimination of a neoplastic disease, disorder, or condition in the subject.

In some embodiments, a therapeutically effective amount of a radioimmunoconjugate or pharmaceutical composition of the invention is administered to a subject to treat a neoplastic disease or disorder in the subject, such as cancer.

In other embodiments of the invention, radioimmunoconjugates and pharmaceutical compositions of the invention can be used in combination with other agents that are effective for treatment of neoplastic diseases or disorders.

Also provided are radioimmunoconjugates and pharmaceutical compositions as described herein for use in selectively targeting neoplastic cells for radiotherapy and/or for treating a neoplastic disease or disorder; and use of a radioimmunoconjugate or pharmaceutical compositions as described herein in the manufacture of a medicament for selectively targeting neoplastic cells for radiotherapy and/or for treating a neoplastic disease or disorder.

EXAMPLES

The following examples of the invention are to further illustrate the nature of the invention. It should be understood that the following examples do not limit the invention and that the scope of the invention is to be determined by the appended claims.

Example 1: Synthesis and Chelation Efficiency of Macrocyclic Chelators Having Different Positions of Linker Substitution Two chelators based on the macrocyclic chelator N,N'-bis[(6-carboxy-2-pyridil)methyl]-4,13-diaza-18-crown-6 (H₂bp18c6) were synthesized to study the effect of linker position on chelation efficiency of actinium-225 ($^{225}$Ac). In particular, H2bp18c6-benzyl-isopentyl and H2bp18c6-benzyl-phenyl were synthesized:

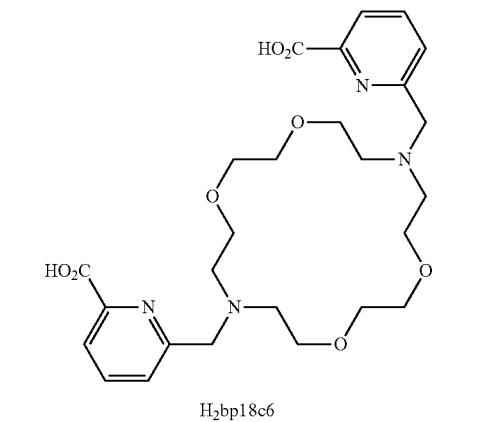

H₂bp18c6

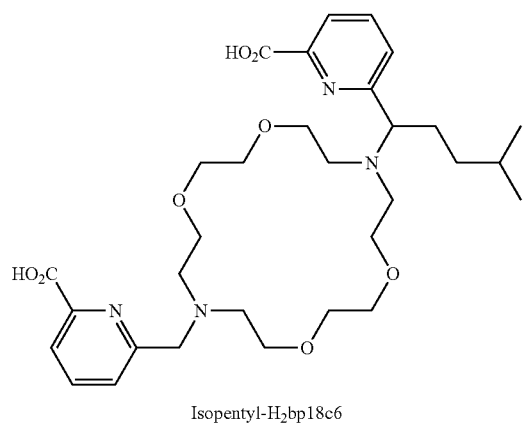

Isopentyl-H₂bp18c6

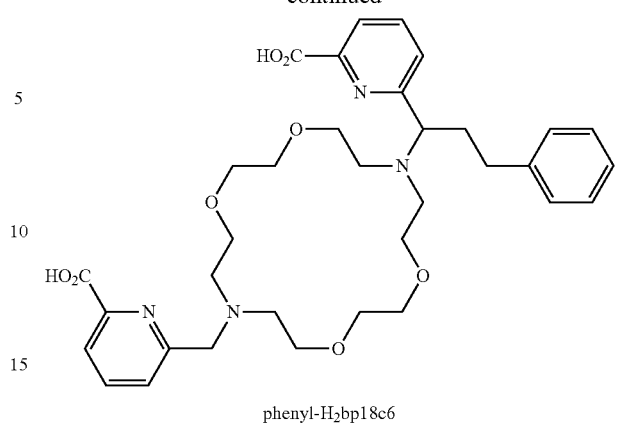

phenyl-H₂bp18c6

Synthesis and Characterization of H2bp18c6-Benzyl-Isopentyl

H2bp18c6-benzyl-isopentyl was synthesized according to Scheme 1.

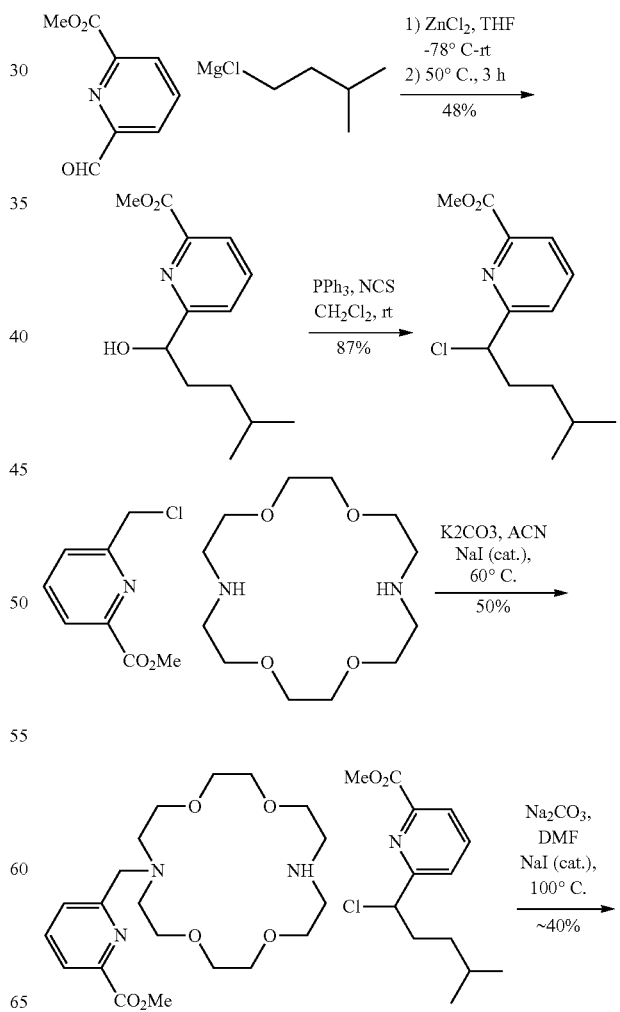

Scheme 1: Synthesis of H2bp18cb-benzyl-isopentyl

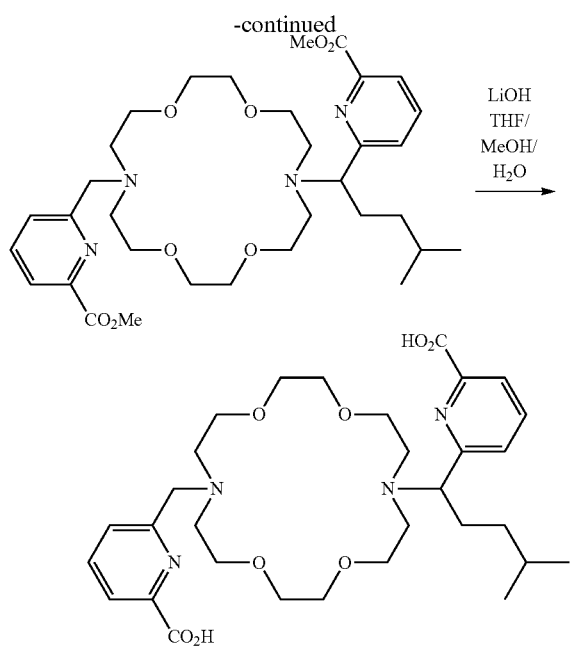

To a solution of ZnCl$_2$ (1.9 M in 2-methyltetrahydrofuran, 3.50 mL, 6.65 mmol) and THF (25 mL) at −78° C. was added dropwise isopentylmagnesium chloride (2 M in Et$_2$O, 3.33 mL, 6.66 mmol). The milky mixture was stirred at room temperature for 1 hr and then cooled to 0° C. A solution of methyl 6-formylpicolinate (1.00 g, 6.1 mmol) in THF (10 mL) was added. The mixture was heated at 50° C. for 3 hr. The cooled reaction mixture was poured into saturated NH$_4$Cl aqueous solution and extracted with EtOAc three times. The combined extracts were dried over Na$_2$SO$_4$. Filtration and concentration of the filtrate gave the crude product as brown oil. Chromatography on silica gel (heptane to 50% EtOAc in heptane) gave 693 mg (48% yield) of the product as yellow oil.

To a solution of methyl 6-(1-hydroxy-4-methylpentyl)picolinate (91 mg, 0.38 mmol) in CH$_2$Cl$_2$ (3 mL) at room temperature were added PPh$_3$ (120 mg, 0.46 mmol) and NBS (56 mg, 0.42 mmol). The reaction solution was stirred at room temperature for 1 hr and then concentrated. Chromatography on silica gel (heptane to 30% EtOAc in heptane) gave 85 mg (87% yield) of the product as colorless oil.

To a stirred mixture of 1,4,10,13-tetraoxa-7,16-diazacyclooctadecane (315 mg, 1.2 mmol) and K$_2$CO$_3$ (691 mg, 5 mmol) in ACN (30 mL) at 60° C. was added slowly a solution of methyl 6-(chloromethyl)picolinate in ACN (5 mL) in one hour using a syringe pump. After addition, the reaction mixture was stirred at 60° C. for 6 hr and then was filtered. The filtrate was concentrated, and the residue was purified by chromatography on silica gel (CH$_2$Cl$_2$ to 10% MeOH in CH$_2$Cl$_2$) to give 206 mg (50% yield) of the product as yellowish foam solid.

To a mixture of methyl 6-((1,4,10,13-tetraoxa-7,16-diazacyclooctadecan-7-yl)methyl)picolinate (31 mg, 0.075 mmol), Na$_2$CO$_3$ (40 mg, 0.38 mmol) and NaI (1.5 mg) in DMF (0.5 mL) was added methyl 6-(1-chloro-4-methylpentyl)picolinate (29 mg, 0.11 mmol). The reaction mixture was heated at 100° C. for 20 hr. Chromatography on silica gel (EtOAc to 10% MeOH in CH$_2$Cl$_2$) gave 18.9 mg (40% yield of the product as yellow film stuck on the flask wall.

A solution of methyl 6-((16-(1-(6-(methoxycarbonyl)pyridin-2-yl)-4-methylpentyl)-1,4,10,13-tetraoxa-7,16-diazacyclooctadecan-7-yl)methyl)picolinate (3 mg, 0.005 mmol) in THF/MeOH/H$_2$O (4:1:1 v/v/v, 0.6 mL) was treated with LiOH (1N, 0.1 mL). After the reaction mixture was stirred at room temperature for 1 hr, it was concentrated to dryness. The residue was dissolved in 0.95 mL of metal free water and neutralized with 0.05 mL of 2N HCl to provide a solution of H2bp18c6-benzyl-isopentyl in water (~3 mg/mL=~5 mM, pH~6).

H2bp18c6-benzyl-isopentyl (MW=602 Da) was characterized by high performance liquid chromatography (HPLC) and liquid chromatography-mass spectrometry (LC-MS). HPLC analysis showed a major peak at an elution time of 17.181 minutes corresponding to the free chelator. LC-MS analysis showed mass ion peaks (ES, m/z) at 603 [M+H$^+$], 625 [M+Na$^+$] and 302 [M+2H$^+$], confirming the synthesis of H2bp18c6-benzyl-isopentyl.

HPLC method: XBridge C18 3.5 μm 150×4.6 mm, 100 column; Mobile phase A: 0.1% TFA in H$_2$O, B: 0.1% TFA in ACN; gradient 10% to 30% B in 0-20 min, gradient 30% to 100% B in 20-20.1 min, isocratic at 100% B in 20.1-25 min, gradient 100% to 10% B in 25-25.1 min, isocratic at 10% B in 25.1-30 min; postrun 3 min; flow rate 1 mL/min; column temperature 30° C.; injection volume 5 uL.

Synthesis and Characterization of H2bp18c6-Benzyl-Phenyl

H2bp18c6-benzyl-phenyl was synthesized according to Scheme 2.

Scheme 2: Synthesis of H2bp18C6-benzyl-phenyl

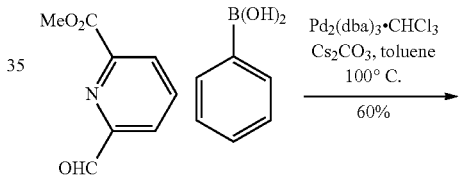

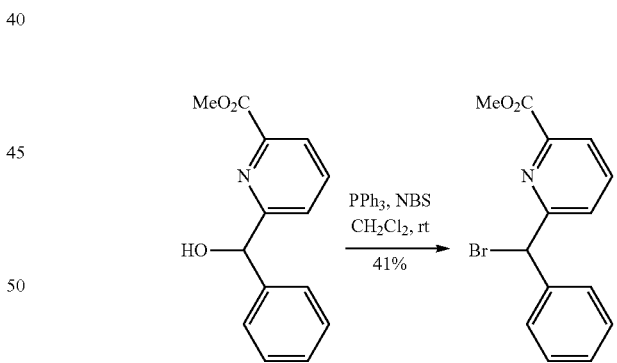

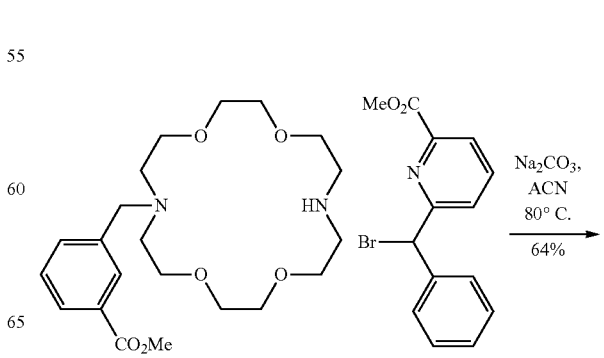

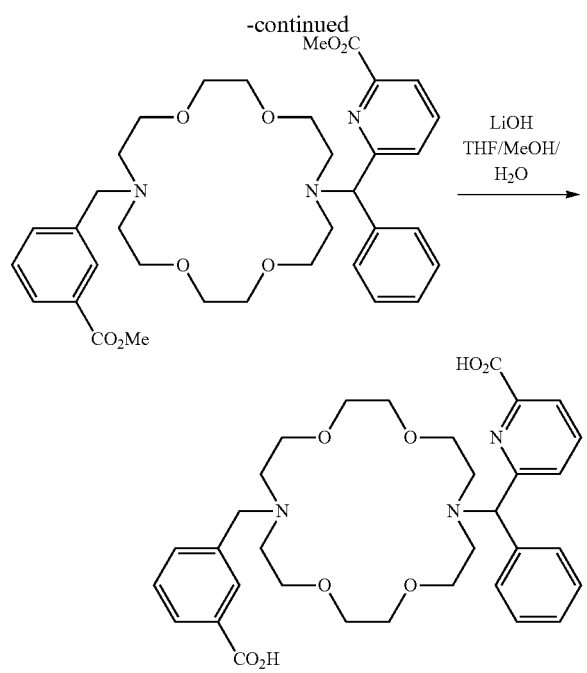

A mixture of methyl 6-formylpicolinate (165 mg, 1.0 mmol), phenylboronic acid (244 mg, 2.0 mmol), $Cs_2CO_3$ (326 mg, 1.0 mmol), $Pd_2(dba)_3 \cdot CHCl_3$ (52 mg, 0.05 mmol), and $PPh_3$ (26 mg, 0.1 mmol) was put under $N_2$ in a sealed vial. Toluene (3 mL) was added via syringe and the mixture was heated at 100° C. in a microwave for 4 hr. After the cooled reaction mixture was filtered through Celite, the filtrate was concentrated. Chromatography on silica gel (heptane to 50% EtOAc in heptane) gave 146 mg (60% yield) of product as yellow oil.

A solution of methyl 6-(hydroxy(phenyl)methyl)picolinate (141 mg, 0.58 mmol), $PPh_3$ (183 mg, 0.70 mmol) and NBS (113 mg, 0.64 mmol) in $CH_2Cl_2$ (8 mL) was stirred at room temperature for 1 hr. More $PPh_3$ (133 mg, 0.70 mmol) and NBS (113 mg, 0.64 mmol) were added and the solution was further stirred for one hour at room temperature. The reaction mixture was concentrated and purified by chromatography on silica gel (heptane to 30% EtOAc in heptane) to give 73 mg (41% yield) of product as colorless oil.

A mixture of methyl 6-((1,4,10,13-tetraoxa-7,16-diazacyclooctadecan-7-yl)methyl)picolinate (33 mg, 0.080 mmol), methyl 6-(bromo(phenyl)methyl)picolinate (37 mg, 0.12 mmol) and $Na_2CO_3$ (42 mg, 0.40 mmol) in ACN (1.0 mL) was heated at 80° C. for 3 hr. The reaction mixture was filtered, and the filtrate was concentrated. Chromatography on silica gel (EtOAc to 10% MeOH in $CH_2Cl_2$) gave 51 mg (64% yield) of the product as white solid.

A solution of methyl 6-((16-((6-(methoxycarbonyl)pyridin-2-yl)(phenyl)methyl)-1,4,10,13-tetraoxa-7,16-diazacyclooctadecan-7-yl)methyl)picolinate (16 mg, 0.025 mmol) in $THF/MeOH/H_2O$ (4:1.1 v/v/v, 1.2 mL) was treated with LiH (1N, 0.2 mL). After the reaction mixture was stirred at room temperature for 1 hr, it was concentrated to dryness. The residue was dissolved in 5.2 mL of metal free water and neutralized with 0.10 mL of 2N HCl to obtain a solution of H2bp18c6-benzyl-phenyl in water (~3 mg/mL=~5 mM, pH~6).

H2bp18c6-benzyl-phenyl (MW=608 Da) was characterized by high performance liquid chromatography (HPLC) and liquid chromatography-mass spectrometry (LC-MS). HPLC analysis was conducted as described above for isopentane-H2bp18c6. HPLC analysis showed a major peak at an elution time of 14.137 minutes corresponding to the free chelator. LC-MS analysis showed mass ion peaks (ES, m/z) at 609 [M+H$^+$], 631 [M+Na$^+$], and 305 [M+2H$^+$], confirming the synthesis of H2bp18c6-benzyl-phenyl.

Chelation Test with Lanthanum (III)

An aqueous solution of H2bp18c6-benzyl-isopentyl in water (~3 mg/mL=~5 mM, 20 µL, 0.1 µmol) was treated with $La(NO_3)_3$ (10 mM in metal free water, 50 µL, 0.5 µmol). An aqueous solution of H2bp18c6-benzyl-phenyl in water (~3 mg/mL=~5 mM, 20 µL, 0.1 µmol) was treated with $La(NO_3)_3$ (10 mM in metal free water, 50 µL, 0.5 µmol). After thorough mixing, each solution was analyzed by LCMS and HPLC to determine whether complexes of the chelator and $La^{3+}$ formed.

Both isopentane-H2bp18c6 and H2bp18c6-benzyl-phenyl chelators showed rapid and stoichiometric chelation with $La^{3+}$ at room temperature as demonstrated by a significant shift in HPLC peak retention time analyzed according to the method described above for the synthesis of H2bp18c6 (FIGS. 1A and 1B). Complex formation was also confirmed by LCMS. LCMS analysis of isopentane-H2bp18c6 after mixing with $La(NO_3)_3$ showed a mass ion peak (ES, m/z) at 739 (H2bp18c6-benzyl-isopentyl+La$^{+3}$-2H$^+$); and LC-MS analysis of H2bp18c6-benzyl-phenyl after mixing with $La(NO_3)_3$ showed a mass ion peak (ES, m/z) at 745 (H2bp18c6-benzyl-phenyl+La$^{+3}$-2H$^+$), confirming complex formation with both chelators.

Chelation of H2bp18c6-Benzyl-Isopentyl with $^{225}$Ac(III)

(i) Chelation with $^{225}$Ac(III) at Low $^{225}$Ac/Chelator Ratio

To a plastic vial were sequentially added tetramethylammonium acetate (1M in water, 10 µL), H2bp18c6-benzyl-isopentyl (1.66 mM in water, 2 µL, ~3.32 nmol) and $^{225}$Ac(NO$_3$)$_3$ (10 mCi/mL in 0.1 N HCl, 3 µL, 30 µCi). After mixing, the pH was ~6.5 by pH paper. The reaction solution was left standing still at room temperature for 1.5 hr.

iTLC-SG Analysis:

0.5 µL of the reaction solution was spotted onto an iTLC-SG, which was developed with 10 mM EDTA. The dried iTLC-SG was left at room temperature for overnight before it was scanned on a Bioscan AR-2000 radio-TLC scanner. Under the conditions described here, bounded Ac-225 stays at the base-line of the iTLC-SG, while free Ac-225 migrates with the solvent to the solvent front. No radioactivity was observed at the solvent front of the iTLC-SG, indicating that the chelator successfully chelated $^{225}$Ac ion.

HPLC Analysis:

5 µL of the reaction mixture was diluted with 95 µL of PBS buffer. The diluted mixture was analyzed by HPLC. After HPLC, the fractions were collected in one-minute intervals. The collected fractions were left at room temperature for overnight then counted in a gamma counter. The HPLC radio-trace was constructed from the activities of the fractions.

HPLC analysis confirmed that the $^{225}$Ac complex was formed based on a shift in retention time similar to that shown in the HPLC chromatograms in FIG. 1A.

DTPA Challenge:

0.5 µL of the reaction mixture was mixed with 15 µL of 10 mM DTPA solution and the mixture was incubated for 30 min. 10 µL of the mixture was spotted onto an iTLC-SG, which was developed with 10 mM EDTA. The dried iTLC-SG was left at room temperature for overnight before it was scanned on a Bioscan AR-2000 radio-TLC scanner. Under the conditions described here, stably chelated Ac-225 stays at the base-line of the iTLC-SG, while free Ac-225 migrates with the solvent to the solvent front. No radioactivity was observed at the solvent front of the iTLC-SG after DTPA challenge, indicating that a stable complex with $^{225}$Ac ion was formed.

(ii) Chelation with $^{225}$Ac(III) at High $^{225}$Ac/Chelator Ratio

To a plastic vial were sequentially added tetramethylammonium acetate (1M in water, 10 μL), H2bp18c6-benzyl-isopentyl (0.33 mM in water, 2 μL, ~0.66 nmol) and $^{225}$Ac(NO$_3$)$_3$ (10 mCi/mL in 0.1 N HCl, 5 μL, 50 μCi). After mixing, the pH was ~6.5 by pH paper. The reaction solution was left standing still at room temperature for 1.5 hr. Then the reaction was analyzed by iTLC-SG and DTPA challenge as described above. No free $^{225}$Ac was detected before or after DTPA challenge, indicating that a stable complex with $^{225}$Ac ion was formed.

Chelation of H2bp18c6-Benzyl-Phenyl with $^{225}$Ac(III)

(i) Chelation with $^{225}$Ac(III) at Low $^{225}$Ac/Chelator Ratio

To a plastic vial were sequentially added tetramethylammonium acetate (1M solution in water, 10 μL), H2bp18c6-benzyl-phenyl (1.64 mM in water, 2 μL, ~3.28 nmol) and $^{225}$Ac(NO$_3$)$_3$ (10 mCi/mL in 0.1 N HCl, 3 μL, 30 μCi). After mixing, the pH was ~6.5 by pH paper. The reaction solution was left standing still at room temperature for 2 hr. No free $^{225}$Ac ion was detected indicating that the chelator successfully chelated $^{225}$Ac ion iTLC-Sg Analysis:

0.5 μL of the reaction solution was spotted onto an iTLC-SG, which was developed with 10 mM EDTA. The dried iTLC-SG was left at room temperature for overnight before it was scanned on a Bioscan AR-2000 radio-TLC scanner. Under the conditions described here, bounded Ac-225 stays at the base-line of the iTLC-SG, while free Ac-225 migrates with the solvent to the solvent front. No radioactivity was observed at the solvent front of the iTLC-SG, indicating successful chelation of Ac-225.

HPLC Analysis:

5 μL of the reaction mixture was diluted with 95 μL of PBS buffer. The diluted mixture was analyzed by HPLC. After HPLC, the fractions were collected in one-minute intervals. The collected fractions were left at room temperature for overnight then counted in a gamma counter. The HPLC radioactive trace was constructed from the activities of the fractions. HPLC analysis confirmed that the $^{225}$Ac complex was formed based on a shift in retention time similar to that shown in the HPLC chromatograms in FIG. 1B.

DTPA Challenge:

0.5 μL of the reaction mixture was mixed with 15 μL of 10 mM DTPA solution and the mixture was incubated for 30 min. 10 μL of the mixture was spotted onto an iTLC-SG, which was developed with 10 mM EDTA. The dried iTLC-SG was left at room temperature for overnight before it was scanned on a Bioscan AR-2000 radio-TLC scanner. Under the conditions described here, stably chelated Ac-225 stays at the base-line of the iTLC-SG, while free Ac-225 migrates with the solvent to the solvent front. No free $^{225}$Ac was detected after DTPA challenge, indicating that a stable complex with $^{225}$Ac ion was formed. No radioactivity was observed at the solvent front of the iTLC-SG before or after DTPA challenge, indicating that a stable complex with $^{225}$Ac ion was formed.

(ii) Chelation with $^{225}$Ac(III) at High $^{225}$Ac/Chelator Ratio

To a plastic vial were sequentially added tetramethylammonium acetate (1M solution in water, 10 μL), H2bp18c6-benzyl-phenyl (0.16 mM in water, 2 μL, ~0.33 nmol) and $^{225}$Ac(NO$_3$)$_3$ (10 mCi/mL in 0.1 N HCl, 5 μL, 50 μCi). After mixing, the pH was ~6.5 by pH paper. The reaction solution was left standing still at room temperature for 2 hr. Then the reaction was analyzed by iTLC-SG and DTPA challenge as described above. No free $^{225}$Ac was detected before or after DTPA challenge, indicating that a stable complex with $^{225}$Ac ion was formed.

Summary

Taken together, the above results indicate that H2bp18c6 derivatized at the "benzyl" carbon efficiently chelates $^{225}$Ac at room temperature with rapid chelation kinetics forming a stable complex. The results also indicate that high specific activity (i.e., lower ratio of chelator to $^{225}$Ac) can be achieved by linkage through the "benzyl" position.

Example 2: Synthesis and Chelation Efficiency of H2bp18c6 Derivatives Bearing a DBCO "Click" Linker The following H2bp18c6 derivatives bearing a DBCO linker for subsequent conjugation to targeting ligands via click chemistry reactions can be synthesized:

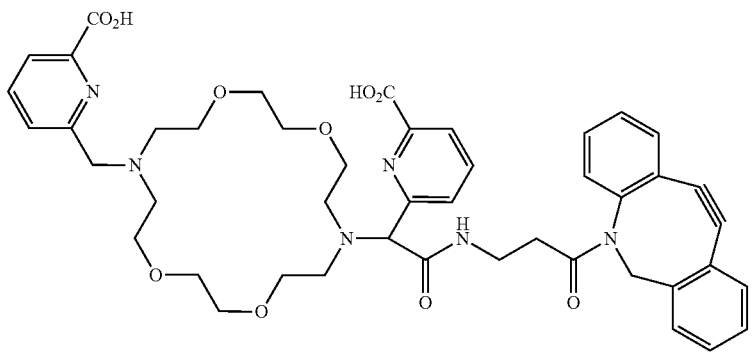

H$_2$bp18c6-benzyl-acetate-DBCO

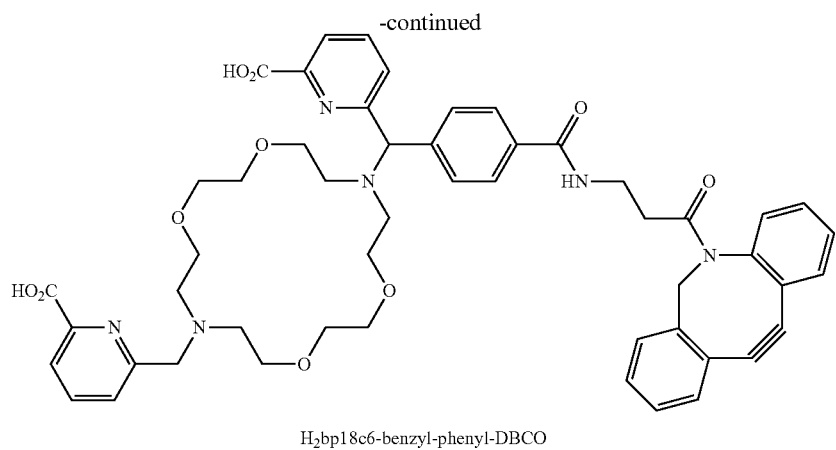
H₂bp18c6-benzyl-phenyl-DBCO
For example, H2bp18c6-acetate-DBCO can be synthesized according to Scheme 3.
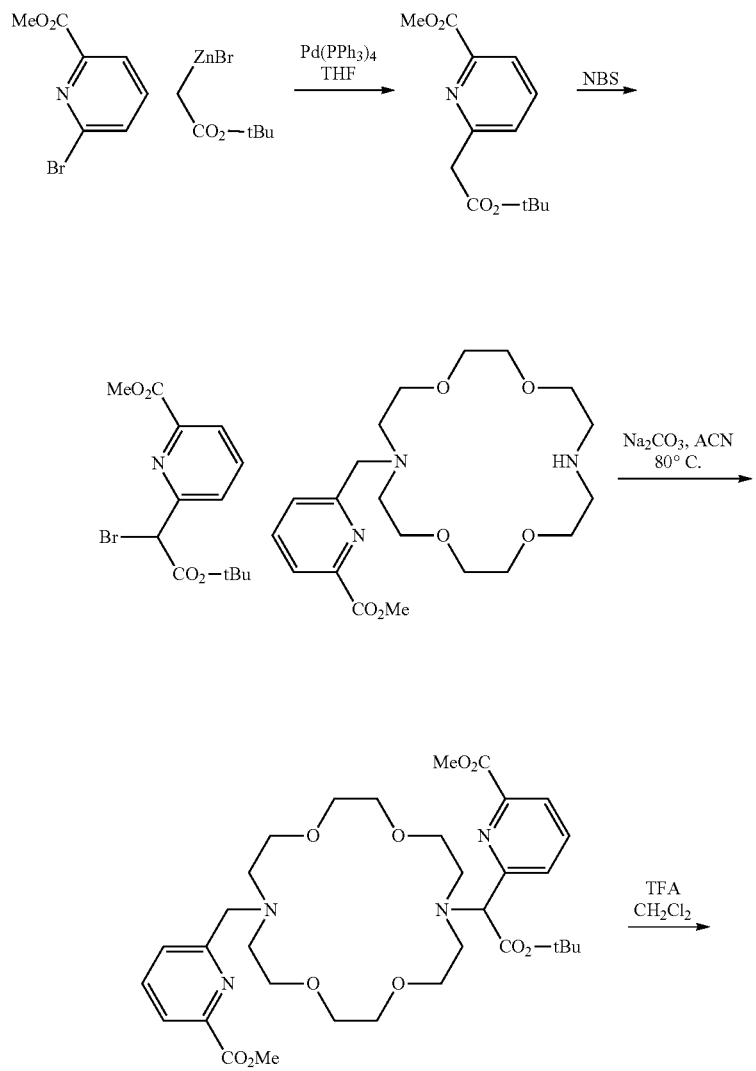
Scheme 3: Synthesis of H₂bp18c6-benzyl-acetate-DBCO -continued

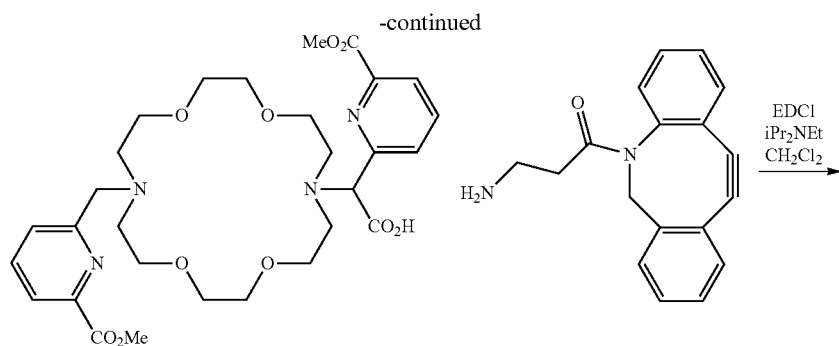

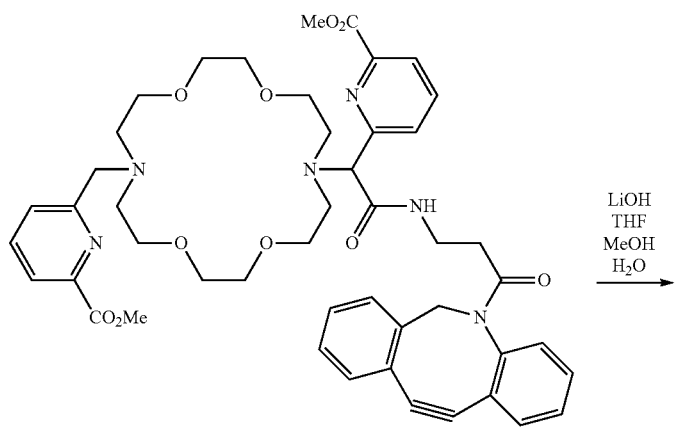

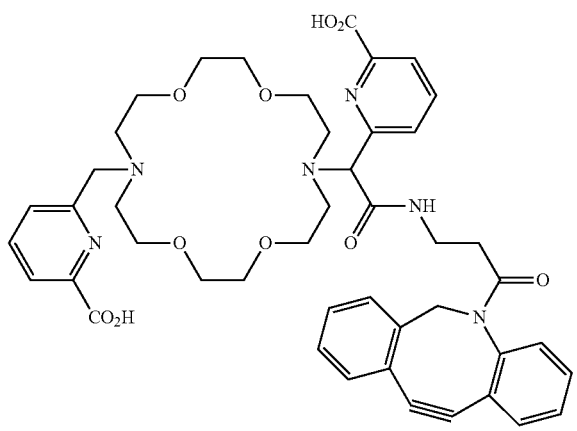

Methyl 6-bromopicolinate can be reacted with 2-tert-butoxy-2-oxoethylzinc bromide in the presence of palladium catalyst to afford methyl 6-(2-(tert-butoxy)-2-oxoethyl)picolinate. Subsequent bromination with NBS and AIBN can yield methyl 6-(1-bromo-2-(tert-butoxy)-2-oxoethyl)picolinate. The substitution reaction of methyl 6-(1-bromo-2-(tert-butoxy)-2-oxoethyl)picolinate with methyl 6-(((1,4,10,13-tetraoxa-7,16-diazacyclooctadecan-7-yl)methyl)picolinate under basic reaction conditions can produce methyl 6-(2-(tert-butoxy)-1-(16-(((6-(methoxycarbonyl)pyridin-2-yl)methyl)-1,4,10,13-tetraoxa-7,16-diazacyclooctadecan-7-yl)-2-oxoethyl)picolinate. In the presence of TFA, the tert-butyl ester can be hydrolyzed to carboxylic acid. Amide bond formation with dibenzocyclooctyne-amine and the subsequent hydrolysis of methyl esters by lithium hydroxide can afford H2bp18c6-benzyl-acetate-DBCO.

H₂bp18c6-benzyl-phenyl-DBCO is synthesized according to Scheme 4.

Scheme 4: Synthesis of H₂bp18c6-bezyl-phenyl-DBCO
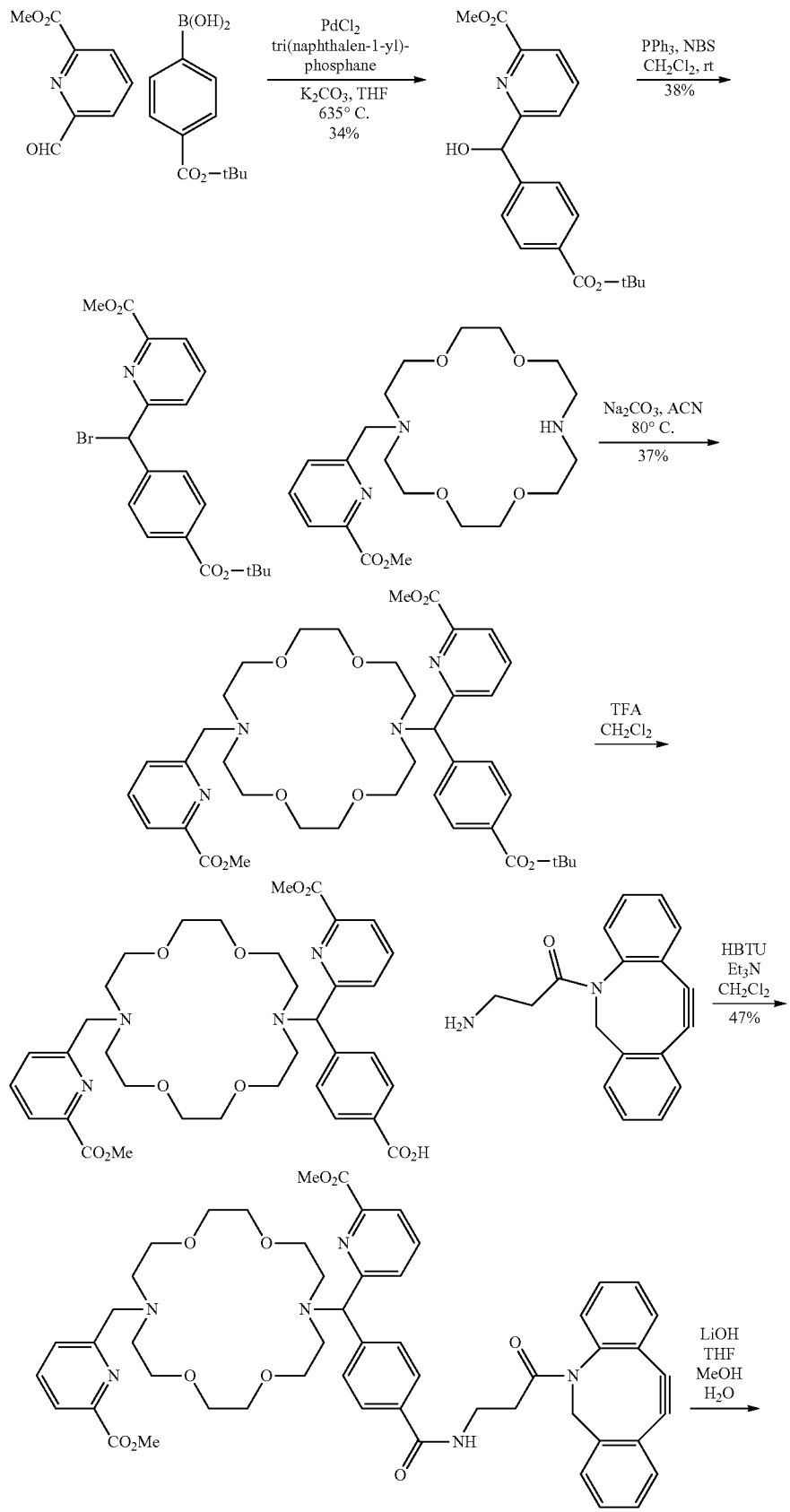

-continued

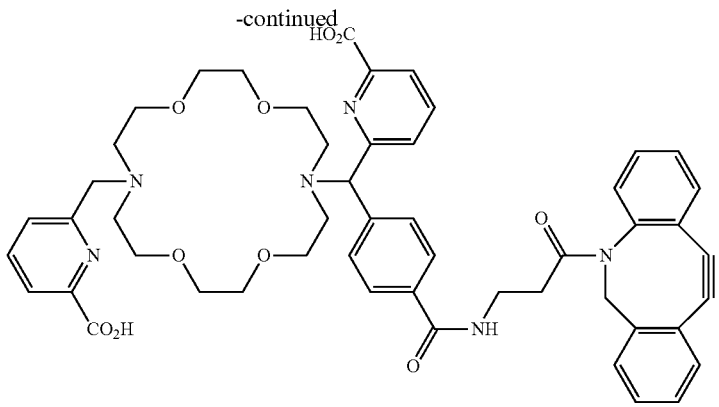

THE (5 mL) was added to a mixture of methyl 6-formylpicolinate (165 mg, 1.0 mmol), (4-(tert-butoxycarbonyl)phenyl)boronic acid (444 mg, 2.0 mmol), $PdCl_2$ (8.9 mg, 0.05 mmol), tri(naphthalen-1-yl)phosphane (20.6 mg, 0.05 mmol) and $K_2CO_3$ (415 mg, 3.0 mmol) under $N_2$ at −78° C. The mixture was purged with $N_2$ and stirred at room temperature for 0.5 hr, then heated at 65° C. for 24 hr. The cooled reaction mixture was filtered through Celite and the filtrate was concentrated. Chromatography on silica gel (heptane to 50% EtOAc in heptane) gave 116 mg (34% yield) of the product as a yellow oil.

A solution of methyl 6-((4-(tert-butoxycarbonyl)phenyl)(hydroxy)methyl)picolinate (138 mg, 0.40 mmol), $PPh_3$ (126 mg, 0.48 mmol) and NBS (79 mg, 0.44 mmol) in $CH_2Cl_2$ (5 mL) was stirred at room temperature for 1 hr. More $PPh_3$ (63 mg, 0.24 mmol) and NBS (39 mg, 0.22 mmol) were added and it was stirred for one more hour. The reaction solution was loaded onto a silica gel column. Chromatography (heptane to 30% EtOAc in heptane) gave 62 mg (38% yield) of the product as a yellowish film stuck on the flask wall.

A mixture of methyl 6-((1,4,10,13-tetraoxa-7,16-diazacyclooctadecan-7-yl)methyl)picolinate (56 mg, 0.14 mmol), methyl 6-(bromo(4-(tert-butoxycarbonyl)phenyl)methyl)picolinate (60 mg, 0.15 mmol) and $Na_2CO_3$ (72 mg, 0.68 mmol) in ACN (1 mL) was heated at 80° C. for 13 hr. The cooled reaction mixture was filtered, and the filtrate was concentrated. Chromatography on silica gel ($CH_2Cl_2$ to 10% MeOH in $CH_2Cl_2$) give 37 mg (37% yield) of the product as a white solid.

To a solution of methyl 6-((4-(tert-butoxycarbonyl)phenyl)(16-((6-(methoxycarbonyl)pyridin-2-yl)methyl)-1,4,10,13-tetraoxa-7,16-diazacyclooctadecan-7-yl)methyl)picolinate (22 mg, 0.03 mmol) in $CH_2Cl_2$ (1.5 mL) at room temperature was added TFA (0.5 mL). The solution was stirred for 1 hr. The reaction solution was concentration to give the crude product as a yellowish residue, which was used for the next step reaction without further purification.

To a solution of the above crude product in $CH_2Cl_2$ (0.5 mL) at 0° C. were added $Et_3N$ (42 µL, 0.3 mmol) and then HBTU (15 mg, 0.04 mmol). After the solution was stirred for 5 min at 0° C., dibenzocyclooctyne-amine in $CH_2Cl_2$ (0.5 mL) was added. The cold bath was removed, and it was stirred at room temperature for 18 hr. Water was added to the reaction mixture and it was extracted with $CH_2Cl_2$ three times. The combined extracts were washed with saturated $NaHCO_3$ aqueous solution and then brine, dried ($Na_2SO_4$) and filtered. The filtrate was concentrated to give the crude product. Chromatography on silica gel ($CH_2Cl_2$ to 10% MeOH in $CH_2Cl_2$) gave 13.2 mg (47% yield) of the product as a colorless film stuck on the flask wall.

To a solution of the dimethyl ester of H2bp18c6-benzyl-phenyl-DBCO (4.8 mg, 0.005 mmol) in $THF/MeOH/H_2O$ (4:1:1 v/v/v, 0.6 mL) at room temperature was added NaOH (1N, 0.1 mL). After the reaction mixture was stirred at room temperature for 1 hr, it was neutralized with HCl (1 N) to pH=6.5. The reaction mixture was concentrated on a rotovap at room temperature to remove the volatile solvents. The residue was dissolved in $H_2O$ (4 mL) and ACN (1 mL). After lyophilization, it gave the crude product as white solid.

Chelation of H2bp18c6-Benzyl-Phenyl-DBCO with La(III)

A solution of H2bp18c6-benzyl-phenyl-DBCO (~1.55 mg/mL=~1.7 mM in 4:1 v/v of $H_2O$/ACN, pH ~6.5 by pH paper) was prepared from the above crude product.

The above solution of H2bp18c6-benzyl-phenyl (~1.55 mg/mL=~1.7 mM, 50 µL, 0.085 µmol) was treated with $La(NO_3)_3$ (10 mM in metal free water, 50 µL, 0.5 µmol). After thorough mixing, the solution was analyzed by LCMS and HPLC. MS (ES, m/z) 1047 (H2bp18c6-benzyl-phenyl-DBCO+$La^{+3}$-2H$^+$).

HPLC method: XBridge C18 3.5 µm 150×4.6 mm, 100 Å column; Mobile phase A: 0.1% TFA in $H_2O$, B: 0.1% TFA in ACN; gradient 10% to 50% B in 0-20 min, gradient 50% to 100% B in 20-20.1 min, isocratic at 100% B in 20.1-25 min, gradient 100% to 10% B in 25-25.1 min, isocratic at 10% B in 25.1-30 min; flow rate 1 mL/min; column temperature 30° C.; injection volume 5 µL.

Chelation of H2bp18c6-Benzyl-Phenyl-DBCO with $^{225}$Ac (III)

(i) Chelation with $^{225}$Ac(III) at Low $^{225}$Ac/Chelator Ratio

To a plastic vial were sequentially added tetramethylammonium acetate (1M solution in water, 10 µL), H2bp18c6-benzyl-phenyl-DBCO (1.7 mM in H$_2$O/ACN, 2 µL, ~3.4 nmol) and $^{225}$Ac(NO$_3$)$_3$ (10 mCi/mL in 0.1 N HCl, 3 µL, 30 µCi). After mixing, the pH was ~6.5 by pH paper. The reaction solution was left standing still at room temperature for 1 hr.

iTLC-SG Analysis: 0.5 µL of the Reaction Solution was Spotted onto an iTLC-SG, which was developed with 10 mM EDTA. The dried iTLC-SG was left at room temperature for overnight before it was scanned on a Bioscan AR-2000 radio-TLC scanner. Under the conditions described here, free Ac-225 migrates with the solvent to the solvent front. No radioactivity activity was observed at the solvent front of the iTLC-SG indicating that there was no free Ac-225 in the reaction solution after 1 hr.

HPLC Analysis:

5 µL of the reaction mixture was diluted with 95 µL of PBS buffer. The diluted mixture was analyzed by HPLC. After HPLC, the fractions were collected in one-minute intervals. The collected fractions were left at room temperature for overnight then counted in a gamma counter. The HPLC radioactive trace was constructed from the activities of the fractions.

DTPA Challenge:

0.5 µL of the reaction mixture was mixed with 15 µL of 10 mM DTPA solution and the mixture was incubated for 30 min. 10 µL of the mixture was spotted onto an iTLC-SG, which was developed with 10 mM EDTA. The dried iTLC-SG was left at room temperature for overnight before it was scanned on a Bioscan AR-2000 radio-TLC scanner. No radioactivity was detected at the solvent front of the iTLC-SG.

(ii) Chelation with $^{225}$Ac(III) at High $^{225}$Ac/Chelator Ratio

To a plastic vial were sequentially added tetramethylammonium acetate (1M solution in water, 10 µL), H2bp18c6-benzyl-phenyl-DBCO (0.17 mM in water, 2 µL, ~0.34 nmol) and $^{225}$Ac(NO$_3$)$_3$ (10 mCi/mL in 0.1 N HCl, 5 µL, 50 µCi). After mixing, the pH was ~6.5 by pH paper. The reaction solution was left standing still at room temperature for 2 hr. Then the reaction was analyzed by iTLC-SG and DTPA challenge as described above.

Example 3: Preparation of H2bp18c6-Benzyl-Phenyl-DBCO-IgG4 and $^{225}$Ac(III) Labeling General Method to Prepare Radioimmunoconjugates:

Radioimmunoconjugates containing a radiometal complex of the invention covalently linked to an antibody are produced by click radiolabeling. See FIGS. 2A-2D for a schematic representation of an exemplary method of click radiolabeling to produce a radioimmunoconjugate of the invention.

Random Conjugation of Azide-Handle to an Antibody

A stock solution of antibody (1-10 mg/mL) in 10 mM sodium acetate pH 5.2, phosphate-buffered saline pH 7, or other compatible buffer was mixed with 20% (v/v) of 1 M sodium carbonate buffer pH 9 to a final pH of ~9. NHS-PEG4-azide (Thermo catalog #26130) was dissolved in DMSO to a final concentration of 100 mM, and 0.2% (v/v) of the stock was added to produce a molar excess of ~3-10 relative to the antibody (Ab). The reaction was incubated at 22° C. for 10 minutes followed by quenching with the addition of 1 M Tris pH 7.5 to a final concentration of 50 mM Tris.

The azide-mAb conjugate was purified and exchanged into a compatible buffer (PBS; 20 mM HEPES 150 mM, NaCl pH 7.5; or 10 mM sodium acetate pH 5.2) using a method such as Zeba desalting columns with 7K MW cutoff (Thermo); dialysis; standard protein A affinity chromatography; or another compatible method. After purification, the conjugate was concentrated to 10-20 mg/mL using Amicon concentrators with 50K MW cutoff (Millipore). Conjugation efficiency was determined by LC-MS.

Site-Specific Incorporation of Azido Sugars into Antibody Glycans

Antibody glycans were trimmed with GlycINATOR (Genovis), a bacterial endoglycosidase specific for the β-1,4 linkage between the core GlcNac residues in the Fc-glycosylation site(s) leaving the inner most GlcNAc intact on the Fc, which can then be used for site-specific incorporation of azido sugars. More specifically, immobilized GlycINATOR on agarose beads packed into a column (Genovis) was equilibrated in Tris-buffered saline pH 7.4 (TBS). 1 mL of mAb at 5-10 mg/mL was added to the resin and incubated on a rocker for 1 hour at RT. mAb was eluted by spinning at 100×g for 1 minute. The column was eluted 3 more times with 0.5 mL TBS. The elutions containing trimmed mAb were pooled, and the supplied buffer additive (Genovis) was added along with UDP-GalNaz azido sugar substrate and GalT galactosyltransferase enzyme. The reaction was incubated overnight at 30° C. The final azido mAb was purified using an mAb Select column (GE) on an AKTA Avant instrument. Azide modification was confirmed by LC-MS.

Conjugation of Chelator to Azido-Ab

Chelators of the invention comprising a DBCO group, such as:

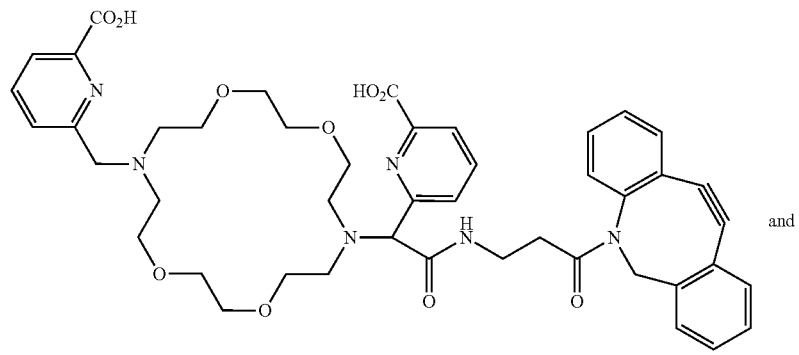

and

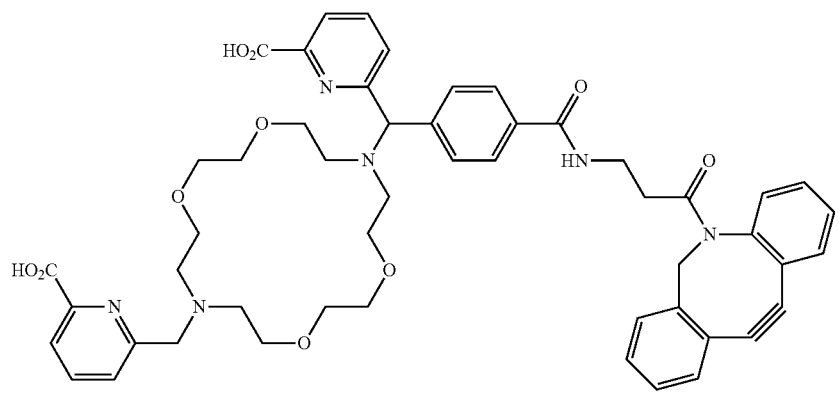

are coordinated to radiometal ion, such as $^{225}$Ac as described in Example 1 to produce a radiocomplex. Random or site-specific azide-modified antibody in PBS or other compatible buffer (10-20 mg/mL) is added to a solution of the radiocomplex. The reaction solution is gently agitated and allowed to stand still at room temperature for 3 h before purification, e.g., with a PD-10 column (GE Healthcare) pre-conditioned with 15 mL of NaOAc buffer, 10 mM, pH 6-6.5 or another compatible buffer. Purity is assessed by iTLC-SG. The product solution is analyzed by HPLC for chemical and radiochemical purity. The antibody concentration in the product solution is determined by UV absorption using a standard curve. The activity of the product solution is quantified using a Capintec CRC-55TW dose calibrator.

Analytical Characterization of Click-Labeled Radioimmunoconjugates

Radiochemical conversion (% RA conversion) is determined by iTLC-SG (Instant Thin Layer Chromatography (iTLC). Radiochemical purity (% RA purity) of Ac-225 chelates is determined by SE-HPLC (size exclusion HPLC).

Direct Chelation of 225Ac(III) to H2bp18c6-Phenyl-IgG4

The following method of preparing a radioimmunoconjugate may be referred to as a "one-step direct radiolabeling" method (e.g., as schematically illustrated in FIG. 2C). The radiolabeling was successfully performed under non-metal free conditions, further exemplifying the chelator's ability to be resistant to metal contaminants.

The IgG4 used in this example is an isotype control, which binds to a respiratory syncytial Virus (RSV) antigen. The amino acid sequences of the heavy chain (HC) and light chain (LC) of the IgG4 are provided below as SEQ ID NO:1 and SEQ ID NO:2, respectively:

mAb HC

SEQ ID NO: 1

QITLKESGPTLVKPTQTLTLTCTFSGFSLSTSGMGVSWIRQPPGKALEWL

AHIYWDDDKRYNPSLKSRLTITKDTSKNQVVLTMTNMDPVDTATYYCARL

YGFTYGFAYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK mAb LC

SEQ ID NO: 2

DIVMTQSPDSLAVSLGERNATINCRASQSVDYNGISYMHWYQQKPGQPPK

LLIYAASNPESGVPDRFSGSGSGTDFTLTISSLQAEDVAVYYCQQIIEDP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Scheme 5: Direct chelation of 224Ac(III) to H2bp18c6-phenyl-IGg4 (formed by click reaction of H2bp18c6-benzyl-phenyl-DBCO to Site Specific Azide-IgG4)

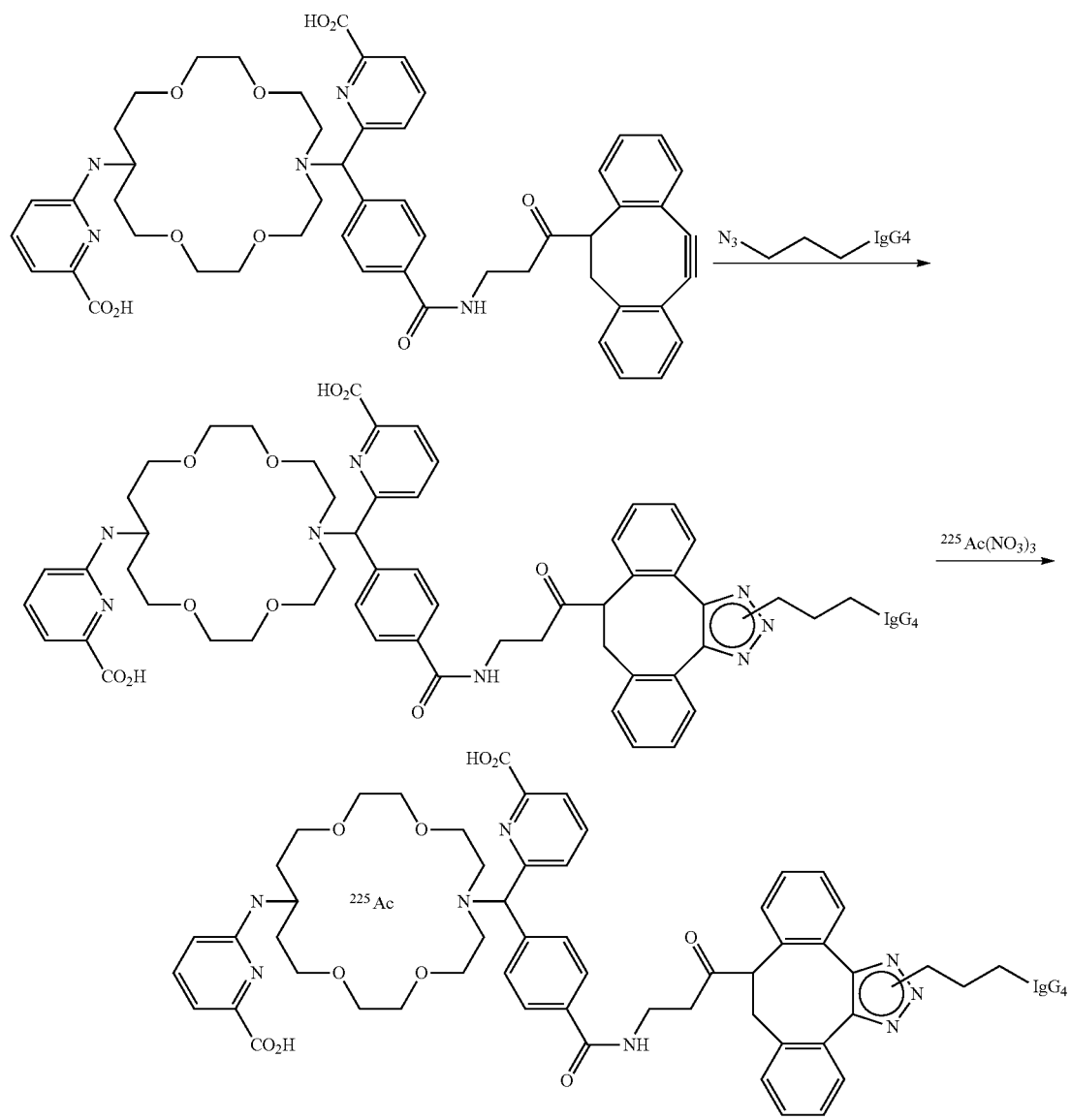

Azide Modification of mAb and Click Reaction:

The above mAb IgG4 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 20 mM Hepes, 100 mM NaCl pH 7.5 using 7K Zeba desalting columns. 10× molar excess of H2bp18c6-benzyl-phenyl-DBCO was reacted with site specific azide-IgG4 (DOL=2) at 37° C. for 1 hour without shaking. Completion of the DBCO-azide click reaction was monitored by intact mass spectrometry. Excess free chelator was removed by desalting the conjugate over a Zeba 7K desalting column into 20 mM Hepes, 100 mM NaCl pH 7.5 followed by three sequential 15× dilution and concentration steps in 20 mM Hepes, 100 mM NaCl pH 7.5 using a 30K MWCO Amicon concentrator device by spinning at 3800×g. This provided the final site specific H2bp18c6-benzyl-phenyl-DBCO-IgG4 conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 µL.

Labeling:

To a solution of NaOAc (3 M in $H_2O$, 20 µL) in a plastic vial was added sequentially $^{225}Ac(N_3)_3$ (~5 mCi/mL in 0.1 N HCl, 20 µL, 0.098 mCi) and H2bp18c6-benzyl-phenyl-DBCO-IgG4 (site specific, CAR=2, 1.7 mg/mL in 20 mM Hepes, 100 mM NaCl pH 7.5, 36 µL, 61.2 µg). After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 µL of fraction #3 collected after PD-10 column was mixed with 15 µL of 10 mM DTPA solution (pH 6.5), and incubated for 30 min. 10 µL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 µm column; column temperature: room temperature; the column was eluted with DPBS buffer (×1, without calcium and magnesium); flow rate: 0.7 mL/min; 20 min run; injection volume: 30 µL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-IgG4 peak on HPLC UV trace.

Example 4: Preparation of H2bp18c6-Benzyl-Phenyl-DBCO-PSMB127 and $^{225}$Ac(III) Labeling

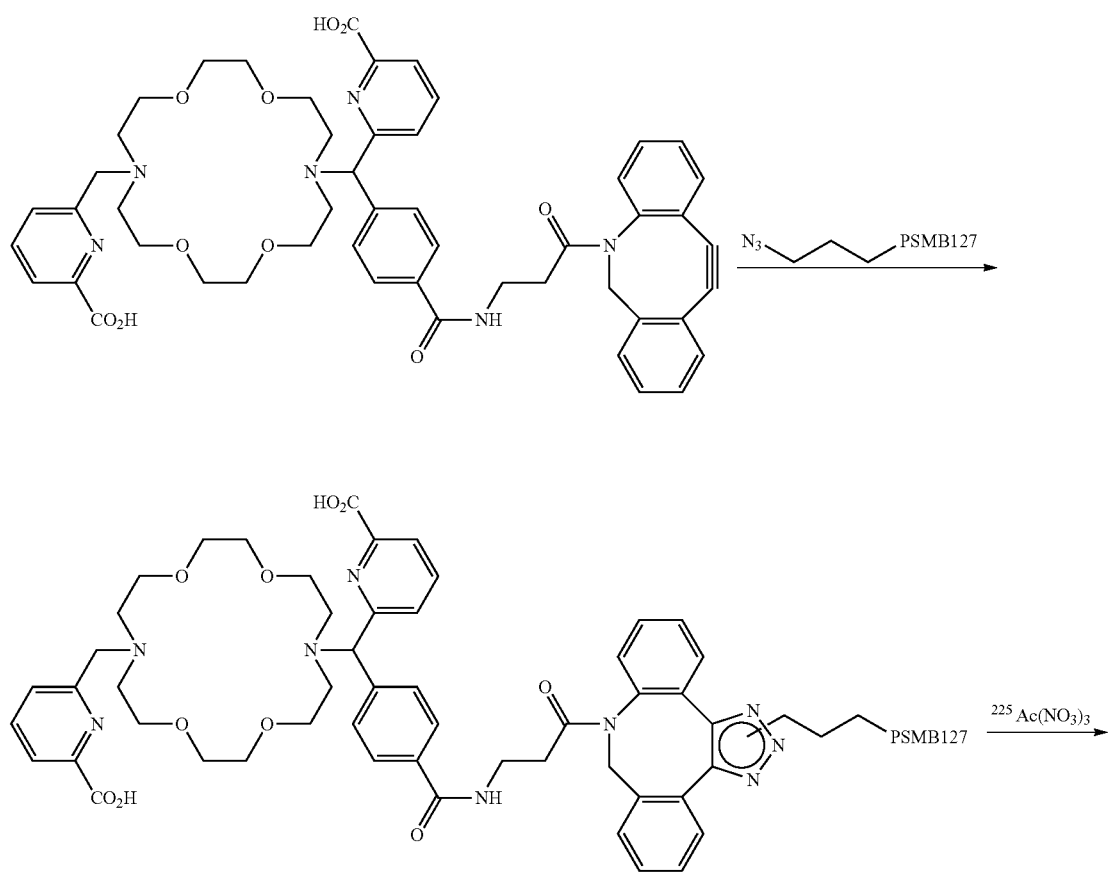

Scheme 6. Direct chelation of $^{225}$Ac(III) to H2bp18c6-benzyl-phenyl-DBCO-PSMB127
(formed by click reaction of H2bp18c6-benzyl-phenyl-DBCO to Site Specific azide-PSMB127)

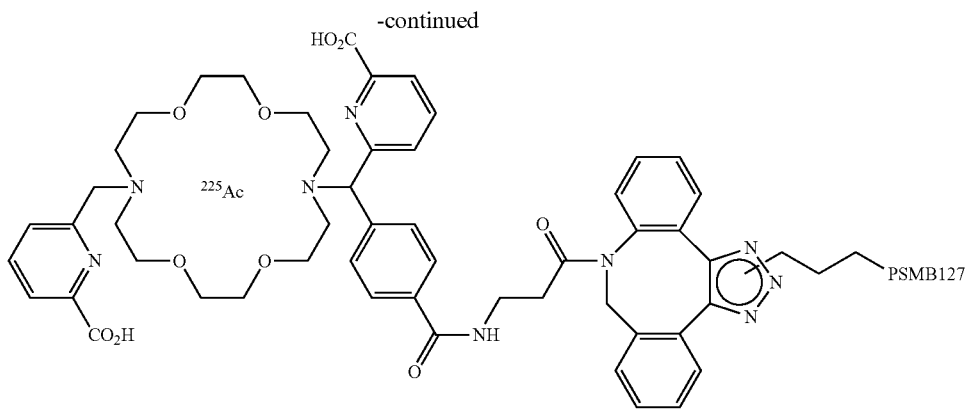

Azide Modification of mAb and Click Reaction:

PSMB127 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 20 mM Hepes, 100 mM NaCl pH 7.5 using 7K Zeba desalting columns. Ox molar excess of H2bp18c6-benzyl-phenyl-DBCO was reacted with site specific azide-PSMB127 (DOL=2) at 37° C. for 1 hour without shaking. Completion of the DBCO-azide click reaction was monitored by intact mass spectrometry. Excess free chelator was removed by desalting the conjugate over a Zeba 7K desalting column into 20 mM Hepes, 100 mM NaCl pH 7.5 followed by three sequential 15× dilution and concentration steps in 20 mM Hepes, 100 mM NaCl pH 7.5 using a 30K MWCO Amicon concentrator device by spinning at 3800×g. This provided the final site specific H2bp18c6-benzyl-phenyl-DBCO-PSMB127 conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 µL.

Labeling:

To a solution of NaOAc (3 M in $H_2O$, 20 µL) in a plastic vial was added sequentially $^{225}Ac(NO_3)_3$ (~5 mCi/mL in 0.1 N HCl, 20 µL, 0.098 mCi) and H2bp18c6-benzyl-phenyl-DBCO-PSMB127 (site specific, CAR=2, 2.8 mg/mL in 20 mM Hepes, 100 mM NaCl pH 7.5, 22 µL, 61.6 µg). After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 µL of fraction #3 collected after PD-10 column was mixed with 15 µL of 10 mM DTPA solution (pH 6.5), and incubated for 30 min. 10 µL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 µm column; column temperature: room temperature; the column was eluted with DPBS buffer (×1, without calcium and magnesium); flow rate: 0.7 mL/min; 20 min run; injection volume: 30 µL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-PSMB127 peak on HPLC UV trace.

Example 5: Preparation of
H2bp18c6-Benzyl-Phenyl-DBCO-Pertuzumab and
$^{225}$Ac(III) Labeling

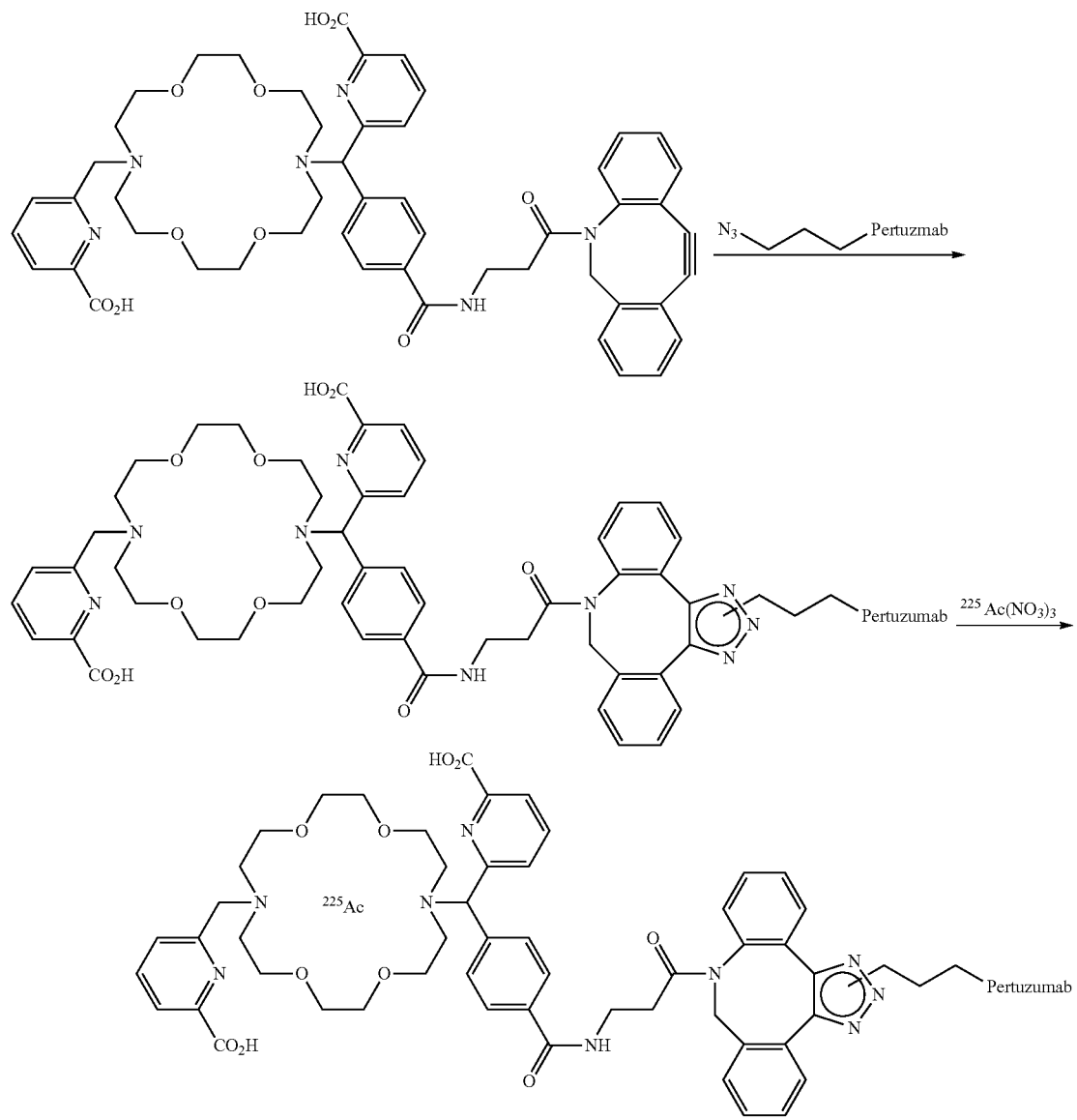

Scheme 7. Direct chelation of $^{225}$Ac(III) to H2bp18c6-benzyl-phenyl-DBCO-Pertuzumab
(formed by click reaction of H2bp18c6-benzyl-phenyl-DBCO to Site Specific azide-Pertuzumab)

Azide Modification of mAb and Click Reaction:

Pertuzumab was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 1×dPBS using 7K Zeba desalting columns. 1× molar excess of H2bp18c6-benzyl-phenyl-DBCO was reacted with site specific azide-Pertuzumab (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-DBCO-Pertuzumab conjugate with CAR=2. The final conjugate was confirmed to be monomeric by analytical size exclusion chromatography on a Tosoh TSK-gel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 µL.

Labeling:

To a solution of NaOAc (3 M in H$_2$O, 10 µL) in a plastic vial was added sequentially $^{225}$Ac(NO$_3$)$_3$ (~5 mCi/mL in 0.1 N HCl, 10 µL, 0.042 mCi) and H2bp18c6-benzyl-phenyl-DBCO-Pertuzumab (site specific, CAR=2, 2.4 mg/mL in PBS buffer solution, 12.5 µL, 30 µg). After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 µL of fraction #3 collected after PD-10 column was mixed with 15 µL of 10 mM DTPA solution (pH 6.5), and incubated for 30 min. 10 µL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 µm column; column temperature: room temperature; the column was eluted with DPBS buffer (×1, without calcium and magnesium); flow rate: 0.7 mL/min; 20 min run; injection volume: 30 µL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-Pertuzumab peak on HPLC UV trace.

Example 6: Preparation of H2bp18c6-Benzyl-Phenyl-DBCO-Cetuximab and $^{225}$Ac(III) Labeling Scheme 8. Direct chelation of $^{225}$Ac(III) to H2bp18c6-benzyl-phenyl-DBCO-Cetuximab
(formed by click reaction of H2bp18c6-benzyl-phenyl-DBCO to Site Specific azide-Cetuximab)

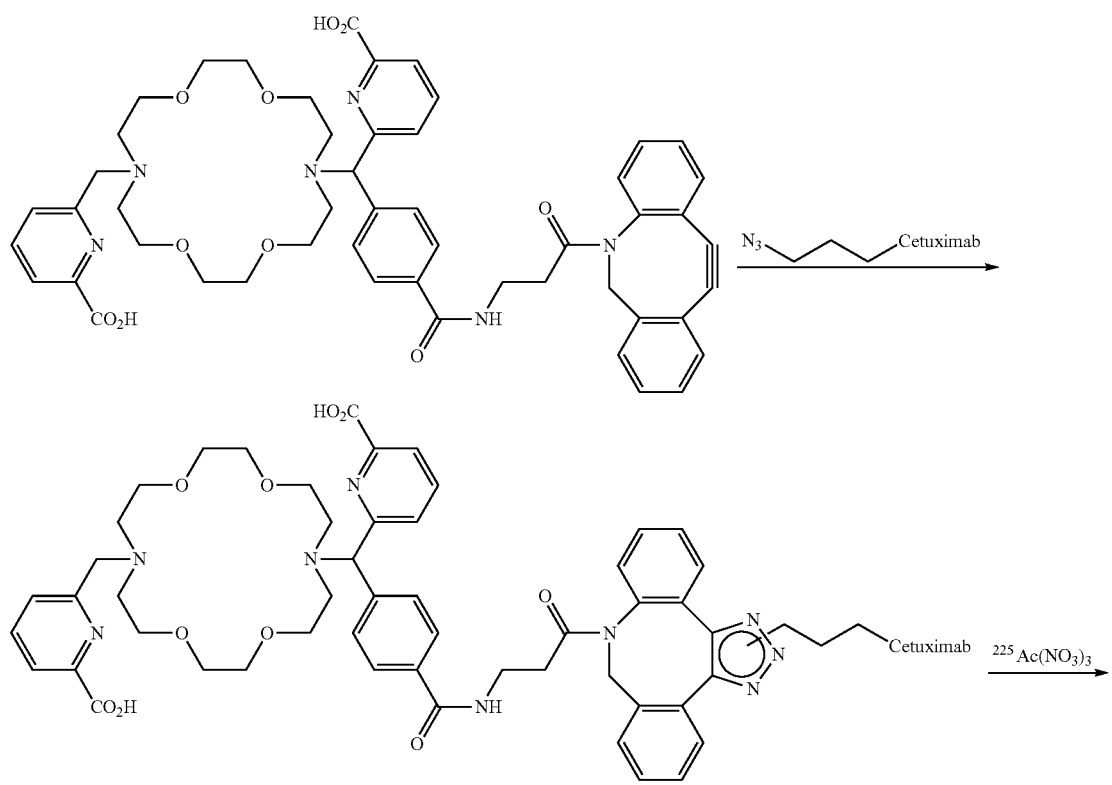

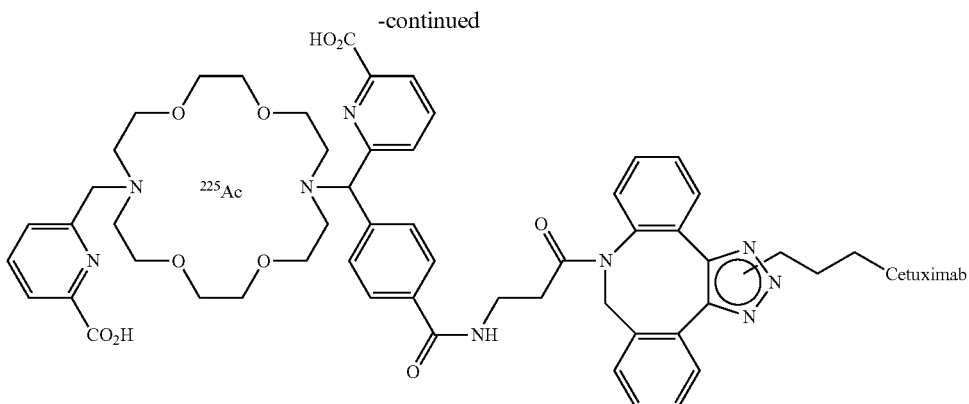

Azide Modification of mAb and Click Reaction:

Cetuximab was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-benzyl-phenyl-DBCO was reacted with site specific azide-Cetuximab (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-DBCO-Cetuximab conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling:

To a solution of NaOAc (3 M in $H_2O$, 10 μL) in a plastic vial was added sequentially $^{225}Ac(NO_3)_3$ (~5 mCi/mL in 0.1 N HCl, 10 μL, 0.044 mCi) and H2bp18c6-benzyl-phenyl-DBCO-Cetuximab (site specific, CAR=2, 1.8 mg/mL in PBS buffer solution, 16.7 μL, 30 μg). After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 μL of fraction #3 collected after PD-10 column was mixed with 15 μL of 10 mM DTPA solution (pH 6.5), and incubated for 30 min. 10 μL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 μm column; column temperature: room temperature; the column was eluted with DPBS buffer (×1, without calcium and magnesium); flow rate: 0.7 mL/min; 20 min run; injection volume: 30 μL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-Cetuximab peak on HPLC UV trace.

Example 7: Preparation of H2bp18c6-Benzyl-Phenyl-DBCO-Panitumumab and $^{225}$Ac(III) Labeling

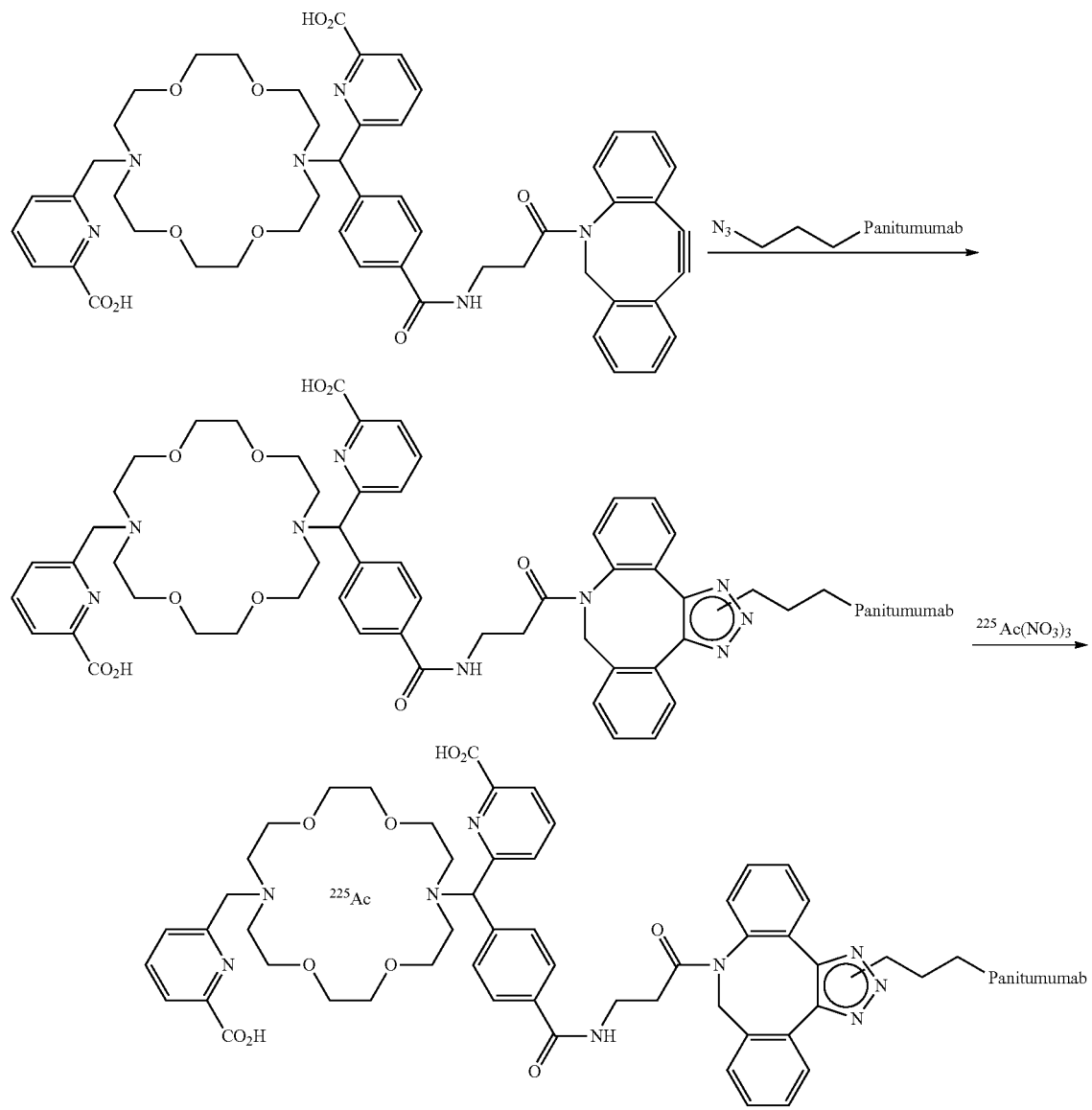

Scheme 9. Direct chelation of $^{225}$Ac(III) to H2bp18c6-benzyl-phenyl-DBCO-Panitumumab (formed by click reaction of H2bp18c6-benzyl-phenyl-DBCO to Site Specific azide-Panitumumab)

Azide Modification of mAb and Click Reaction:

Panitumumab was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 1×dPBS using 7K Zeba desalting columns. 1× molar excess of H2bp18c6-benzyl-phenyl-DBCO was reacted with site specific azide-Panitumumab (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-DBCO-Panitumumab conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling:

To a solution of NaOAc (3 M in H₂O, 10 μL) in a plastic vial was added sequentially ²²⁵Ac(NO₃)₃ (~5 mCi/mL in 0.1 N HCl, 10 μL, 0.043 mCi) and H2bp18c6-benzyl-phenyl-DBCO-Panitumumab (site specific, CAR=2, 2.6 mg/mL in PBS buffer solution, 11.5 μL, 30 μg). After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 μL of fraction #3 collected after PD-10 column was mixed with 15 μL of 10 mM DTPA solution (pH 6.5), and incubated for 30 min. 10 μL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 μm column; column temperature: room temperature; the column was eluted with DPBS buffer (×1, without calcium and magnesium); flow rate: 0.7 mL/min; 20 min run; injection volume: 30 μL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-Panitumumab peak on HPLC UV trace.

Example 8: Preparation of H2bp18c6-Benzyl-Phenyl-DBCO-Herceptin and ²²⁵Ac(III) Labeling Scheme 10. Direct chelation of ²²⁵Ac(III) to H2bp18c6-benzyl-phenyl-DBCO-Herceptin (formed by click reaction of H2bp18c6-benzyl-phenyl-DBCO to Site Specific azide-Herceptin)

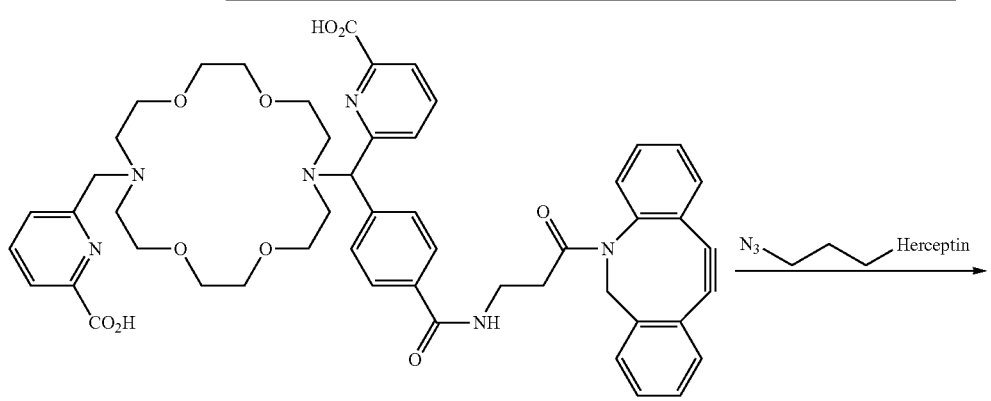

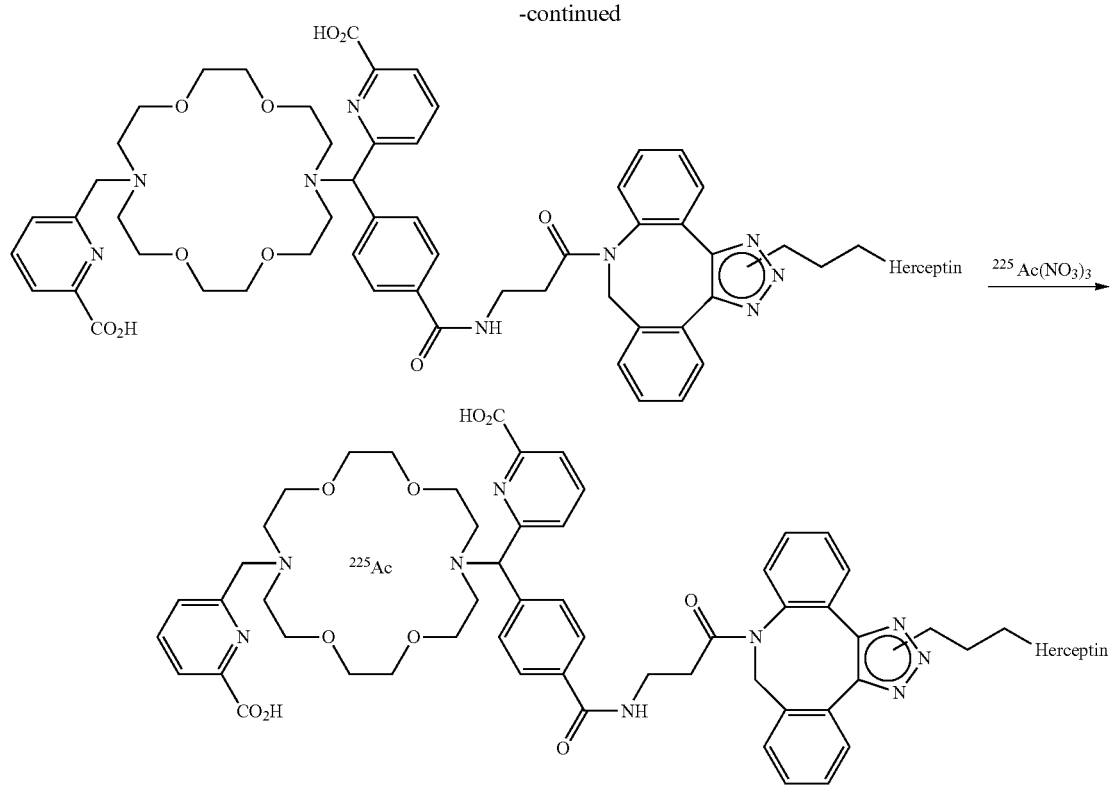

Azide Modification of mAb and Click Reaction:

Herceptin was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 ml GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-benzyl-phenyl-DBCO was reacted with site specific azide-Herceptin (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-DBCO-Herceptin conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling:

To a solution of NaOAc (3 M in $H_2O$, 10 μL) in a plastic vial was added sequentially $^{225}Ac(NO_3)_3$ (~5 mCi/mL in 0.1 N HCl, 10 μL, 0.041 mCi) and H2bp18c6-benzyl-phenyl-DBCO-Herceptin (site specific, CAR=2, 1.7 mg/mL in PBS buffer solution, 17.6 μL, 30 μg). After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 μL of fraction #3 collected after PD-10 column was mixed with 15 μL of 10 mM DTPA solution (pH 6.5), and incubated for 30 min. 10 μL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 μm column; column temperature: room temperature; the column was eluted with DPBS buffer (×1, without calcium and magnesium); flow rate: 0.7 mL/min; 20 min run; injection volume: 30 μL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-Herceptin peak on HPLC UV trace.

Example 9: Preparation of H2bp18c6-Benzyl-Phenyl-DBCO-H11B6 and $^{225}$Ac(III) Labeling

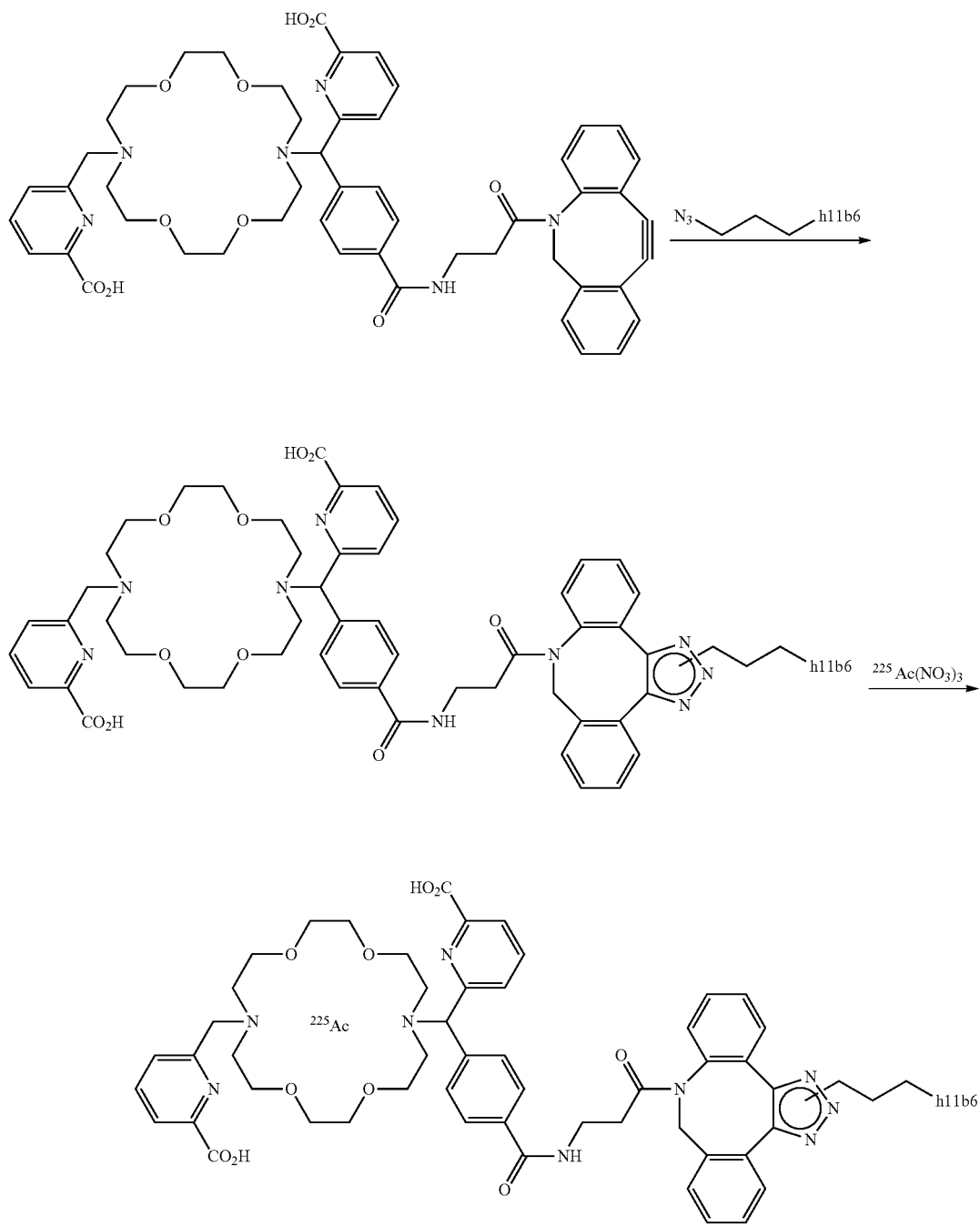

Scheme 11. Direct chelation of $^{225}$Ac(III) TO H2bp18c6-benzyl-phenyl-DBCO-H11b6 (formed by click reaction of H2bp18c6-benzyl-phenyl-DBCO to Site Specific azide-H11B6)

Azide Modification of mAb and Click Reaction:

H11B6 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 ml GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-benzyl-phenyl-DBCO was reacted with site specific azide-H11B6 (DOL=1.82) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-DBCO-H11B6 conjugate with CAR=1.82. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling:

To a solution of NaOAc (3 M in $H_2O$, 10 μL) in a plastic vial was added sequentially $^{225}Ac(NO_3)_3$ (~5 mCi/mL in 0.1 N HCl, 10 μL, 0.043 mCi) and H2bp18c6-phenyl-DBCO-H11B6 (site specific, CAR=1.82, 1.2 mg/mL in PBS buffer solution, 25.0 μL, 30 μg). After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 μL of fraction #3 collected after PD-10 column was mixed with 15 μL of 10 mM DTPA solution (pH 6.5), and incubated for 30 min. 10 μL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 μm column; column temperature: room temperature; the column was eluted with DPBS buffer (×1, without calcium and magnesium); flow rate: 0.7 mL/min; 20 min run; injection volume: 30 μL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-DBCO-H11B6 peak on HPLC UV trace.

Example 10: Synthesis of H2bp18c6-Phenyl-BCN

Sheme 12.

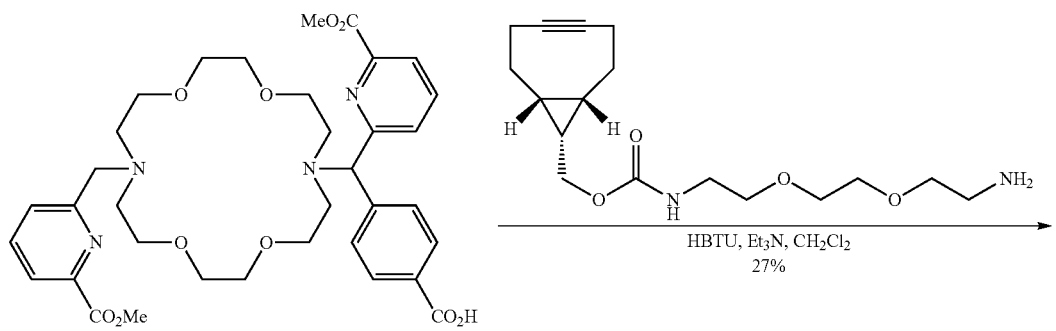

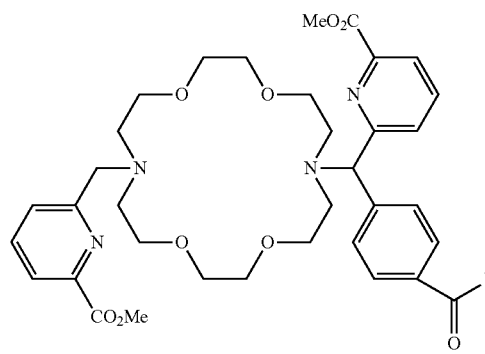 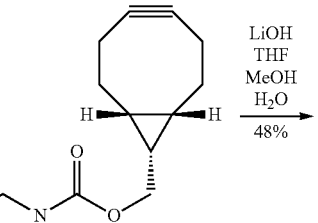

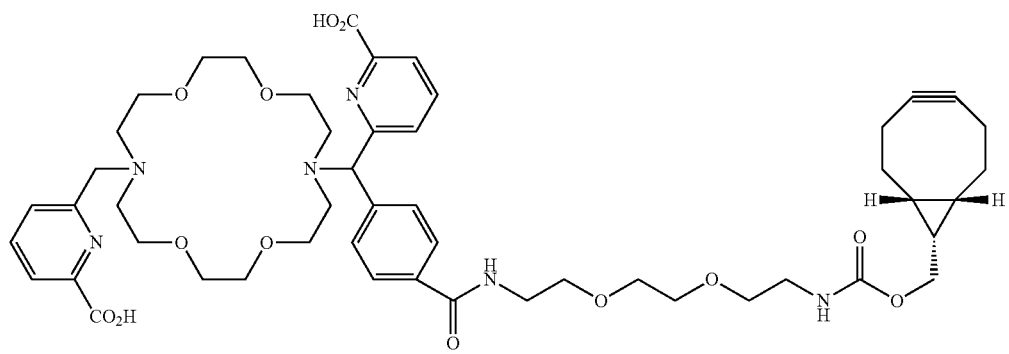

To a solution of 4-((6-(methoxycarbonyl)pyridin-2-yl) (16-((6-(methoxycarbonyl)pyridin-2-yl)methyl)-1,4,10,13-tetraoxa-7,16-diazacyclooctadecan-7-yl)methyl)benzoic acid (50 mg, 0.073 mmol) and Et$_3$N (0.1 mL, 0.73 mmol) in CH$_2$Cl$_2$ (2.5 mL) at 0° C. were added HATU (37 mg, 0.10 mmol). After the solution was stirred for 5 min at 0° C., N-[(1R,8S,9s)-bicyclo[6.1.0]non-4-yn-9-ylmethyloxycarbonyl]-1,8-diamino-3,6-dioxaoctane in CH$_2$Cl$_2$ (1 mL) was added. The cold bath was removed, and it was stirred at room temperature for 18 h. The mixture was concentrated and the residue was purified by chromatography on amine functionalized silica gel (CH$_2$Cl$_2$ to 10% MeOH in CH$_2$Cl$_2$) to give 19.8 mg (27% yield) of the product as a colorless film stuck on the flask wall. LC-MS analysis showed mass/ion peaks at 987.6 [M+H$^+$].

To a solution of methyl 6-((4-((1-((1R,8S,9s)-bicyclo[6.1.0]non-4-yn-9-yl)-3-oxo-2,7,10-trioxa-4-azadodecan-12-yl)carbamoyl)phenyl)(16-((6-(methoxycarbonyl)pyridin-2-yl)methyl)-1,4,10,13-tetraoxa-7,16-diazacyclooctadecan-7-yl)methyl)picolinate (14.5 mg, 0.015 mmol) in THF/MeOH/H$_2$O (4:11 v/v/v, 1.8 mL) at room temperature was added LiOH (1N, 0.3 mL). After the reaction mixture was stirred at room temperature for 1 h, it was neutralized with HCl (1 N) to pH=6.5. The reaction mixture was concentrated under vacuum. The residue was purified by chromatography on amine functionalized silica gel (CH$_2$Cl$_2$ to 10% MeOH in CH$_2$Cl$_2$) to give 9.5 mg (48% yield) of H2bp18c6-benzyl-phenyl-BCN as a colorless film, which was dissolved in H$_2$O (4 mL) and ACN (1 mL). After lyophilization, it gave the product as white solid. H NMR (CD$_3$OD, 400 MHz) δ 7.91 (d, J=8 Hz, 2H), 7.84 (t, J=8 Hz, 2H), 7.81 (d, J=8 Hz, 2H), 7.60 (d, J=8 Hz, 2H), 7.53 (d, J=8 Hz, 1H), 7.46 (d, J=8 Hz, 1H), 5.24 (s, 1H), 4.10 (d, J=8 Hz, 2H), 3.91 (brs, 2H), 3.75-3.58 (m, 22H), 3.56 (t, J=4 Hz, 2H), 3.51 (t, J=4 Hz, 2H), 3.23 (t, J=4 Hz, 2H), 2.97 (dt, J=8, 4 Hz, 2H), 2.92-2.82 (m, 4H), 2.78 (dt, J=8, 4 Hz, 2H), 2.28-2.08 (m, 6H), 1.65-1.50 9m, 2H), 1.39-1.27 (m, 1H), 0.96-0.84 (m, 2H). MS (ESI) 981.4 [M+Na$^+$].

Example 11: Preparation of H2bp18c6-Benzyl-Phenyl-BCN-PSMB127 and $^{225}$Ac(III) Labeling

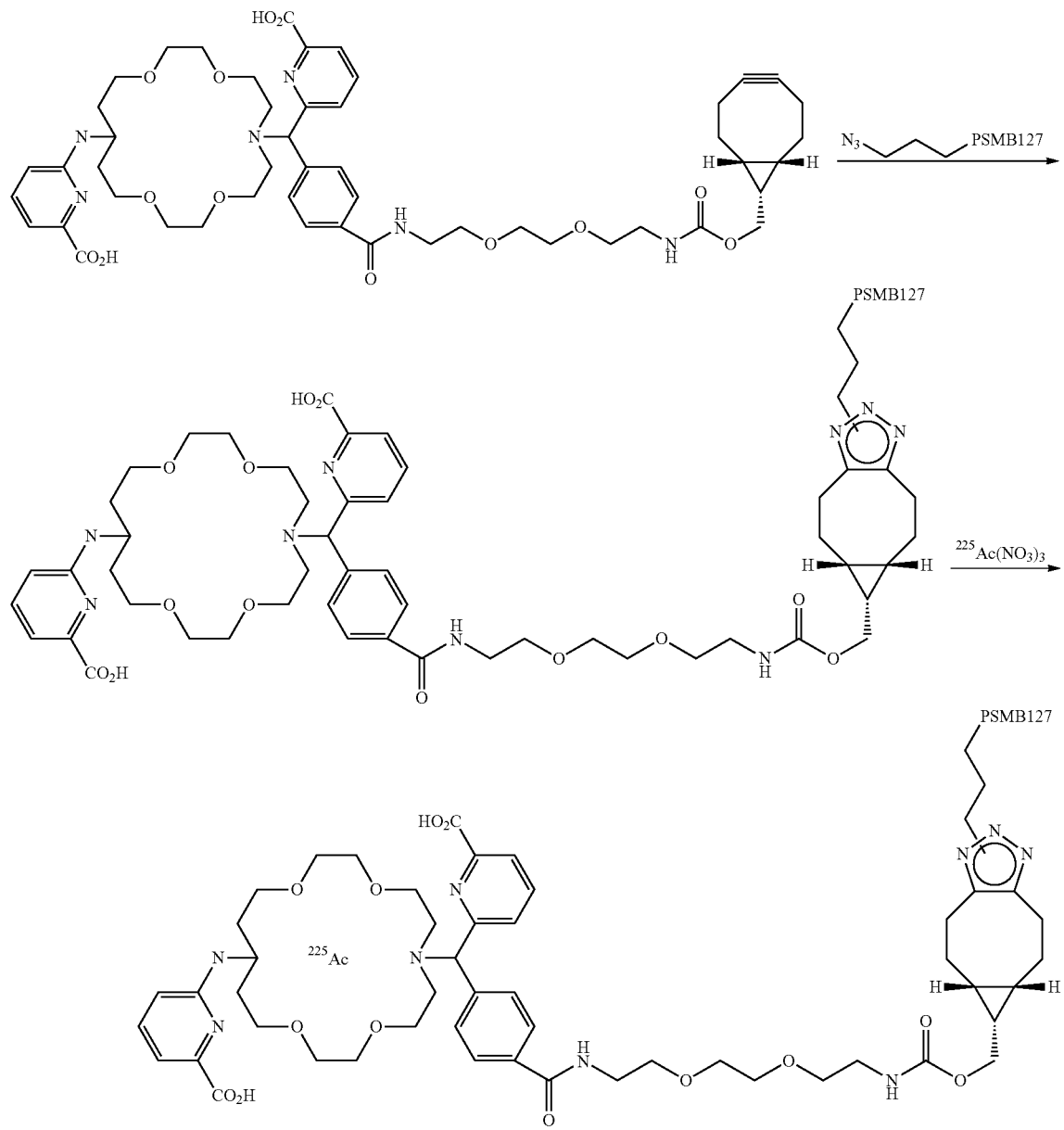

Scheme 13. Direct chelation of $^{225}$Ac(III) to H2bp18c6-benzyl-phenyl-BCN-PSMB127 (formed by click reaction of H2bp18c6-benzyl-phenyl-BCN to Site Specific azide-PSMB127)

Azide Modification of mAb and Click Reaction:

PSMB127 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-benzyl-phenyl-BCN was reacted with site specific azide-PSMB127 (DOL=2) in 1×dPBS at 37° C. for 1 hour without shaking. Completion of the BCN-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-benzyl-phenyl-BCN-PSMB127 conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 µL.

Labeling:

To a solution of NaOAc (3 M in H$_2$O, 10 µL) in a plastic vial was added sequentially $^{225}$Ac(N$_3$)$_3$ (~5 mCi/mL in 0.1 N HCl, 10 µL, 0.046 mCi) and H2bp18c6-benzyl-phenyl-BCN-PSMB127 (site specific, CAR=2, 2.3 mg/mL in PBS buffer solution, 13.0 µL, 30 µg). After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 µL of fraction #3 collected after PD-10 column was mixed with 15 µL of 10 mM DTPA solution (pH 6.5), and incubated for 30 min. 10 µL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 µm column; column temperature: room temperature; the column was eluted with DPBS buffer (×1, without calcium and magnesium); flow rate: 0.7 mL/min; 20 min run; injection volume: 40 µL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-benzyl-phenyl-BCN-PSMB127 peak on HPLC UV trace.

Example 12: Synthesis of H2bp18c6-Off Macrocycle-Ethyl Sulfide-DBCO

H2bp18c6 derivatives substituted at a carbon atom of the macrocyclic ring with linkers for conjugation to a targeting ligand are synthesized generally according to Scheme 14a and Scheme 14b below:

Scheme 14a: Synthesis of H$_2$bp18c6 Ring Derivatives Substituted at Carbon Atom of Macrocyclic Ring with Linker for Conjugation

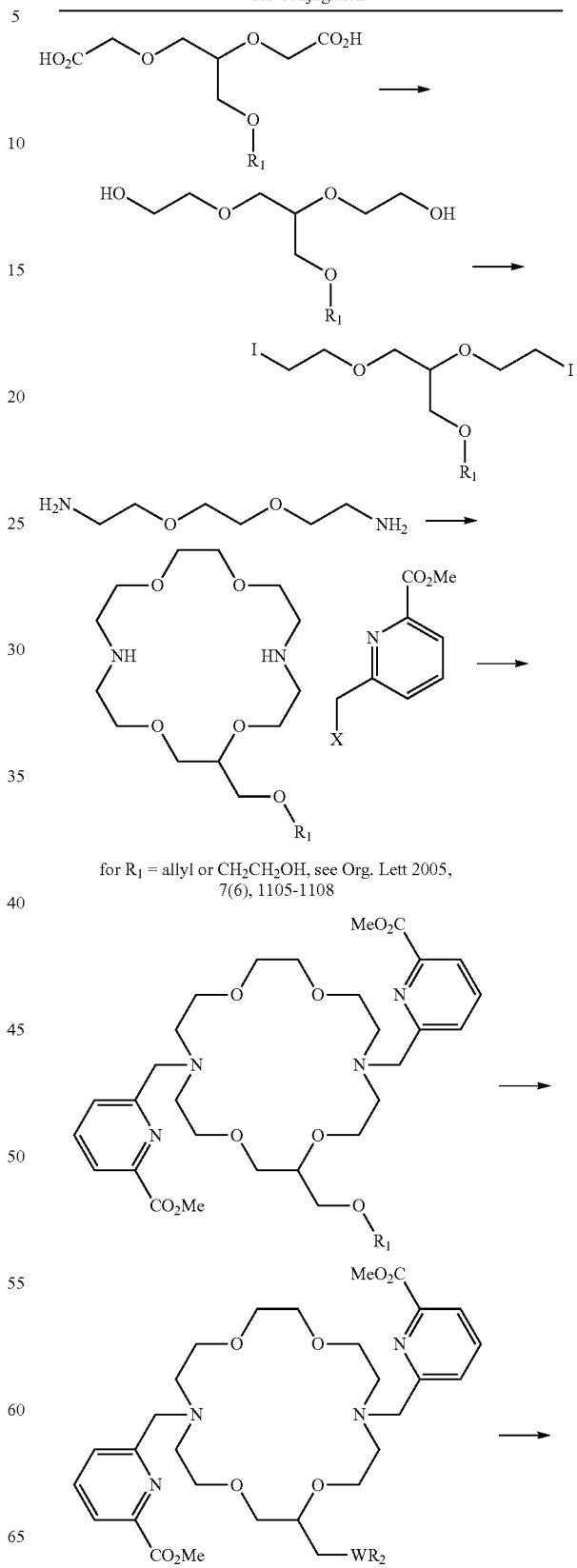

for R$_1$ = allyl or CH$_2$CH$_2$OH, see Org. Lett 2005, 7(6), 1105-1108

-continued

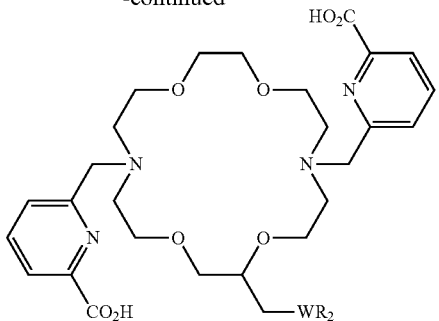

OR₁ could be converted to other functional groups for ligation WR₂.
R₂ is NH₂, N₃, aldehyde, carboxylate, alkyne and the like.
W is absent or a linker such as hetroatom, alkyl, akyl with hetroatom(s), substituted aryl and the like.

Synthesis of diaza-18-crown-6 substituted with —CH$_2$OR$_1$ is synthesized using procedures described in *Org. Lett.* 2005, 7(6), 1105-1108, which is subsequently reacted with a derivative of 6-(halomethyl)picolinic acid as described above with respect to Schemes 3 and 4. The functional group OR$_1$ can be converted to another functional group WR$_2$ for ligation or conjugation to a linker, targeting ligand, etc., including but not limited to NH$_2$, N$_3$, aldehyde, carboxylate, alkyne and the like, with or without a linker W, which is a heteroatom, alkyl, alkyl with heteroatom(s), substituted aryl and the like. In Scheme 6a, X is leaving group, e.g., halo, mesylate, tosylate and the like; R$_1$ is allyl, benzyl, alcohol and the like; W is absent or a linker, e.g., heteroatom, alkyl, heteroalkyl, substituted aryl and the like; R$_2$ is NH$_2$, N$_3$ aldehyde, carboxylate, alkynyl, and the like.

Scheme 14b: Synthesis of H$_2$bp18c6 Ring Derivatives Substituted at Carbon Atom of Macrocyclic Ring with Linker for Conjugation

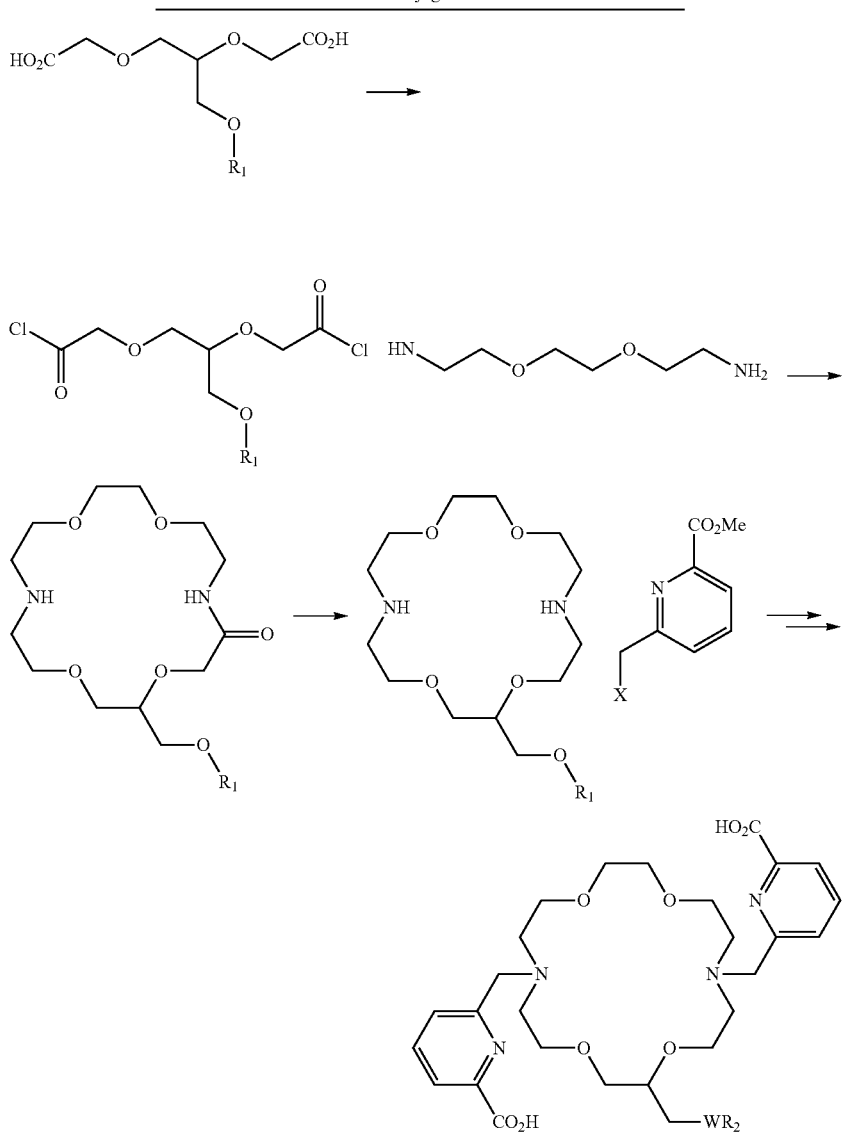

Diaza-18-crown-6 substituted with —CH$_2$OR$_1$ could also be synthesized using procedures described in *Journal of Organic Chemistry*, 1988, 53(14), 3190-5 and *Journal of Heterocyclic Chemistry*, 1986, 23(2), 609-13, which is subsequently reacted with a derivative of 6-(halomethyl)picolinic acid as described above with respect to Schemes 3 and 4. The functional group OR$_1$ can be converted to another functional group R$_2$ for ligation or conjugation to a linker, targeting ligand, etc., including but not limited to NH$_2$, N$_3$, aldehyde, carboxylate, alkyne and the like, with or without a linker W, which is a heteroatom, alkyl, alkyl with heteroatom(s), substituted aryl and the like.

Next, the synthesis of H2bp18c6-off Macrocycle-ethyl sulfide-DBCO is described.

Scheme 15.

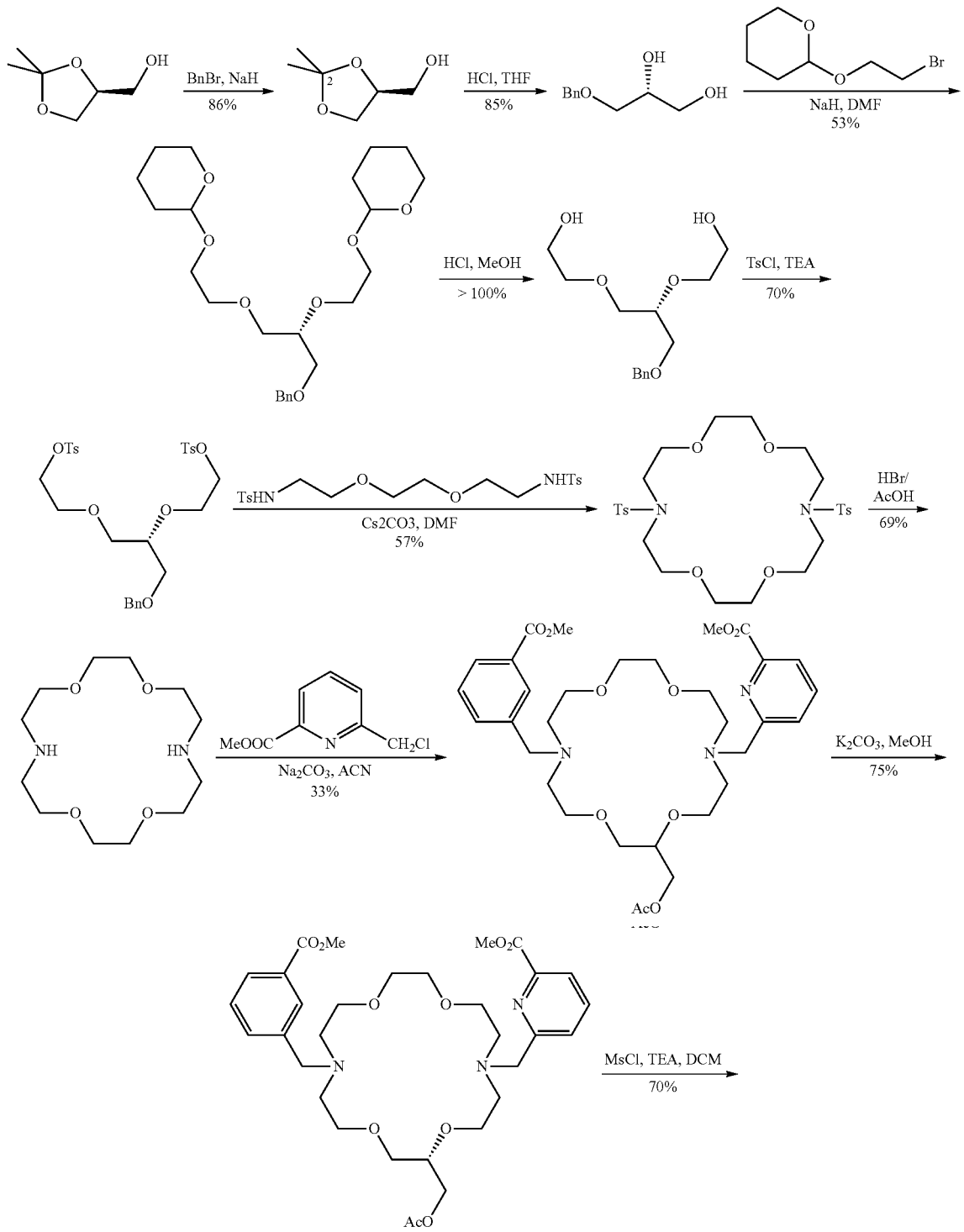

117
-continued
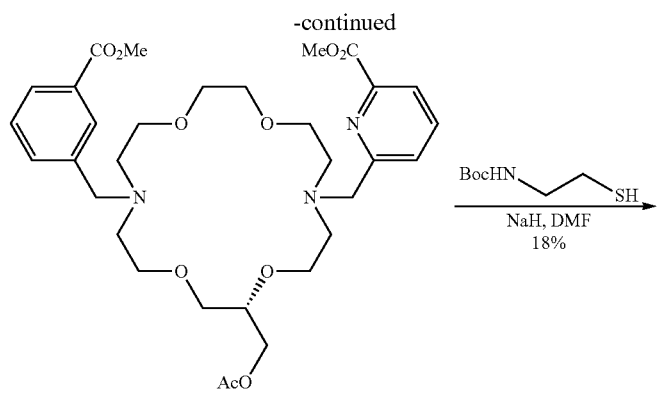
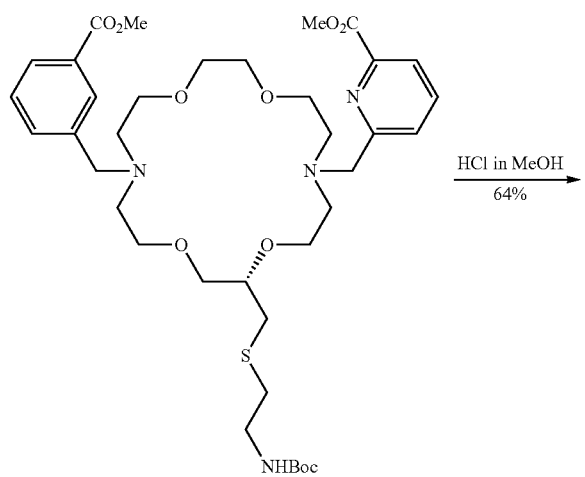
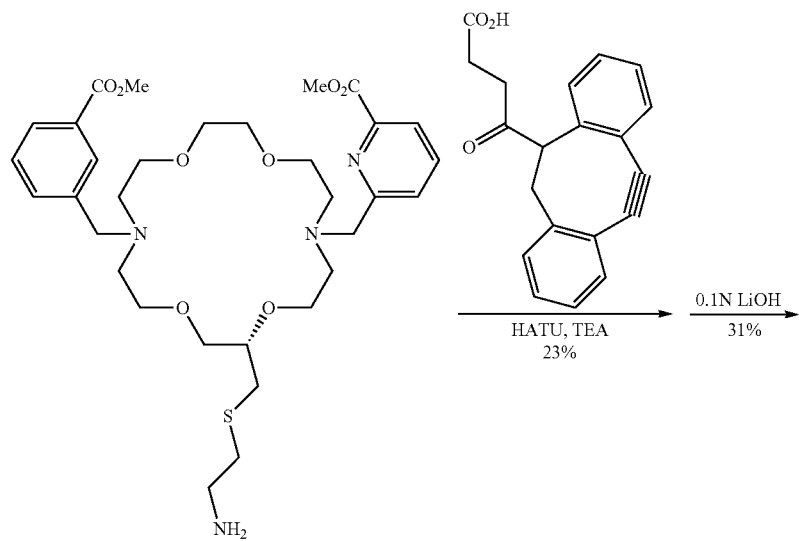
118

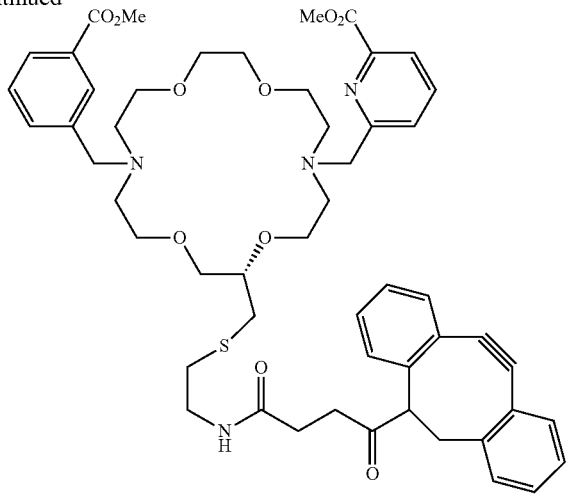

Sodium hydride (18.16 g, 60% in mineral oil, 454 mmol) was added to solution of (S)-(+)-2,2-dimethyl-1,3-dioxolane-4-methanol (50 g, 378 mmol) in anhydrous DMF (500 mL) at 0° C. After stirring at this temperature for 10 minutes, benzyl bromide (77.63 g, 454 mmol) was added slowly to this suspension. The reaction was brought to room temperature after 30 min and stirred for an additional 8 h. The reaction mixture was quenched using saturated ammonium chloride solution and was extracted with dichloromethane (2×500 mL). The combined organic layer was washed with brine and dried over sodium sulfate. After removal of solvent, the residue was purified by flash column chromatography (silica gel, 230-400 mesh) using petroleum ether and ethyl acetate to yield (S)-4-((benzyloxy)methyl)-2,2-dimethyl-1,3-dioxolanethe (72 g, 86%) as a colorless liquid.

To a solution of (S)-4-((benzyloxy)methyl)-2,2-dimethyl-1,3-dioxolane (72 g, 324 mmol) in THF (100 mL) was added 1.5 N HCl (100 mL) followed by stirring at room temperature for 16 h. The reaction mixture was diluted with ethyl acetate (500 mL) and neutralized with 10% sodium bicarbonate solution. The reaction mixture was extracted with ethyl acetate (2×500 mL), washed with brine, dried over sodium sulfate, filtered and concentrated under reduced pressure. The residue was purified by flash column chromatography (silica gel, 230-400 mesh) using petroleum ether and ethyl acetate to yield (R)-3-(benzyloxy)propane-1,2-diol (51 g, 85%) as a colorless oil.

To a suspension of sodium hydride (26.29 g, 60% in mineral oil, 686 mmol) in DMF (20 mL) was added (R)-3-(benzyloxy)propane-1,2-diol (25.0 g, 137 mmol) in DMF (100 mL) dropwise at 0° C. The reaction mixture was allowed to stir at room temperature for 2 h. It was cooled again to 0° C. and 2-(2-bromoethoxy)tetrahydro-2H-pyran (85.89 g, 411 mmol) in DMF (100 mL) was added dropwise. The reaction mixture was allowed to reach room temperature and stirred for 16 h. The reaction was quenched with saturated ammonium chloride and extracted with ethyl acetate (3×300 mL). Combined organic layer was washed with water, dried over sodium sulfate, filtered and concentrated. The crude oil was purified by silica gel (230-400 mesh) flash chromatography using ethyl acetate in petroleum ether (0-40%) to give 2,2'-(((((R)-3-(benzyloxy)propane-1,2-diyl)bis(oxy))bis(ethane-2,1-diyl))bis(oxy))bis(tetrahydro-2H-pyran) (32 g, 53%) as a colorless liquid.

To a solution of 2,2'-(((((R)-3-(benzyloxy)propane-1,2-diyl)bis(oxy))bis(ethane-2,1-diyl))bis(oxy))bis(tetrahydro-2H-pyran) (32 g, 73.05 mmol) in 500 mL of methanol was added 5 mL of HCl in dioxane. The reaction was stirred at reflux for 1 h, cooled, and evaporated. The crude product (R)-2,2'-((3-(benzyloxy)propane-1,2-diyl)bis(oxy))bis (ethan-1-ol) (20 g) was used in the next step without purification.

To a solution of (R)-2,2'-((3-(benzyloxy)propane-1,2-diyl)bis(oxy))bis(ethan-1-ol) (20 g, 74.07 mmol) in dichloromethane (250 mL) and triethylamine (53 mL, 370 mmol) at 10° C. was added solid p-toluene sulfonyl chloride (42.2 g, 222 mmol) portion wise. The mixture was stirred at ambient temperature for 16 h. After completion of the reaction, the suspension was diluted with 1000 mL of dichloromethane, washed with cold 1 M HCl (3×100 mL), followed by 2×500 mL portions of ice-cold water, dried over sodium sulfate, and evaporated to a solid gum. The crude material was purified by flash chromatography (silica gel, 230-400 mesh) using ethyl acetate in petroleum ether (0-40%) to give (R)-((3-(benzyloxy)propane-1,2-diyl)bis (oxy))bis(ethane-2,1-diyl) bis(4-methylbenzenesulfonate) (30 g, 70%) as a colorless liquid.

A mixture of (R)-((3-(benzyloxy)propane-1,2-diyl)bis (oxy))bis(ethane-2,1-diyl) bis(4-methylbenzenesulfonate) (30 g, 51.9 mmol) and cesium carbonate (50.76 g, 155.7 mmol) in 200 mL of dry DMF was stirred for 1.5 h at ambient temperature. To the suspension, was added N,N'-((ethane-1,2-diylbis(oxy))bis(ethane-2,1-diyl))bis(4-methylbenzenesulfonamide) (23.56 g, 51.9 mmol) in 200 mL of DMF dropwise over a period of 2 h. The mixture was stirred for additional 20 h at ambient temperature. The solvent was removed under reduced pressure to obtain a solid paste. This was suspended in 1000 mL of dichloromethane and stirred for 30 min. The precipitated solids were filtered off and the filtrate was evaporated at high vacuum. The crude material was purified by flash chromatography (silica gel, 230-400 mesh) using ethyl acetate in petroleum ether (0-40%) to give (R)-2-((benzyloxy)methyl)-7,16-ditosyl-1,4,10,13-tetraoxa-7,16-diazacyclooctadecane (24 g, 67%) as a colorless liquid.

To a solution of (R)-2-((benzyloxy)methyl)-7,16-ditosyl-1,4,10,13-tetraoxa-7,16-diazacyclooctadecane (24 g, 34.78 mmol) in hydrobromic acid in acetic acid (50%, 100 mL) was added phenol (16.35 g, 174 mmol) at room temperature. The reaction was heated at 60° C. for 6 h. After completion of the reaction, it was cooled to room temperature, acetic acid was removed under high vacuum. The crude product was purified on reverse phase column using 0-100% acetonitrile in water (0.1% TFA) to give (S)-(1,4,10,13-tetraoxa-7,16-diazacyclooctadecan-2-yl)methyl acetate (8.0 g, 69%) as a colorless liquid.

A suspension of (S)-(1,4,10,13-tetraoxa-7,16-diazacyclooctadecan-2-yl)methyl acetate (8.0 g, 23.95 mmol), methyl 6-(chloromethyl)picolinate (11.07 g, 59.88 mmol) and sodium carbonate (12.69 g, 119.75 mmol) in dry acetonitrile (100 mL) was heated at 90° C. for 16 h. After completion of the reaction, reaction mixture was cooled to room temperature, filtered through Celite and concentrated under reduced pressure. The crude material was purified by flash chromatography (silica gel, 230-400 mesh) using methanol in dichloromethane (0-10%) to give dimethyl 6,6'-((2-(acetoxymethyl)-1,4,10,13-tetraoxa-7,16-diazacyclooctadecane-7,16-diyl)bis(methylene))(S)-dipicolinate (5.0 g, 33%) as a brown liquid.

To a solution of dimethyl 6,6'-((2-(acetoxymethyl)-1,4,10,13-tetraoxa-7,16-diazacyclooctadecane-7,16-diyl)bis(methylene))(S)-dipicolinate (5.0 g, 7.91 mmol) in methanol (50 mL) was added potassium carbonate (0.11 g, 0.79 mmol) at room temperature, and stirred for 10 min. After completion of the reaction, it was concentrated under reduced pressure. The residue was purified by flash chromatography over silica (230-400 mesh) eluting with a gradient of 0-10% methanol in dichloromethane to give dimethyl 6,6'-((2-(hydroxymethyl)-1,4,10,13-tetraoxa-7,16-diazacyclooctadecane-7,16-diyl)bis(methylene))(R)-dipicolinate (3.5 g, 75%) as a brown liquid.

To a solution of dimethyl 6,6'-((2-(hydroxymethyl)-1,4,10,13-tetraoxa-7,16-diazacyclooctadecane-7,16-diyl)bis(methylene))(R)-dipicolinate (1.0 g, 1.7 mmol) in dichloromethane (20 mL) was added triethylamine (0.51 g, 0.70 mL, 5.1 mmol). Mesyl chloride (0.39 g, 0.26 mL, 3.4 mmol) was added dropwise to this solution at 0° C. The reaction was stirred for 30 min at room temperature. The reaction progress was monitored by TLC. After completion of the reaction, it was concentrated and the crude was purified by column chromatography (alumina—neutral) using methanol in dichloromethane (1-2%) as eluent to give dimethyl 6,6'-((2-(((methylsulfonyl)oxy)methyl)-1,4,10,13-tetraoxa-7,16-diazacyclooctadecane-7,16-diyl)bis(methylene))(S)-dipicolinate (0.7 g, 62%) as a brown liquid.

To a solution of tert-butyl (2-mercaptoethyl)carbamate (53 mg, 0.3 mmol) in DMF (2 mL) was added sodium hydride (12 mg, 60% in mineral oil, 0.3 mmol) at 0° C. The reaction mixture was stirred for 10 minutes at room temperature. To the reaction mixture, was added dimethyl 6,6'-((2-(((methylsulfonyl)oxy)methyl)-1,4,10,13-tetraoxa-7,16-diazacyclooctadecane-7,16-diyl)bis(methylene))(S)-dipicolinate (100 mg, 0.15 mmol) in DMF (1 mL) at 0° C. The reaction was stirred for 2 h at room temperature. The reaction progress was monitored by TLC. After completion of the reaction, the reaction mixture was quenched with saturated ammonium chloride solution and extracted with ethyl acetate (3×5 mL). The combined organic layer was washed with water, brine, dried over anhydrous sodium sulphate and concentrated. The crude product was purified by preparative HPLC using acetonitrile in water (0.1% TFA) to give dimethyl 6,6'-((2-(((2-((tert-butoxycarbonyl)amino)ethyl)thio)methyl)-1,4,10,13-tetraoxa-7,16-diazacyclooctadecane-7,16-diyl)bis(methylene))(S)-dipicolinate (20 mg, 18%) as brown liquid.

To dimethyl 6,6'-((2-(((2-((tert-butoxycarbonyl)amino)ethyl)thio)methyl)-1,4,10,13-tetraoxa-7,16-diazacyclooctadecane-7,16-diyl)bis(methylene))(S)-dipicolinate (100 mg, 0.15 mmol), a cold solution of HCl in methanol (2 mL, 4 N) was added and the solution was stirred for 2 h. The reaction mixture was concentrated under reduced pressure to yield dimethyl 6,6'-((2-(((2-aminoethyl)thio)methyl)-1,4,10,13-tetraoxa-7,16-diazacyclooctadecane-7,16-diyl)bis(methylene))(S)-dipicolinate as yellow liquid (55 mg, 64%).

To a solution of dimethyl 6,6'-((2-(((2-aminoethyl)thio)methyl)-1,4,10,13-tetraoxa-7,16-diazacyclooctadecane-7,16-diyl)bis(methylene))(S)-dipicolinate (60 mg, 0.09 mmol) in dichloromethane (0.5 mL) at 0° C. were added triethylamine (0.04 mL, 0.27 mmol) and then HATU (51 mg, 0.13 mmol). After the solution was stirred for 5 min at 0° C., DBCO-acid (27 mg, 0.09 mmol) in dichloromethane (0.5 mL) was added. The cold bath was removed, and it was stirred at room temperature for 18 h. Water was added to the reaction mixture and it was extracted with dichloromethane (2 mL×3). The combined extracts were washed with saturated $NaHCO_3$ aqueous solution, brine, dried over sodium sulfate and filtered. The filtrate was concentrated to give the crude product. Chromatography on silica gel using dichloromethane and methanol yielded the dimethyl ester of H2bp18c6-off Macrocycle-ethyl sulfide-DBCO (20 mg, 23%) as colorless liquid.

To a solution of the dimethyl ester of H2bp18c6-off Macrocycle-ethyl sulfide-DBCO (20 mg, 0.02 mmol) in methanol (0.5 mL) at room temperature was added LiOH in $H_2O$ (0.64 mL, 0.1N, 0.06 mmol). After stirring at room temperature for 16 h, it was neutralized with acetic acid to pH=6.5. The reaction mixture was concentrated on a rotavapor at room temperature to remove the volatile solvents. The residue was purified by preparative HPLC to give H2bp18c6-off Macrocycle-ethyl sulfide-DBCO (6 mg, 31%) as an off white solid. LC-MS APCI: Calculated for C48H56N6O10S 909.07; Observed m/z $[M+H]^+$ 909.4. Purity by LC-MS: 92.92% RT: 1.86. Purity by HPLC: 91.56% RT: 3.87. $^1$H NMR (400 MHz, $D_2O$): δ 7.83-7.76 (m, 4H), 7.54-7.17 (m, 10H), 4.97-4.90 (m, 1H), 4.80 (s, 4H), 4.23 (s, 4H), 3.78-3.42 (m, 18H), 3.04-3.00 (m, 2H), 2.51-2.39 (m, 3H), 2.31-2.29 (m, 2H), 2.10-2.04 (m, 3H)

Example 13: Preparation of H2bp18c6-Off Macrocycle-Ethyl Sulfide-DBCO-PSMB127 and $^{225}$Ac(III) Labeling Scheme 16. Direct chelation of $^{225}$Ac(III) to H2bp18c6-off Macrocycle-ethyl sulfide-DBCO-PSMB127 (formed by click reaction of H2bp18c6-off Macroycycle-ethyl sulfide-DBCO to Site Specific azide-PSMB127)

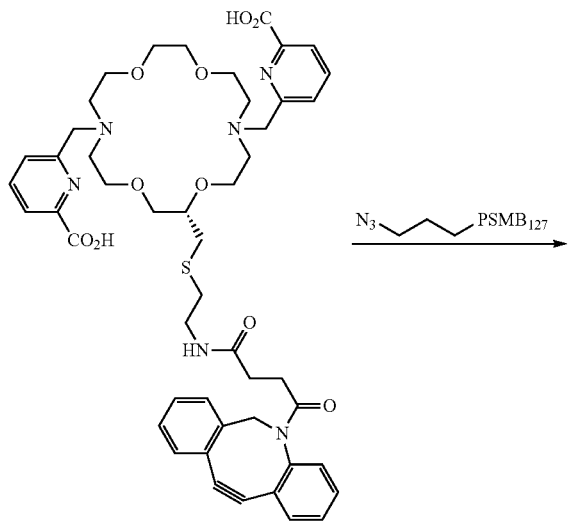

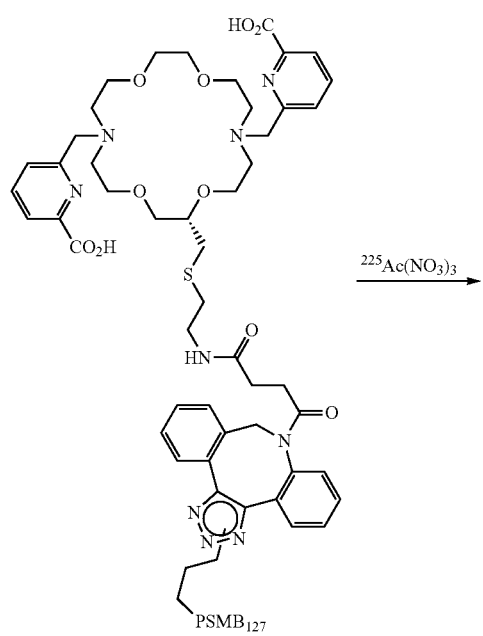

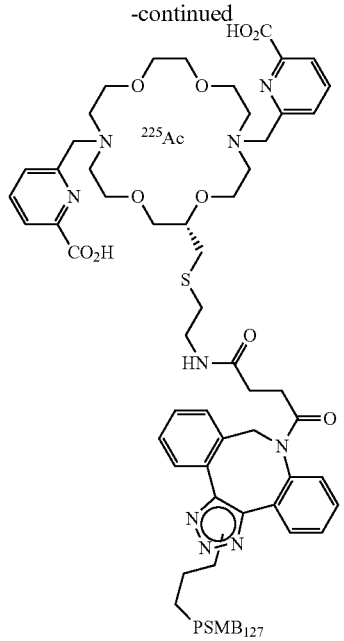

Azide Modification of mAb and Click Reaction:

PSMB127 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 ml GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-off Macrocycle-ethyl sulfide-DBCO was reacted with site specific azide-PSMB127 (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-off Macrocycle-ethyl sulfide-DBCO-PSMB127 conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling:

To a solution of NaOAc (3 M in H$_2$O, 10 μL) in a plastic vial was added sequentially $^{225}$Ac(N$_3$)$_3$ (~5 mCi/mL in 0.1 N HCl, 10 μL, 0.048 mCi) and H2bp18c6-off Macrocycle-ethyl sulfide-DBCO-PSMB127 (site specific, CAR=2, 2.4 mg/mL in PBS buffer solution, 10 μL, 24 μg). After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) though column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 μL of fraction #3 collected after PD-10 column was mixed with 15 μL of 10 mM DTPA solution (pH 6.5), and incubated for 30 min. 10 μL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 μm column; column temperature: room temperature; the column was eluted with DPBS buffer (×1, without calcium and magnesium); flow rate: 0.7 mL/min; 20 min run; injection volume: 40 μL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-off Macrocycle-ethyl sulfide-DBCO-PSMB127 peak on HPLC UV trace.

Example 14: Synthesis of H2bp18c6-Off Macrocycle-Pentyl Sulfide-DBCO

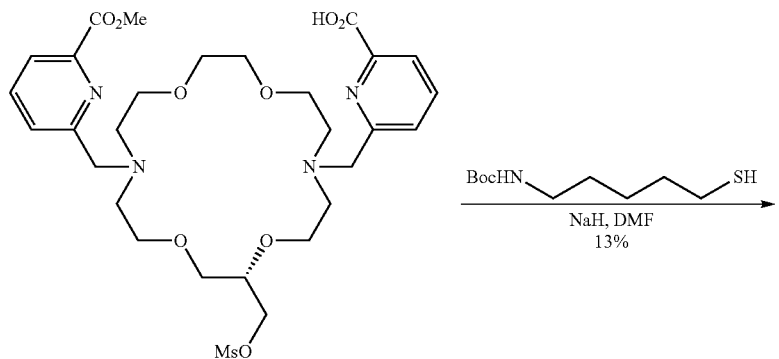

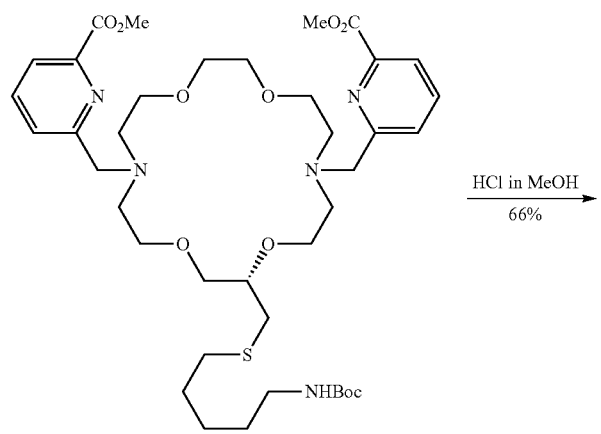

-continued
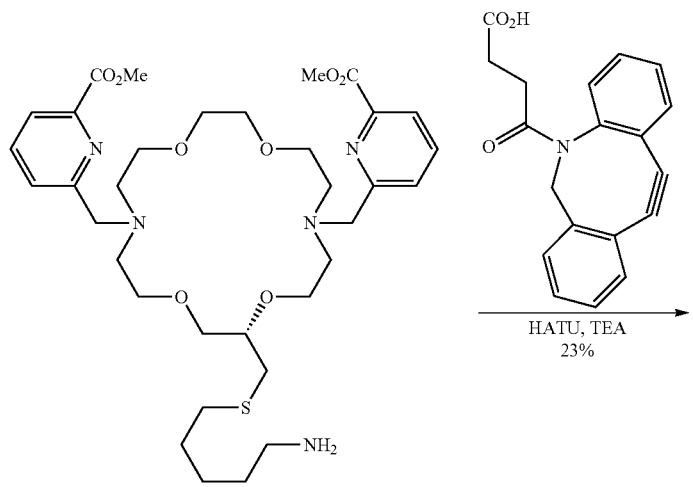
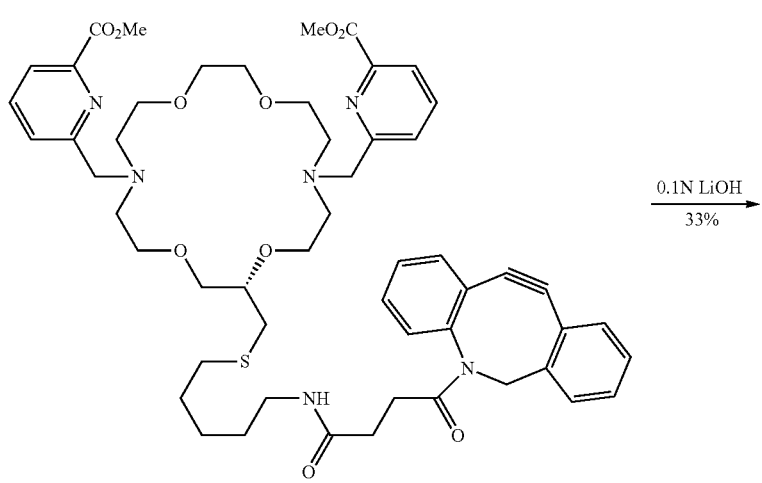
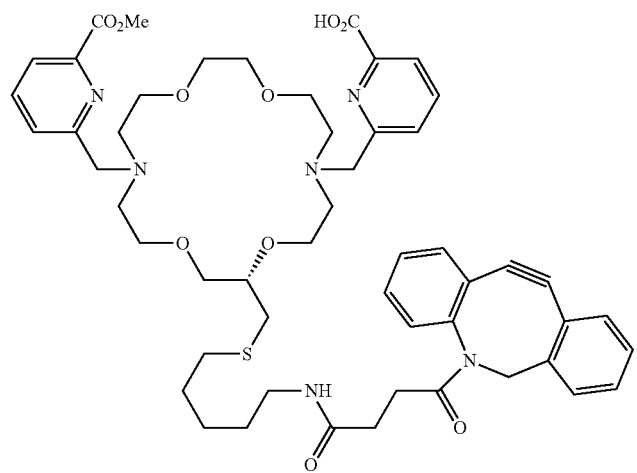

To a solution of tert-butyl (5-mercaptopentyl)carbamate (65 mg, 0.3 mmol) in DMF (2 mL) was added sodium hydride (12 mg, 60% in mineral oil, 0.3 mmol) at 0° C. The reaction mixture was stirred for 10 min at room temperature. To the reaction mixture, was added dimethyl 6,6'-((2-(((methylsulfonyl)oxy)methyl)-1,4,10,13-tetraoxa-7,16-diazacyclooctadecane-7,16-diyl)bis(methylene))(S)-dipicolinate (100 mg, 0.15 mmol) in DMF (1 mL) at 0° C. The reaction was stirred for 2 h at room temperature. The reaction progress was monitored by TLC. After completion of the reaction, it was concentrated and the residue was purified by preparative HPLC using acetonitrile and 0.1% TFA in water to give dimethyl 6,6'-((2-(((5-((tert-butoxycarbonyl)amino)pentyl)thio)methyl)-1,4,10,13-tetraoxa-7,16-diazacyclooctadecane-7,16-diyl)bis(methylene))(S)-dipicolinate (15 mg, 13%) as a brown liquid.

To dimethyl 6,6'-((2-(((5-((tert-butoxycarbonyl)amino)pentyl)thio)methyl)-1,4,10,13-tetraoxa-7,16-diazacyclooctadecane-7,16-diyl)bis(methylene))(S)-dipicolinate (120 mg, 0.15 mmol), a cold solution of HCl in methanol (2 mL, 4N) was added and stirred for 2 h. The reaction mixture was concentrated under reduced pressure to yield dimethyl 6,6'-((2-(((5-aminopentyl)thio)methyl)-1,4,10,13-tetraoxa-7,16-diazacyclooctadecane-7,16-diyl)bis(methylene))(S)-dipicolinate (70 mg, 66%) as yellow liquid.

To a solution of dimethyl 6,6'-((2-(((5-aminopentyl)thio)methyl)-1,4,10,13-tetraoxa-7,16-diazacyclooctadecane-7,16-diyl)bis(methylene))(S)-dipicolinate (50 mg, 0.07 mmol) in dichloromethane (0.5 mL) at 0° C. were added triethylamine (0.03 mL, 0.21 mmol) and then HATU (38 mg, 0.10 mmol). After the solution was stirred for 5 min at 0° C., DBCO-acid (21 mg, 0.07 mmol) in dichloromethane (0.5 mL) was added. The cold bath was removed, and it was stirred at room temperature for 18 h. Water was added to the reaction mixture and it was extracted with dichloromethane (2 mL×3). The combined extracts were washed with saturated $NaHCO_3$ aqueous solution, brine, dried over sodium sulphate and filtered. The filtrate was concentrated to give the crude product. Chromatography on silica gel using dichloromethane and methanol yielded the dimethyl ester of H2bp18c6-off Macrocycle-pentyl sulfide-DBCO (16 mg, 23%) as colorless liquid.

To a solution of the dimethyl ester of H2bp18c6-off Macrocycle-pentyl sulfide-DBCO (16 mg, 0.01 mmol) in methanol (0.5 mL) at room temperature was added LiOH in $H_2O$ (0.49 mL, 0.1N, 0.05 mmol). After stirring at room temperature for 16 h, it was neutralized with acetic acid to pH=6.5. The reaction mixture was concentrated on a rotavapor at room temperature to remove the volatile solvents. The residue was purified by preparative HPLC to give H2bp18c6-off Macrocycle-pentyl sulfide-DBCO (5 mg, 33%) as an off white solid. LC-MS APCI: Calculated for $C_{51}H_{62}N_6O_{10}S$; 951.15; Observed m/z $[M+H]^+$ 951.4. Purity by LC-MS: 94.51% RT: 1.98. Purity by HPLC: 98.41% RT: 4.13. $^1$H NMR (400 MHz, $D_2O$): δ 7.81-7.75 (m, 4H), 7.52-7.17 (m, 10H), 4.97-4.90 (m, 1H), 4.80 (s, 4H), 4.14 (s, 3H), 3.77-3.46 (m, 16H), 3.10 (s, 7H), 2.83-2.80 (m, 2H), 2.55-2.53 (m, 2H), 2.42-2.38 (m, 3H), 2.11-2.08 (m, 3H), 1.39-1.35 (m, 2H), 1.20-1.10 (m, 4H).

Example 15: Preparation of H2bp18c6-Off Macrocycle-Pentyl Sulfide-DBCO-PSMB127 and $^{225}$Ac(III) Labeling Scheme 18. Direct chelation of $^{225}$Ac(III) to H2bp18c6-off Macrocycle-pentyl sulfide-DBCO-PSMB127 (formed by click reaction of H2bp18c6-off Macrocycle-pentyl sulfide-DBCO to Site Specific azide-PSMB127)

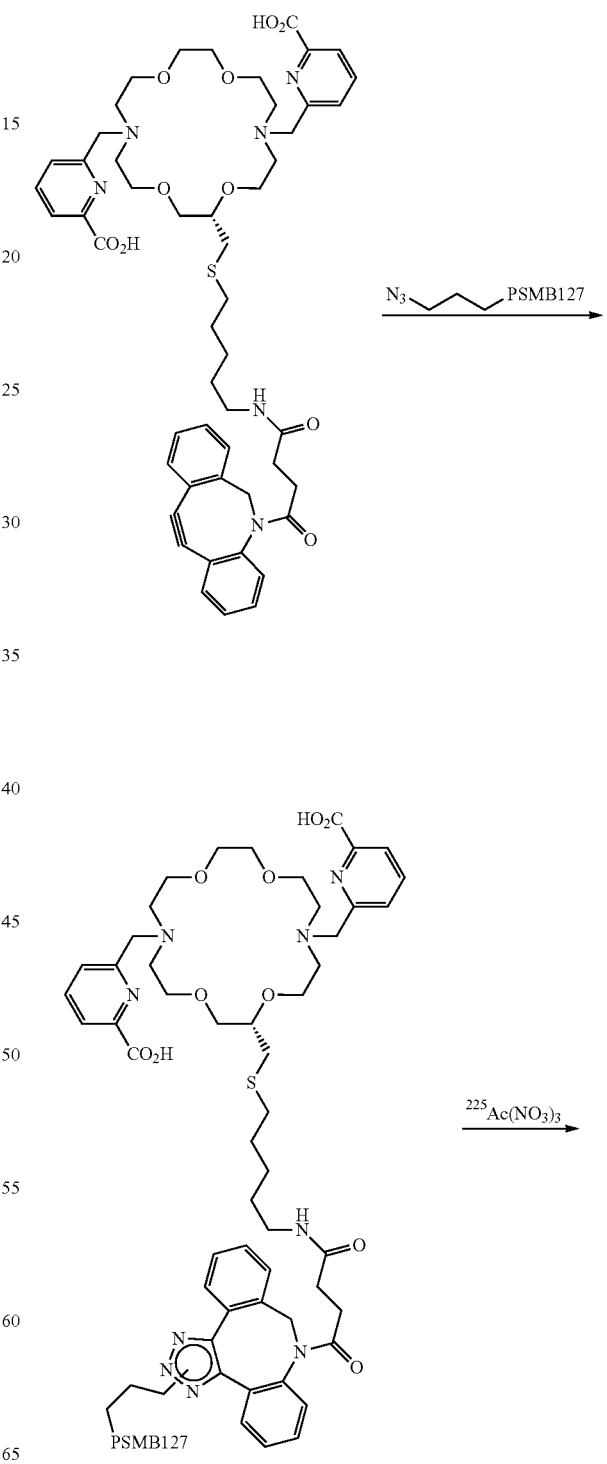

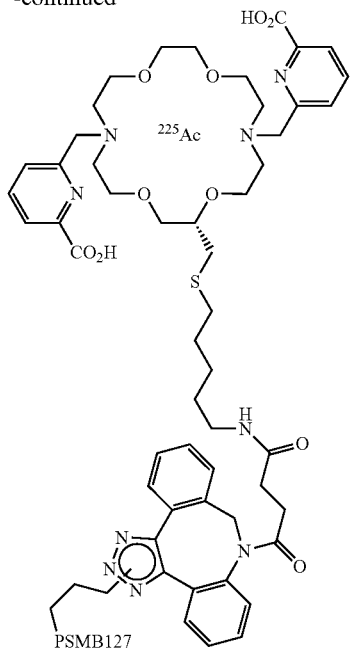

PSMB127

Azide Modification of mAb and Click Reaction:

PSMB127 was site-selectively modified with 100× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 mL GE Healthcare MabSelect column. Azido-mAb is eluted from the resin using 100 mM sodium citrate pH 3.0 and then exchanged into 1×dPBS using 7K Zeba desalting columns. 10× molar excess of H2bp18c6-off Macrocycle-pentyl sulfide-DBCO was reacted with site specific azide-PSMB127 (DOL=2) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific H2bp18c6-off Macrocycle-pentyl sulfide-DBCO-PSMB127 conjugate with CAR=2. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 µL.

Labeling:

To a solution of NaOAc (3 M in H$_2$O, 10 µL) in a plastic vial was added sequentially $^{225}$Ac(NO$_3$)$_3$ (~5 mCi/mL in 0.1 N HCl, 10 µL, 0.047 mCi) and H2bp18c6-off Macrocycle-pentyl sulfide-DBCO-PSMB127 (site specific, CAR=2, 2.8 mg/mL in PBS buffer solution, 8 µL, 22 µg). After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Purification:

The reaction mixture was purified on a PD-10 column: The PD-10 resin was conditioned in NaOAc buffer solution by passing 5 mL×3 of NaOAc buffer (10 mM, pH 6-6.5) through column and discarding the washings. The entire reaction mixture was applied to the reservoir of the column and the eluate collected in pre-numbered plastic tubes. The reaction vial was washed with 0.2 mL×3 NaOAc buffer (10 mM, pH 6-6.5) solution and the washings pipetted into the reservoir of the PD-10 column and the eluate collected. Each tube contained ~1 mL of the eluate. Continued application of NaOAc buffer (10 mM, pH 6-6.5) into the reservoir of the PD-10 column occurred until a total elution volume of 10 mL was reached.

DTPA Challenge:

10 µL of fraction #3 collected after PD-10 column was mixed with 15 µL of 10 mM DTPA solution (pH 6.5), and incubated for 30 min. 10 µL of the mixture was loaded onto an iTLC-SG, which was developed with 10 mM EDTA and dried overnight. It was scanned on a Bioscan AR-2000 radio-TLC scanner. Under the conditions described herein, free Ac-225 migrates with the solvent to the solvent front. No radioactivity signal was observed at the solvent front of the iTLC-SG indicating that there was no free Ac-225 in the fraction #3.

HPLC Analysis:

The fraction #3 collected after PD-10 column was analyzed by HPLC. HPLC method: Tosoh TSKgel G3000SWxl 7.8 mm×30 cm, 5 µm column; column temperature: room temperature; the column was eluted with DPBS buffer (×1, without calcium and magnesium); flow rate: 0.7 mL/min; 20 min run; injection volume: 40 µL. After HPLC, the fractions were collected in time intervals of 30 seconds or 1 minute. The collected HPLC fractions were left at room temperature overnight. The radioactivity in each of the collected fractions was counted in a gamma counter. The HPLC radio trace was constructed from the radioactivity in each HPLC fraction. HPLC radio trace showed a radioactive peak corresponding to the H2bp18c6-off Macrocycle-pentyl sulfide-DBCO-PSMB127 peak on HPLC UV trace.

Example 16: Preparation of DOTA-DBCO-H11B6 (Site Specific) and $^{225}$Ac(III) Labeling Scheme 19. Direct chelation of $^{225}$Ac(III) to DOTA-H11b6 (site specific, formed by click reaction of DOTA-DBCO to Site Specific azide-H11B6)

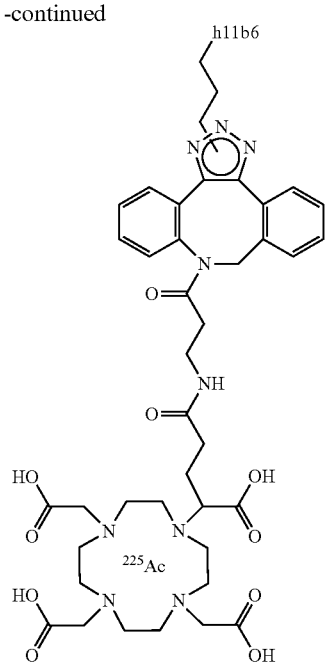

Azide Modification of mAb and Click Reaction:

H11B6 was site-selectively modified with 200× molar excess of 3-azido propylamine and microbial transglutaminase (MTG; Activa TI) at 37° C. The addition of two azides on the heavy chains of the mAb was monitored by intact mass ESI-TOF LC-MS on an Agilent G224 instrument. Excess 3-azido propylamine and MTG was purified away using a 1 ml GE Healthcare MabSelect column. Azido-mAb is eluted from the resin using 100 mM sodium citrate pH 3.0 and then exchanged into 1×dPBS using 7K Zeba desalting columns. 10× molar excess of DOTA-DBCO was reacted with site specific azide-H11B6 (DOL=1.94) in 1×dPBS at 37° C. for 1 hour without shaking. Completion of the DBCO-azide click reaction was monitored by intact mass spectrometry. Excess free chelator was removed by desalting the conjugate over a Zeba 7K desalting column into 1×dPBS followed by three sequential 15× dilution and concentration steps in PBS using a 30K MWCO Amicon concentrator device by spinning at 3800×g. This provided the final site specific DOTA-DBCO-H11B6 conjugate with CAR=1.94. The final conjugate was confirmed to be monomeric by analytical size exclusion chromatography on a Tosoh TSKgel G3000SWxl 7.8 mm×30 cm, 5 u column; column temperature: room temperature; the column was eluted with DPBS buffer (×1, without calcium and magnesium); flow rate: 0.7 mL/min; 18 min run; injection volume: 18 μL.

Labeling with the Ratio of H11B6:

Ac-225 at 50:1: To a solution of NaOAc (3 Min H$_2$O, 10 μL) in a plastic vial was added sequentially $^{225}$Ac(NO$_3$)$_3$ (~10 mCi/mL in 0.1 N HCl, 5 μL) and DOTA-H11B6 (site specific, CAR=1.94, 2.4 mg/mL in PBS buffer solution, 12.5 μL, 30 μg). The ratio of H11B6:Ac-225 is 50:1. After mixing, the pH was ~6.5 by pH paper. The reaction solution was left standing still at 37° C. for 2 h. 0.5 μL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. 21% radioactivity signal was observed at the solvent front of the iTLC-SG indicating that 79% Ac-225 was chelated in the reaction solution after 2 h.

Example 17: Labeling DOTA-DBCO-H11B6 (Random Conjugation) with $^{225}$Ac(III) Targeting Various SA Scheme 20. Direct chelation of $^{225}$Ac(III) to DOTA-H11B6 (random site)

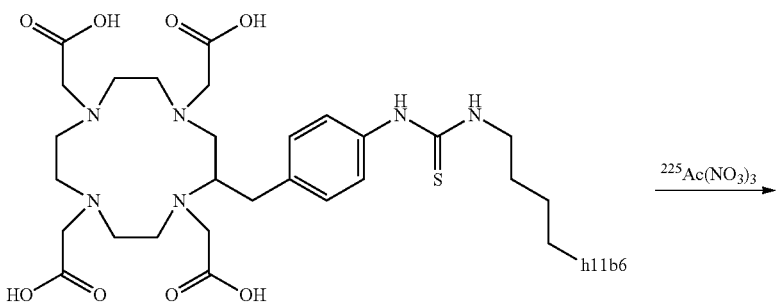

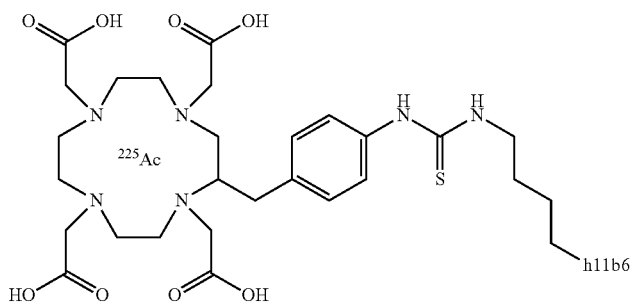

Labeling with the ratio of H11B6:Ac-225 at 880:1: To a solution of NaOAc (3 M in H$_2$O, 20 µL) in a plastic vial was added sequentially $^{225}$Ac(NO$_3$)$_3$ (~10 mCi/mL in 0.1 N HCl, 5 µL), DOTA-H11B6 (random conjugate, CAR~2.5, 10 mg/mL in 25 mM acetate buffer solution, pH 5.5, 50 µL, 500 µg) and NaOH solution (0.1 M, 2 µL). The ratio of H11B6:Ac-225 is 880:1. After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Labeling with the ratio of H11B6: Ac-225 at 440:1: To a solution of NaOAc (3 M in H$_2$O, 20 µL) in a plastic vial was added sequentially $^{225}$Ac(NO$_3$)$_3$ (~10 mCi/mL in 0.1 N HCl, 5 µL), DOTA-H11B6 (random conjugate, CAR~2.5, 10 mg/mL in 25 mM acetate buffer solution, pH 5.5, 25 µL, 250 µg) and NaOH solution (0.1 M, 1 µL). The ratio of H11B6:Ac-225 is 440:1. After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. No radioactivity signal was observed at the solvent front of the iTLC-SG indicating that all Ac-225 was fully chelated in the reaction solution after 2 h.

Labeling with the ratio of H11B6: Ac-225 at 220:1: To a solution of NaOAc (3 M in H$_2$O, 20 µL) in a plastic vial was added sequentially $^{225}$Ac(NO$_3$)$_3$ (~10 mCi/mL in 0.1 N HCl, 5 µL), DOTA-H11B6 (random conjugate, CAR~2.5, 10 mg/mL in 25 mM acetate buffer solution, pH 5.5, 12.5 µL, 125 µg) and NaOH solution (0.1 M, 1 µL). The ratio of H11B6:Ac-225 is 220:1. After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. 5% radioactivity signal was observed at the solvent front of the iTLC-SG indicating that 95% Ac-225 was chelated in the reaction solution after 2 h.

Labeling with the Ratio of H11B6:

Ac-225 at 110:1: To a solution of NaOAc (3 M in $H_2O$, 10 µL) in a plastic vial was added sequentially $^{225}Ac(NO_3)_3$ (~10 mCi/mL in 0.1 N HCl, 5 µL), DOTA-H11B6 (random conjugate, CAR~2.5, 10 mg/mL in 25 mM acetate buffer solution, pH 5.5, 6.25 µL, 62.5 µg) and NaOH solution (0.1 M, 1 µL). The ratio of H11B6:Ac-225 is 110:1. After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. 71% radioactivity signal was observed at the solvent front of the iTLC-SG indicating that 29% Ac-225 was chelated in the reaction solution after 2 h.

Labeling with the Ratio of H11B6:

Ac-225 at 55:1: To a solution of NaOAc (3 M in $H_2O$, 10 µL) in a plastic vial was added sequentially $^{225}Ac(NO_3)_3$ (~10 mCi/mL in 0.1 N HCl, 5 µL) DOTA-H11B6 (random conjugate, CAR~2.5, 10 mg/mL in 25 mM acetate buffer solution, pH 5.5, 3.13 µL, 31.3 µg) and NaOH solution (0.1 M, 1 µL). The ratio of H11B6:Ac-225 is 55:1. After mixing, the pH was ~6.5 by pH paper. The reaction solution was left standing still at 37° C. for 2 h. 0.5 µL of reaction mixture was then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. 64% radioactivity signal was observed at the solvent front of the iTLC-SG indicating that 36% Ac-225 was chelated in the reaction solution after 2 h.

Conclusion: Examples 9, 16 and 17 demonstrated that the DOTA containing chelators have poorer actinium chelation efficacy compared to the H2bp18c6 containing chelators.

Example 18: Synthesis of H2bp18c6-Cis-Cyclopentyl-Fused Macrocycle and $^{225}Ac(III)$ Chelation

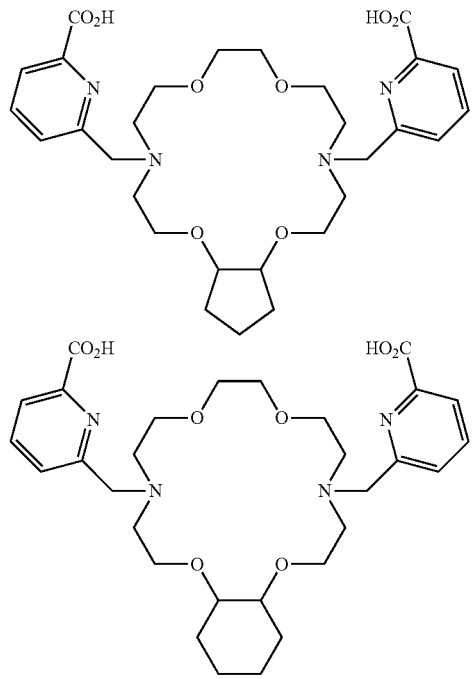

The above H2bp18c6 derivatives having ring fusion on the macrocyclic ring are synthesized generally according to Scheme 21 below:

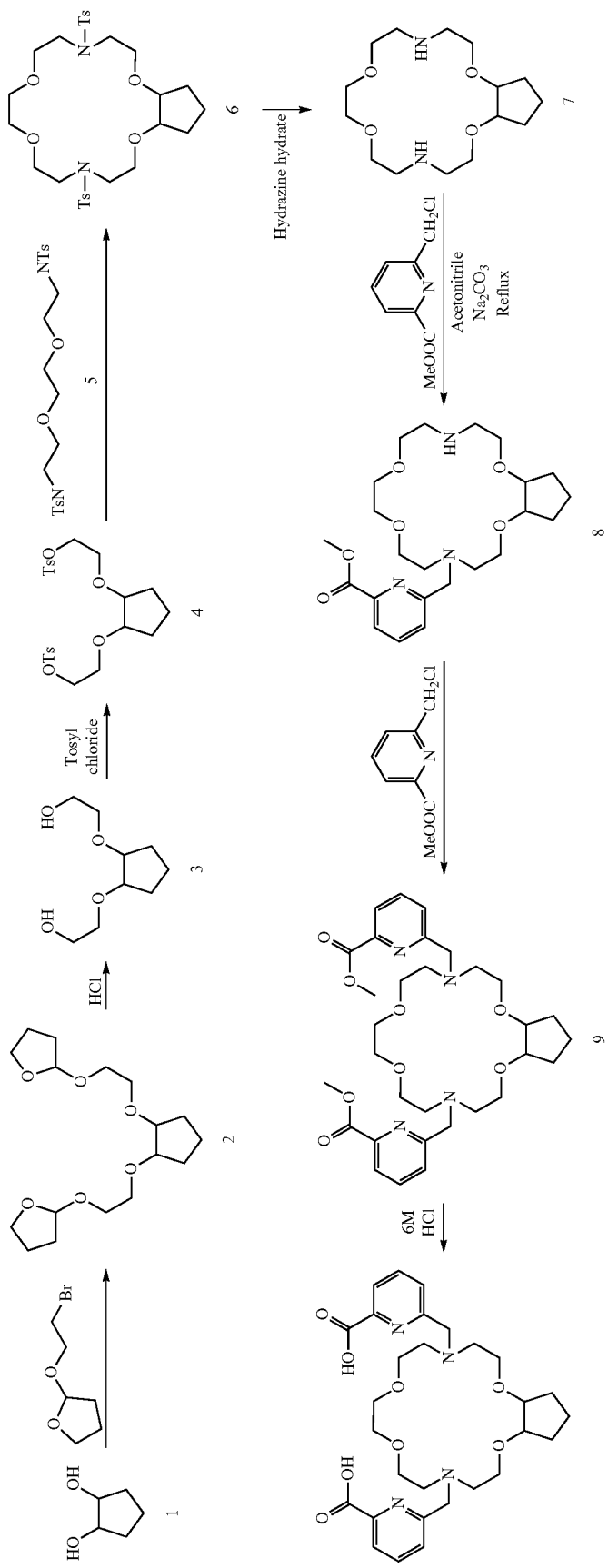
Scheme 21: Synthesis of H2bp18c6 Fused Ring Derivatives

A linker for conjugation to a targeting ligand can be introduced at, for example, the "benzylic" position by reacting intermediate 7 with methyl 6-(bromo(4-(tert-butoxycarbonyl)phenyl)methyl)picolinate as described above with respect to Schemes 3 and 4. Cyclopentane 1,2-diol (compound 1) can be replaced with cyclohexane 1,2-diol to obtain the H2bp18c6 derivative having cyclohexyl ring fusion.

Next, the synthesis of H2bp18c6-cis-cyclopentyl-fused Macrocycle is described.

Scheme 22. Synthesis of H2bp18c6-cis-cyclopentyl-fuesd Macrocycle

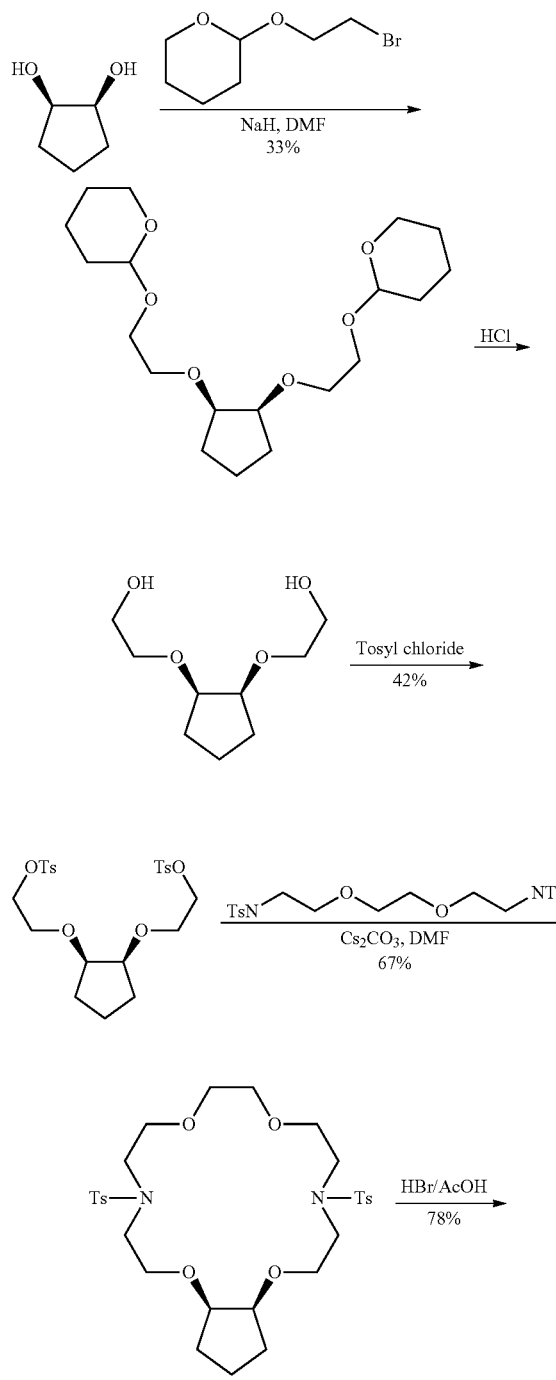

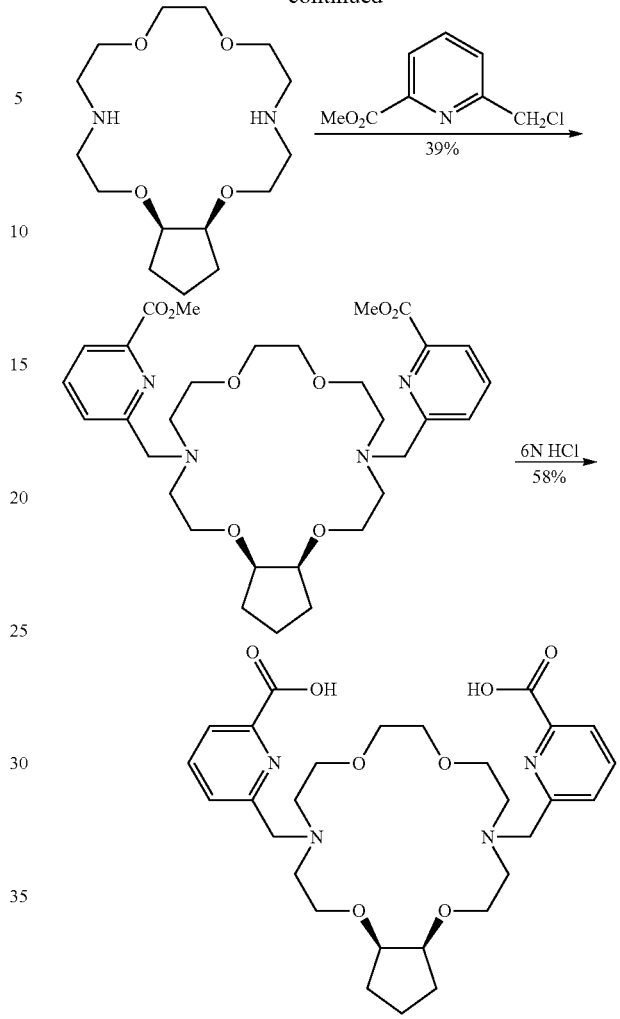

To a suspension of sodium hydride (5.63 g, 60% in mineral oil, 147.05 mmol) in DMF (30 mL) was added (1R,2S)-cyclopentane-1,2-diol (3.0 g, 29.41 mmol) in DMF (30 mL) dropwise at 0° C. The reaction mixture was allowed to stir at room temperature for 2 h. It was cooled again to 0° C. and 2-(2-bromoethoxy)tetrahydro-2H-pyran (18.44 g, 88.23 mmol) in DMF (30 mL) was added dropwise. The reaction mixture was allowed to reach room temperature and stirred for 16 h. The reaction was quenched with saturated ammonium chloride and extracted with ethyl acetate (3×500 mL). Combined organic layer was washed with water, dried over sodium sulfate, filtered and concentrated. The crude oil was purified by silica gel (230-400 mesh) flash chromatography using ethyl acetate in petroleum ether (0-40%) to give (1R,2S)-1,2-bis(2-((tetrahydro-2H-pyran-2-yl)oxy)ethoxy)cyclopentane (3.5 g, 33%) as a colorless liquid.

To a solution of (1R,2S)-1,2-bis(2-((tetrahydro-2H-pyran-2-yl)oxy)ethoxy)cyclopentane (3.5 g, 9.77 mmol) in 100 mL of methanol was added 1 mL of HCl in dioxane, stirred at reflux for 1 h, cooled, and evaporated to give 2,2'-(((1R, 2S)-cyclopentane-1,2-diyl)bis(oxy))bis(ethan-1-ol) (2.0 g), which was used in the next step without purification.

To a solution of 2,2'-(((1R,2S)-cyclopentane-1,2-diyl)bis (oxy))bis(ethan-1-ol) 2 (2.0 g, 10.52 mmol) in dichloromethane (50 mL) and triethylamine (7.60 mL, 52.63 mmol) at 10° C., was added p-toluene sulfonyl chloride (6.0 g, 31.56 mmol) portion wise. The mixture was stirred at ambient temperature for 16 h. After completion of reaction, the suspension was diluted with 200 mL of dichloromethane, washed with cold 1 M HCl (3×100 mL), followed by ice-cold water (2×100 mL), dried over sodium sulfate, and evaporated to yield a solid gum. The crude material was purified by flash chromatography (silica gel, 230-400 mesh) using ethyl acetate in petroleum ether (0-40%) to give (((1R,2S)-cyclopentane-1,2-diyl)bis(oxy))bis(ethane-2,1-diyl) bis(4-methylbenzenesulfonate) (2.2 g, 42%) as a colorless liquid.

A mixture of (((1R,2S)-cyclopentane-1,2-diyl)bis(oxy))bis(ethane-2,1-diyl) bis(4-methylbenzenesulfonate) (2.2 g, 4.42 mmol) and cesium carbonate (4.32 g, 13.25 mmol) in 50 mL of dry DMF was stirred for 1.5 h at ambient temperature. To the suspension, was added 1,2-bis(2-(tosyl-λ²-azaneyl)ethoxy)ethane (2.06 g, 4.42 mmol) in 50 mL of DMF dropwise over a period of 2 h. The mixture was stirred for additional 20 h at ambient temperature. The solvent was removed under reduced pressure to obtain a solid paste. This was suspended in 200 mL of dichloromethane and stirred for 30 min. The precipitated solids were filtered off and the filtrate was evaporated at high vacuum. The crude material was purified by flash chromatography (silica gel, 230-400 mesh) using ethyl acetate in petroleum ether (0-40%) to give (16aR,19aS)-4,13-ditosyltetradecahydro-2H,11H,17H-cyclopenta[b][1,4,10,13]tetraoxa[7,16]diazacyclooctadecine (1.8 g, 67%) as a colorless liquid.

To a solution of (16aR,19aS)-4,13-ditosyltetradecahydro-2H,11H,17H-cyclopenta[b][1,4,10,13]tetraoxa[7,16]diazacyclooctadecine (1.8 g, 2.95 mmol) in hydrobromic acid in acetic acid (50%, 10 mL) was added phenol (1.38 g, 14.75 mmol) at room temperature. The reaction was heated at 60° C. for 6 h. After completion of the reaction, it was cooled to room temperature and acetic acid was removed under high vacuum. The residue was purified by reverse phase column purification using 0-100% acetonitrile in water (0.1% TFA) to yield (16aR,19aS)-tetradecahydro-2H,11H,17H-cyclopenta[b][1,4,10,13]tetraoxa[7,16]diazacyclooctadecine (0.7 g, 78%) as a colorless liquid.

A suspension of (16aR,19aS)-tetradecahydro-2H,11H,17H-cyclopenta[b][1,4,10,13]tetraoxa[7,16]diazacyclooctadecine (0.7 g, 2.32 mmol), methyl 6-(chloromethyl)picolinate (1.73 g, 5.80 mmol) and sodium carbonate (0.74 g, 6.96 mmol) in dry acetonitrile (10 mL) was heated at 90° C. for 16 h. After completion of the reaction, reaction mixture was cooled to room temperature, filtered through Celite and concentrated under reduced pressure. The crude material was purified by flash chromatography (silica gel, 230-400 mesh) using methanol in dichloromethane (0-10%) to give dimethyl 6,6'-(((16aR,19aS)-tetradecahydro-4H,13H,17H-cyclopenta[b][1,4,10,13]tetraoxa[7,16]diazacyclooctadecine-4,13-diyl)bis(methylene))dipicolinate (0.55 g, 39%) as a brown liquid.

A solution of dimethyl 6,6'-(((16aR,19aS)-tetradecahydro-4H,13H,17H-cyclopenta[b][1,4,10,13]tetraoxa[7,16]diazacyclooctadecine-4,13-diyl)bis(methylene))dipicolinate (0.55 g, 0.92 mmol) in 6N hydrochloric acid (5 mL) was heated at 80° C. for 5 h. After completion of reaction, the reaction mixture was concentrated under reduced pressure. The crude was purified by preparative HPLC to yield H2bp18c6-cis-cyclopentyl-fused Macrocycle (0.3 g, 58%) as a colorless gummy solid. LC-MS APCI: Calculated for C29H40N4O8 572.66; Observed m/z [M+H]$^+$ 572.9. Purity by LC-MS: 99.27% RT: 1.17. Purity by HPLC: 99.05% RT: 2.12. $^1$H NMR (400 MHz, DMSO-d$_6$): δ 7.86-7.84 (m, 4H), 7.59-7.56 (m, 2H), 3.80 (s, 4H), 3.60-3.49 (m, 10H), 3.44-3.41 (m, 4H), 2.75-2.68 (m, 8H), 1.57-1.47 (m, 6H).

Scheme 23. Chelation of H2bp18c6-cis-cyclopentyl-fused Marcocycle with $^{225}$Ac(III)

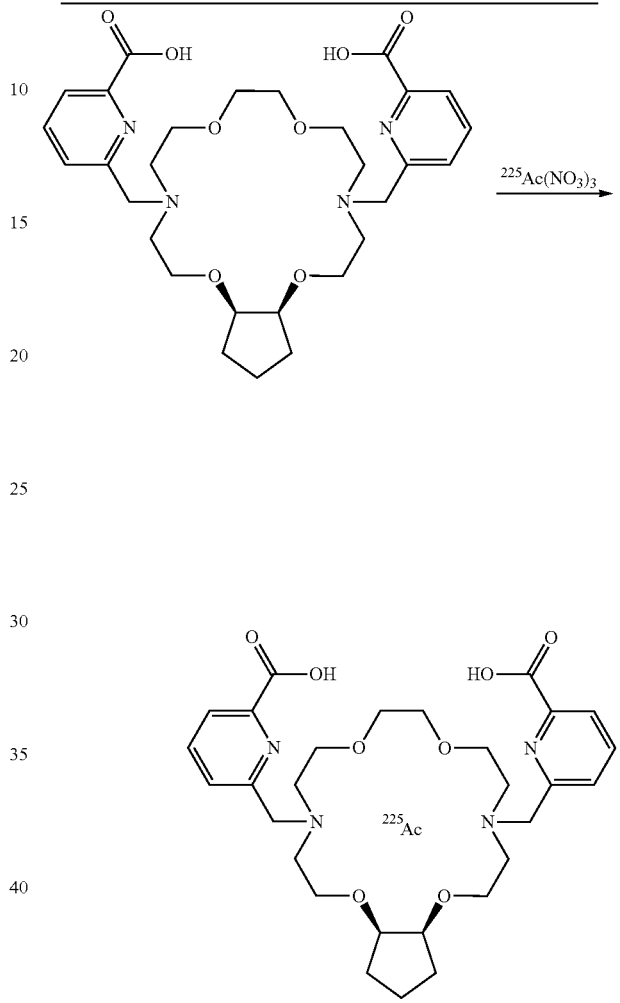

Chelation with $^{225}$Ac(II):

Tetramethylammonium acetate (1M, 10 µL), H2bp18c6-cis-cyclopentyl-fused Macrocycle (2 mg/mL in water, 3 µL), $^{225}$Ac(NO$_3$)$_3$ in 0.1 N HCl (10 mCi/mL, 3 µL, 30 µCi) were added to a plastic vial sequentially. The pH was ~6.5 by pH paper. The vial was put on a heat at 37° C. for 2 h.

0.5 µL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 µL of reaction mixture was mixed with 15 µL 10 mM DTPA (pH 6.5) and incubated for 30 min. 10 µL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 19: Synthesis of H2bp18c6-Trans-Cyclopentyl-Fused Macrocycle and $^{225}$Ac(III) Chelation

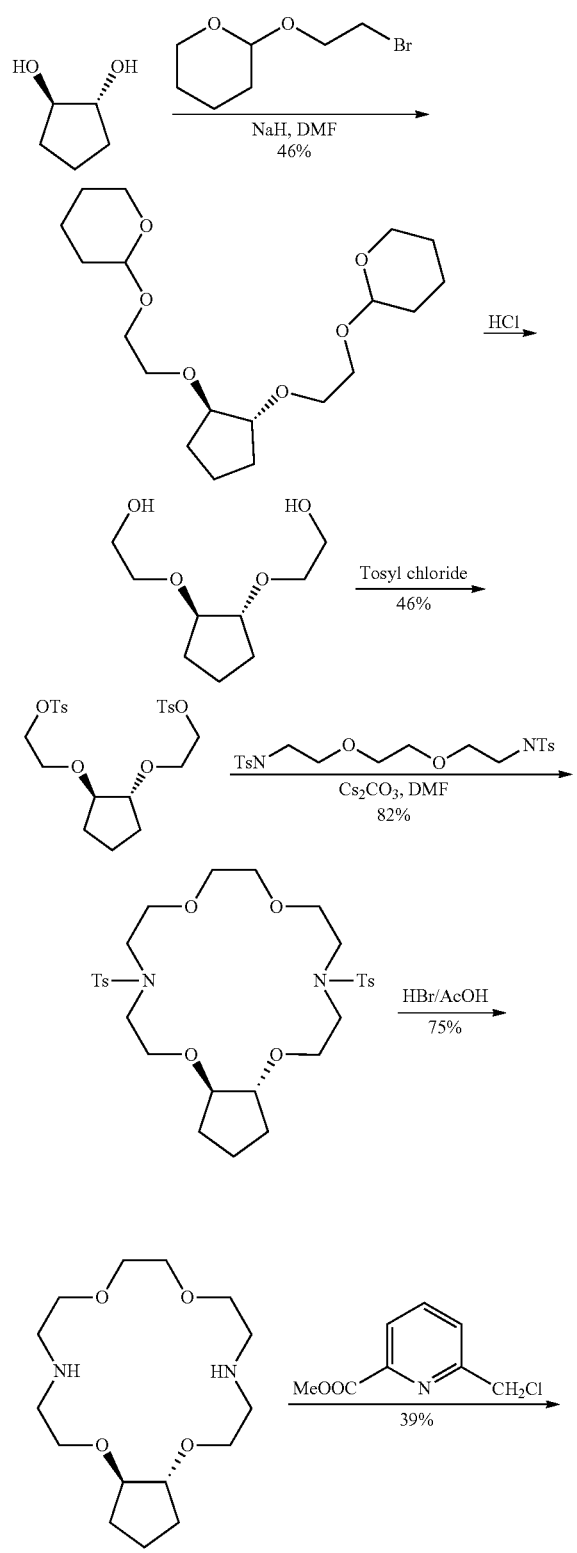

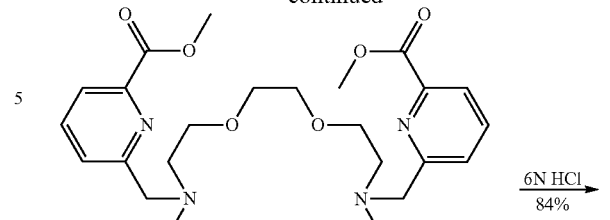

To a suspension of sodium hydride (5.63 g, 60% in mineral oil, 147.05 mmol) in DMF (30 mL) was added (1R,2R)-cyclopentane-1,2-diol (3.0 g, 29.41 mmol) in DMF (30 mL) dropwise at 0° C. The reaction mixture was allowed stir at room temperature for 2 h. It was cooled again to 0° C., added 2-(2-bromoethoxy)tetrahydro-2H-pyran (18.44 g, 88.23 mmol) in DMF (30 mL) dropwise. The reaction mixture was allowed to reach room temperature and stirred for 16 h. Reaction was quenched with saturated ammonium chloride and extracted with ethyl acetate (3×500 mL). Combined organic layer was washed with water, dried over sodium sulfate, filtered and concentrated. The crude oil was purified by silica gel (230-400 mesh) flash chromatography using ethyl acetate in petroleum ether (0-40%) to yield (1R,2R)-1,2-bis(2-((tetrahydro-2H-pyran-2-yl)oxy)ethoxy)cyclopentane (4.8 g, 46%) as a colorless liquid.

To a solution of (1R,2R)-1,2-bis(2-((tetrahydro-2H-pyran-2-yl)oxy)ethoxy)cyclopentane (4.8 g, 13.40 mmol) in 100 mL of methanol was added 1 mL of HCl in dioxane, stirred at reflux for 1 h, cooled, and evaporated to give 2'-(((1R,2R)-cyclopentane-1,2-diyl)bis(oxy))bis(ethan-1-ol) (2.9 g), which was used in the next step without purification.

To 2'-(((1R,2R)-cyclopentane-1,2-diyl)bis(oxy))bis(ethan-1-ol) (2.9 g, 10.52 mmol) in dichloromethane (50 mL) and triethylamine (11.03 mL, 76.31 mmol) at 10° C. was added p-toluene sulfonyl chloride (8.70 g, 45.78 mmol) portion wise. The mixture was stirred at ambient temperature for 16 h. After completion of reaction, the suspension was diluted with 200 mL of dichloromethane, washed with cold 1 M HCl (3×100 mL), followed by ice-cold water (2×100), dried over sodium sulphate, and evaporated to give a solid gum. The crude material was purified by flash chromatography (silica gel, 230-400 mesh) using ethyl acetate in petroleum ether (0-40%) to yield (((1R,2R)- cyclopentane-1,2-diyl)bis(oxy))bis(ethane-2,1-diyl) bis(4-methylbenzenesulfonate) (3.5 g, 46%) as a colorless liquid.

A mixture of (((1R,2R)-cyclopentane-1,2-diyl)bis(oxy)) bis(ethane-2,1-diyl) bis(4-methylbenzenesulfonate) (3.5 g, 7.03 mmol) and cesium carbonate (6.87 g, 21.08 mmol) in 50 mL of dry DMF was stirred for 1.5 h at ambient temperature. To the suspension, was added 1,2-bis(2-(tosyl-λ²-azaneyl)ethoxy)ethane ((3.19 g, 7.03 mmol) in 50 mL of DMF dropwise over a period of 2 h. The mixture was stirred for additional 20 h at ambient temperature. The solvent was removed under reduced pressure to obtain a solid paste. This was suspended in 200 mL of dichloromethane and stirred for 30 min. The precipitated solids were filtered off and the filtrate was evaporated at high vacuum. The crude material was purified by flash chromatography (silica gel, 230-400 mesh) using ethyl acetate in petroleum ether (0-40%) to yield (16aR,19aR)-4,13-ditosyltetradecahydro-2H,11H,17H-cyclopenta[b][1,4,10,13]tetraoxa[7,16]diazacyclooctadecine (3.5 g, 82%) as a colorless liquid.

To a solution of (16aR,19aR)-4,13-ditosyltetradecahydro-2H,11H,17H-cyclopenta[b][1,4,10,13]tetraoxa[7,16]diazacyclooctadecine (3.5 g, 5.73 mmol) in hydrobromic acid in acetic acid (50%, 15 mL) was added phenol (2.70 g, 28.68 mmol) at room temperature. The reaction was heated at 60° C. for 6 h. After completion of the reaction, it was cooled to room temperature and acetic acid was removed under high vacuum. The crude material was purified by reverse phase column purification using 0-100% acetonitrile in water (0.1% TFA) to yield (16aR,19aR)-tetradecahydro-2H,11H,17H-cyclopenta[b][1,4,10,13]tetraoxa[7,16]diazacyclooctadecine (1.3 g, 75%) as a colorless liquid.

A suspension of (16aR,19aS)-tetradecahydro-2H,11H,17H-cyclopenta[b][1,4,10,13]tetraoxa[7,16]diazacyclooctadecine (1.3 g, 4.30 mmol), methyl 6-(chloromethyl)picolinate (1.99 g, 10.76 mmol) and sodium carbonate (1.37 g, 12.90 mmol) in dry acetonitrile (20 mL) was heated at 90° C. for 16 h. After completion of the reaction, the reaction mixture was cooled to room temperature, filtered through Celite and concentrated under reduced pressure. The crude material was purified by flash chromatography (silica gel, 230-400 mesh) using methanol in dichloromethane (0-10%) to yield dimethyl 6,6'-(((16aR,19aR)-tetradecahydro-4H,13H,17H-cyclopenta[b][1,4,10,13]tetraoxa[7,16]diazacyclooctadecine-4,13-diyl)bis(methylene))dipicolinate (1.0 g, 39%) as a brown liquid.

A solution of dimethyl 6,6'-(((16aR,19aR)-tetradecahydro-4H,13H,17H-cyclopenta[b][1,4,10,13]tetraoxa[7,16] diazacyclooctadecine-4,13-diyl)bis(methylene))dipicolinate (1.0 g, 1.66 mmol) in 6N hydrochloric acid (10 mL) was heated at 80° C. for 5 h. After completion of reaction, the reaction mixture was concentrated under reduced pressure. The crude was purified by preparative HPLC to give H2bp18c6-trans-cyclopentyl-fused Macrocycle (0.8 g, 84%) as a colorless gummy solid. LC-MS APCI: Calculated for C29H40N4O8 572.66; Observed m/z [M+H]⁺ 573.0. Purity by LC-MS: 96.10% RT: 1.18. Purity by HPLC: 97.77% RT: 2.29. ¹H NMR (400 MHz, DMSO-d₆): δ 13.42 (s, 1H), 9.70 (s, 1H), 8.15-8.09 (m, 4H), 7.80-7.78 (m, 2H), 4.69 (s, 4H), 3.93-3.55 (m, 22H), 1.90-1.85 (m, 2H), 1.57-1.52 (m, 2H), 1.46-1.39 (m, 2H).

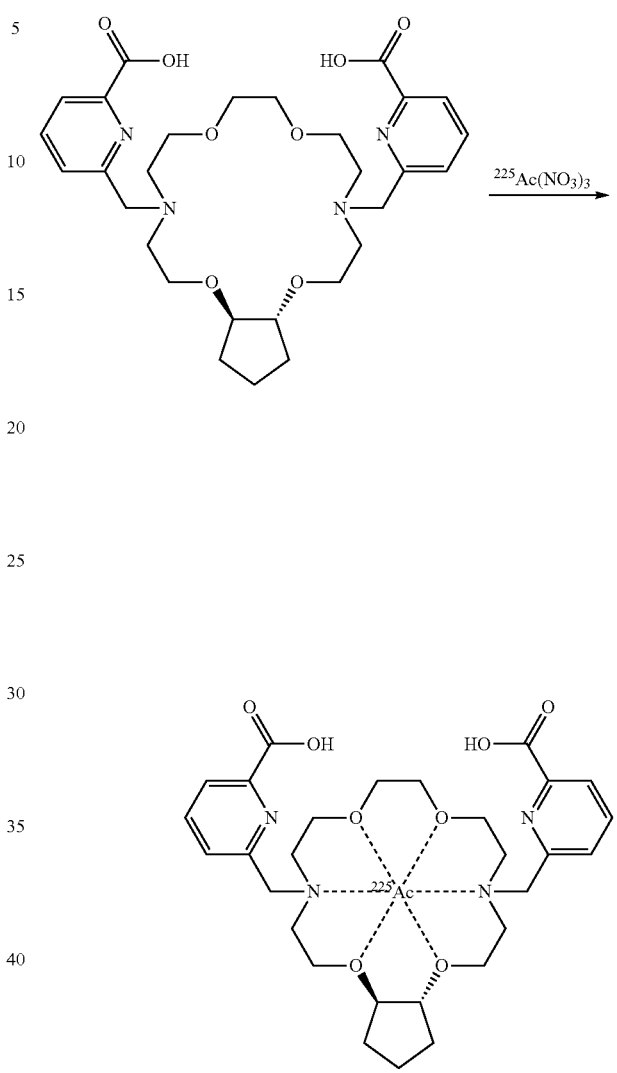

Scheme 25. Chelation of H2bp18c6-trans-cyclopentyl-fused Macrocycle with ²²⁵Ac(III)

Chelation with ²²⁵Ac(III):

Tetramethylammonium acetate (1M, 10 µL), H2bp18c6-trans-cyclopentyl-fused Macrocycle (2 mg/mL in water, 3 µL), ²²⁵Ac(NO₃)₃ in 0.1 N HCl (10 mCi/mL, 3 µL, 30 µCi) were added to a plastic vial sequentially. The pH was ~6.5 by pH paper. The vial was put on a heat at 37° C. for 2 h.

0.5 µL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 µL of reaction mixture was mixed with 15 µL 10 mM DTPA (pH 6.5) and incubated for 30 min. 10 µL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 20: Synthesis of H2bp18c6-Cis-Cyclohexyl-Fused Macrocycle and $^{225}$Ac(III) Chelation

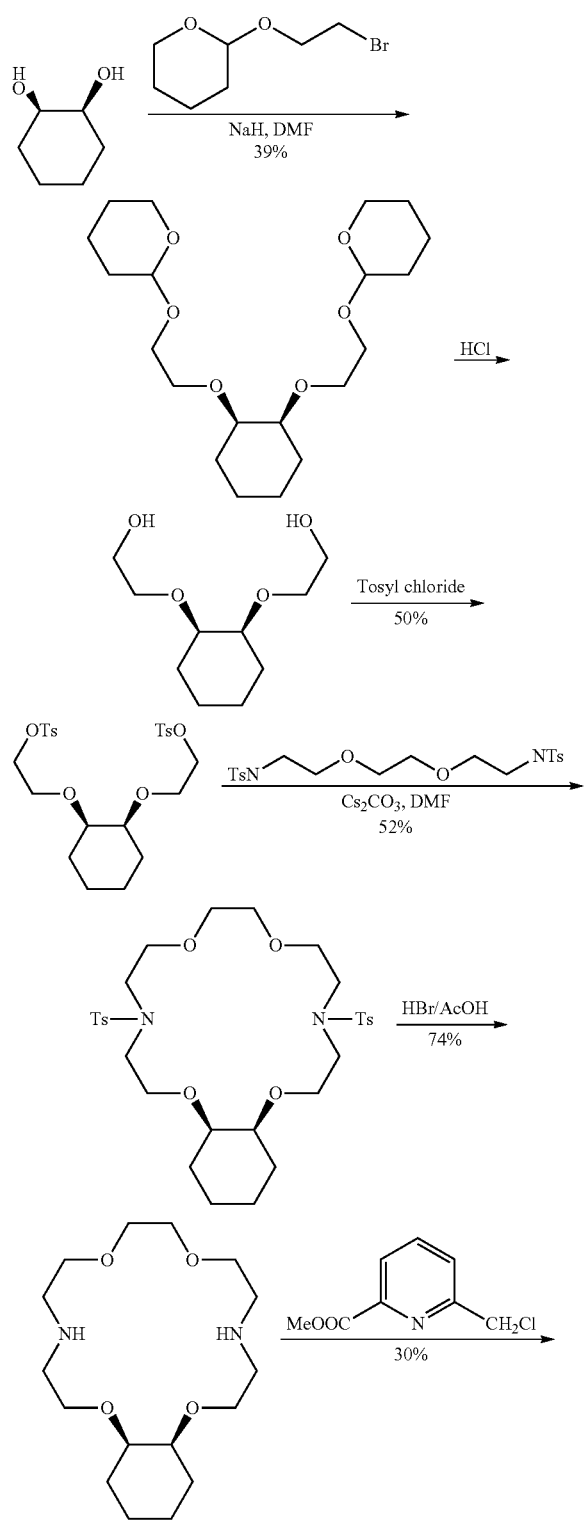

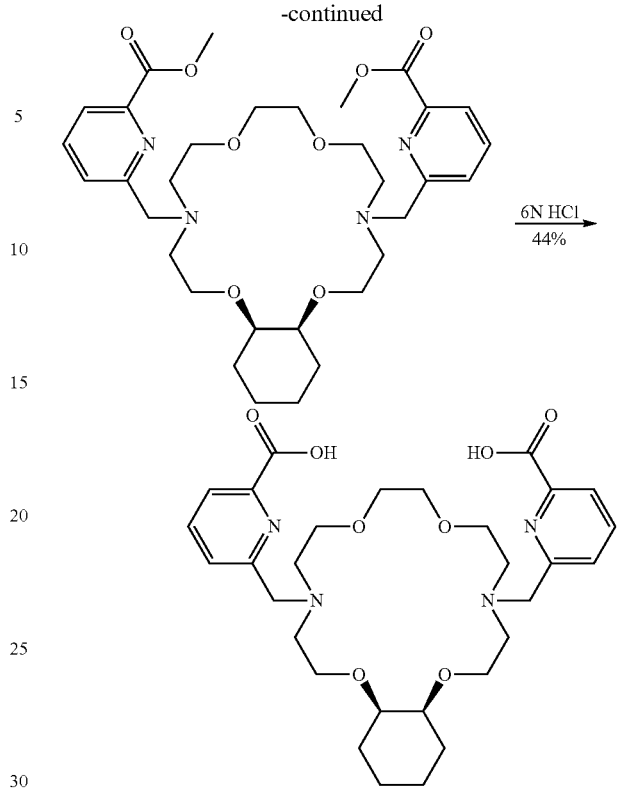

To a suspension of sodium hydride (3.3 g, 60% in mineral oil, 86.20 mmol) in DMF (20 mL) was added (1R,2S)-cyclohexane-1,2-diol (2.0 g, 17.24 mmol) in DMF (20 mL) dropwise at 0° C. The reaction mixture was allowed to stir at room temperature for 2 h. It was cooled again to 0° C. and 2-(2-bromoethoxy)tetrahydro-2H-pyran (10.81 g, 51.72 mmol) in DMF (20 mL) was added dropwise. The reaction mixture was allowed to reach room temperature and stirred for 16 h. The reaction was quenched with saturated ammonium chloride and extracted with ethyl acetate (3×500 mL). The combined organic layer was washed with water, dried over sodium sulfate, filtered and concentrated. The crude oil was purified by silica gel (230-400 mesh) flash chromatography using ethyl acetate in petroleum ether (0-40%) to give (1R,2S)-1,2-bis(2-((tetrahydro-2H-pyran-2-yl)oxy)ethoxy)cyclohexane (2.5 g, 39%) as a colorless liquid.

To a solution of 1R,2S)-1,2-bis(2-((tetrahydro-2H-pyran-2-yl)oxy)ethoxy)cyclohexane (2.5 g, 6.7 mmol) in 100 mL of methanol was added 1 mL of HCl in dioxane, stirred at reflux for 1 h, cooled, and evaporated. The crude 2,2'-(((1R,2S)-cyclohexane-1,2-diyl)bis(oxy))bis(ethan-1-ol) (1.5 g) was used in the next step without purification.

To a solution of 2,2'-(((1R,2S)-cyclohexane-1,2-diyl)bis(oxy))bis(ethan-1-ol) (1.5 g, 7.35 mmol) in dichloromethane (25 mL) and triethylamine (5.31 mL, 36.76 mmol) at 10° C. was added p-toluene sulfonyl chloride (4.20 g, 22.05 mmol) portion wise. The mixture was stirred at ambient temperature for 16 h. After completion of reaction, the suspension was diluted with 200 mL of dichloromethane, washed with cold 1 M HCl (3×100 mL), followed by ice-cold water (2×100), dried over sodium sulfate, and evaporated to give a solid gum. The crude material was purified by flash chromatography (silica gel, 230-400 mesh) using ethyl acetate in petroleum ether (0-40%) to yield (((1R,2S)- cyclohexane-1,2-diyl)bis(oxy))bis(ethane-2,1-diyl) bis(4-methylbenzenesulfonate) (1.9 g, 50%) as a colorless liquid.

A mixture of (((1R,2S)-cyclohexane-1,2-diyl)bis(oxy))bis(ethane-2,1-diyl) bis(4-methylbenzenesulfonate) (1.9 g, 3.71 mmol) and cesium carbonate (3.63 g, 11.13 mmol) in 50 mL of dry DMF was stirred for 1.5 h at ambient temperature. To the suspension was added 1,2-bis(2-(tosyl-$\lambda^2$-azaneyl)ethoxy)ethane (1.68 g, 3.71 mmol) in 50 mL of DMF dropwise over a period of 2 h. The mixture was stirred for additional 20 h at ambient temperature. The solvent was removed under reduced pressure to obtain a solid paste. This was suspended in 200 mL of dichloromethane and stirred for 30 min. The precipitated solids were filtered off and the filtrate was evaporated at high vacuum. The crude material was purified by flash chromatography (silica gel, 230-400 mesh) using ethyl acetate in petroleum ether (0-40%) to yield (16aR,20aS)-4,13-ditosylhexadecahydro-2H,11H-benzo[b][1,4,10,13]tetraoxa[7,16]diazacyclooctadecine (1.2 g, 52%) as a colorless liquid.

To a solution of (16aR,20aS)-4,13-ditosylhexadecahydro-2H,11H-benzo[b][1,4,10,13]tetraoxa[7,16]diazacyclooctadecine (1.2 g, 1.92 mmol) in hydrobromic acid in acetic acid (50%, 5 mL) was added phenol (0.9 g, 9.61 mmol) at room temperature. The reaction was heated at 60° C. for 6 h. After completion of the reaction, it was cooled to room temperature and acetic acid was removed under high vacuum. The residue was purified by reverse phase column purification using 0-100% acetonitrile in water (0.1% TFA) to yield (16aR,20aS)-hexadecahydro-2H,11H-benzo[b][1,4,10,13]tetraoxa[7,16]diazacyclooctadecine (0.45 g, 74%) as a colorless liquid.

A suspension of (16aR,20aS)-hexadecahydro-2H,11H-benzo[b][1,4,10,13]tetraoxa[7,16]diazacyclooctadecine (0.45 g, 1.42 mmol), methyl 6-(chloromethyl)picolinate (0.65 g, 3.56 mmol) and sodium carbonate (0.45 g, 4.26 mmol) in dry acetonitrile (10 mL) was heated at 90° C. for 16 h. The reaction mixture was cooled to room temperature, filtered through Celite and concentrated under reduced pressure. The crude material was purified by flash chromatography (silica gel, 230-400 mesh) using methanol in dichloromethane (0-10%) to yield dimethyl 6,6'-(((16aR,20aS)-hexadecahydro-4H,13H-benzo[b][1,4,10,13]tetraoxa[7,16]diazacyclooctadecine-4,13-diyl)bis(methylene))dipicolinate (0.26 g, 30%) as a brown liquid.

A solution of dimethyl 6,6'-(((16aR,20aS)-hexadecahydro-4H,13H-benzo[b][1,4,10,13]tetraoxa[7,16]diazacyclooctadecine-4,13-diyl)bis(methylene))dipicolinate (0.26 g, 0.42 mmol) in 6N hydrochloric acid (5 mL) was heated at 80° C. for 5 h. The reaction mixture was concentrated under reduced pressure. The residue was purified by preparative HPLC to get the product H2bp18c6-cis-cyclohexyl-fused Macrocycle (0.11 g, 44%) as off white solid. LC-MS APCI: Calculated for C30H42N4O8 586.69; Observed m/z [M+H]$^+$ 587.0. Purity by LC-MS: 98.15% RT: 1.31. Purity by HPLC: 97.78% RT: 2.32. $^1$H NMR (400 MHz, DMSO-d6): δ 13.35 (s, 1H), 9.84 (s, 1H), 8.15-8.09 (m, 4H), 7.80-7.78 (m, 2H), 4.70 (s, 4H), 3.97-3.54 (m, 22H), 1.70-1.23 (m, 8H).

Scheme 27. Chelation of H2bp18c6-cis-cyclohexyl-fused Macrocycle with $^{225}$Ac(III)

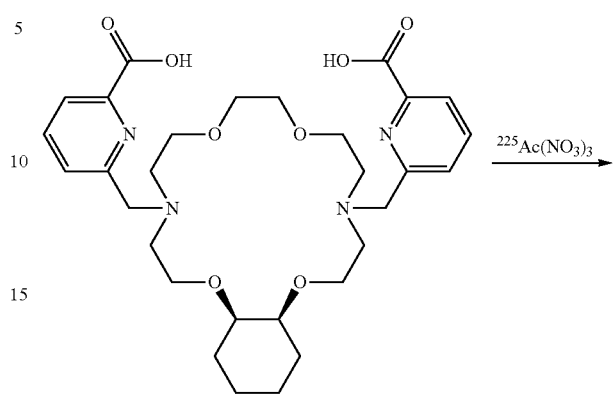

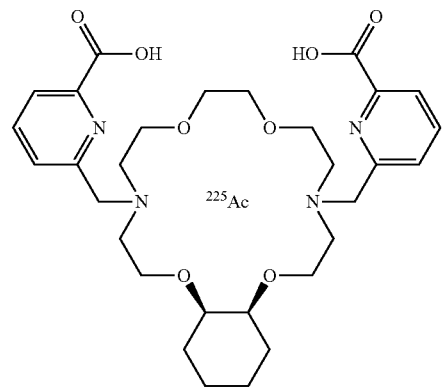

Chelation with $^{225}$Ac(I):

Tetramethylammonium acetate (1M, 10 µL), H2bp18c6-cis-cyclohexyl-fused Macrocycle (2 mg/mL in water, 3 µL), $^{225}$Ac(NO$_3$)$_3$ in 0.1 N HCl (10 mCi/mL, 3 µL, 30 µCi) were added to a plastic vial sequentially. The pH was ~6.5 by pH paper. The vial was put on a heat at 37° C. for 2 h.

0.5 µL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 µL of reaction mixture was mixed with 15 µL 10 mM DTPA (pH 6.5) and incubated for 30 min. 10 µL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 21: Synthesis of H2bp18c6-Trans-Cyclohexyl-Fused Macrocycle and $^{225}$Ac(III) Chelation Scheme 28. Synthesis of H2bp18c6-trans-cyclohexyl-fuesd Macrocycle

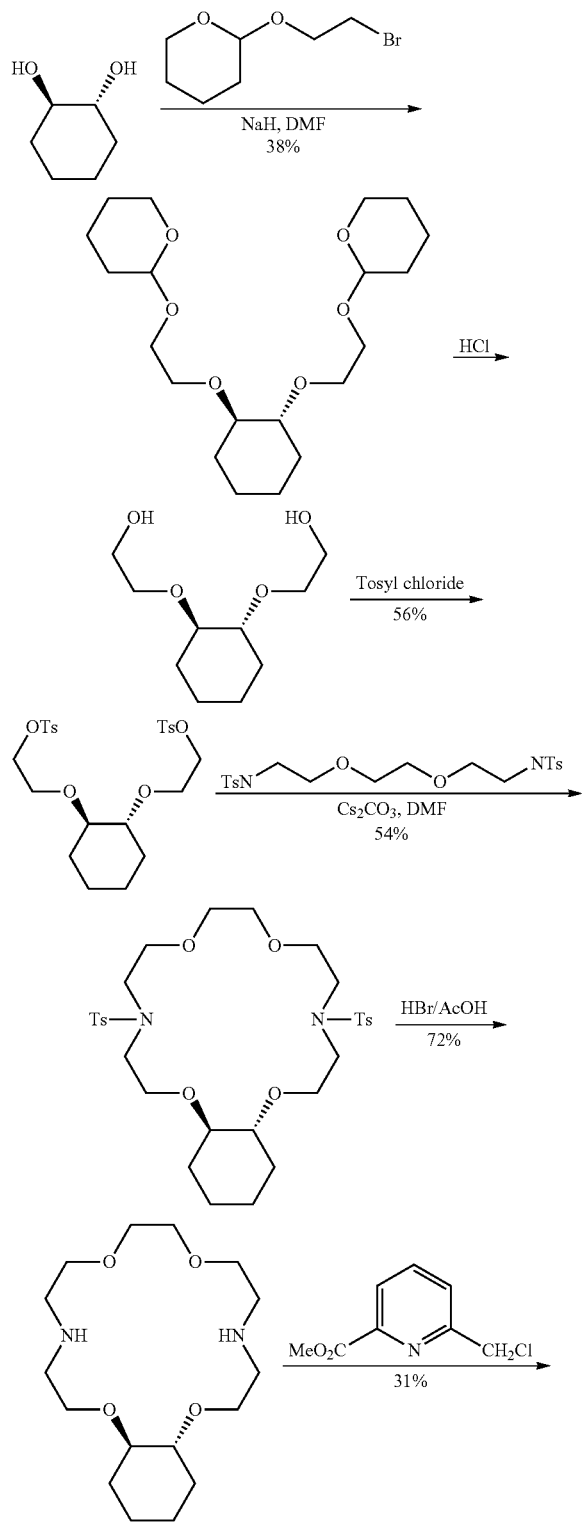

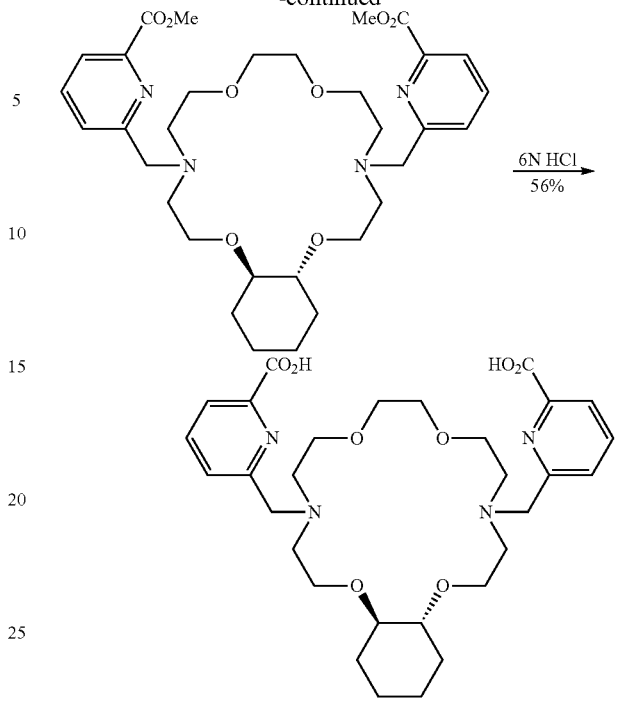

To a suspension of sodium hydride (3.3 g, 60% in mineral oil, 86.20 mmol) in DMF (20 mL) was added (1R,2R)-cyclohexane-1,2-diol (2.0 g, 17.24 mmol) in DMF (20 mL) dropwise at 0° C. The reaction mixture was allowed stir at room temperature for 2 h. It was cooled again to 0° C. and 2-(2-bromoethoxy)tetrahydro-2H-pyran (10.81 g, 51.72 mmol) in DMF (20 mL) was added dropwise. The reaction mixture was allowed to reach room temperature and stirred for 16 h. The reaction was quenched with saturated ammonium chloride and extracted with ethyl acetate (3×500 mL). The combined organic layer was washed with water, dried over sodium sulfate, filtered and concentrated. The crude oil was purified by silica gel (230-400 mesh) flash chromatography using ethyl acetate in petroleum ether (0-40%) to yield (1R,2R)-1,2-bis(2-((tetrahydro-2H-pyran-2-yl)oxy)ethoxy) cyclohexane (2.45 g, 38%) as a colorless liquid.

To a solution of (1R,2R)-1,2-bis(2-((tetrahydro-2H-pyran-2-yl)oxy)ethoxy)cyclohexane (2.45 g, 6.5 mmol) in 100 mL of methanol was added 1 mL of HCl in dioxane, stirred at reflux for 1 h, cooled, and evaporated. The crude 2,2'-(((1R,2R)-cyclohexane-1,2-diyl)bis(oxy))bis(ethan-1-ol) (1.5 g) was used in the next step without purification.

To a solution of 2,2'-(((1R,2R)-cyclohexane-1,2-diyl)bis(oxy))bis(ethan-1-ol) (1.5 g, 7.35 mmol) in dichloromethane (25 mL) and triethylamine (5.31 mL, 36.76 mmol) at 10° C. was added p-toluene sulfonyl chloride (4.20 g, 22.05 mmol) portion wise. The mixture was stirred at ambient temperature for 16 h. The suspension was diluted with a further 200 mL of dichloromethane, washed with cold 1 M HCl (3×100 mL), followed by ice-cold water (2×100 mL), dried over sodium sulfate, and evaporated to give a solid gum. The crude material was purified by flash chromatography (silica gel, 230-400 mesh) using ethyl acetate in petroleum ether (0-40%) to yield (((1R,2R)-cyclohexane-1,2-diyl)bis(oxy)) bis(ethane-2,1-diyl) bis(4-methylbenzenesulfonate) (2.1 g, 56%) as a colorless liquid.

A mixture of (((1R,2R)-cyclohexane-1,2-diyl)bis(oxy)) bis(ethane-2,1-diyl) bis(4-methylbenzenesulfonate) (2.1 g, 4.1 mmol) and cesium carbonate (4.01 g, 12.30 mmol) in 30 mL of dry DMF was stirred for 1.5 h at ambient temperature. To the suspension was added 1,2-bis(2-(tosyl-λ²-azaneyl)ethoxy)ethane (1.86 g, 4.1 mmol) in 30 mL of DMF dropwise over a period of 2 h. The mixture was stirred for additional 20 h at ambient temperature. The solvent was removed under reduced pressure to obtain a solid paste. This was suspended in 200 mL of dichloromethane and stirred for 30 min. The precipitated solids were filtered off and the filtrate was evaporated at high vacuum. The residue was purified by flash chromatography (silica gel, 230-400 mesh) using ethyl acetate in petroleum ether (0-40%) to yield (16aR,20aR)-4,13-ditosylhexadecahydro-2H,11H-benzo[b][1,4,10,13]tetraoxa[7,16]diazacyclooctadecine (1.35 g, 54%) as a colorless liquid.

To a solution of (16aR,20aR)-4,13-ditosylhexadecahydro-2H,11H-benzo[b][1,4,10,13]tetraoxa[7,16]diazacyclooctadecine (1.35 g, 2.16 mmol) in hydrobromic acid in acetic acid (50%, 5 mL) was added phenol (1.01 g, 1.81 mmol) at room temperature. The reaction was heated at 60° C. for 6 h. It was cooled to room temperature and acetic acid was removed under high vacuum. The residue was purified by reverse phase column purification using 0-100% acetonitrile in water (0.1% TFA) to yield (16aR,20aR)-hexadecahydro-2H,11H-benzo[b][1,4,10,13]tetraoxa[7,16]diazacyclooctadecine (0.5 g, 72%) as a colorless liquid.

A suspension of (16aR,20aR)-hexadecahydro-2H,11H-benzo[b][1,4,10,13]tetraoxa[7,16]diazacyclooctadecine (0.5 g, 1.58 mmol), methyl 6-(chloromethyl)picolinate (0.73 g, 3.95 mmol) and sodium carbonate (0.5 g, 4.74 mmol) in dry acetonitrile (10 mL) was heated at 90° C. for 16 h. The reaction mixture was cooled to room temperature, filtered through Celite and concentrated under reduced pressure. The residue was purified by flash chromatography (silica gel, 230-400 mesh) using methanol in dichloromethane (0-10%) to yield dimethyl 6,6'-(((16aR,20aR)-hexadecahydro-4H,13H-benzo[b][1,4,10,13]tetraoxa[7,16]diazacyclooctadecine-4,13-diyl)bis(methylene))dipicolinate (0.3 g, 31%) as a brown liquid.

A solution of dimethyl 6,6'-(((16aR,20aR)-hexadecahydro-4H,13H-benzo[b][1,4,10,13]tetraoxa[7,16]diazacyclooctadecine-4,13-diyl)bis(methylene))dipicolinate (0.3 g, 0.49 mmol) in 6N hydrochloric acid (5 mL) was heated at 80° C. for 5 h. The reaction mixture was concentrated under reduced pressure. The residue was purified by preparative HPLC to yield H2bp18c6-trans-cyclohexyl-fused Macrocycle (0.16 g, 56%) as off white solid. LC-MS APCI: Calculated for C30H42N4O8 586.69; Observed m/z [M+H]+ 587.0. Purity by LC-MS: 98.97% RT: 1.31. Purity by HPLC: 97.08% RT: 2.27. ¹H NMR (400 MHz, DMSO-d₆): δ 13.35 (s, 1H), 9.84 (s, 1H), 8.16-8.10 (m, 4H), 7.80-7.78 (m, 2H), 4.71 (s, 4H), 4.00-3.82 (m, 8H), 3.73-3.53 (m, 12H), 3.20-3.18 (m, 2H), 2.03-2.00 (m, 2H), 1.61-1.60 (m, 2H), 1.15-1.02 (m, 4H).

Scheme 29. Chelation of H2bp18c6-trans-cyclohexyl-fused Macrocycle with ²²⁵Ac(III)

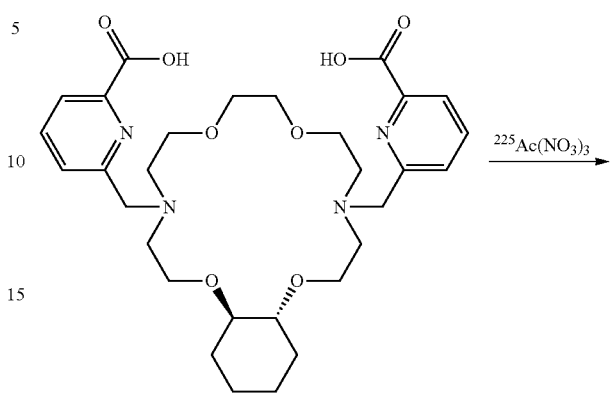

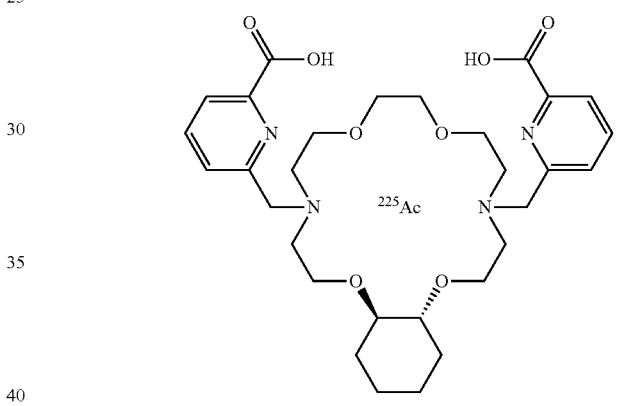

Chelation with ²²⁵Ac(I):

Tetramethylammonium acetate (1M, 10 µL), H2bp18c6-trans-cyclohexyl-fused Macrocycle (2 mg/mL in water, 3 µL), ²²⁵Ac(NO₃)₃ in 0.1 N HCl (10 mCi/mL, 3 µL, 30 µCi) were added to a plastic vial sequentially. The pH was ~6.5 by pH paper. The vial was put on a heat at 37° C. for 2 h.

0.5 µL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 µL of reaction mixture was mixed with 15 µL 10 mM DTPA (pH 6.5) and incubated for 30 min. 10 µL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 22: Synthesis of H2bp18c6-Off Macrocycle-Hydroxylmethyl Isomer I and $^{225}$Ac(III) Chelation
Scheme 30. Synthesis of H2bp18c6-off Macrocycle-hydroxylmethyl isomer I
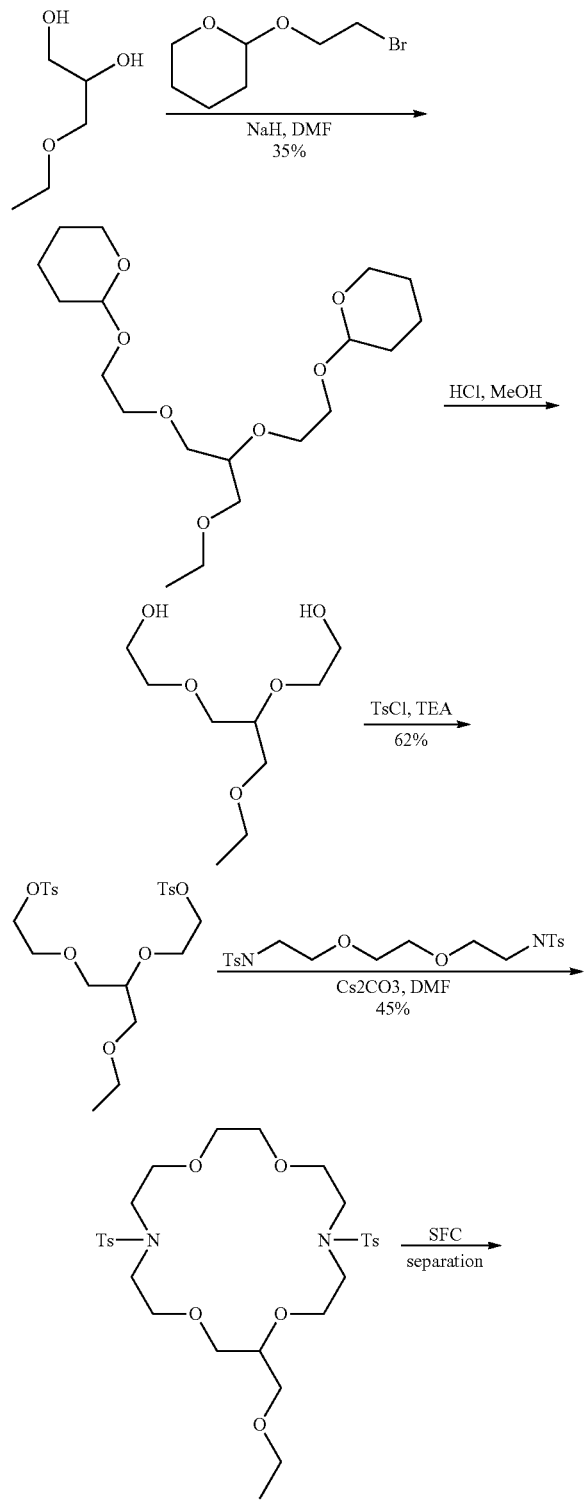
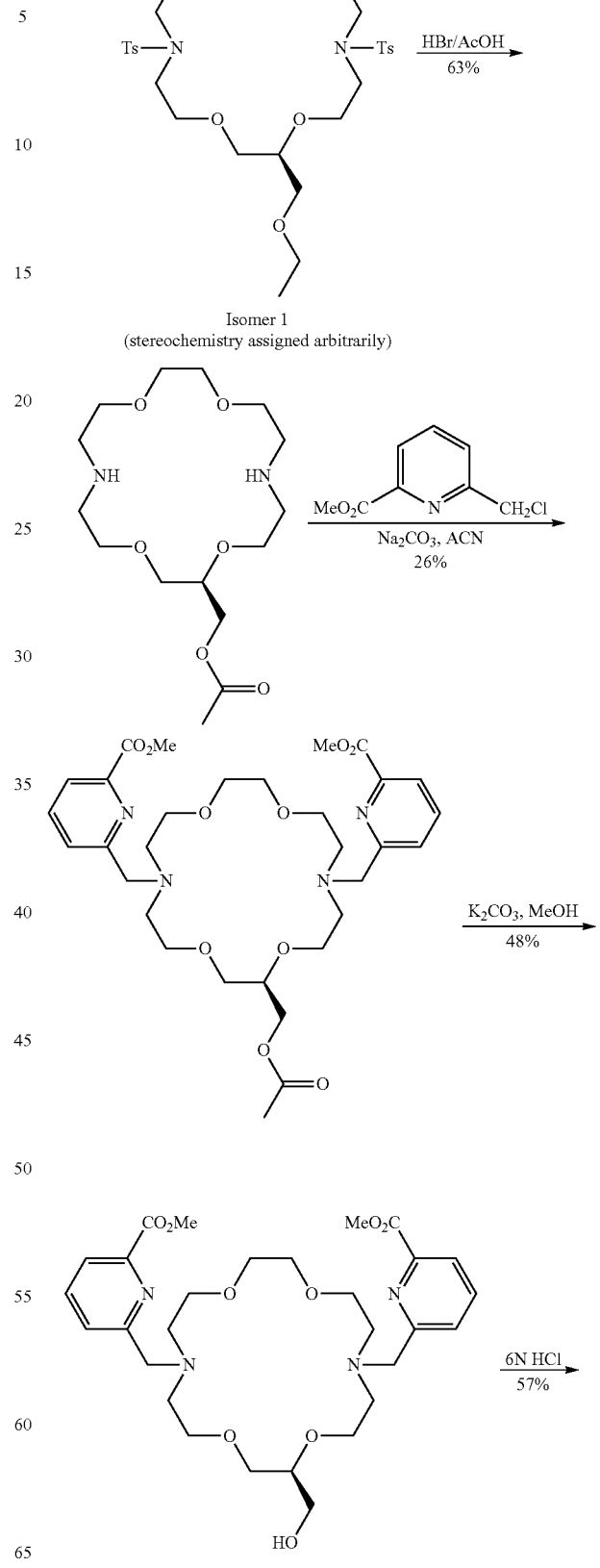
Isomer 1
(stereochemistry assigned arbitrarily)

-continued

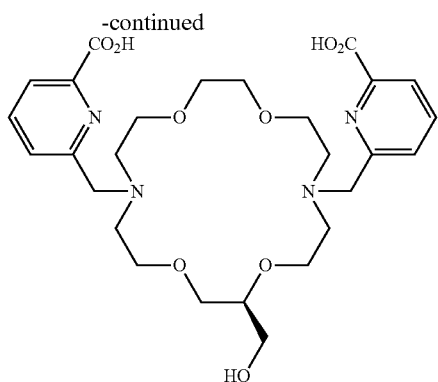

To a suspension of sodium hydride (3.33 g, 60% in mineral oil, 83.33 mmol) in DMF (20 mL) was added 3-ethoxypropane-1,2-diol (2.0 g, 16.66 mmol) in DMF (20 mL) dropwise at 0° C. The reaction mixture was allowed to stir at room temperature for 2 h. It was cooled again to 0° C. and 2-(2-bromoethoxy)tetrahydro-2H-pyran (10.44 g, 49.98 mmol) in DMF (20 mL) was added dropwise. The reaction mixture was allowed to reach room temperature and stirred for 16 h. The reaction was quenched with saturated ammonium chloride and extracted with ethyl acetate (3×500 mL). The combined organic layer was washed with water, dried over sodium sulfate, filtered and concentrated. The residue oil was purified by silica gel (230-400 mesh) flash chromatography using ethyl acetate in petroleum ether (0-40%) to yield 2,2'-((((3-ethoxypropane-1,2-diyl)bis(oxy))bis(ethane-2,1-diyl))bis(oxy))bis(tetrahydro-2H-pyran) (2.2 g, 35%) as a colorless liquid.

To a solution of 2,2'-((((3-ethoxypropane-1,2-diyl)bis(oxy))bis(ethane-2,1-diyl))bis(oxy))bis(tetrahydro-2H-pyran) (2.2 g, 5.85 mmol) in 50 mL of methanol was added 1 mL of HCl in dioxane. The reaction was stirred at reflux for 1 h, cooled, and evaporated. The crude 2,2'-((3-ethoxypropane-1,2-diyl)bis(oxy))bis(ethan-1-ol) (1.3 g) was used in the next step without purification.

To a solution of 2,2'-((3-ethoxypropane-1,2-diyl)bis(oxy))bis(ethan-1-ol) (1.3 g, 6.25 mmol) in dichloromethane (30 mL) and triethylamine (4.51 mL, 31.25 mmol) at 10° C. was added p-toluene sulfonyl chloride (3.56 g, 18.75 mmol) portion wise. The mixture was stirred at ambient temperature for 16 h. The suspension was diluted with 200 mL of dichloromethane, washed with cold 1 M HCl (3×100 mL), ice-cold water (1×100 mL), dried over sodium sulfate, and evaporated to give a solid gum. The crude material was purified by flash chromatography (silica gel, 230-400 mesh) using ethyl acetate in petroleum ether (0-40%) to yield ((3-ethoxypropane-1,2-diyl)bis(oxy))bis(ethane-2,1-diyl) bis(4-methylbenzenesulfonate) (2.0 g, 62%) as a colorless liquid.

A mixture of ((3-ethoxypropane-1,2-diyl)bis(oxy))bis(ethane-2,1-diyl) bis(4-methylbenzenesulfonate) (2.0 g, 3.87 mmol) and cesium carbonate (3.79 g, 11.62 mmol) in 25 mL of dry DMF was stirred for 1.5 h at ambient temperature. To the suspension, was added 1,2-bis(2-(tosyl-$\lambda^2$-azaneyl)ethoxy)ethane (1.75 g, 3.87 mmol) in 25 mL of DMF dropwise over a period of 2 h. The mixture was stirred for additional 20 h at ambient temperature. The solvent was removed under reduced pressure to obtain a solid paste. This was suspended in 200 mL of dichloromethane and stirred for 30 min. The precipitated solids were filtered off and the filtrate was evaporated at high vacuum. The residue was purified by flash chromatography (silica gel, 230-400 mesh) using ethyl acetate in petroleum ether (0-40%) to yield 2-(ethoxymethyl)-7,16-ditosyl-1,4,10,13-tetraoxa-7,16-diazacyclooctadecane (1.1 g, 45%) as a colorless liquid. The product was further purified by SFC to resolve the two enantiomers isomer-I (0.3 g, 12%) and isomer-II (0.26 g, 11%). The stereochemistry of isomers I and II was assigned arbitrarily.

To a solution of (S)-2-(ethoxymethyl)-7,16-ditosyl-1,4,10,13-tetraoxa-7,16-diazacyclooctadecane (isomer I, 0.3 g, 0.48 mmol) in hydrobromic acid in acetic acid (50%, 1 mL) was added phenol (0.22 g, 2.39 mmol) at room temperature. The reaction was heated at 60° C. for 6 h. It was cooled to room temperature and acetic acid was removed under high vacuum. The residue was purified by reverse phase column using 0-100% acetonitrile in water (0.1% TFA) to yield (R)-(1,4,10,13-tetraoxa-7,16-diazacyclooctadecan-2-yl)methyl acetate (stereochemistry assigned arbitrarily) (0.1 g, 63%) as a colorless liquid.

A suspension of (R)-(1,4,10,13-tetraoxa-7,16-diazacyclooctadecan-2-yl)methyl acetate (stereochemistry assigned arbitrarily) (100 mg, 0.30 mmol), methyl 6-(chloromethyl) picolinate (138 mg, 0.75 mmol) and sodium carbonate (159 mg, 1.5 mmol) in dry acetonitrile (3 mL) was heated at 90° C. for 16 h. The reaction mixture was cooled to room temperature, filtered through Celite and concentrated under reduced pressure. The residue was purified by flash chromatography (silica gel, 230-400 mesh) using methanol in dichloromethane (0-10%) to yield dimethyl 6,6'-((2-(acetoxymethyl)-1,4,10,13-tetraoxa-7,16-diazacyclooctadecane-7,16-diyl)bis(methylene)-(R)-dipicolinate (stereochemistry assigned arbitrarily) (50 mg, 26%) as a brown liquid.

To a solution of dimethyl 6,6'-((2-(acetoxymethyl)-1,4,10,13-tetraoxa-7,16-diazacyclooctadecane-7,16-diyl)bis(methylene)-(R)-dipicolinate (stereochemistry assigned arbitrarily) (50 mg, 0.08 mmol) in methanol (1 mL) was added potassium carbonate (1 mg, 0.008 mmol) at room temperature and stirred for 10 min. It was concentrated under reduced pressure. The residue was purified by flash chromatography (silica gel, 230-400 mesh) using methanol in dichloromethane (0-10%) to yield dimethyl 6,6'-((2-(hydroxymethyl)-1,4,10,13-tetraoxa-7,16-diazacyclooctadecane-7,16-diyl)bis(methylene))-(S)-dipicolinate (stereochemistry assigned arbitrarily) (22 mg, 48%) as a brown liquid.

A solution of dimethyl 6,6'-((2-(hydroxymethyl)-1,4,10,13-tetraoxa-7,16-diazacyclooctadecane-7,16-diyl)bis(methylene))-(S)-dipicolinate (stereochemistry assigned arbitrarily) (22 mg, 0.04 mmol) in 6 N hydrochloric acid (0.5 mL) was heated at 80° C. for 5 h. The reaction mixture was concentrated under reduced pressure. The residue was purified by preparative HPLC to H2bp18c6-off Macrocycle-hydroxylmethyl isomer I (12 mg, 57%) as gummy solid. LC-MS APCI: Calculated for C27H38N4O9 562.62; Observed m/z [M+H]+ 562.8. Purity by LC-MS: 96.89% RT: 1.61. Purity by HPLC: 96.47% RT: 1.57. $^1$H NMR (400 MHz, DMSO-$d_6$): δ 3.39 (s, 1H), 9.81 (s, 1H), 8.14-8.09 (m, 4H), 7.80-7.78 (m, 2H), 4.70 (s, 4H), 3.98-3.85 (m, 10H), 3.60-3.42 (m, 15H).

161

Scheme 31. Chelation of H2bp18c6-off Macrocycle-hydroxylmethyl isomer I with $^{225}$Ac(III)

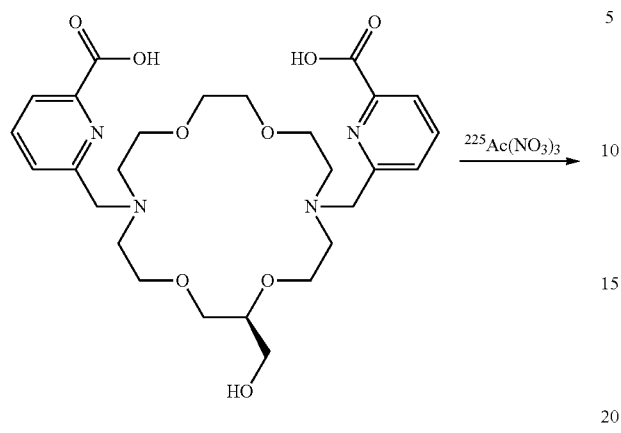

162

Example 23: Synthesis of H2bp18c6-Off Macrocycle-Hydroxylmethyl Isomer II and $^{225}$Ac(III) Chelation Scheme 32. Synthesis of H2bp18c6-off Macrocycle-hydroxylmethyl isomer II

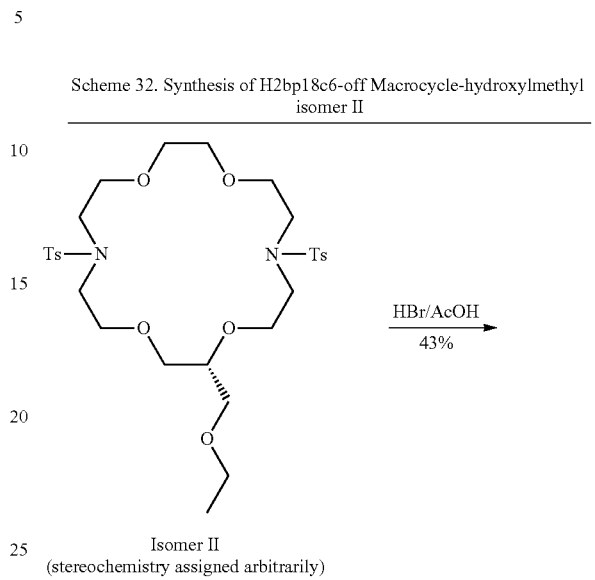

Isomer II
(stereochemistry assigned arbitrarily)

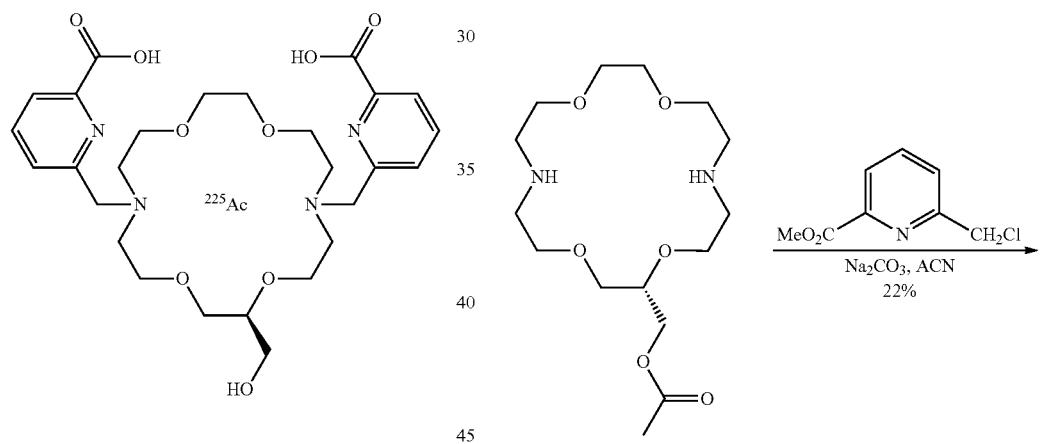

Chelation with $^{225}$Ac(III):

Tetramethylammonium acetate (1M, 10 µL), H2bp18c6-off Macrocycle-hydroxylmethyl isomer I (2 mg/mL in water, 3 µL), $^{225}$Ac(NO$_3$)$_3$ in 0.1 N HCl (10 mCi/mL, 3 µL, 30 µCi) were added to a plastic vial sequentially. The pH was ~6.5 by pH paper. The vial was put on a heat at 37° C. for 2 h.

0.5 µL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 µL of reaction mixture was mixed with 15 µL 10 mM DTPA (pH 6.5) and incubated for 30 min. 10 µL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

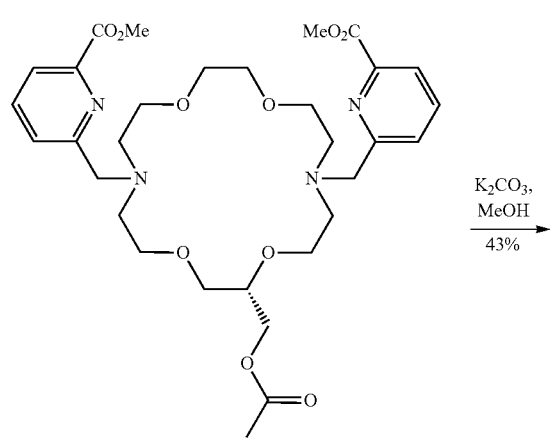

-continued

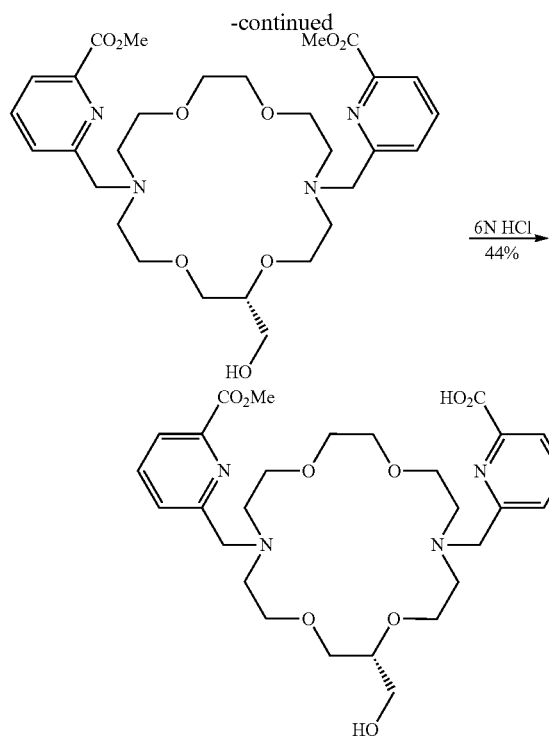

To a solution of (R)-2-(ethoxymethyl)-7,16-ditosyl-1,4,10,13-tetraoxa-7,16-diazacyclooctadecane (stereochemistry assigned arbitrarily) (isomer II, 0.26 g, 0.42 mmol) in hydrobromic acid in acetic acid (50%, 1 mL) was added phenol (197 mg, 2.07 mmol) at room temperature. The reaction was heated at 60° C. for 6 h. It was cooled to room temperature and acetic acid was removed under high vacuum. The residue was purified by reverse phase column purification using 0-100% acetonitrile in water (0.1% TFA) to yield (S)-(1,4,10,13-tetraoxa-7,16-diazacyclooctadecan-2-yl)methyl acetate (stereochemistry assigned arbitrarily) (0.06 g, 43%) as a colorless liquid.

A suspension of (S)-(1,4,10,13-tetraoxa-7,16-diazacyclooctadecan-2-yl)methyl acetate (stereochemistry assigned arbitrarily) (0.06 g, 0.18 mmol), methyl 6-(chloromethyl)picolinate (0.083 g, 0.45 mmol) and sodium carbonate (0.095 g, 0.9 mmol) in dry acetonitrile (3 mL) was heated at 90° C. for 16 h. The reaction mixture was cooled to room temperature, filtered through Celite and concentrated under reduced pressure. The residue was purified by flash chromatography (silica gel, 230-400 mesh) using methanol in dichloromethane (0-10%) to give dimethyl 6,6'-((2-(acetoxymethyl)-1,4,10,13-tetraoxa-7,16-diazacyclooctadecane-7,16-diyl)bis(methylene))-(S)-dipicolinate (stereochemistry assigned arbitrarily) (0.025 g, 22%) as a brown liquid.

To a solution of dimethyl 6,6'-((2-(acetoxymethyl)-1,4,10,13-tetraoxa-7,16-diazacyclooctadecane-7,16-diyl)bis(methylene))-(S)-dipicolinate (stereochemistry assigned arbitrarily) (0.025 g, 0.04 mmol) in methanol (0.5 mL) was added potassium carbonate (0.5 mg, 0.004 mmol) at room temperature. The mixture was stirred for 10 min. It was concentrated under reduced pressure. The crude was purified by flash chromatography over silica (230-400 mesh) eluting with a gradient of 0-10% methanol in dichloromethane to yield dimethyl 6,6'-((2-(hydroxymethyl)-1,4,10,13-tetraoxa-7,16-diazacyclooctadecane-7,16-diyl)bis(methylene))-(R)-dipicolinate (0.01 g, 43%) as a brown liquid.

A solution of dimethyl 6,6'-((2-(hydroxymethyl)-1,4,10,13-tetraoxa-7,16-diazacyclooctadecane-7,16-diyl)bis(methylene))-dipicolinate (0.01 g, 0.02 mmol) in 6 N hydrochloric acid (0.5 mL) was heated at 80° C. for 3 h. The reaction mixture was concentrated under reduced pressure. The crude was purified by preparative HPLC to yield H2bp18c6-off Macrocycle-hydroxylmethyl isomer II (4 mg, 44%) as gummy liquid. LC-MS APCI: Calculated for C27H38N4O9 562.62; Observed m/z [M+H]+ 562.8. Purity by LC-MS: 96.89% RT: 6.31. Purity by HPLC: 93.97% RT: 6.67. $^1$H NMR (400 MHz, DMSO-$d_6$): δ 13.34 (s, 1H), 9.86 (s, 1H), 8.13-8.11 (m, 4H), 7.80-7.78 (m, 2H), 4.70 (s, 4H), 3.95-3.84 (m, 10H), 3.58-3.42 (m, 15H).

Scheme 33. Chelation of H2bp18c6-off Macrocycle-hydroxylmethyl isomer II with $^{225}$Ac(III)

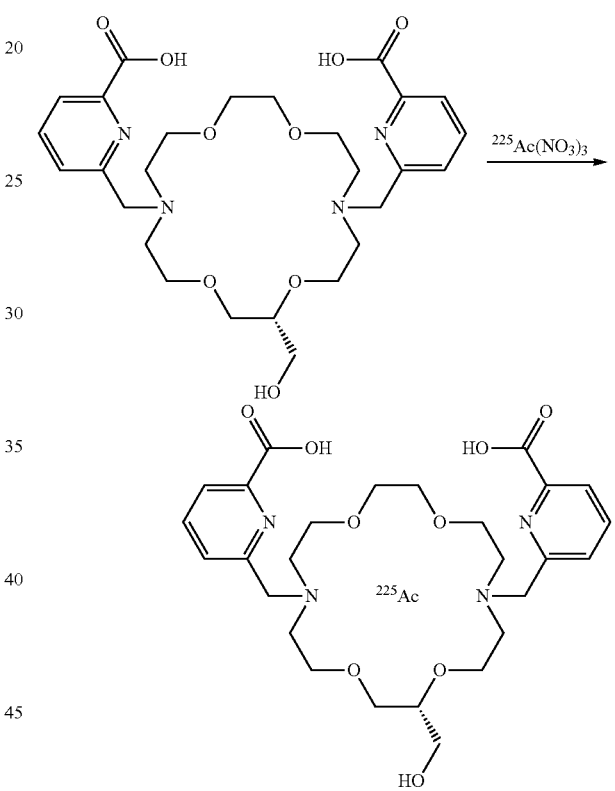

Chelation with $^{225}$Ac(III):

Tetramethylammonium acetate (1M, 10 μL), H2bp18c6-off Macrocycle-hydroxylmethyl isomer II (2 mg/mL in water, 3 μL), $^{225}$Ac(NO$_3$)$_3$ in 0.1 N HCl (10 mCi/mL, 3 μL, 30 μCi) were added to a plastic vial sequentially. The pH was ~6.5 by pH paper. The vial was put on a heat at 37° C. for 2 h.

0.5 μL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 μL of reaction mixture was mixed with 15 μL 10 mM DTPA (pH 6.5) and incubated for 30 min. 10 μL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 24: Synthesis of H2bp18c6-Off Macrocycle-Ethoxylmethyl Isomer I and $^{225}$Ac(III) Chelation Scheme 34. Synthesis of H2bp18c6-off Macrocycle-ethoxylmethyl isomer I

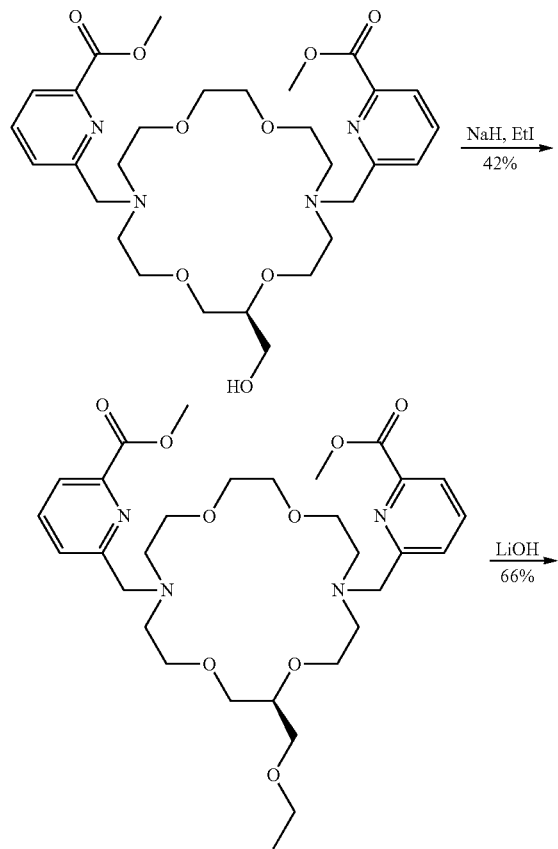

To a stirred solution of dimethyl 6,6'-((2-(hydroxymethyl)-1,4,10,13-tetraoxa-7,16-diazacyclooctadecane-7,16-diyl)bis(methylene))(S)-dipicolinate (100 mg, 0.17 mmol) (stereochemistry arbitrarily assigned) in DMF (2 mL) at 0° C. under nitrogen was added sodium hydride (10 mg, 60% dispersion in mineral oil, 0.25 mmol) slowly. The reaction mixture was allowed to reach room temperature and then stirred for 10 minutes. The reaction mixture was cooled again to 0° C. and added a solution of ethyl iodide (39 mg, 0.25 mmol, 20 uL) in DMF (1 ml) dropwise. The reaction mixture was allowed to reach room temperature and then stirred at this temperature for 2 h. After completion of the reaction (monitored by LCMS), reaction mixture was quenched with saturated NH$_4$Cl solution and extracted with ethyl acetate. Then combined organic extracts were dried over anhydrous sodium sulphate and concentrated. The residue was purified by silica gel (230-400 mesh) flash column chromatography using 5% methanol in dichloromethane as eluent to yield the product dimethyl 6,6'-((2-(ethoxymethyl)-1,4,10,13-tetraoxa-7,16-diazacyclooctadecane-7,16-diyl)bis(methylene))(S)-dipicolinate (stereochemistry arbitrarily assigned) (45 mg, 42%) as brown colour liquid.

To a stirred solution of dimethyl 6,6'-((2-(ethoxymethyl)-1,4,10,13-tetraoxa-7,16-diazacyclooctadecane-7,16-diyl)bis(methylene))(S)-dipicolinate (45 mg, 0.07 mmol) (stereochemistry arbitrarily assigned) in THF (0.25 mL), water (0.5 mL) and methanol (0.25 mL) was added lithium hydroxide monohydrate (9 mg, 0.21 mmol). The reaction mixture was stirred at room temperature for 4 h. After completion of the reaction (monitored by UPLC-MS), pH of the reaction was adjusted to 3-4 using 1.5M aqueous HCl solution and concentrated. The residue was purified by preparative HPLC to give H2bp18c6-off Macrocycle-ethoxylmethyl isomer I (28 mg, 66%) as a gummy liquid. LC-MS APCI: Calculated for C29H42N4O9 590.30; Observed m/z [M+H]$^+$ 591.2. Purity by LC-MS: 99.59% RT: 1.19. Purity by HPLC: 96.12% RT: 2.01. $^1$H NMR (400 MHz, DMSO-d$_6$): δ 13.40 (s, 1H), 9.75 (s, 1H), 8.16-8.09 (m, 4H), 7.80-7.78 (m, 2H), 4.69 (s, 4H), 3.98-3.34 (m, 28H), 1.06 (t, J=6.80 Hz, 3H).

Scheme 35. Chelation of H2bp18c6-off Macrocycle-ethoxylmethyl isomer I with $^{225}$Ac(III)

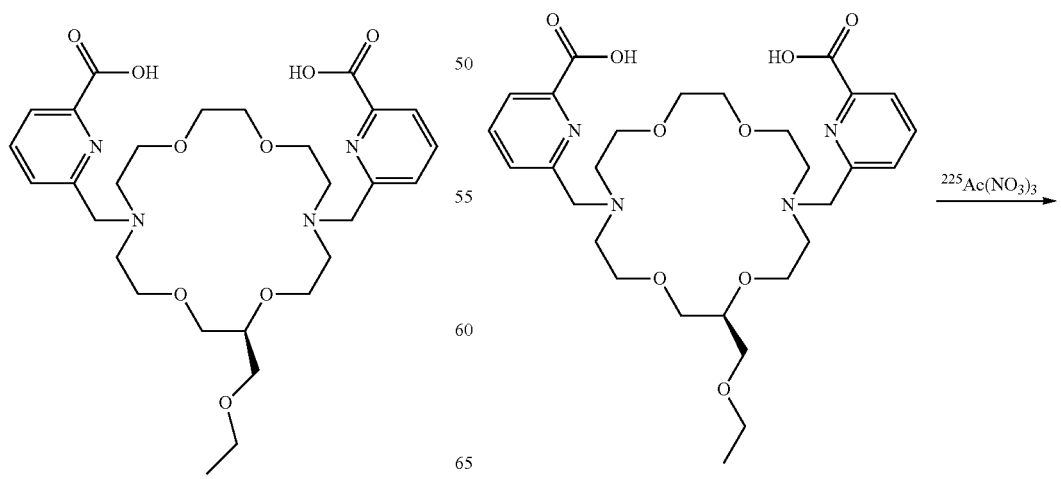

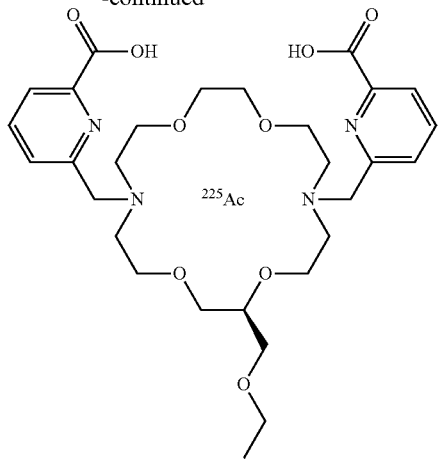

Chelation with $^{225}$Ac(III):

Tetramethylammonium acetate (1M, 10 μL), H2bp18c6-off Macrocycle-ethoxylmethyl isomer I (1 mg/mL in water, 1 μL), $^{225}$Ac(NO$_3$)$_3$ in 0.1 N HCl (10 mCi/mL, 3 μL, 30 μCi) were added to a plastic vial sequentially. The pH was ~6.5 by pH paper. The vial was put on a heat at 37° C. for 2 h.

0.5 μL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 μL of reaction mixture was mixed with 15 μL 10 mM DTPA (pH 6.5) and incubated for 30 min. 10 μL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 25: Synthesis of H2bp18c6-Off Macrocycle-Ethoxylmethyl Isomer II and $^{225}$Ac(III) Chelation Scheme 36. Synthesis of H2bp18c6-off Macrocycle-ethoxymethyl isomer II

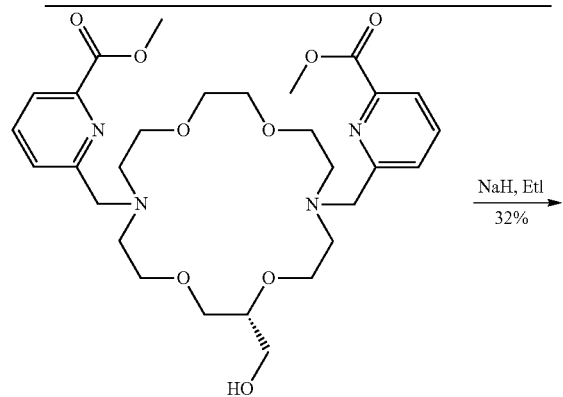

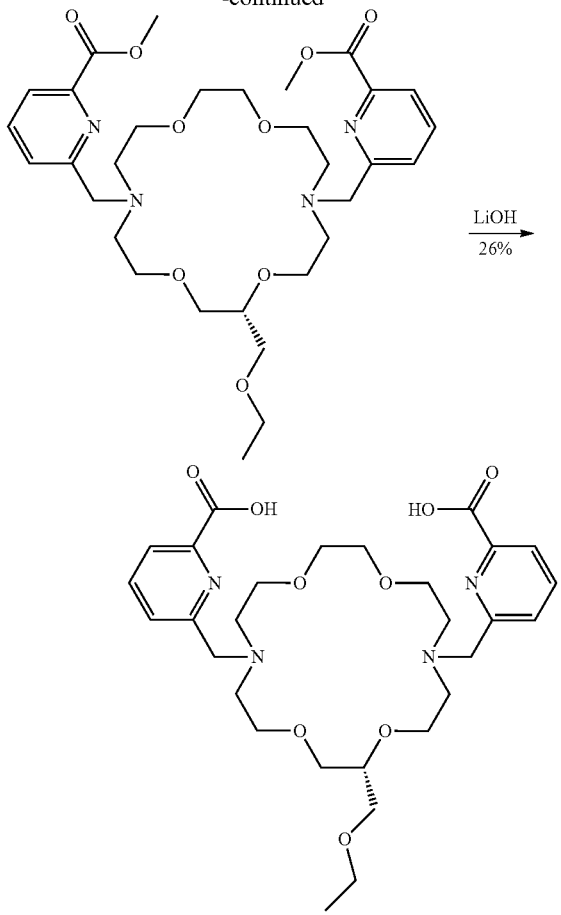

To a stirred solution of dimethyl 6,6'-((2-(hydroxymethyl)-1,4,10,13-tetraoxa-7,16-diazacyclooctadecane-7,16-diyl)bis(methylene))(R)-dipicolinate (stereochemistry arbitrarily assigned) (60 mg, 0.1 mmol) in DMF (1.5 mL) at 0° C. under nitrogen was added sodium hydride (6 mg, 60% dispersion in mineral oil, 0.15 mmol) slowly. The reaction mixture was allowed to reach room temperature and then stirred for 10 minutes. The reaction mixture was cooled again to 0° C. and added a solution of ethyl iodide (23 mg, 0.15 mmol, 12 uL) in DMF (0.5 ml) dropwise. The reaction mixture was allowed to reach room temperature and then stirred at this temperature for 2 h. After completion of the reaction (monitored by LCMS), reaction mixture was quenched with saturated NH$_4$Cl solution and extracted with ethyl acetate. Then combined organic extracts were dried over anhydrous sodium sulphate and concentrated. The residue was purified by silica gel (230-400 mesh) flash column chromatography using 5% methanol in dichloromethane as eluent to yield dimethyl 6,6'-((2-(ethoxymethyl)-1,4,10,13-tetraoxa-7,16-diazacyclooctadecane-7,16-diyl)bis(methylene))(R)-dipicolinate (stereochemistry arbitrarily assigned) (20 mg, 32%) as brown colour liquid.

To a stirred solution of dimethyl 6,6'-((2-(ethoxymethyl)-1,4,10,13-tetraoxa-7,16-diazacyclooctadecane-7,16-diyl)bis(methylene))(R)-dipicolinate (stereochemistry arbitrarily assigned) (20 mg, 0.03 mmol) in THF (0.1 mL), Water (0.25 mL) and Methanol (0.1 mL) was added lithium hydroxide monohydrate (4 mg, 0.09 mmol). The reaction mixture was stirred at room temperature for 4 h. After completion of the reaction (monitored by UPLC-MS), pH of the reaction was adjusted to 3-4 using 1.5M aqueous HCl solution and concentrated. The residue was purified by preparative HPLC to give H2bp18c6-off Macrocycle-ethoxylmethyl isomer II (5 mg, 26%) as a gummy liquid. LC-MS APCI: Calculated for C29H42N4O9 590.30; Observed m/z [M+H]+ 591.3. Purity by LC-MS: 99.28%, RT: 1.199. Purity by HPLC: 97.60% RT: 2.01. 1H NMR 1H-NMR (400 MHz, DMSO-$d_6$): δ 13.40 (s, 1H), 9.72 (s, 1H), 8.16-8.00 (m, 4H), 7.80-7.77 (m, 2H), 4.69 (s, 4H), 4.34-3.38 (m, 28H), 1.06 (t, J=6.80 Hz, 3H).

Chelation with $^{225}$Ac(II):

Tetramethylammonium acetate (1M, 10 μL), H2bp18c6-off Macrocycle-ethoxylmethyl isomer II (1 mg/mL in water, 1 μL), $^{225}$Ac(NO$_3$)$_3$ in 0.1 N HCl (10 mCi/mL, 3 μL, 30 μCi) were added to a plastic vial sequentially. The pH was ~6.5 by pH paper. The vial was put on a heat at 37° C. for 2 h.

0.5 μL of the reaction mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

0.5 μL of reaction mixture was mixed with 15 μL 10 mM DTPA (pH 6.5) and incubated for 30 min. 10 μL of the mixture was loaded onto a iTLC-SG, which was developed with 10 mM EDTA. The dried iTLC was scanned after 20 h on a Bioscan AR-2000 radio-TLC scanner. Under the elution conditions described herein, any free Ac-225 would migrate with the solvent to the solvent front. iTLC showed 99% chelated Ac-225.

Example 26: Synthesis of H2bp18c6-Off Macrocycle-NCS

Scheme 38. Synthesis of H2bp18c6-off Macrocycle-ethylsulfide amine

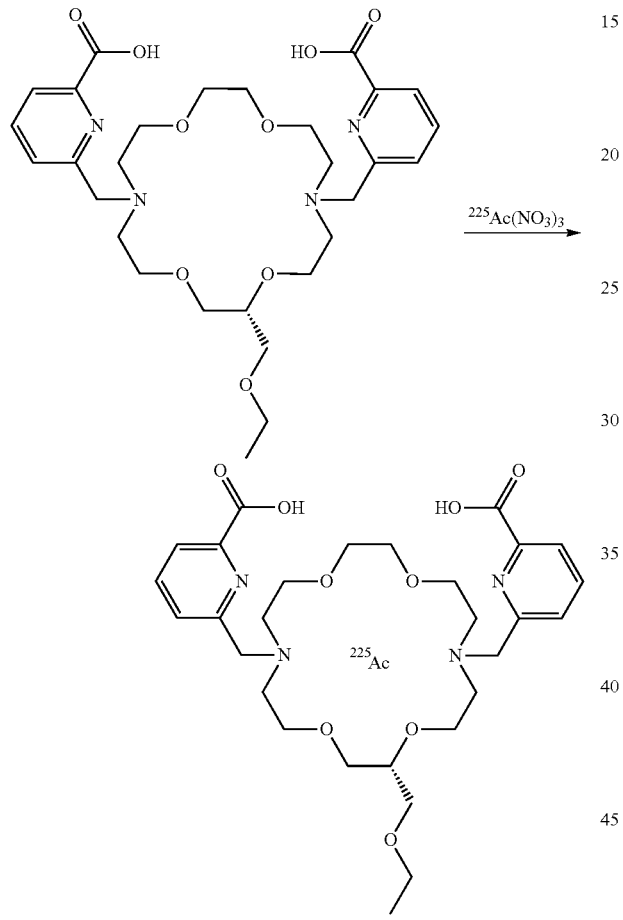

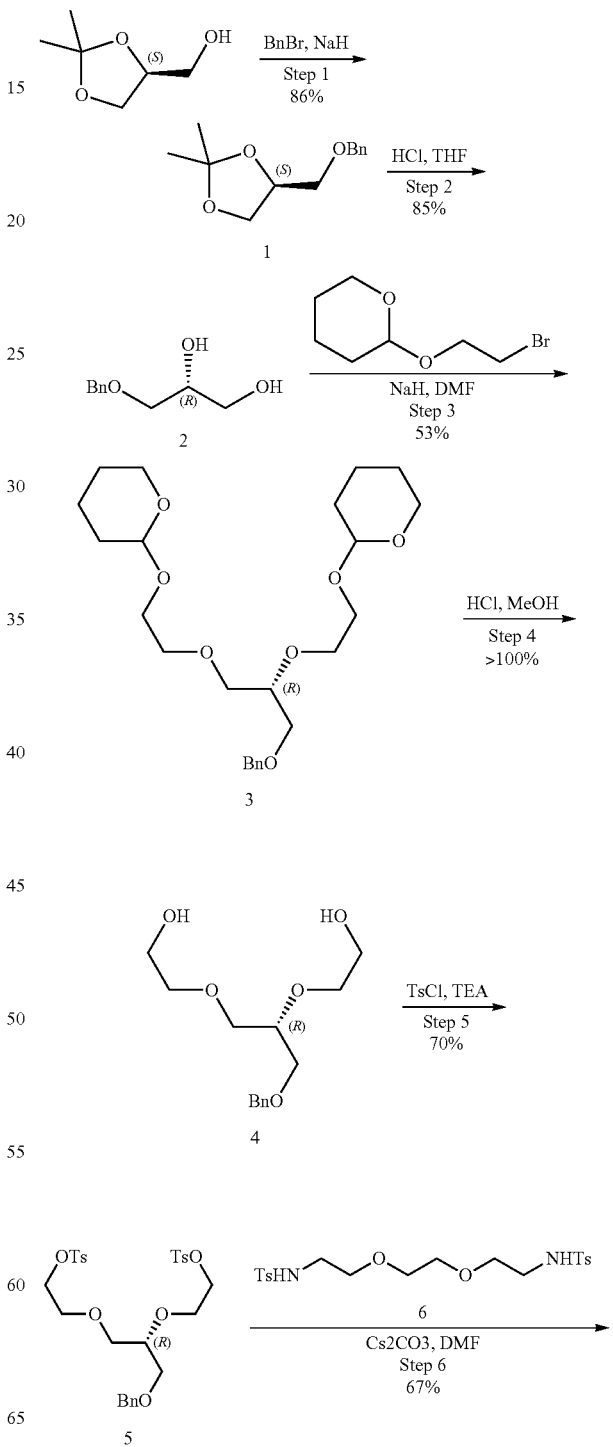

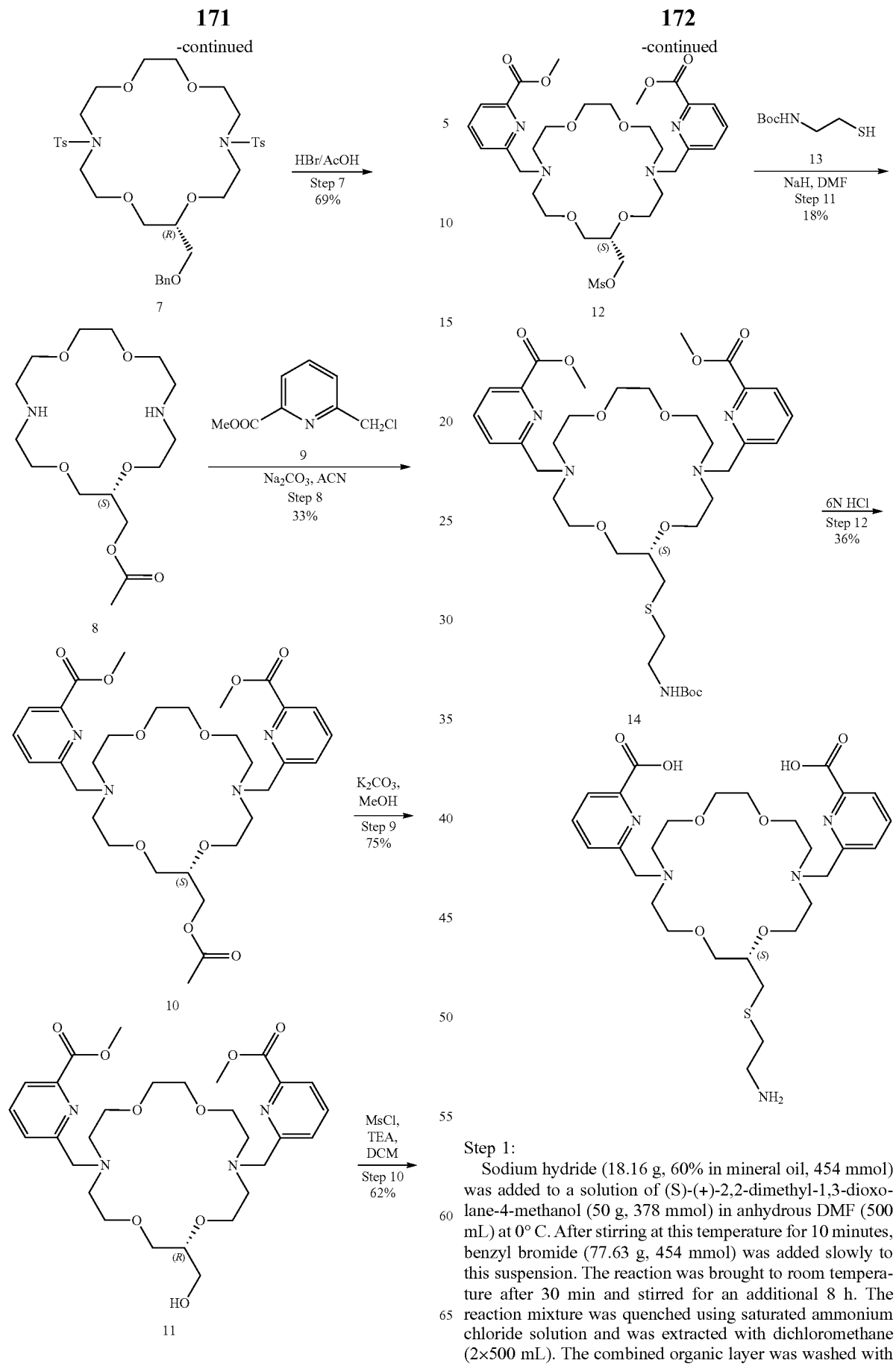

Step 1:

Sodium hydride (18.16 g, 60% in mineral oil, 454 mmol) was added to a solution of (S)-(+)-2,2-dimethyl-1,3-dioxolane-4-methanol (50 g, 378 mmol) in anhydrous DMF (500 mL) at 0° C. After stirring at this temperature for 10 minutes, benzyl bromide (77.63 g, 454 mmol) was added slowly to this suspension. The reaction was brought to room temperature after 30 min and stirred for an additional 8 h. The reaction mixture was quenched using saturated ammonium chloride solution and was extracted with dichloromethane (2×500 mL). The combined organic layer was washed with brine and dried over sodium sulphate. After removal of solvent, the residue was purified by flash column chromatography (silica gel, 230-400 mesh) using petroleum ether and ethyl acetate to yield the compound 1 (72 g, 86%) as a colorless liquid.

Step 2:

Compound 1 (72 g, 324 mmol) was dissolved in THF (100 mL), added aq. HCl (1.5N, 100 mL) and stirred at room temperature for 16 h. The reaction mixture was diluted with ethyl acetate (500 mL) and neutralised with 10% sodium bicarbonate solution. The solution was extracted with ethyl acetate (2×500 mL) and the combined organic layer was washed with water, brine, dried over sodium sulphate, filtered and concentrated under reduced pressure. The residue was purified by flash column chromatography (silica gel, 230-400 mesh) using petroleum ether and ethyl acetate to yield compound 2 (51 g, 85%) as a colorless oil.

Step 3:

To a suspension of sodium hydride (26.29 g, 60% in mineral oil, 686 mmol) in DMF (20 mL) was added compound 2 (25.0 g, 137 mmol) in DMF (100 mL) dropwise at 0° C. The reaction mixture was allowed stir at room temperature for 2 h. It was cooled again to 0° C., added 2-(2-bromoethoxy)tetrahydro-2H-pyran ((85.89 g, 411 mmol) in DMF (100 mL) dropwise. The reaction mixture was allowed to reach room temperature and stirred for 16 h. Reaction was quenched using saturated ammonium chloride solution and extracted with ethyl acetate (3×300 mL). Combined organic layer was washed with water, dried over sodium sulphate, filtered and concentrated. The crude oil was purified by silica gel (230-400 mesh) flash chromatography using ethyl acetate in petroleum ether (0-40%). The product 3 (32 g, 53%) was obtained as a colourless liquid.

Step 4:

To a solution of compound 3 (32 g, 73.05 mmol) in 500 mL of methanol was added 5 mL of HCl in dioxane, stirred at reflux for 1 h, cooled and evaporated. The crude material 4 (20 g) was used in the next step without purification.

Step 5:

Compound 4 (20 g, 74.07 mmol) was dissolved in dichloromethane (250 mL) and triethylamine (53 mL, 370 mmol). The solution was cooled to 10° C., and solid p-toluene sulfonyl chloride (42.20 g, 222 mmol) was added portion wise. The mixture was stirred at ambient temperature for 16 h. After completion of reaction, the suspension was diluted further with 1000 mL of dichloromethane, washed with cold aq. HCl (1 M, 3×200 mL), ice-cold water (2×200 mL), dried over sodium sulphate and evaporated to a solid gum. The crude material was purified by flash chromatography (silica gel, 230-400 mesh) using ethyl acetate in petroleum ether (0-40%). The product 5 (30 g, 70%) was obtained as a colourless liquid.

Step 6:

A mixture of compound 5 (30 g, 51.9 mmol) and cesium carbonate (50.76 g, 155.7 mmol) in 200 mL of dry DMF was stirred for 1.5 h at ambient temperature. To the suspension, was added compound 6 (23.56 g, 51.9 mmol) in 200 mL of DMF dropwise over a period of 2 h. The mixture was stirred for additional 20 h at ambient temperature. The solvent was removed under reduced pressure to obtain a solid paste. This was suspended in 1000 mL of dichloromethane and stirred for 30 min. The precipitated solids were filtered off and the filtrate was evaporated at high vacuum. The crude material was purified by flash chromatography (silica gel, 230-400 mesh) using ethyl acetate in petroleum ether (0-40%). The product 7 (24 g, 67%) was obtained as a colourless liquid.

Step 7:

To a solution of compound 7 (24 g, 34.78 mmol) in hydrobromic acid (50% in acetic acid, 100 mL) was added phenol (16.35 g, 174 mmol) at room temperature. The reaction was heated at 60° C. for 6 h. After completion of the reaction, it was cooled to room temperature, acetic acid was removed under high vacuum. Crude was purified by reverse phase column purification using acetonitrile and 0.1% TFA in water to get the compound 8 (8.0 g, 69%) as a colourless liquid.

Step 8:

A suspension of compound 8 (8.0 g, 23.95 mmol), compound 9 (11.07 g, 59.88 mmol) and sodium carbonate (12.69 g, 119.75 mmol) in dry acetonitrile (100 mL) was heated at 90° C. for 16 h. After completion of the reaction, reaction mixture was cooled to room temperature, filtered through celite and concentrated under reduced pressure. The crude material was purified by flash chromatography (silica gel, 230-400 mesh) using methanol in dichloromethane (0-10%). The product 10 (5.0 g, 33%) was obtained as a brown liquid.

Step 9:

To a solution of compound 10 (5.0 g, 7.91 mmol) in methanol (50 mL) was added potassium carbonate (0.11 g, 0.79 mmol) at room temperature and stirred for 10 min. After completion of the reaction, it was concentrated under reduced pressure. The residue was purified by flash chromatography over silica (230-400 mesh) eluting with a gradient of 0-10% methanol in dichloromethane. The product 11 (3.5 g, 75%) was obtained as a brown liquid.

Step 10:

To a solution of compound 11 (1.0 g, 1.7 mmol) in dichloromethane (20 mL) was added triethylamine (0.51 g, 0.70 mL, 5.1 mmol). Added mesyl chloride (0.39 g, 0.26 mL, 3.4 mmol) dropwise to this solution at 0° C. The reaction was stirred for 30 min at room temperature. The reaction progress was monitored by TLC. After completion of the reaction, it was concentrated and the crude was purified by column chromatography (alumina—neutral) using methanol in dichloromethane (1-2%) as eluent to get compound 12 (0.7 g, 62%) as a brown liquid.

Step 11:

To a solution of compound 13 (53 mg, 0.3 mmol) in DMF (2 mL) was added sodium hydride (12 mg, 60% in mineral oil, 0.3 mmol) at 0° C. The reaction mixture was stirred for 10 minutes at room temperature. To the reaction mixture, was added compound 12 (100 mg, 0.15 mmol) in DMF (1 mL) at 0° C. The reaction was stirred for 2 h at room temperature. The reaction progress was monitored by TLC. After completion of the reaction, the reaction mixture was quenched with saturated ammonium chloride solution and extracted with ethyl acetate (3×5 mL). The combined organic layer was washed with water, brine, dried over anhydrous sodium sulphate and concentrated. The crude product was purified by preparative HPLC using acetonitrile and 0.1% TFA in water to get the compound 14 (20 mg, 18%) as brown liquid.

Step 12:

A solution of compound 14 (20 mg, 0.02 mmol) in 6N hydrochloric acid (0.5 mL) was stirred overnight at room temperature. After completion of reaction, the reaction mixture was concentrated under reduced pressure. The crude was purified by preparative HPLC to get the product H2bp18c6-off Macrocycle-ethylsulfide amine (6 mg, 36%) as gummy solid. LC-MS APCI: Calculated for $C_{29}H_{43}N_5O_8S$ 621.75; Observed m/z $[M+H]^+$ 622.2. Purity by LC-MS: 97.94% RT: 1.38. Purity by HPLC: 94.11% RT: 2.94. $^1$H NMR (400 MHz, DMSO-d6): δ

11.02-11.00 (m, 2H), 8.21 (s, 2H), 8.16-8.09 (m, 4H), 7.93-7.90 (m, 2H), 4.78-4.75 (m, 4H), 4.15-3.93 (m, 9H), 3.56-3.50 (m, 14H), 2.97-2.96 (m, 2H), 2.81-2.79 (m, 2H), 2.70-2.67 (m, 2H).

Scheme 39. Synthesis of H2bp18c6-off Macrocycle-ethylsulfide NCS

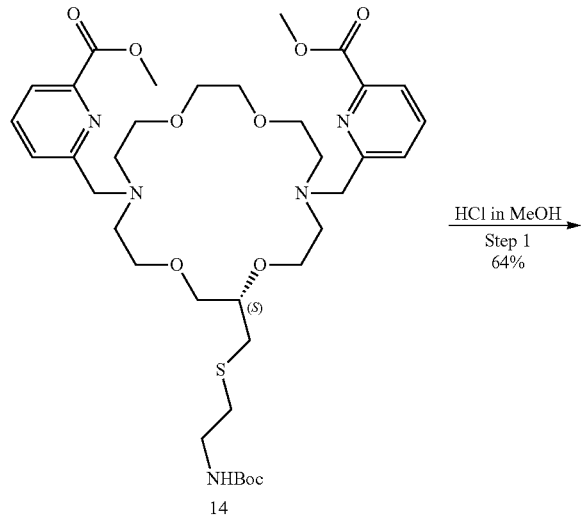

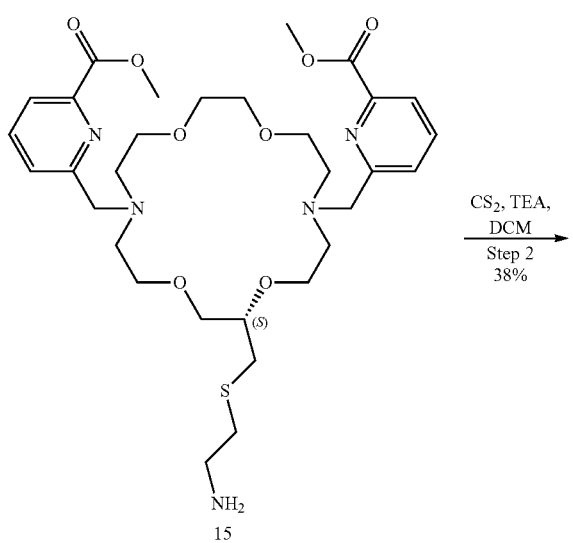

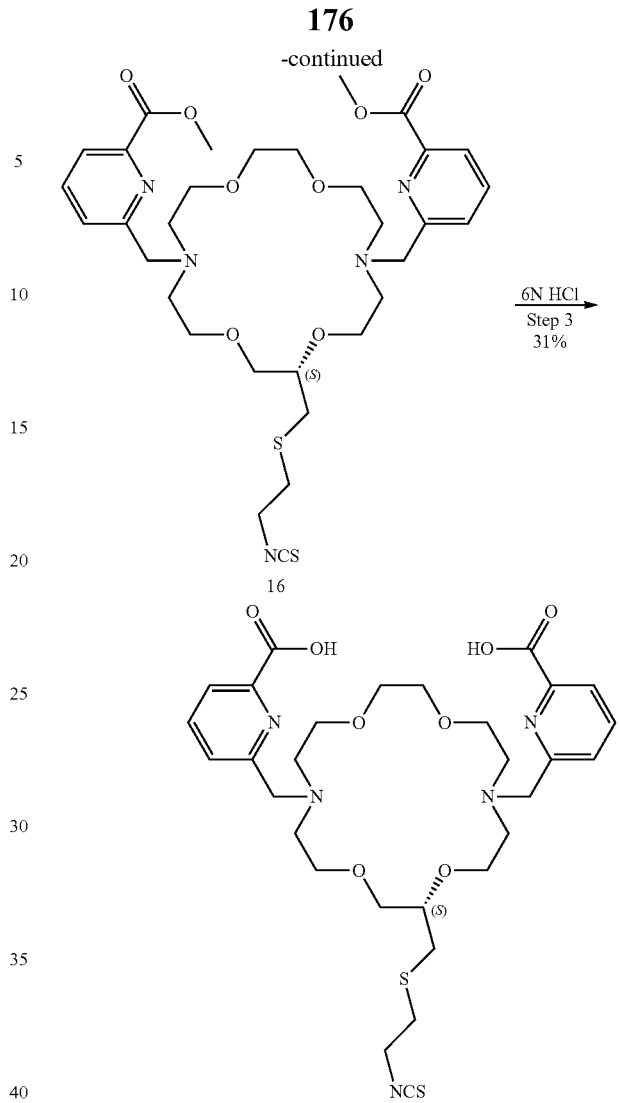

Step 1:
To compound 14 (100 mg, 0.15 mmol), a cold solution of HCl in methanol (2 mL, 4N) was added and stirred for 2 h. The reaction mixture was concentrated under reduced pressure to yield compound 2 as yellow liquid (55 mg, 64%).

Step 2:
To a solution of compound 15 (50 mg, 0.08 mmol) and triethylamine (24 mg, 0.24 mmol) in dry dichloromethane (2 mL) in a pressure vial was added carbon disulfide (12 mg, 0.16 mmol). The vial was subjected to MW-irradiation (150 W power) at 90° C. for 30 min. Thereafter, the reaction mixture was diluted with dichloromethane (10 mL), washed successively with water (5 mL), 1M HCl (5 mL), water (5 mL) and dried over anhydrous sodium sulphate. After concentration, the crude product was purified by flash chromatography on silica gel (230-400 mesh) using 0-10% methanol in dichloromethane as eluent to yield compound 16 (20 mg, 38%) as a yellow solid.

Step 3:
A solution of compound 16 (20 mg, 0.03 mmol) in hydrochloric acid (6N, 0.5 mL) was stirred overnight at room temperature. After completion of the reaction, it was concentrated under reduced pressure. The residue was purified by preparative HPLC to yield H2bp18c6-off Macrocycle-ethylsulfide NCS (6 mg, 31%) as a white solid.

LC-MS APCI: Calculated for C30H41N5O8S2: 663.81; Observed m/z [M+H]+ 664.2. Purity by LC-MS: 99.94% RT: 1.41. Purity by HPLC: 98.77% RT: 2.76. ¹H NMR (400 MHz, DMSO-d6): δ 9.78 (s, 1H), 8.10 (s, 4H), 7.78 (d, J=6.00 Hz, 2H), 4.69 (s, 4H), 3.96-3.52 (m, 23H), 2.85 (t, J=6.40 Hz, 2H), 2.70 (t, J=8.00 Hz, 2H).
Scheme 40. Synthesis of H2bp18c6-off Macrocycle-pentylsulfide amine
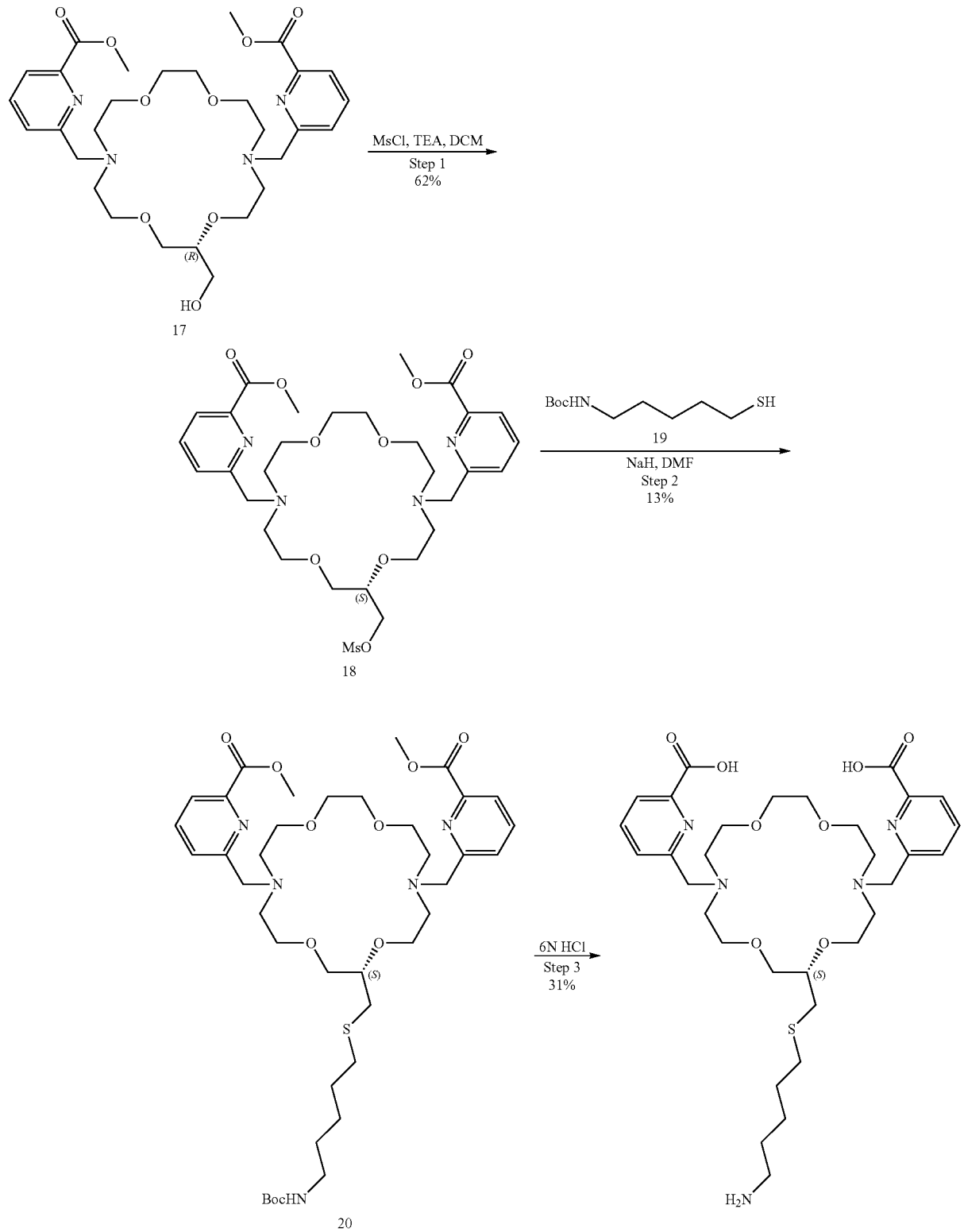

Step 1:
To a solution of compound 17 (1.0 g, 1.7 mmol) in dichloromethane (20 mL) was added triethylamine (0.51 g, 0.70 mL, 5.1 mmol). Added mesyl chloride (0.39 g, 0.26 mL, 3.4 mmol) dropwise to this solution at 0° C. The reaction was stirred for 30 min at room temperature. The reaction progress was monitored by TLC. After completion of the reaction, it was concentrated and the residue was purified by column chromatography (alumina-neutral) using methanol in dichloromethane (1-2%) as eluent to yield compound 18 (0.7 g, 62%) as brown liquid.

Step 2:
To a solution of compound 19 (65 mg, 0.3 mmol) in DMF (2 mL) was added sodium hydride (12 mg, 60% in mineral oil, 0.3 mmol) at 0° C. The reaction mixture was stirred for 10 min at room temperature. To the reaction mixture, was added compound 18 (100 mg, 0.15 mmol) in DMF (1 mL) at 0° C. The reaction was stirred for 2 h at room temperature. The reaction progress was monitored by TLC. After completion of the reaction, it was concentrated and the residue was purified by preparative HPLC using acetonitrile and 0.1% TFA in water to get the compound 20 (15 mg, 13%) as a brown liquid.

Step 3:
A solution of compound 20 (15 mg, 0.02 mmol) in hydrochloric acid (6N, 0.5 mL) was stirred overnight at room temperature. After completion of the reaction, it was concentrated under reduced pressure. The residue was purified by preparative HPLC to get the product H2bp18c6-off Macrocycle-pentylsulfide amine (4 mg, 33%) as gummy liquid. LC-MS APCI: Calculated for $C_{32}H_{49}N_5O_8S$ 663.83; Observed m/z $[M+H]^+$ 664.2. Purity by LC-MS: 90.31% RT: 1.43. Purity by HPLC: 90.69% RT: 3.11. $^1$H NMR (400 MHz, DMSO-d6): δ 7.85-7.83 (m, 2H), 7.79-7.75 (m, 2H), 7.30 (dd, J=6.80, 24.00 Hz, 2H), 4.01-3.38 (m, 29H), 2.89-2.85 (m, 4H), 1.80-1.60 (m, 2H), 1.44-1.39 (m, 4H).

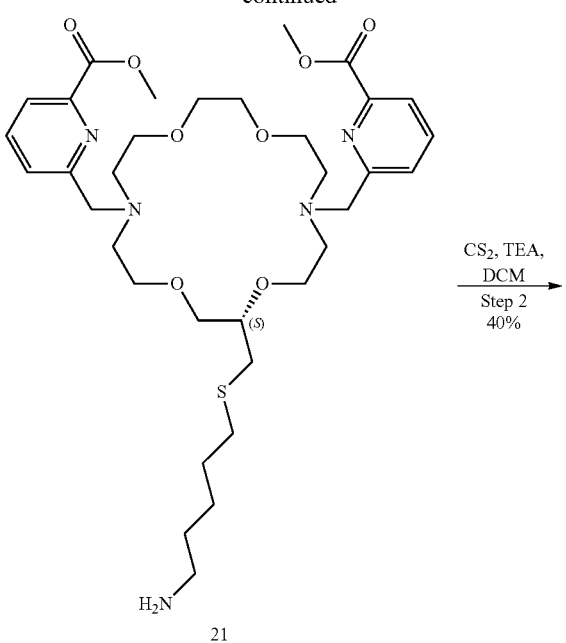

Scheme 41. Synthesis of
H2bp18c6-off Macrocycle-pentylsulfide NCS

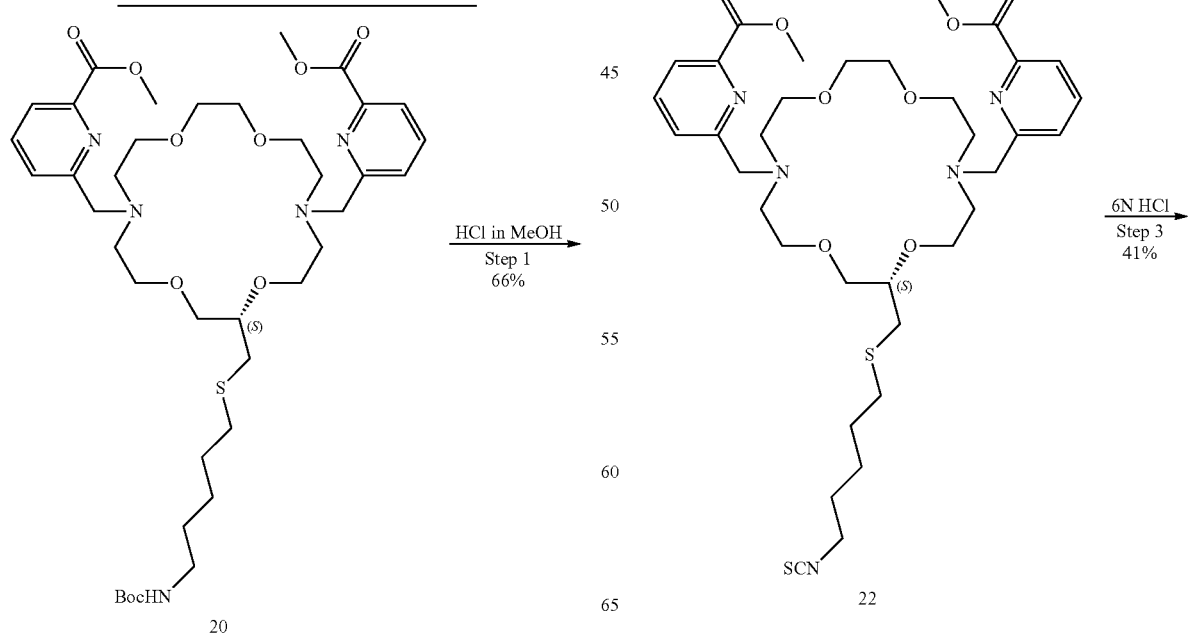

-continued

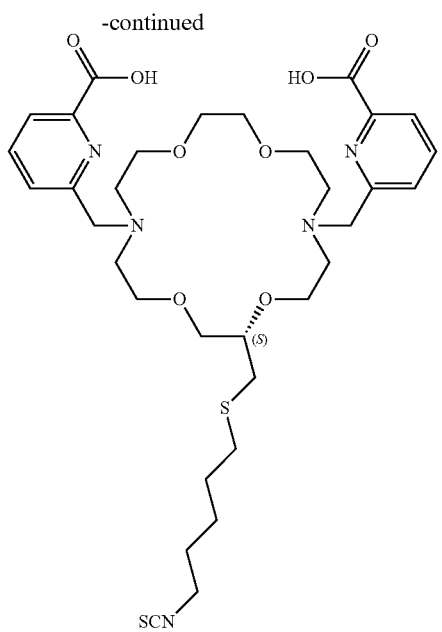

Step 1:
To compound 20 (120 mg, 0.15 mmol), a cold solution of HCl in methanol (2 mL, 4N) was added and stirred for 2 h. The reaction mixture was concentrated under reduced pressure to yield compound 21 as yellow liquid (70 mg, 66%).

Step 2:
To a solution of compound 21 (70 mg, 0.1 mmol) and triethylamine (20 mg, 0.2 mmol) in dry dichloromethane (2 mL) in a pressure vial was added carbon disulfide (15 mg, 0.2 mmol). The vial was subjected to MW-irradiation (150 W power) at 90° C. for 30 min. Thereafter, the reaction mixture was diluted with dichloromethane (10 mL), washed successively with water (5 mL), 1M HCl (5 mL), water (5 mL) and dried over anhydrous sodium sulphate. After concentration, the crude product was purified by flash chromatography on silica gel (230-400 mesh) using 0-10% methanol in dichloromethane as eluent to yield compound 22 (30 mg, 40%) as a yellow solid.

Step 3:
A solution of compound 22 (30 mg, 0.04 mmol) in hydrochloric acid (6N, 0.5 mL) was stirred overnight at room temperature. After completion of the reaction, it was concentrated under reduced pressure. The residue was purified by preparative HPLC to yield H2bp18c6-off Macrocycle-pentylsulfide NCS (12 mg, 41%) as a white solid. LC-MS APCI: Calculated for $C_{33}H_{47}N_5O_8S_2$: 705.89; Observed m/z $[M+H]^+$ 706.2. Purity by LC-MS: 99.33% RT: 1.58. Purity by HPLC: 98.92% RT: 2.76. $^1$H NMR 1H-NMR (400 MHz, DMSO-d6): δ 13.40 (s, 1H), 9.90 (s, 1H), 8.17-8.09 (i, 4H), 7.78 (d, J=6.80 Hz, 2H), 4.70 (s, 4H), 3.93-3.17 (m, 27H), 2.68-2.67 (m, 2H), 1.64-1.60 (m, 2H), 1.53-1.49 (m, 2H), 1.40-1.38 (n, 2H).

Example 26: Properties of Radioimmunoconjugate

Table 1 summarizes the chelation efficiency of the radioimmunoconjugates prepared in the examples.

TABLE 1

Summary of Chelation Efficiency

| Name | Chelation efficacy before DTPA | Chelation efficacy after DTPA | Chelator:Ac-225 Ratio |
|---|---|---|---|
| H2bp18c6-Benzyl-Phenyl-DBCO IgG4 | 99% | — | 100:1 |
| H2bp18c6-Benzyl-Phenyl-DBCO PSMB127 | 99% | — | 100:1 |
| H2bp18c6-Benzyl-Phenyl-DBCO Pertuzumab | 99% | 96% | 100:1 |
| H2bp18c6-Benzyl-Phenyl-DBCO Cetuximab | 99% | 95% | 100:1 |
| H2bp18c6-Benzyl-Phenyl-DBCO Herceptin | 99% | 93% | 100:1 |
| H2bp18c6-Benzyl-Phenyl-DBCO Panitumuma | 99% | 85% | 100:1 |
| H2bp18c6-Benzyl-Phenyl-DBCO H11B6 | 99% | 97% | 91:1 |
| H2bp18c6-Benzyl-Phenyl-BCN PSMB127 | 99% | 97% | 100:1 |
| H2bp18c6-off Macrocycle-ethyl sulfide-DBCO PSMB127 | 99% | 94% | 80:1 |
| H2bp18c6-off Macrocycle-pentyl sulfide-DBCO PSMB127 | 99% | 97% | 76:1 |
| DOTA-H11B6 (site specific) | 79% | | 100:1 |
| DOTA-H11B6 (site random) | 36% | | 130:1 |

Human serum stability of the four $^{225}$Ac-Chelator-mAbs conjugates is measured according to the following method:

$^{225}$Ac-H2bp18c6-benzyl-phenyl-DBCO-PSMB127

$^{225}$Ac-H2bp18c6-off Macrocycle-ethyl sulfide-DBCO-PSMB127

$^{225}$Ac-H2bp18c6-off Macrocycle-pentyl sulfide-DBCO-PSMB127

$^{225}$Ac-H2bp18c6-benzyl-phenyl-BCN-PSMB127

To each solution of 900 µL pooled human serum (BioIVT) is added 100 µL of ~300 µCi/mg of one of the four conjugates. The individual conjugate solution is mixed and then 10 µL is collected at several time-points over seven days. Each 10 µL sample is transferred to a separate plastic vial containing 30 µL of 50 mM DTPA and left standing still for 5 minutes at room temperature. 10 µL of the mixture was collected and then loaded onto an iTLC-SG, which was developed with 10 mM EDTA. The dried iTLC-SG was left at room temperature for overnight before it was scanned on a Bioscan AR-2000 radio-TLC scanner. Under the elution conditions described herein, any free Ac-225 would migrate with the solvent to the solvent front. The stability results are listed in Table 2.

TABLE 2
| $^{225}$Ac Conjugate | Structure | Study days | Stability |
|---|---|---|---|
| $^{225}$Ac H2bp18c6-benzyl-phenyl-DBCO-PSMB127 | 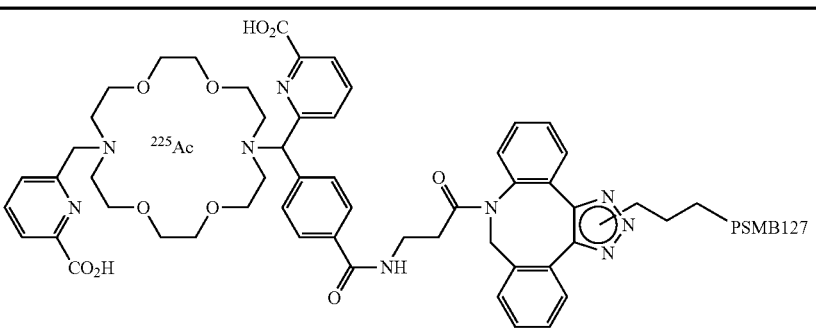 | 14 | Stable |
| $^{225}$Ac H2bp18c6-off Macrocycle-ethyl sulfide-DBCO-PSMB127 | 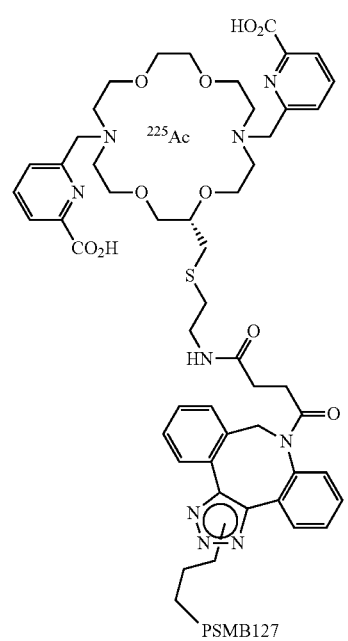 | 7 | Stable |
| $^{225}$Ac H2bp18c6-off Macrocycle-pentyl sulfide-DBCO-PSMB127 | 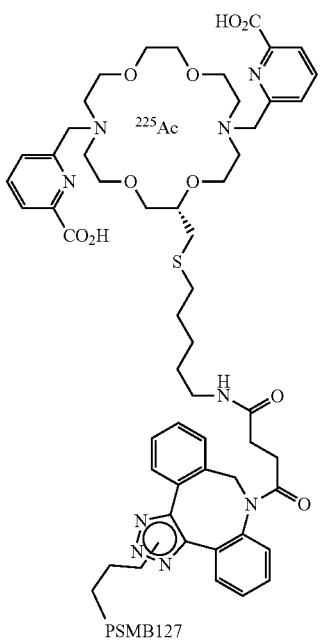 | 7 | Stable |

TABLE 2-continued

| 225Ac Conjugate | Structure | Study days | Stability |
|---|---|---|---|
| 225Ac H2bp18c6-benzyl-phenyl-BCN-PSMB127 | 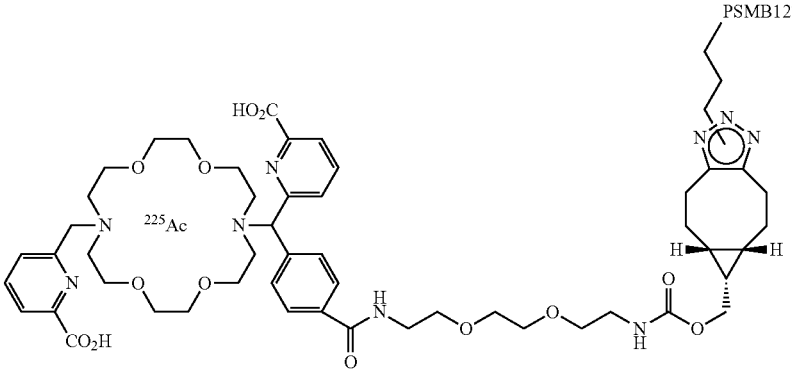 | 7 | Stable |

Example 27: Radioimmunoconjugate Cell Binding Assays

Cell binding of azide-modified antibodies, and azide modified antibodies conjugated to a chelator or radiometal complex of the invention is compared to the parental antibody. Cells expressing the antigen target of the antibody are incubated with parental antibody, azide-modified antibody or conjugated antibody diluted in buffer and then analyzed for cell binding by flow cytometry.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

We claim:

1. A chelator of formula (I):

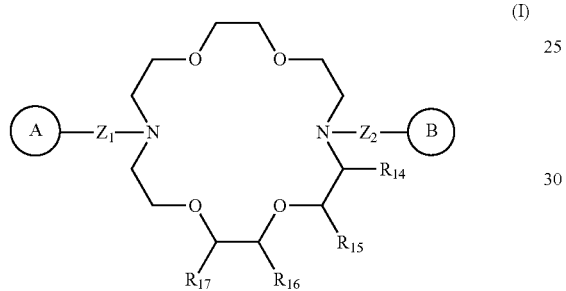

(I)

wherein:
- each of ring A and ring B is independently a 6-10 membered aryl or a 5-10 membered heteroaryl, wherein each of ring A and ring B is optionally substituted with one or more substituents independently selected from the group consisting of halo, alkyl, alkenyl, cycloalkyl, cycloalkenyl, aryl, heterocyclyl, heteroaryl, —$OR_{13}$, —$SR_{13}$, —$(CH_2)_p$ $COOR_{13}$, —$OC(O)R_{13}$, —$N(R_{13})_2$, —$CON(R_{13})_2$, —$NO_2$, —CN —$OC(O)N(R_{13})_2$, and X;
- each of $Z_1$ and $Z_2$ is independently —$(C(R_{12})_2)_m$— or —$(CH_2)_n$—$C(R_{12})(X)$—$(CH_2)_n$—;
- each X is independently -$L_1$-$R_{11}$;
- each n is independently 0, 1, 2, 3, 4, or 5;
- each m is independently 1, 2, 3, 4, or 5;
- each p is independently 0 or 1;
- $L_1$ is absent or a linker;
- $R_{11}$ is a nucleophilic moiety or an electrophilic moiety, or $R_{11}$ comprises a targeting ligand;
- each $R_{12}$ is independently hydrogen, alkyl, cycloalkyl, aryl, heterocyclyl, or heteroaryl;
- each $R_{13}$ is independently hydrogen or alkyl;
- each of $R_{14}$, $R_{15}$, $R_{16}$, and $R_{17}$ is independently hydrogen, alkyl, or X,
- or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
- provided that the chelator comprises at least one X, and when X is present on ring A or ring B, $L_1$ is a linker or at least one of $R_{12}$ and $R_{14}$-$R_{17}$ is not hydrogen wherein L1 is selected from the group consisting of:

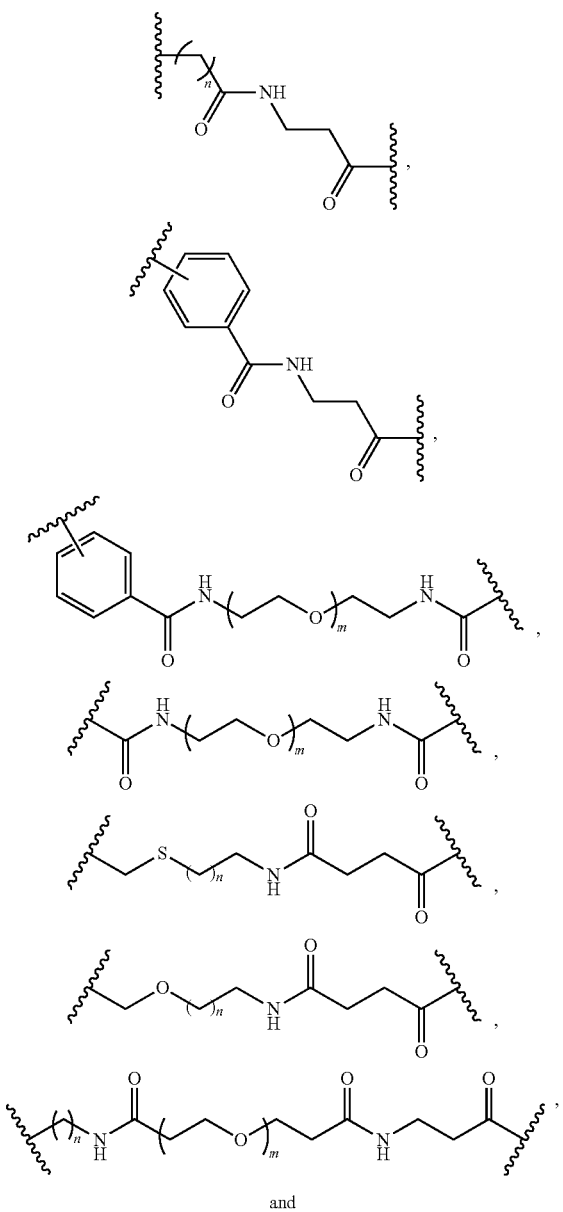

and

-continued

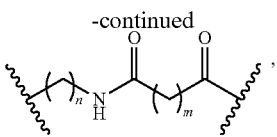

wherein n is an integer of 0 to 10, and m is an integer of 0 to 12.

2. The chelator of claim 1, being a chelator of formula (II):

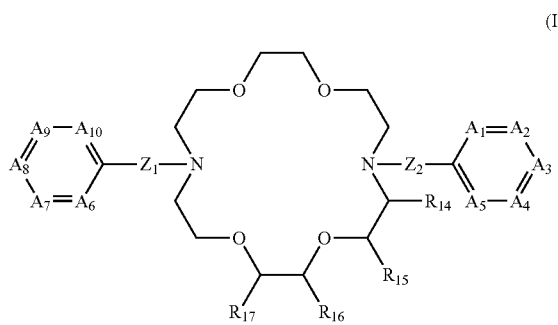

(II)

wherein:
- $A_1$ is N or $CR_1$ or is absent;
- $A_2$ is N or $CR_2$;
- $A_3$ is N or $CR_3$;
- $A_4$ is N or $CR_4$;
- $A_5$ is N or $CR_5$;
- $A_6$ is N or $CR_6$ or is absent;
- $A_7$ is N or $CR_7$;
- $A_8$ is N or $CR_8$;
- $A_9$ is N or $CR_9$;
- $A_{10}$ is N or $CR_{10}$;
- provided that no more than three of $A_1, A_2, A_3, A_4$, and $A_5$ are N, and no more than three of $A_6, A_7, A_8, A_9$, and $A_{10}$ are N;
- each of $R_1, R_2, R_3, R_4, R_5, R_6, R_7, R_8, R_9$, and $R_{10}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_p COOR_{13}$, —$OC(O)R_{13}$, —$N(R_{13})_2$, —$CON(R_{13})_2$, —$NO_2$, —CN, —$OC(O)N(R_{13})_2$, and —X,
- or, alternatively, any two directly adjacent $R_1, R_2, R_3, R_4, R_5, R_6, R_7, R_8, R_9$, and $R_{10}$ are taken together with the atoms to which they are attached to form a five or six-membered substituted or unsubstituted carbocyclic or nitrogen-containing ring;
- each of $Z_1$ and $Z_2$ is independently —$(C(R_{12})_2)_m$— or —$(CH_2)_n$—$C(R_{12})(X)$—$(CH_2)_n$—;
- each X is independently -$L_1$-$R_{11}$;
- each n is independently 0, 1, 2, 3, 4, or 5;
- each m is independently 1, 2, 3, 4, or 5;
- each p is independently 0 or 1;
- $L_1$ is absent or a linker;
- $R_{11}$ is a nucleophilic moiety or an electrophilic moiety, or $R_{11}$ comprises a targeting ligand;
- each $R_{12}$ is independently hydrogen, alkyl, cycloalkyl, aryl, heterocyclyl, or heteroaryl;
- each $R_{13}$ is independently hydrogen or alkyl;
- each of $R_{14}, R_{15}, R_{16}$, and $R_{17}$ is independently hydrogen, alkyl, or X,
- or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
- provided that the chelator comprises at least one X, and when any one of $R_1, R_2, R_3, R_4, R_5, R_6, R_7, R_8, R_9$, and $R_{10}$ is X, then $L_1$ is a linker or at least one of $R_{12}$ and $R_{14}$-$R_{17}$ is not hydrogen.

3. The chelator of claim 1, being a chelator of formula (III):

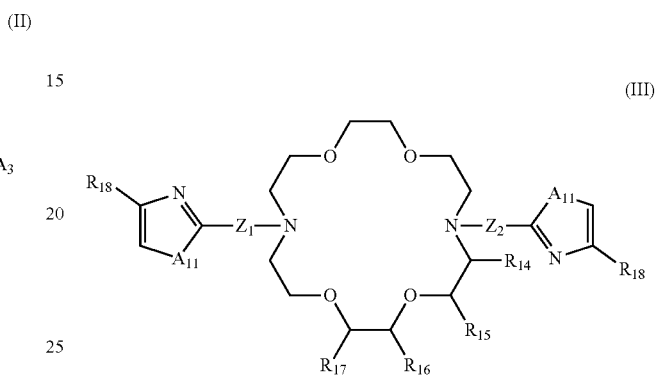

(III)

wherein:
- each $A_{11}$ is independently O, S, NMe, or NH;
- each of $Z_1$ and $Z_2$ is independently —$(C(R_{12})_2)_m$— or —$(CH_2)_n$—$C(R_{12})(X)$—$(CH_2)_n$—;
- each X is independently -$L_1$-$R_{11}$;
- each n is independently 0, 1, 2, 3, 4, or 5;
- each m is independently 1, 2, 3, 4, or 5;
- each p is independently 0 or 1;
- $L_1$ is absent or a linker;
- $R_{11}$ is a nucleophilic moiety or an electrophilic moiety, or $R_{11}$ comprises a targeting ligand;
- each $R_{12}$ is independently hydrogen, alkyl, cycloalkyl, aryl, heterocyclyl, or heteroaryl;
- each $R_{13}$ is independently hydrogen or alkyl;
- each of $R_{14}, R_{15}, R_{16}$, and $R_{17}$ is independently hydrogen, alkyl, or X,
- or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
- each $R_{18}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_p COOR_{13}$, —$OC(O)R_{13}$, —$N(R_{13})_2$, —$CON(R_{13})_2$, —$NO_2$, —CN —$OC(O)N(R_{13})_2$, and —X,
- provided that the chelator comprises at least one X, and when $R_{18}$ is X, then $L_1$ is a linker or at least one of $R_{12}$ and $R_{14}$-$R_{17}$ is not hydrogen.

4. The chelator of claim 1, wherein the chelator is selected from the group consisting of:

209
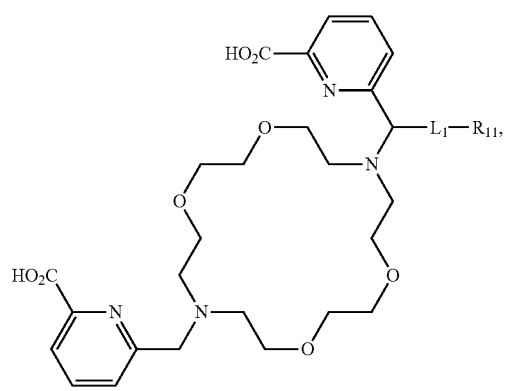
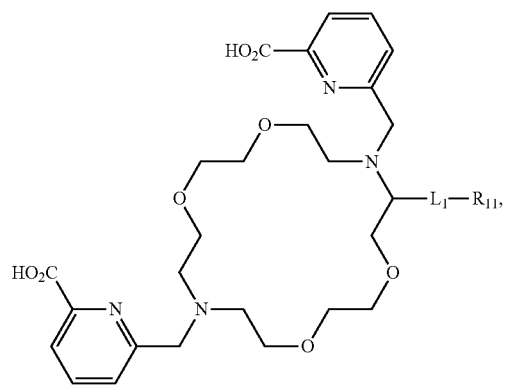
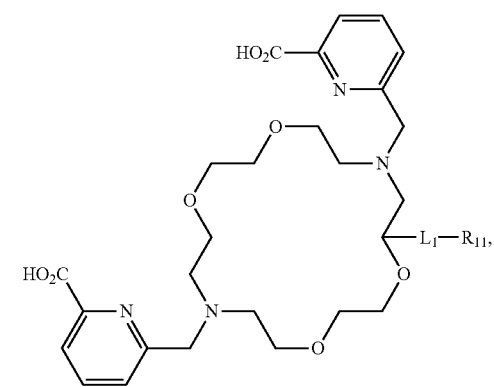
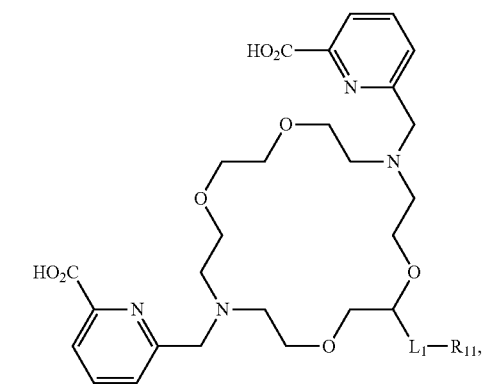
210
-continued
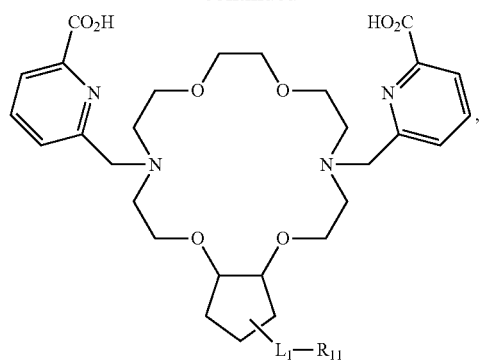
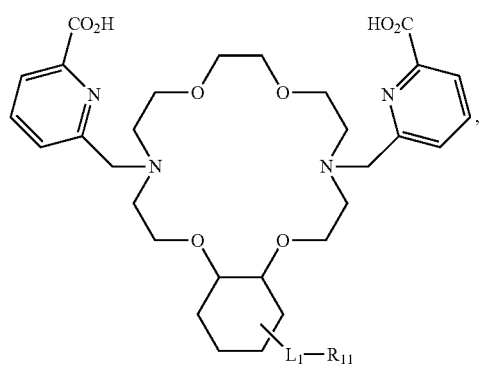
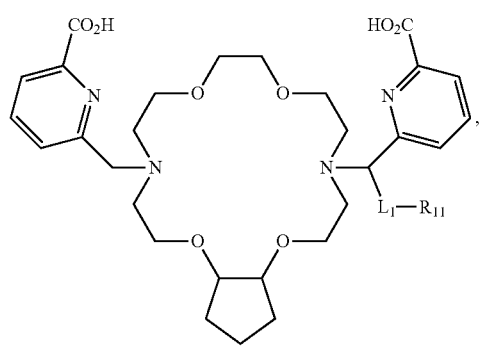
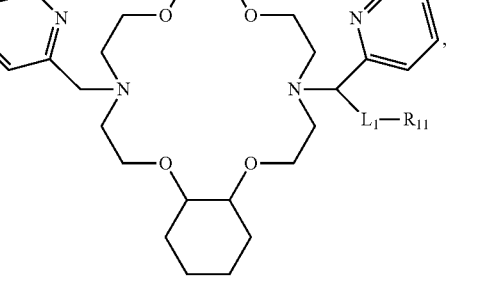
and -continued

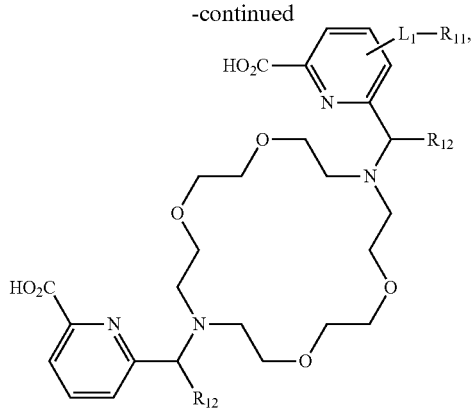

wherein:

$L_1$ is absent or a linker;

$R_{11}$ is a nucleophilic moiety or an electrophilic moiety, or $R_{11}$ comprises a targeting ligand;

each $R_{12}$ is independently hydrogen, —$CH_3$, or —$CH_2CH_3$, provided at least one $R_{12}$ is —$CH_3$ or —$CH_2CH_3$.

5. The chelator of claim 1, wherein $R_{11}$ is —$NH_2$, —NCS, —NCO, —$N_3$, alkynyl, cycloalkynyl, —C(O)$R_{13}$, —COO$R_{13}$, —CON($R_{13}$)$_2$, maleimido, acyl halide, tetrazine, or trans-cyclooctene.

6. The chelator of claim 5, wherein $R_{11}$ is cyclooctynyl or a cyclooctynyl derivative selected from the group consisting of bicyclononynyl (BCN), difluorinated cyclooctynyl (DIFO), dibenzocyclooctynyl (DIBO), keto-DIBO, biarylazacyclooctynonyl (BARAC), dibenzoazacyclooctynyl (DIBAC, DBCO, ADIBO), dimethoxyazacyclooctynyl (DIMAC), difluorobenzocyclooctynyl (DIFBO), monobenzocyclooctynyl (MOBO), and tetramethoxy dibenzocyclooctynyl (TMDIBO).

7. The chelator of claim 6, wherein $R_{11}$ is DBCO or BCN.

8. The chelator of claim 1 wherein $R_{11}$ comprises a targeting ligand, wherein the targeting ligand comprises an antibody or antigen binding fragment thereof, scaffold protein, small molecule, or aptamer.

9. The chelator of claim 1 selected from the group consisting of:

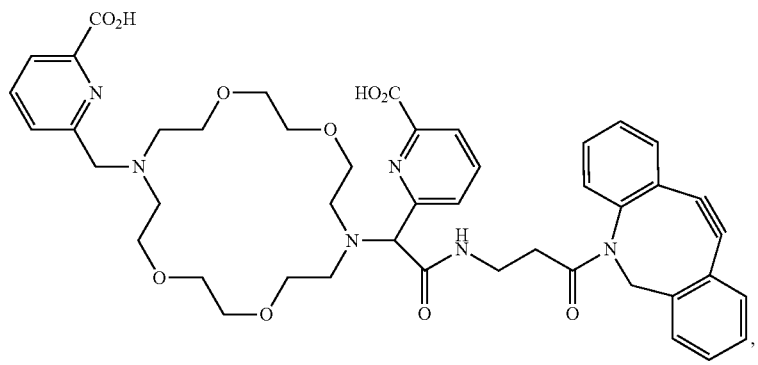

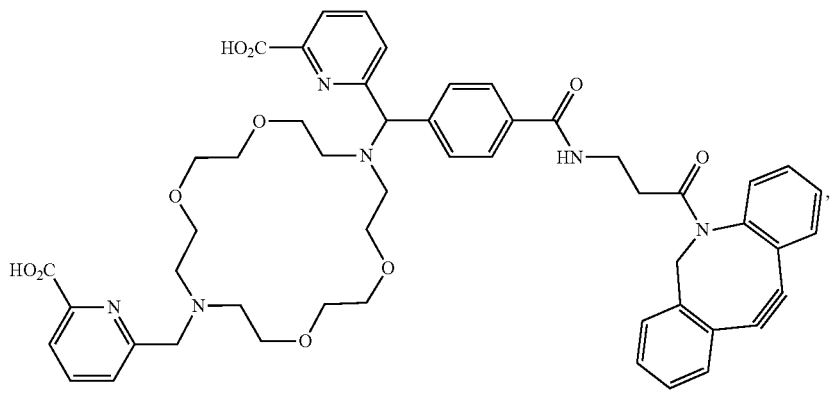

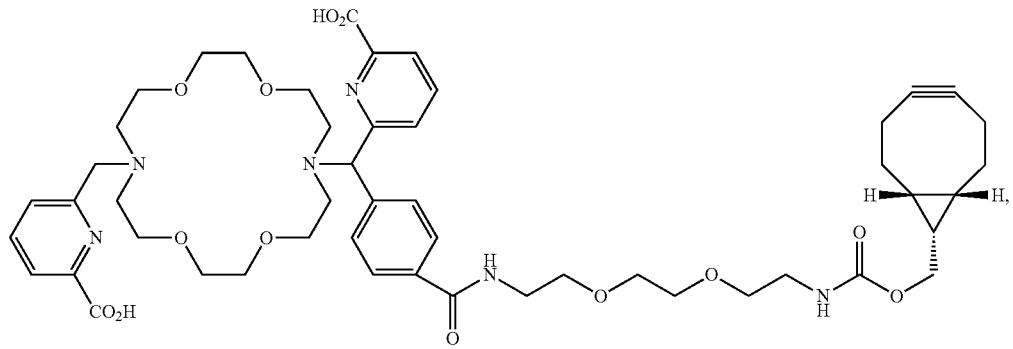

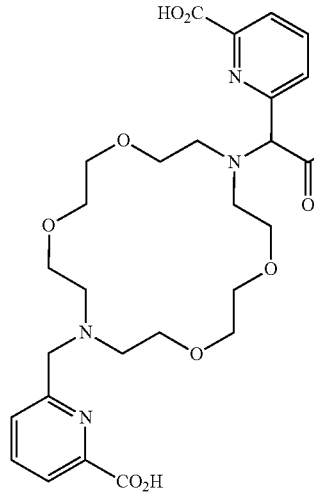
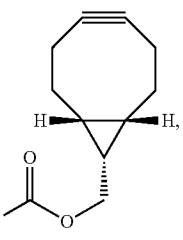
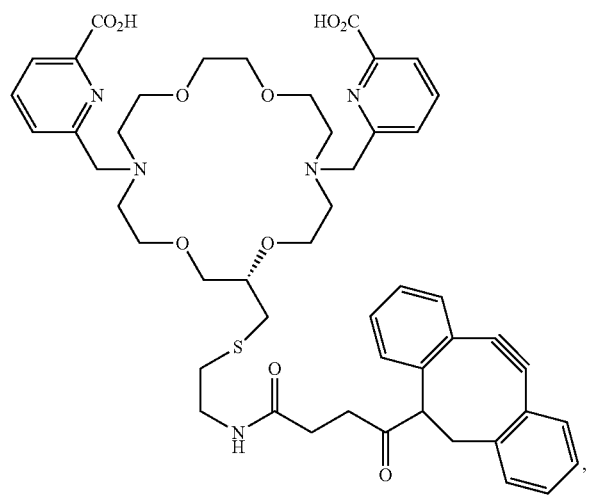
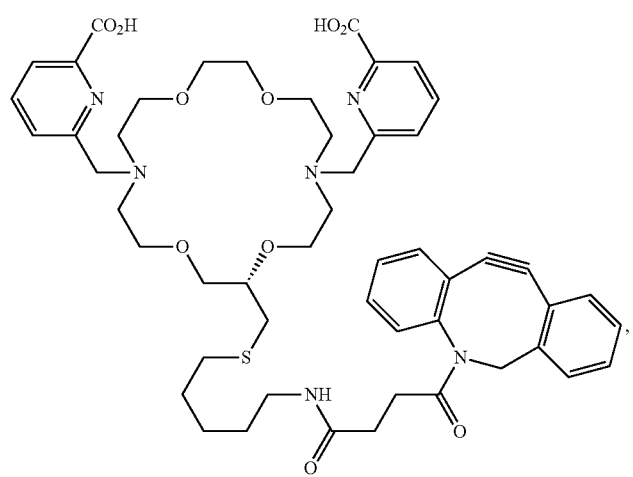
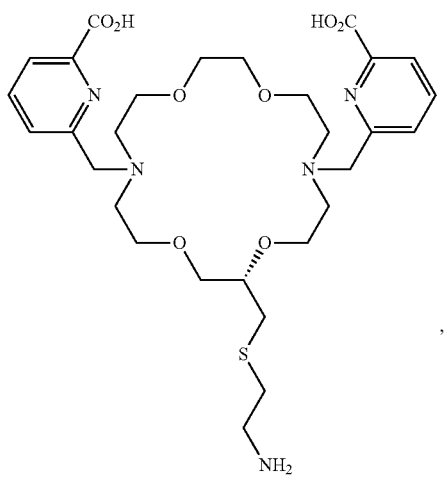

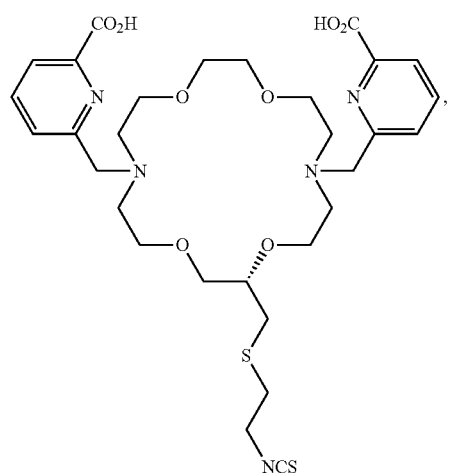

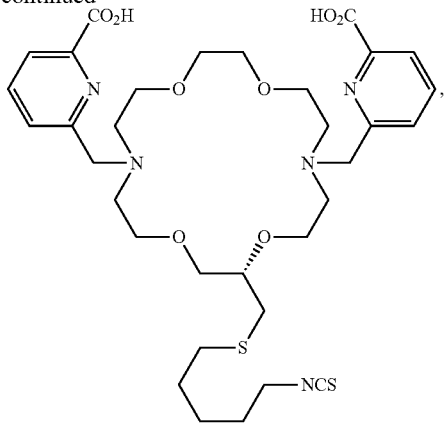

-continued

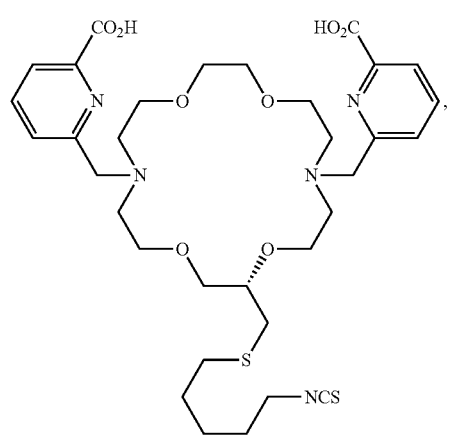

and

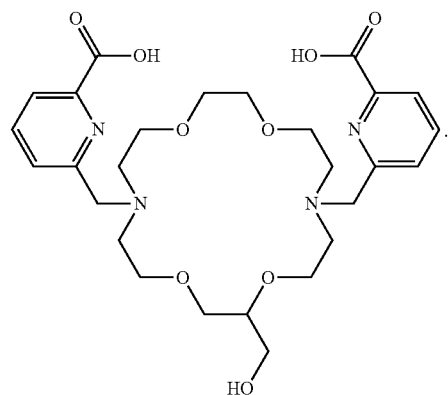

10. The chelator of claim 1, wherein the chelator comprises a radiometal ion bound to the chelator via coordinate bonding thereby forming a radiometal complex.

11. A radiometal complex comprising a chelator bound to an alpha-emitting radiometal ion via coordinate bonding, wherein the radiometal complex has the structure of formula (I-m):

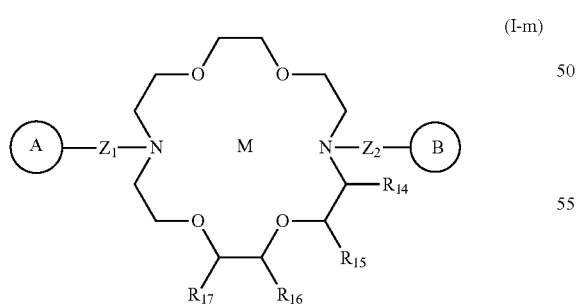

wherein:
M is a radiometal ion;
each of ring A and ring B is independently a 6-10 membered aryl or a 5-10 membered heteroaryl, wherein each of ring A and ring B is optionally substituted with one or more substituents independently selected from the group consisting of halo, alkyl, alkenyl, cycloalkyl, cycloalkenyl, aryl, heterocyclyl, heteroaryl, —$OR_{13}$, —$SR_{13}$, —$(CH_2)_p COOR_{13}$, —$OC(O)R_{13}$, —$N(R_{13})_2$, —$CON(R_{13})_2$, —$NO_2$, —CN —$OC(O)N(R_{13})_2$, and X;

each of $Z_1$ and $Z_2$ is independently —$(C(R_{12})_2)_m$— or —$(CH_2)_n$—$C(R_{12})(X)$—$(CH_2)_n$—;

each X is independently -$L_1$-$R_{11}$;

each n is independently 0, 1, 2, 3, 4, or 5;

each m is independently 1, 2, 3, 4, or 5;

each p is independently 0 or 1;

$L_1$ is absent or a linker;

$R_{11}$ is a nucleophilic moiety or an electrophilic moiety, or $R_{11}$ comprises a targeting ligand;

each $R_{12}$ is independently hydrogen, alkyl, cycloalkyl, aryl, heterocyclyl, or heteroaryl;

each $R_{13}$ is independently hydrogen or alkyl;

each of $R_{14}$, $R_{15}$, $R_{16}$, and $R_{17}$ is independently hydrogen, alkyl, or X, or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;

provided that the radiometal complex comprises at least one X, and when X is present on ring A or ring B, $L_1$ is a linker or at least one of $R_{12}$ and $R_{14}$-$R_{17}$ is not hydrogen wherein L1 is selected from the group consisting of:

wherein n is an integer of 0 to 10, and m is an integer of 0 to 12.

12. The radiometal complex of claim 11, being a radiometal complex of formula (II-m):

(II-m)

wherein:
M is a radiometal ion;
$A_1$ is N or $CR_1$ or is absent;
$A_2$ is N or $CR_2$;
$A_3$ is N or $CR_3$;
$A_4$ is N or $CR_4$;
$A_5$ is N or $CR_5$;
$A_6$ is N or $CR_6$ or is absent;
$A_7$ is N or $CR_7$;
$A_8$ is N or $CR_8$;
$A_9$ is N or $CR_9$;
$A_{10}$ is N or $CR_{10}$;
provided that no more than three of $A_1$, $A_2$, $A_3$, $A_4$, and $A_5$ are N, and no more than three of $A_6$, $A_7$, $A_8$, $A_9$, and $A_{10}$ are N;
each of $R_1$, $R_2$, $R_3$, $R_4$, $R_5$, $R_6$, $R_7$, $R_8$, $R_9$, and $R_{10}$ is independently selected from the group consisting of hydrogen, halo, alkyl, alkenyl, cycloalkyl, cycloalkenyl, aryl, heterocyclyl, heteroaryl, —$OR_{13}$, —$SR_{13}$, —$(CH_2)_pCOOR_{13}$, —$OC(O)R_{13}$, —$N(R_{13})_2$, —$CON(R_{13})_2$, —$NO_2$, —CN —$OC(O)N(R_{13})_2$, and —X,
or, alternatively, any two directly adjacent $R_1$, $R_2$, $R_3$, $R_4$, $R_5$, $R_6$, $R_7$, $R_8$, $R_9$, and $R_{10}$ are taken together with the atoms to which they are attached to form a five or six-membered substituted or unsubstituted carbocyclic or nitrogen-containing ring;
each of $Z_1$ and $Z_2$ is independently —$(C(R_{12})_2)_m$— or —$(CH_2)_n$—$C(R_{12})(X)$—$(CH_2)_n$—;
each X is independently -$L_1$-$R_{11}$;
each n is independently 0, 1, 2, 3, 4, or 5;
each m is independently 1, 2, 3, 4, or 5;
each p is independently 0 or 1;
$L_1$ is absent or a linker;
$R_{11}$ is a nucleophilic moiety or an electrophilic moiety, or $R_{11}$ comprises a targeting ligand;
each $R_{12}$ is independently hydrogen, alkyl, cycloalkyl, aryl, heterocyclyl, or heteroaryl;
each $R_{13}$ is independently hydrogen or alkyl;
each of $R_{14}$, $R_{15}$, $R_{16}$, and $R_{17}$ is independently hydrogen, alkyl, or X,
or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
provided that the radiometal complex comprises at least one X, and when any one of $R_1$, $R_2$, $R_3$, $R_4$, $R_5$, $R_6$, $R_7$, $R_8$, $R_9$, and $R_{10}$ is X, then $L_1$ is a linker or at least one of $R_{12}$ and $R_{14}$-$R_{17}$ is not hydrogen.

13. The radiometal complex of claim 11, being a radiometal complex of formula (III-m):

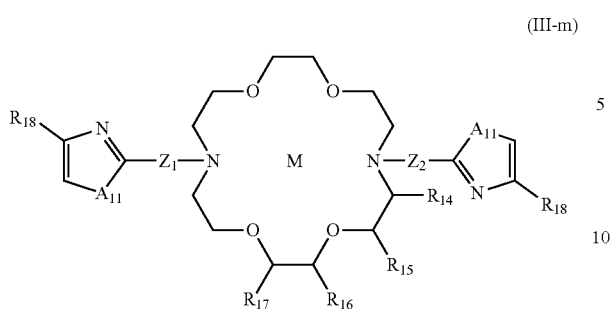

(III-m)

wherein:
- M is a radiometal ion;
- each $A_{11}$ is independently O, S, NMe, or NH;
- each of $Z_1$ and $Z_2$ is independently $-(C(R_{12})_2)_m-$ or $-(CH_2)_n-C(R_{12})(X)-(CH_2)_n-$;
- each X is independently $-L_1-R_{11}$;
- each n is independently 0, 1, 2, 3, 4, or 5;
- each m is independently 1, 2, 3, 4, or 5;
- each p is independently 0 or 1;
- $L_1$ is absent or a linker;
- $R_{11}$ is a nucleophilic moiety or an electrophilic moiety, or $R_{11}$ comprises a targeting ligand;
- each $R_{12}$ is independently hydrogen, alkyl, cycloalkyl, aryl, heterocyclyl, or heteroaryl;
- each $R_{13}$ is independently hydrogen or alkyl;
- each of $R_{14}$, $R_{15}$, $R_{16}$, and $R_{17}$ is independently hydrogen, alkyl, or X,
- or alternatively $R_{14}$ and $R_{15}$ and/or $R_{16}$ and $R_{17}$ are taken together with the carbon atoms to which they are attached to form a 5- or 6-membered cycloalkyl ring optionally substituted with X; and
- each $R_{18}$ is independently selected from the group consisting of hydrogen, halo, alkyl, alkenyl, cycloalkyl, cycloalkenyl, aryl, heterocyclyl, heteroaryl, $-OR_{13}$, $-SR_{13}$, $-(CH_2)_pCOOR_{13}$, $-OC(O)R_{13}$, $-N(R_{13})_2$, $-CON(R_{13})_2$, $-NO_2$, $-CN$, $-OC(O)N(R_{13})_2$, and $-X$,
- provided that the radiometal complex comprises at least one X, and when $R_{18}$ is X, then $L_1$ is a linker or at least one of $R_{12}$ and $R_{14}$-$R_{17}$ is not hydrogen.

14. The radiometal complex of claim 11, wherein the radiometal complex is selected from the group consisting of:

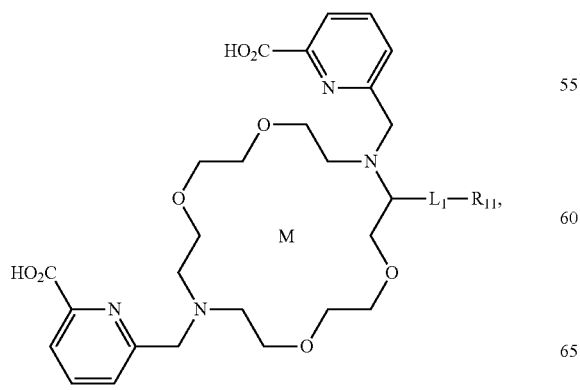

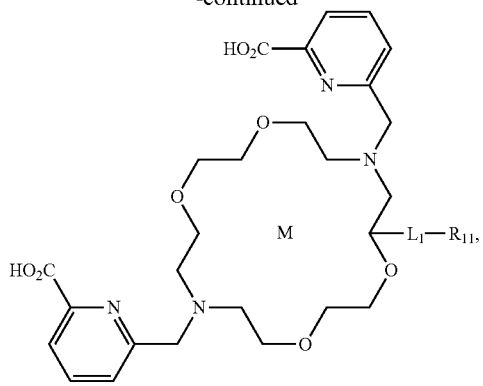

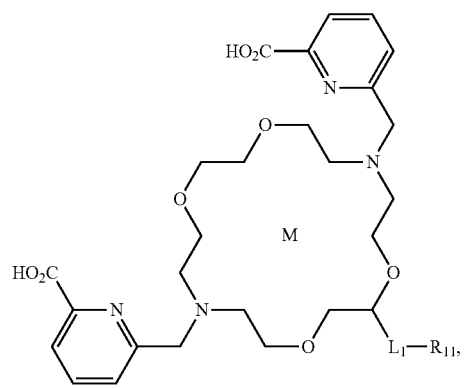

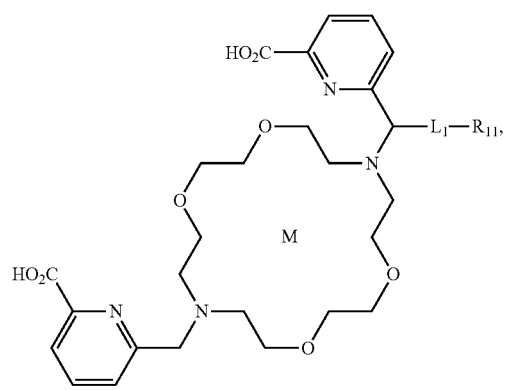

-continued

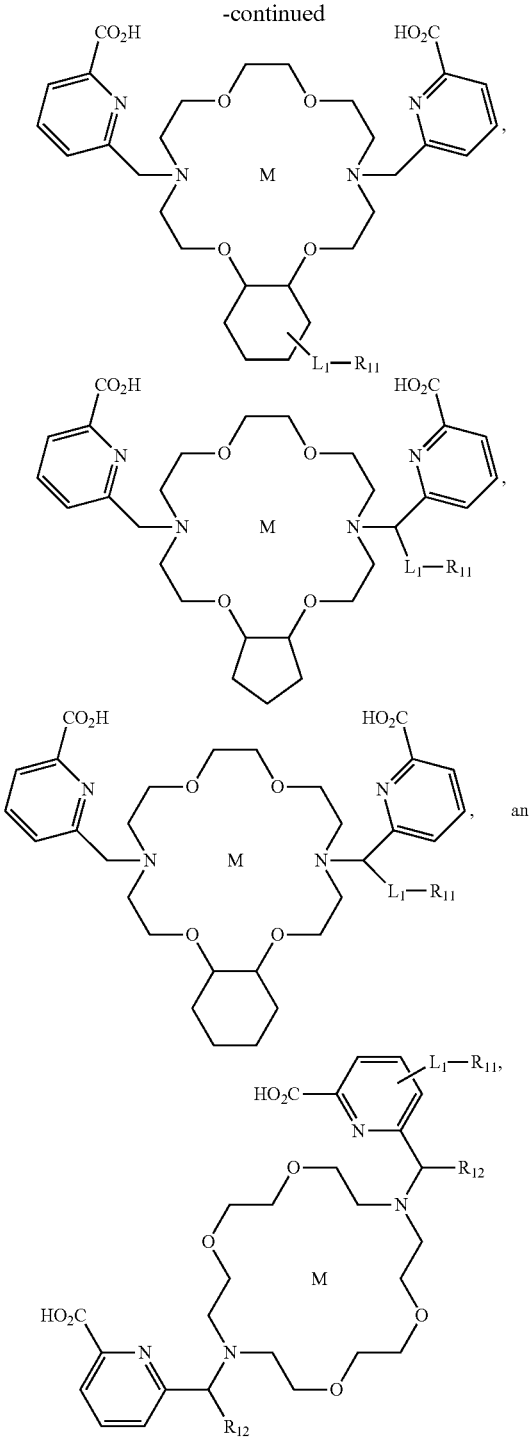

wherein:

M is actinium-225 ($^{225}$Ac), $L_1$ is absent or a linker; and
$R_{11}$ is a nucleophilic moiety or an electrophilic moiety, or $R_{11}$ comprises a targeting ligand; and
each $R_{12}$ is independently hydrogen, —$CH_3$ or —$CH_2CH_3$, provided at least one $R_{12}$ is —$CH_3$ or —$CH_2CH_3$.

15. A radioimmunoconjugate comprising the radiometal complex of claim 11 conjugated to an antibody or antigen binding fragment thereof.

16. The radioimmunoconjugate of claim 15, wherein the antibody or antigen binding fragment thereof is linked to $R_{11}$ of the radiocomplex via a triazole moiety.

17. A radioimmunoconjugate having a structure selected from the group consisting of:

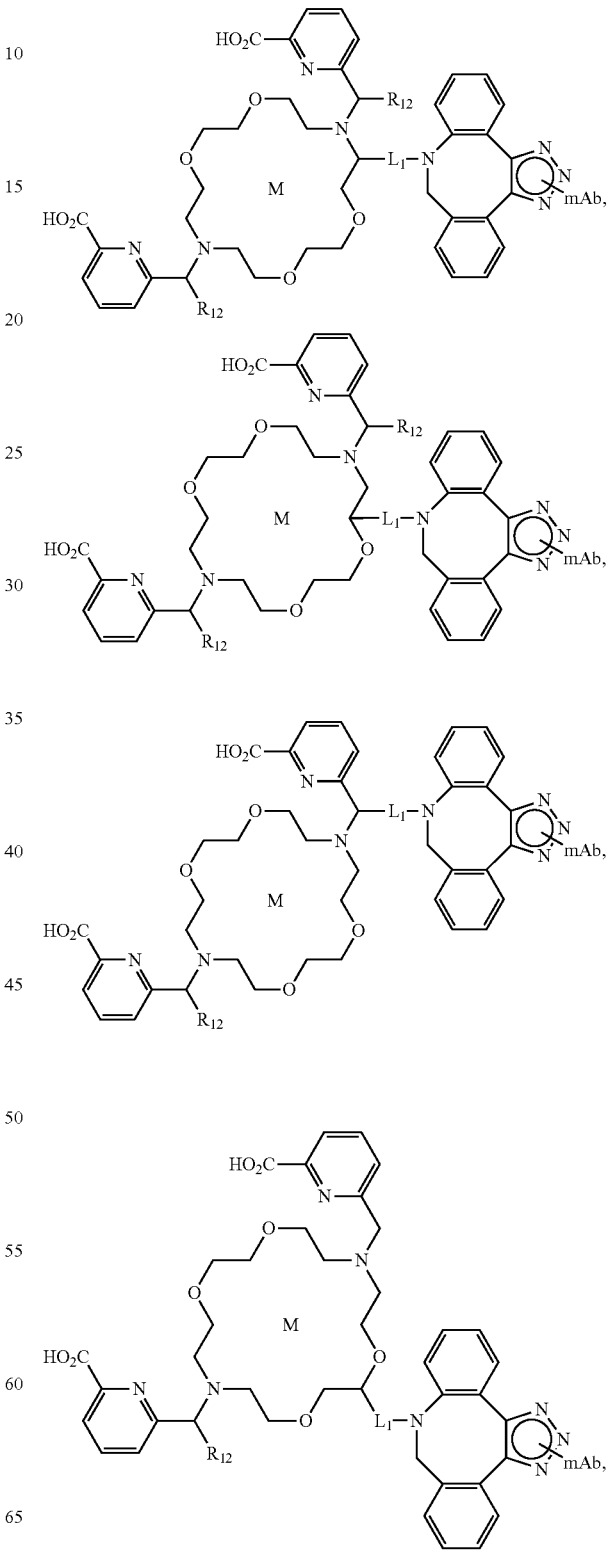

223
-continued
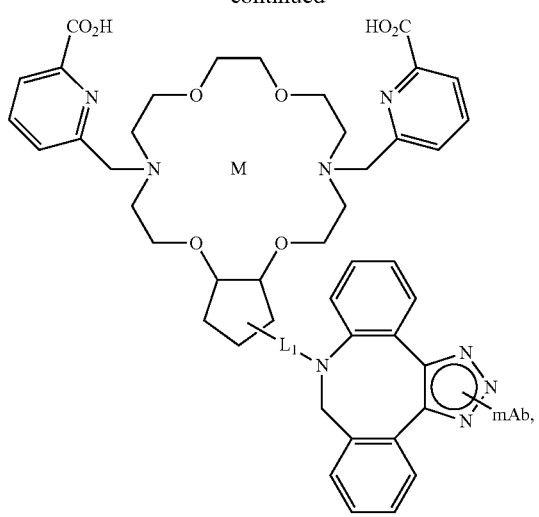
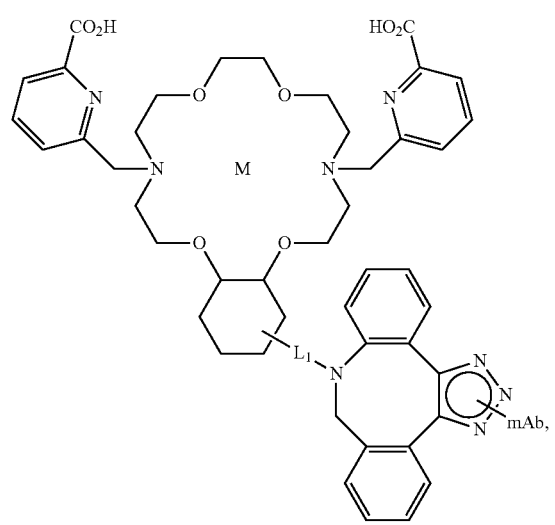
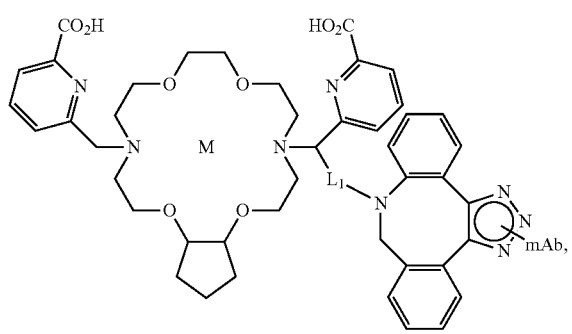
224
-continued
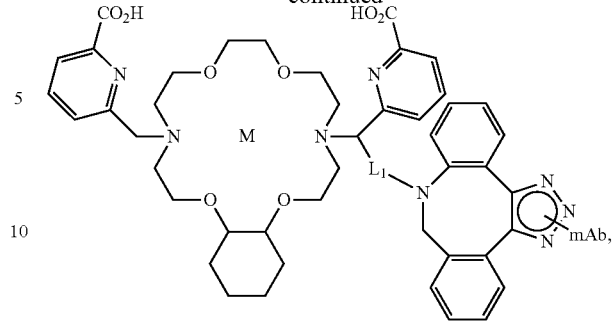
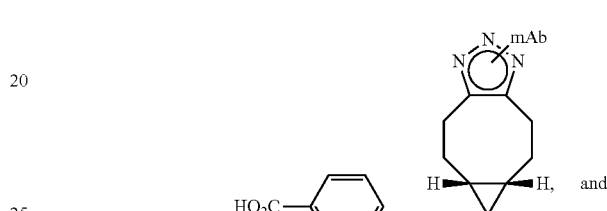
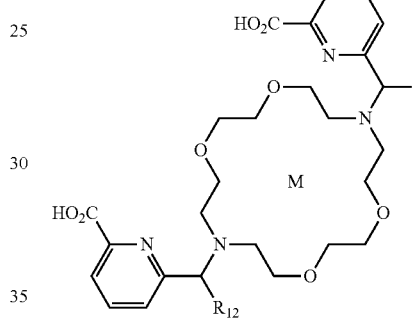
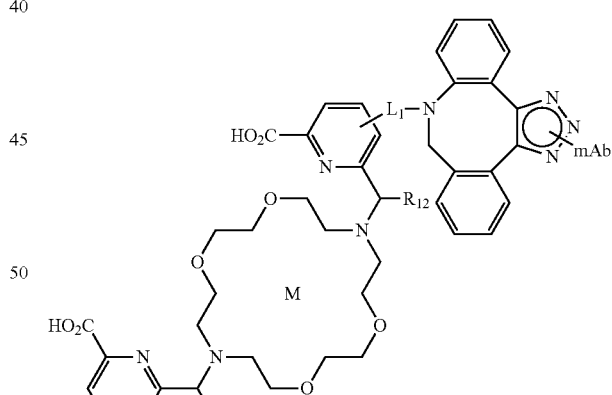
wherein:
M is a radiometal ion;
L₁ is a linker;
mAb is an antibody or antigen binding fragment thereof;
each $R_{12}$ is independently hydrogen, —CH₃, or —CH₂CH₃, provided at least one $R_{12}$ is —CH₃ or —CH₂CH₃.
18. The radioimmunoconjugate of claim 17, wherein the radioimmunoconjugate is selected from the group consisting of:

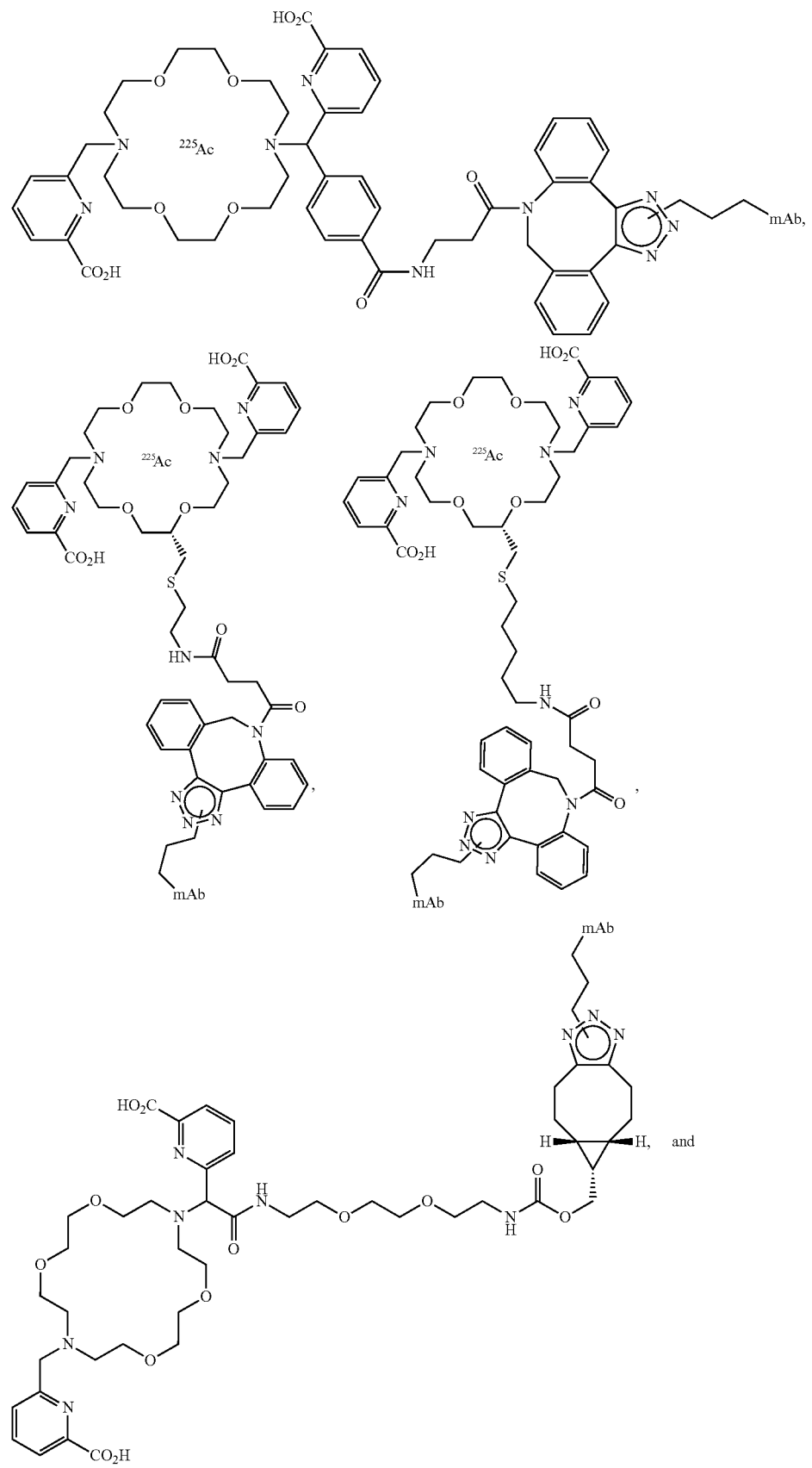

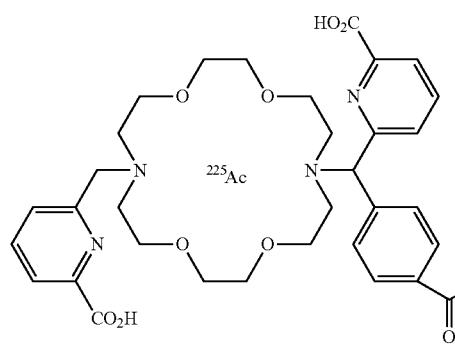
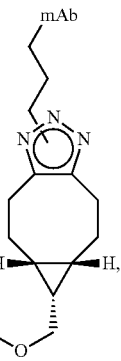

wherein mAb is an antibody or antigen binding fragment thereof.

19. A pharmaceutical composition comprising the radioimmunoconjugate of claim 15, and a pharmaceutically acceptable carrier.

20. A method of selectively targeting neoplastic cells for radiotherapy in a subject in need thereof, the method comprising administering to the subject a therapeutically effective amount of the pharmaceutical composition of claim 19.

21. A method of treating a neoplastic disease or disorder in a subject in need thereof, the method comprising administering to the subject a therapeutically effective amount of the pharmaceutical composition of claim 19.

22. A method of treating cancer in a subject in need thereof, the method comprising administering to the subject a therapeutically effective amount of the pharmaceutical composition of claim 19.

* * * * *